United States Patent [19]

Takaya et al.

[11] Patent Number: 5,252,731
[45] Date of Patent: Oct. 12, 1993

[54] CEPHALOSPORIN INTERMEDIATES

[75] Inventors: Takao Takaya, Kawanishi; Hisashi Takasugi, Osaka; Takashi Masugi, Ikeda; Hideaki Yamanaka, Hirakata; Kohji Kawabata, Osaka, all of Japan

[73] Assignee: Fujisawa Pharmaceutical Co., Ltd., Osaka, Japan

[21] Appl. No.: 831,504

[22] Filed: Feb. 5, 1992

Related U.S. Application Data

[60] Division of Ser. No. 583,304, Sep. 17, 1990, Pat. No. 5,110,921, which is a division of Ser. No. 462,347, Jan. 3, 1990, Pat. No. 4,960,889, which is a continuation of Ser. No. 127,929, Dec. 2, 1987, abandoned, which is a division of Ser. No. 889,189, Jul. 24, 1986, Pat. No. 4,731,443, which is a division of Ser. No. 653,041, Sep. 21, 1984, abandoned, which is a division of Ser. No. 341,621, Jan. 22, 1982, Pat. No. 4,487,927, which is a continuation-in-part of Ser. No. 261,618, May 7, 1981, Pat. No. 4,423,213, which is a continuation-in-part of Ser. No. 205,334, Nov. 10, 1980, Pat. No. 4,409,214.

[30] Foreign Application Priority Data

| | | |
|---|---|---|
| Nov. 19, 1979 [GB] | United Kingdom | 7939985 |
| Feb. 8, 1980 [GB] | United Kingdom | 8004335 |
| Apr. 21, 1980 [GB] | United Kingdom | 8012991 |
| Jul. 14, 1980 [GB] | United Kingdom | 8022920 |

[51] Int. Cl.$^5$ ............................................. C07D 501/18
[52] U.S. Cl. ................................... 540/215; 540/222
[58] Field of Search ........................ 540/222, 230, 215

[56] References Cited

U.S. PATENT DOCUMENTS 3,867,379  2/1975  Dolfini et al. ................. 260/243 C Primary Examiner—Nicholas S. Rizzo
Attorney, Agent, or Firm—Oblon, Spivak, McClelland, Maier & Neustadt

[57] ABSTRACT

Intermediates of the following formula are disclosed:

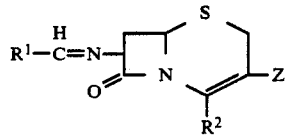

wherein $R^1$ is aryl; $R^2$ is carboxy or protected carboxy; $Z=CH=CH_2$, $CH_2-X^2$, $-CH_2-P^+(R^7)_3 \cdot X^3$ or $CH=P(R^7)_3$ wherein $X^2$ and $X^3$ are each halogen and $R^7$ is aryl.

The compounds are useful as intermediates for cephalosporins.

3 Claims, No Drawings

CEPHALOSPORIN INTERMEDIATES

This is a division of application Ser. No. 07/583,304, filed on Sep. 17, 1990, now U.S. Pat. No. 5,110,921 which is a division of Ser. No. 07/462,347 filed on Jan. 3, 1990 now U.S. Pat. No. 4,960,889, which is a continuation of Ser. No. 07/127,929 filed on Dec. 2, 1987 which is abandoned, which is a division of Ser. No. 06/889,189 filed on Jul. 24, 1986 now U.S. Pat. No. 4,731,443, which is a division of Ser. No. 06/653,041 filed on Sep. 21, 1984 now abandoned, which is a division of Ser. No. 06/341,621 filed on Jan. 22, 1982 now U.S. Pat. No. 4,487,927, which is a continuation-in-part of Ser. No. 06/261,618 filed on May 7, 1981 now U.S. Pat. No. 4,423,273, which is a continuation-in-part of Ser. No. 06/205,334 filed on Nov. 10, 1980 now U.S. Pat. No. 4,409,214.

The present invention relates to novel 7-acylamino-3-vinylcephalosporanic acid derivatives and pharmaceutically acceptable salts thereof.

More particularly, it relates to novel 7-acylamino-3-vinylcephalosporanic acid derivatives and pharmaceutically acceptable salts thereof, which have antimicrobial activity, to processes for the preparation thereof, to a pharmaceutical composition comprising the same, and to a method of using the same therapeutically in the treatment of infectious diseases in human being and animals.

Accordingly, one object of the present invention is to provide novel 7-acylamino-3-vinylcephalosporanic acid derivatives and pharmaceutically acceptable salts thereof, which are highly active against a number of pathogenic microorganisms and are useful as antimicrobial agents, especially for oral administration.

Another object of the present invention is to provide processes for the preparation of novel 7-acylamino-3-vinylcephalosporanic acid derivatives and salts thereof.

A further object of the present invention is to provide a pharmaceutical composition comprising, as active ingredients, said 7-acylamino-3-vinylcephalosporanic acid derivatives and pharmaceutically acceptable salts thereof.

Still further object of the present invention is to provide a method of using said 7-acylamino-3-vinylcephalosporanic acid derivatives and pharmaceutically acceptable salts thereof in the treatment of infectious diseases by pathogenic microorganisms in human being and animals.

The object 7-acylamino-3-vinylcephalosporanic acid derivatives are novel and can be represented by the following general formula:

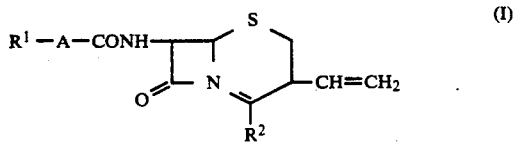
(I)

in which
R$^1$ is amino-substituted-heterocyclic group which may have halogen, protected amino-substituted-heterocyclic group which may have halogen, or a group of the formula:

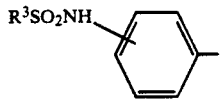

wherein wherein R$^3$ is lower alkyl,
R$^2$ is carboxy or a protected carboxy group, and
A is lower alkylene which may have a substituent selected from the groups consisting of amino, a protected amino group, hydroxy, oxo and a group of the formula: =N~OR$^4$, wherein R$^4$ is hydrogen, cyclo(lower)alkenyl, lower alkynyl, lower alkenyl, lower alkenyl substituted by carboxy or a protected carboxy group, lower alkyl, or lower alkyl substituted by one or more substituent(s) selected from carboxy, a protected carboxy group, amino, a protected amino group, cyano, phosphono, a protected phosphono group and a heterocyclic group which may have suitable substituent(s).

In the object compounds (I) and the corresponding starting compounds (II) to (VI) in Processes 1, 5 and 7 mentioned below, it is to be understood that there may be one or more stereoisomeric pair(s) such as optical and geometrical isomers due to asymmetric carbon atom and double bond in those molecules and such isomers are also included within the scope of the present invention.

With regard to geometrical isomers in the object compounds and the starting compounds, it is to be noted that, for example, the object compounds, wherein A means a group of the formula: =C=N~OR$^4$, include syn isomer, anti isomer and a mixture thereof, and the syn isomer means one geometrical isomer having the partial structure represented by the following formula:

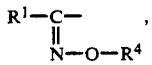

wherein R$^1$ and R$^4$ are each as defined above, and the anti isomer means the other geometrical isomer having the partial structure represented by the following formula:

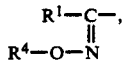

wherein R$^1$ and R$^4$ are each as defined above.

Regarding the other object and starting compounds as mentioned above, the syn isomer and the anti isomer can also be referred to the same geometrical isomers as illustrated for the compounds (I).

Suitable pharmaceutically acceptable salts of the object compounds (I) are conventional non-toxic salts and may include a salt with a base or an acid addition salt such as a salt with an inorganic base, for example, an alkali metal salt (e.g. sodium salt, potassium salt, etc.), an alkaline earth metal salt (e.g. calcium salt, magnesium salt, etc.), an ammonium salt; a salt with an organic base, for example, an organic amine salt (e.g. triethylamine salt, pyridine salt, picoline salt, ethanolamine salt, triethanolamine salt, dicyclohexylamine salt, N,N'-dibenzylethylenediamine salt, etc.) etc.; an inorganic acid addition salt (e.g. hydrochloride, hydrobromide, sulfate, phosphate, etc.); an organic carboxylic or sulfonic acid addition salt (e.g. formate, acetate, trifluoroacetate, maleate, tartrate, methanesulfonate, benzenesulfonate, p-toluenesulfonate, etc.); a salt with a basic or acidic amino acid (e.g. arginine, aspartic acid, glutamic acid, etc.); an intermolecular or intramolecular quaternary salt, and the like. The said intermolecular quaternary salt can be formed in case that the heterocyclic group in $R^4$ in the compounds (I) contains nitrogen atom(s) (e.g. pyridyl, etc.), and suitable intermolecular quaternary salt may include. 1-lower alkylpyridinium lower alkylsulfate (e.g. 1-methylpyridinium methylsulfate, 1-ethylpyridinium ethylsulfate, etc.), 1-loweralkyl-pyridinium halide (e.g. 1-methylpyridinium iodide, etc.) and the like. The said intramolecular salt can be formed in case that heterocyclic group in $R^4$ in the compounds (I) contains nitrogen atom(s) (e.g. pyridyl etc.) and $R^2$ is carboxy, and suitable intramolecular salt may include 1-lower alkylpyridinium carboxylate (e.g. 1-methylpyridinium carboxylate, 1-ethylpyridinium carboxylate, 1-propylpyridinium carboxylate, 1-isopropylpyridinium carboxylate, 1-butylpyridinium carboxylate, etc.); and the like.

According to the present invention, the object compounds (I) and the pharmaceutically acceptable salts thereof can be prepared by the processes as illustrated by the following reaction schemes.

(1) Process 1:

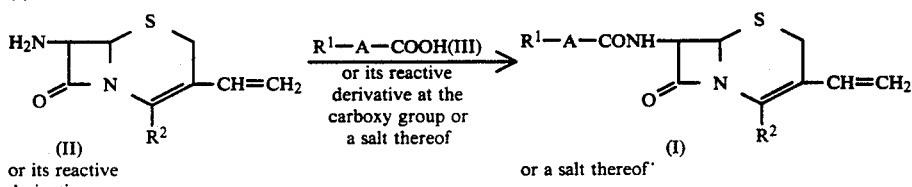

(2) Process 2:

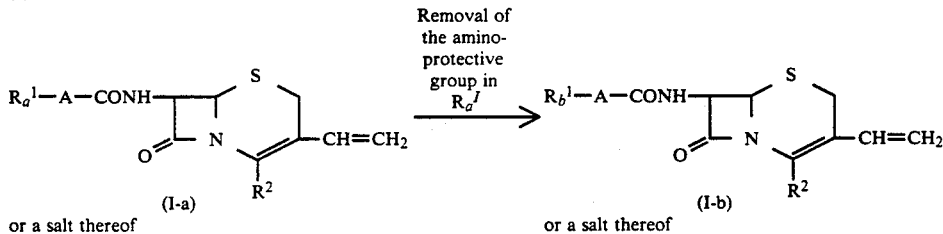

(3) Process 3:

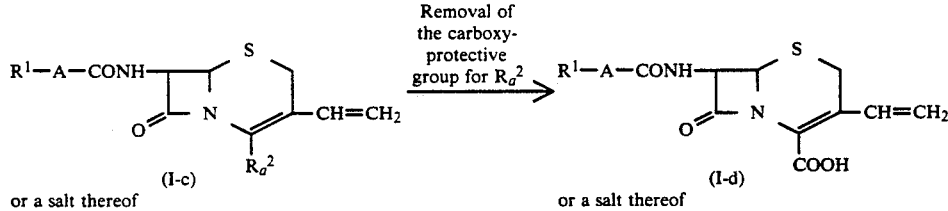

(4) Process 4:

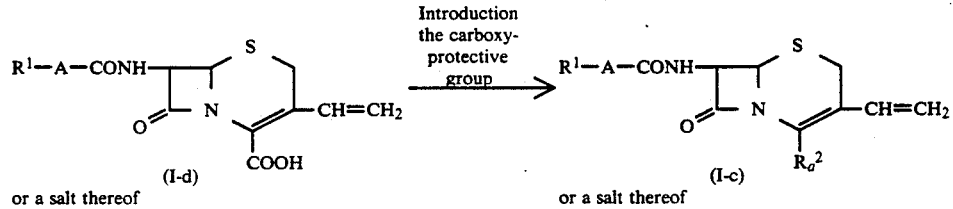

(5) Process 5:

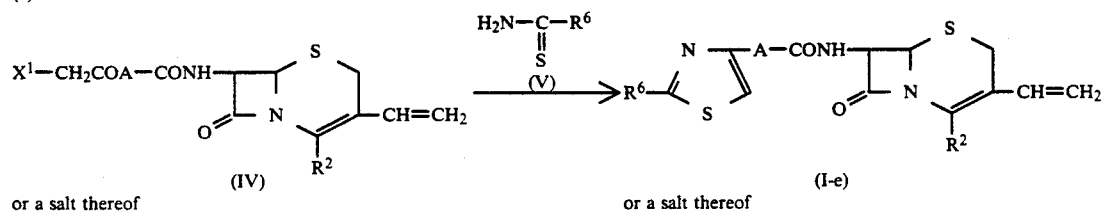

(6) Process 6:

-continued

Removal of the carboxy-protective group or the phosphono-protective group in $A^1$

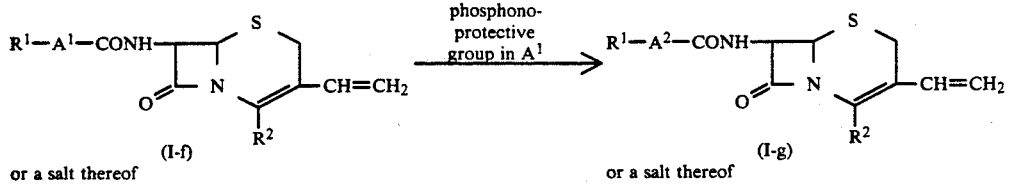

(I-f) or a salt thereof → (I-g) or a salt thereof (7) Process 7:

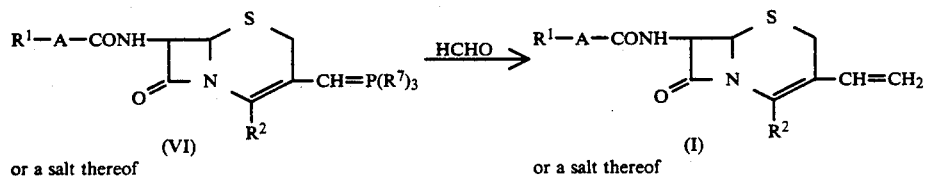

(VI) or a salt thereof → (I) or a salt thereof (8) Process 8:

Removal of the amino- and carboxy-protective groups in $R_b^2$

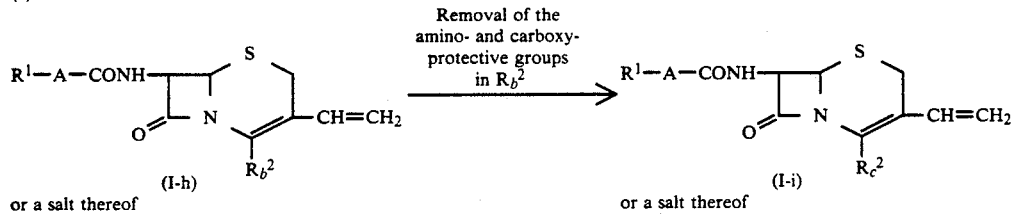

(I-h) or a salt thereof → (I-i) or a salt thereof (9) Process 9:

Removal of the amino- and carboxy-protective groups in $A^3$

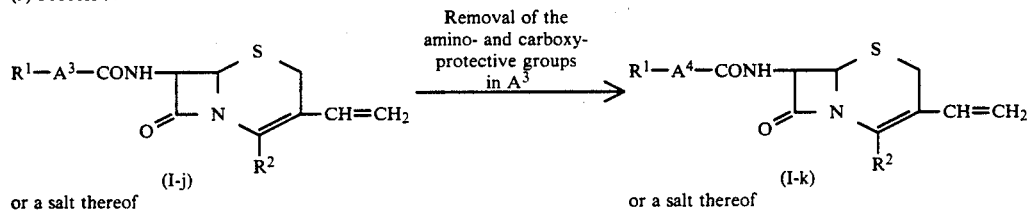

(I-j) or a salt thereof → (I-k) or a salt thereof

(10) Process 10:

Introduction of the carboxy-protective group or the phosphono-protective group in $A^2$

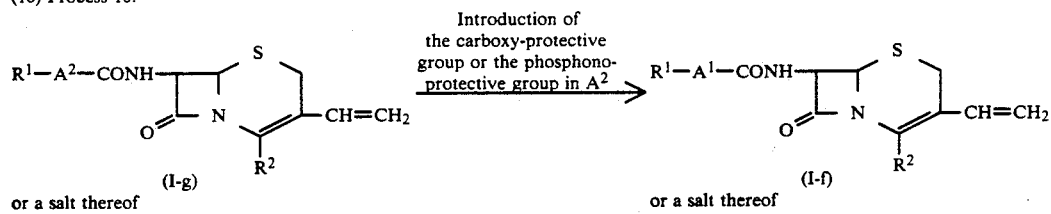

(I-g) or a salt thereof → (I-f) or a salt thereof

(11) Process 11:

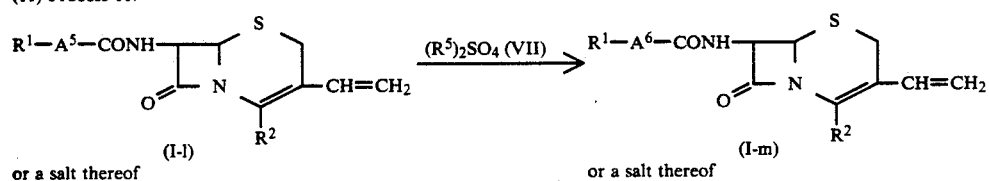

(I-l) or a salt thereof → (I-m) or a salt thereof

(12) Process 12:

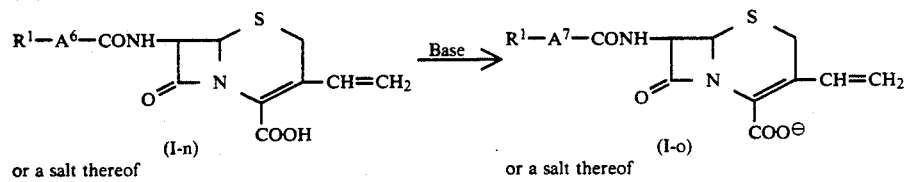

(I-n) or a salt thereof → (I-o) or a salt thereof

(13) Process 13:

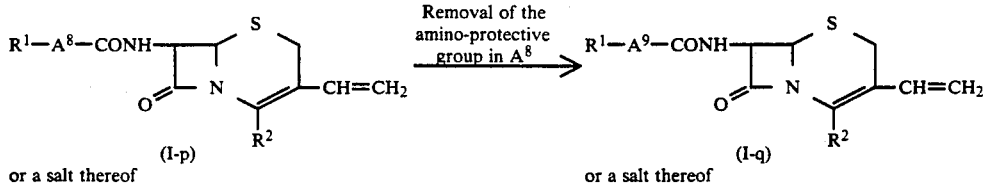

(I-p) or a salt thereof → (I-q) or a salt thereof (Removal of the amino-protective group in $A^8$)

(14) Process 14:

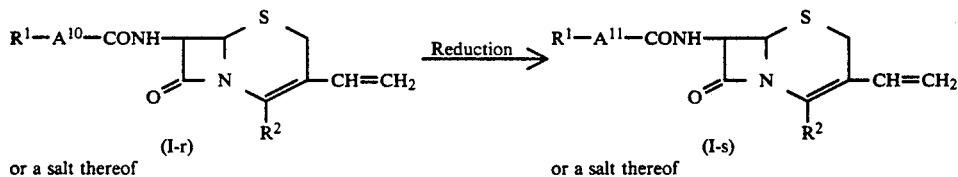

(I-r) or a salt thereof → (I-s) or a salt thereof (Reduction)

(15) Process 15:

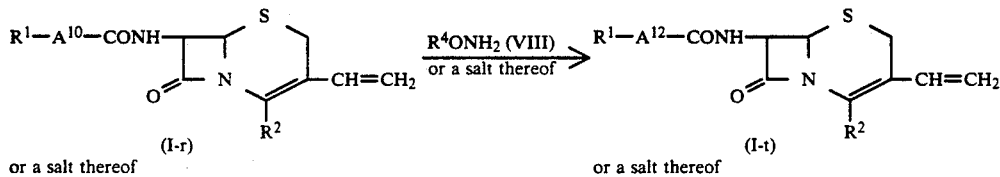

(I-r) or a salt thereof → (I-t) or a salt thereof ($R^4ONH_2$ (VIII) or a salt thereof)

in which $R^1$, $R^2$ and A are each as defined above, $R_a^1$ is protected amino-substituted-heterocyclic group which may have halogen, $R_b^1$ is amino-substituted-heterocyclic group which may have halogen, $R_a^2$ is a protected carboxy group, $R_b^2$ is lower alkoxycarbonyl substituted by a protected amino and a protected carboxy groups, or lower alkoxycarbonyl substituted by a protected carboxy group, $R_c^2$ is lower alkoxycarbonyl substituted by amino and carboxy, or lower alkoxycarbonyl substituted by carboxy, $R^5$ is lower alkyl, $R^6$ is amino or a protected amino group, $R^7$ is aryl, $A^1$ is lower alkylene having a group of the formula: $=N\sim OR_a^4$, wherein $R_a^4$ is lower alkyl substituted by a protected carboxy group or a protected phosphono group, or lower alkenyl substituted by a protected carboxy group, $A^2$ is lower alkylene having a group of the formula: $=N\sim OR_b^4$, wherein $R_b^4$ is lower alkyl substituted by carboxy or phosphono, or lower alkenyl substituted by carboxy, $A^3$ is lower alkylene having a group of the formula: $=N\sim OR_c^4$, wherein $R_c^4$ is lower alkoxycarbonyl(-lower)alkyl substituted by a protected amino and a protected carboxy groups, or lower alkyl substituted by a protected amino and a protected carboxy groups, $A^4$ is lower alkylene having a group of the formula: $=N\sim OR_d^4$, wherein $R_d^4$ is lower alkoxycarbonyl(lower)alkyl substituted by amino and carboxy, or lower alkyl substituted by amino and carboxy, $A^5$ is lower alkylene having a group of the formula: $=N\sim OR_e^4$, wherein $R_e^4$ is lower alkyl substituted by a group of the formula:

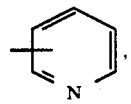

$A^6$ is lower alkylene having a group of the formula: $=N\sim OR_f^4$, wherein $R_f^4$ is lower alkyl substituted by a group of the formula:

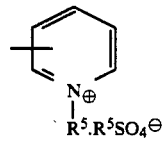

wherein $R^5$ is as defined above, $A^7$ is lower alkylene having a group of the formula: $=N\sim OR_g^4$, wherein $R_g^4$ is lower alkyl substituted by a cation of the formula:

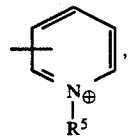

wherein $R^5$ is as defined above, $A^8$ is lower alkylene having a protected amino group, $A^9$ is lower alkylene having amino, $A^{10}$ is lower alkylene having oxo, $A^{11}$ is lower alkylene having hydroxy, $A^{12}$ is lower alkylene having a group of the formula: $=N\sim OR^4$, wherein $R^4$ is as defined above, and $X^1$ is halogen.

Some of the starting compounds (II), (III), (IV), (VI) and (VIII) used in Processes 1, 5, 7 and 15 are new and can be represented by the following general formulae:

① 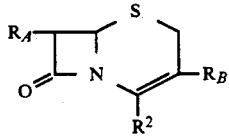 (Compound ①)

in which
R_A is a group of the formula:

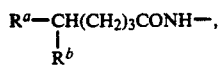

$R^1$—A—CONH— or $R^8$—CH=N—
wherein
$R^8$ is aryl which may have suitable substituent(s),
$R^a$ is a protected amino group,
$R^b$ is a protected carboxy group, and
$R^1$ and A are each as defined above,
$R_B$ is a group of the formula:

—CH$_2$—X$^2$, —CH$_2$P$^\oplus$(R$^7$)$_3$·X$^{3\ominus}$ or —CH=P(R$^7$)$_3$ wherein
X$^2$ and X$^3$ are each halogen, and
R$^7$ is as defined above, and
R$^2$ is as defined above;
provided that, when R_A is a group of the formula:
R$^8$—CH=N—, wherein R$^8$ is as defined above, then
R_B is a group of the formula:

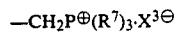

or

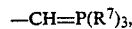

wherein
R$^7$ and X$^3$ are each as defined above,
or a salt thereof; and

② 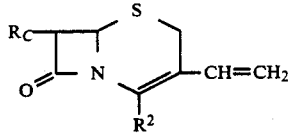 (Compound ②)

in which
R_C is amino or a group of the formula:

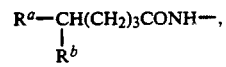

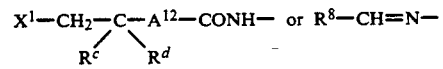

wherein
R$^c$ and R$^d$ are combined to form oxo or a protected oxo group, and
R$^8$, R$^a$, R$^b$, A$^{12}$ and X$^1$ are each as defined above, and
R$^2$ is as defined above;
provided that, when R_C is amino, then R$^2$ is carboxy, or a salt thereof; and ③ 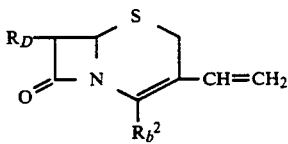 (Compound ③)

in which
R_D is amino or a protected amino group, and
R$_b^2$ is as defined above,
or a salt thereof; and ④ R$_c^1$—A—R$^3$ (Compound ④)

in which
R$_c^1$ is a group of the formula:

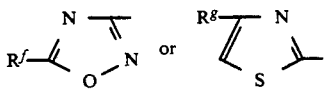

wherein
R$^f$ is amino or trihalomethyl, and
R$^g$ is carboxy or a protected amino group,
R$^e$ is carboxy or a protected carboxy group, and
A is as defined above,
or a salt thereof; and ⑤ R$^1$—A$^{13}$—R$^3$ (Compound ⑤)

in which
A$^{13}$ is lower alkylene having a group of the formula:
=N—OR$_h^4$, wherein R$_h^4$ is lower alkenyl substituted by carboxy or a protected carboxy group, lower alkyl substituted by a protected amino and a protected carboxy groups, lower alkyl substituted by a protected amino- and a protected carboxy-substituted-lower alkoxycarbonyl, or lower alkyl substituted by pyridyl, and
R$^1$ and R$^e$ are each as defined above,
or a salt thereof; and ⑥ R$_d^1$—A$^{14}$—R$^3$ (Compound ⑥)

in which
R$_d^1$ is aminothiazolyl having halogen, protected aminothiazolyl having halogen, aminopyridyl, protected aminopyridyl, aminopyrimidinyl or protected aminopyrimidinyl,
A$^{14}$ is lower alkylene having a group of the formula:
=N~OR$_i^4$, wherein R$_i^4$ is lower alkyl substituted by carboxy or a protected carboxy group, and
R$^e$ is as defined above,
or a salt thereof; and ⑦ R$^h$—O—R$_h^4$ (Compound ⑦)

in which
R$^h$ is amino or phthalimido, and
R$_h^4$ is as defined above,
or a salt thereof; and

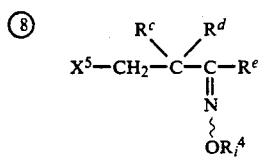 (Compound ⑧)

wherein
 $X^5$ is hydrogen or halogen, and
 $R^c$, $R^d$, $R^e$ and $R_i^A$ are each as defined above,
or a salt thereof; and

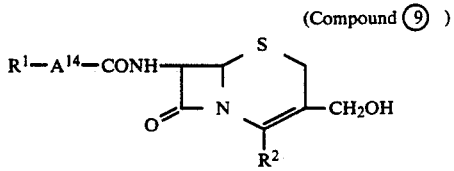 (Compound ⑨)

wherein $R^1$, $R^2$ and $A^{14}$ are each as defined above,
or a salt thereof.

Suitable salts of the starting compounds ① to ⑨ thus formulated may include the same ones as exemplified for the compounds (I).

The starting compounds ① to ⑨ and other starting compounds can be prepared, for example, from the known compounds by the methods in the following Processes ① to 15 or in a similar manner thereto or in a conventional manner.

Process ①-(1):

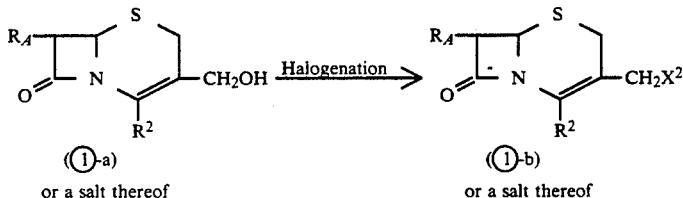

Process ①-(2):

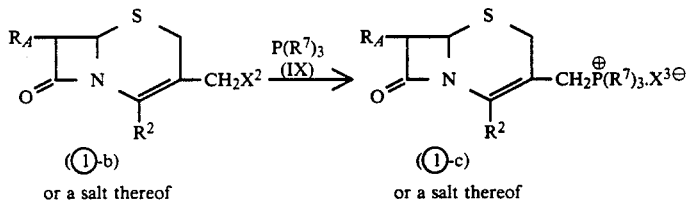

Process ①-(3):

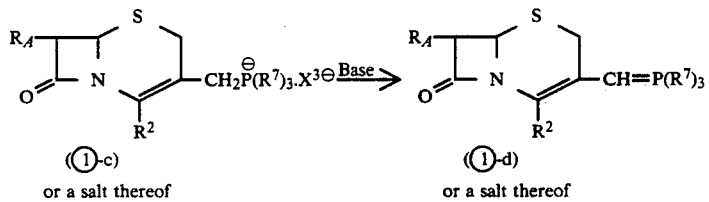

Process ①-(4):

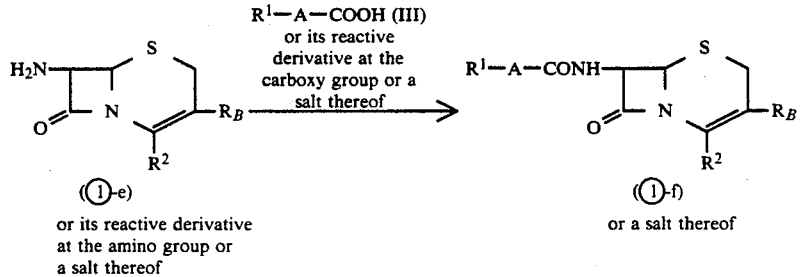

Process ②-(1):

-continued
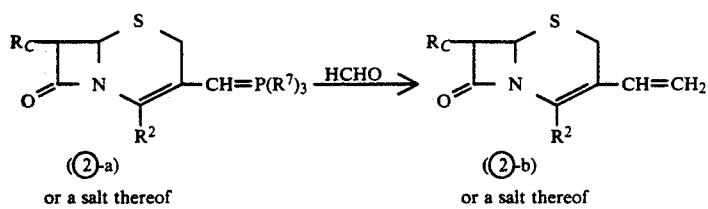
((2)-a)
or a salt thereof
((2)-b)
or a salt thereof
Process a (2)-(2):
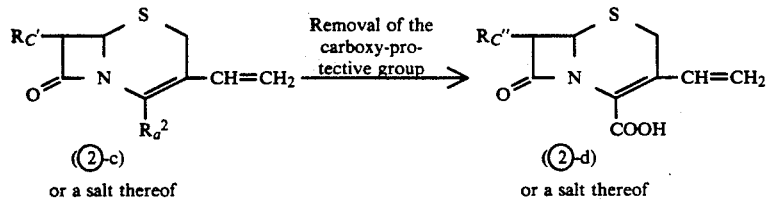
((2)-c)
or a salt thereof
((2)-d)
or a salt thereof
Process (2)-(3):
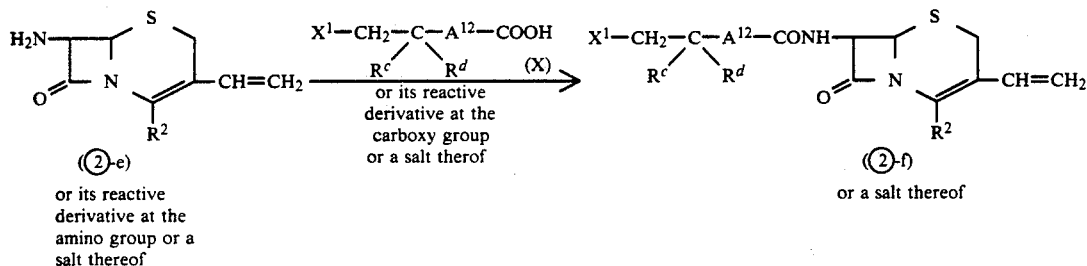
((2)-e)
or its reactive
derivative at the
amino group or a
salt thereof
((2)-f)
or a salt thereof
Process (2)-(4):
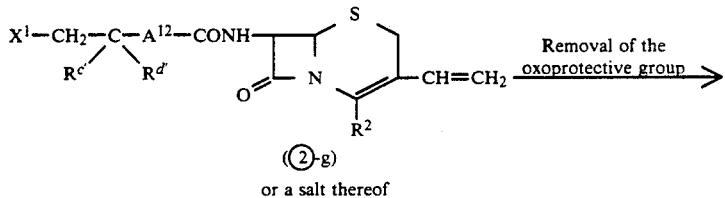
((2)-g)
or a salt thereof
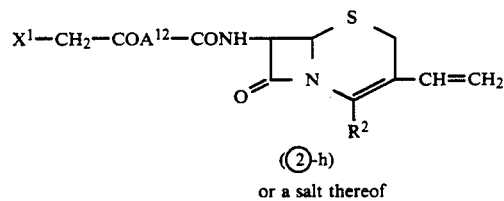
((2)-h)
or a salt thereof
Process (3)-(1):
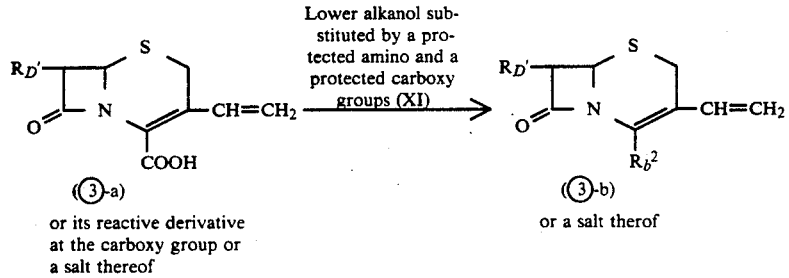
((3)-a)
or its reactive derivative
at the carboxy group or
a salt thereof
((3)-b)
or a salt therof
Process (3)-(2):

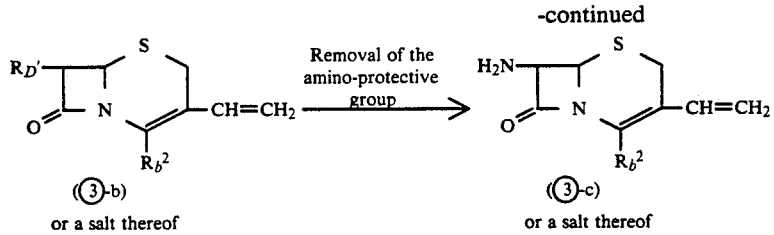
Process ④-(1):
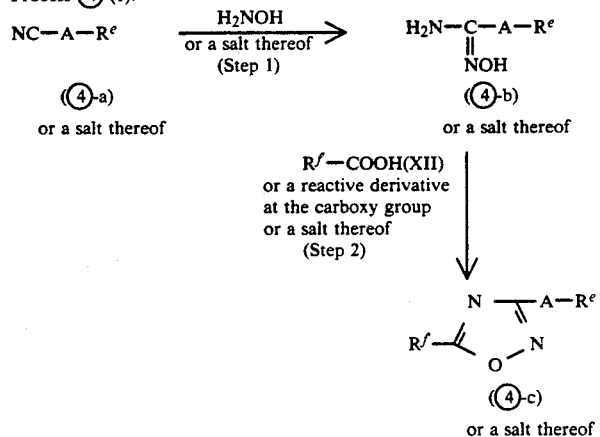
Process ④-(2):
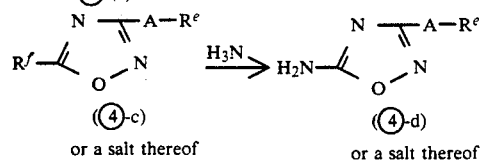
Process ④-(3):
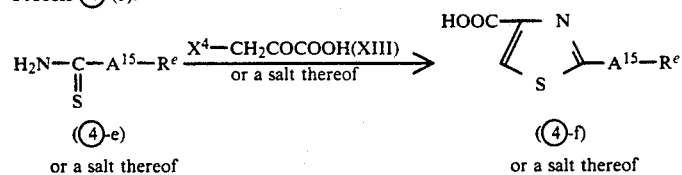
Process ④-(4):
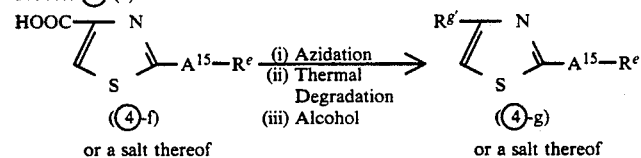
Process ④-(5):
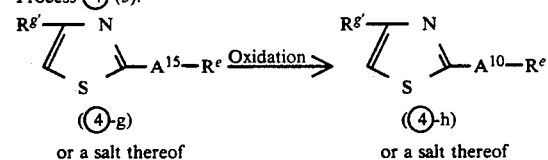
Process ④-(6)
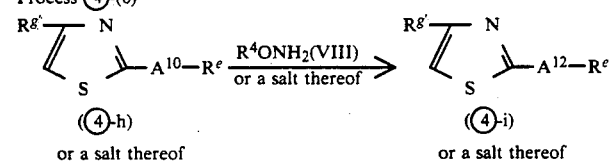

-continued

Process ④-(7):

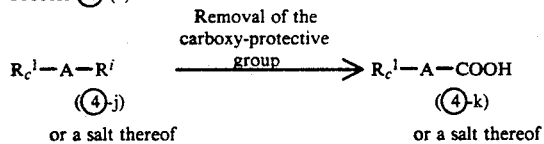

$R_c^1-A-R^i$ → $R_c^1-A-COOH$
(④-j)                  (④-k)
or a salt thereof      or a salt thereof Removal of the carboxy-protective group Process ⑤:

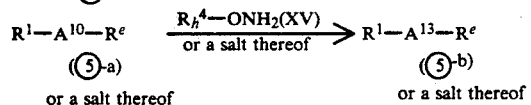

$R^1-A^{10}-R^e$ →(via $R_h^4-ONH_2$(XV) or a salt thereof)→ $R^1-A^{13}-R^e$
(⑤-a)                                                         (⑤-b)
or a salt thereof                                              or a salt thereof Process ⑥:

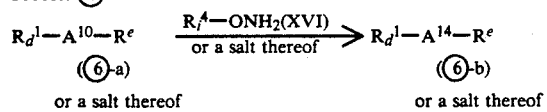

$R_d^1-A^{10}-R^e$ →(via $R_i^4-ONH_2$(XVI) or a salt thereof)→ $R_d^1-A^{14}-R^e$
(⑥-a)                                                          (⑥-b)
or a salt thereof                                               or a salt thereof Process ⑦-(1):

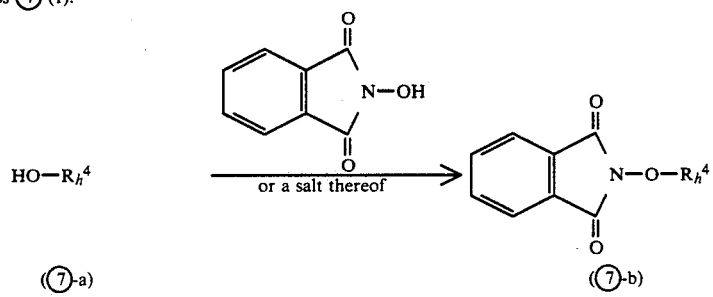

(⑦-a) or a reactive derivative at the hydroxy group → (⑦-b)

Process ⑦-(2):

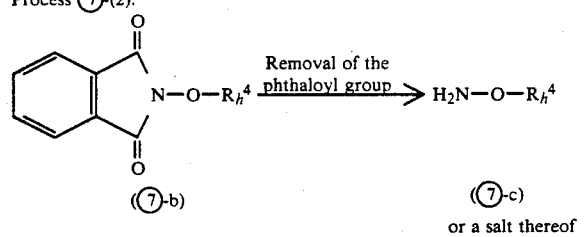

(⑦-b) →Removal of the phthaloyl group→ $H_2N-O-R_h^4$
                                        (⑦-c)
                                        or a salt thereof Process ⑧:

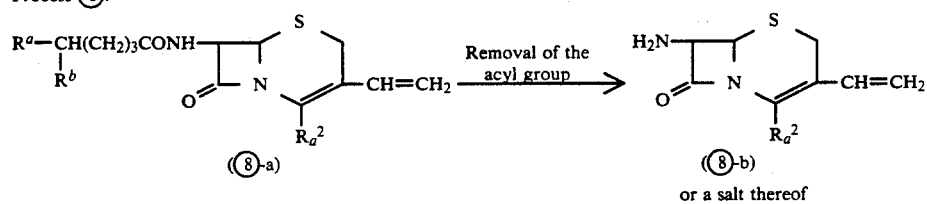

(⑧-a) →Removal of the acyl group→ (⑧-b) or a salt thereof

Process ⑨:

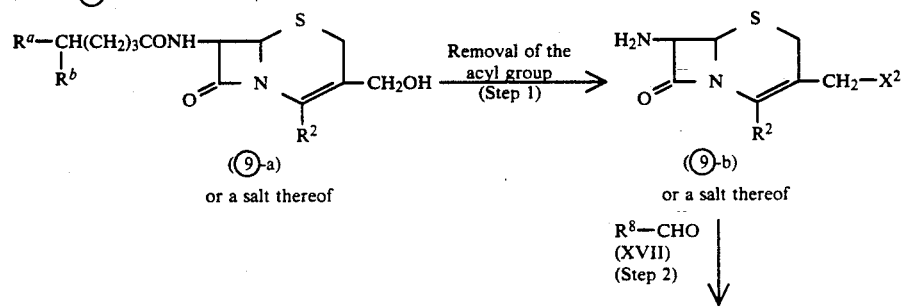

(⑨-a) or a salt thereof →Removal of the acyl group (Step 1)→ (⑨-b) or a salt thereof $R^8-CHO$ (XVII) (Step 2) ↓

-continued

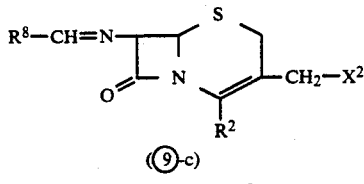

(⑨-c)
or a salt thereof

Process ⑩:

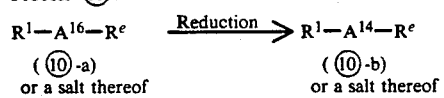

(⑩-a)
or a salt thereof (⑩-b)
or a salt thereof

Process ⑪:

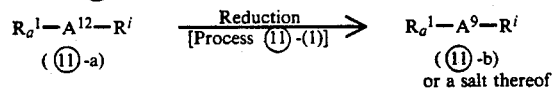

(⑪-a)

(⑪-b)
or a salt thereof

Introduction of the amino-protective group [Process ⑪-(2)]

$R_b^1—A^9—R^i$ (⑪-d)
or a salt thereof $R_a^1—A^8—R^i$ (⑪-c)

Removal of the carboxy-protective group [Process ⑪-(4)]

Removal of the carboxy-protective group [Process ⑪-(3)]

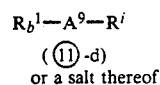

(⑪-e)
or a salt thereof

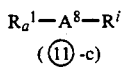

(⑪-f)
or a salt thereof

Introduction of the amino-protective group [Process ⑪-(5)]

Introduction of the amino-protective group [Process ⑪-(6)]

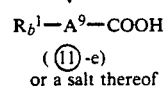

(⑪-g)
or a salt thereof

Process ⑫:

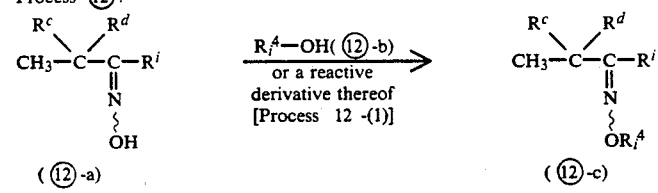

(⑫-a)

(⑫-c)

Halogenation [Process ⑫-(2)]

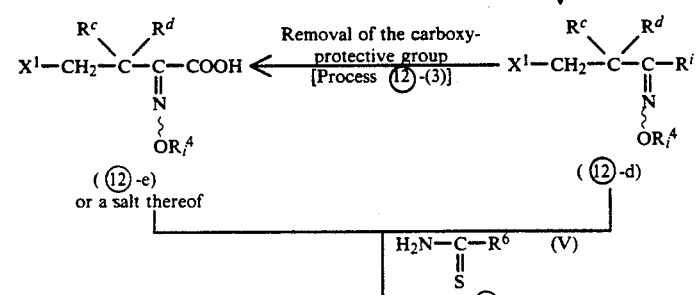

(⑫-e)
or a salt thereof (⑫-d)

$H_2N—C—R^6$ (V)
 ‖
 S

[Process ⑫-(4)]

-continued

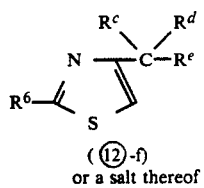

( ⑫ -f)
or a salt thereof

Process ⑬:

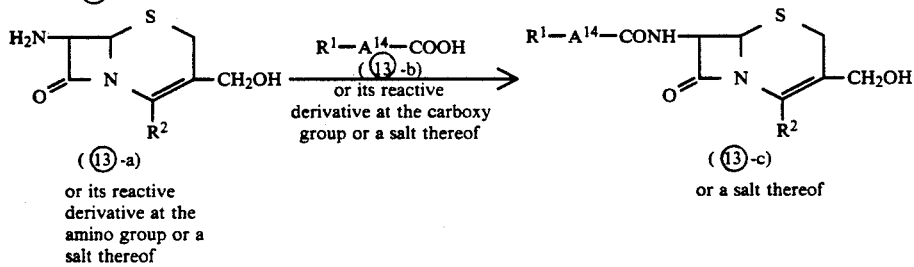

(⑬-a)
or its reactive
derivative at the
amino group or a
salt thereof (⑬-c)
or a salt thereof Process ⑭:

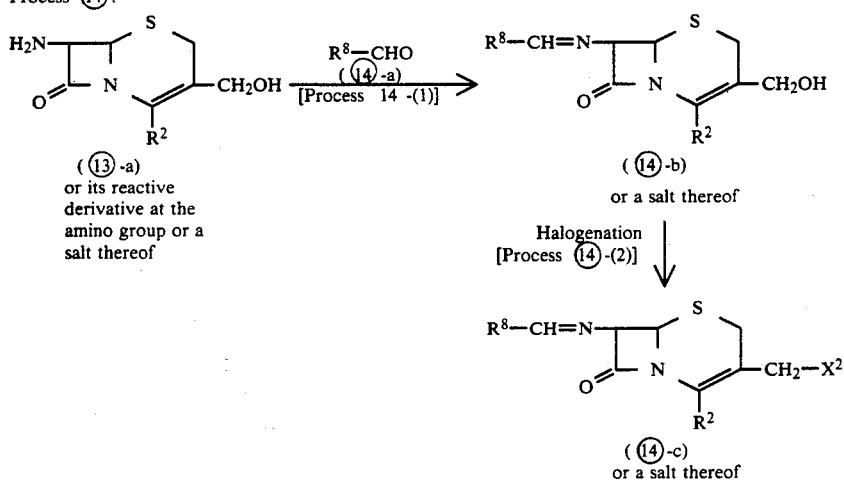

(⑬-a)
or its reactive
derivative at the
amino group or a
salt thereof (⑭-b)
or a salt thereof Halogenation
[Process ⑭-(2)]

(⑭-c)
or a salt thereof

Process ⑮:

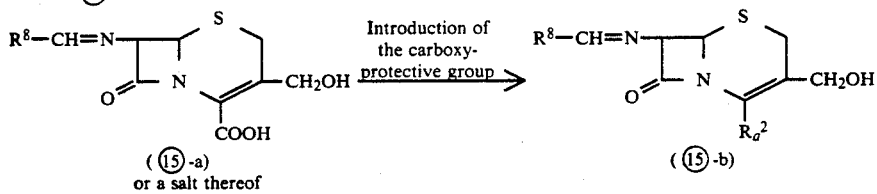

(⑮-a)
or a salt thereof (⑮-b)

or a salt thereof in which
$R_A, R_B, R_C, R^1, R_a^1, R_b^1, R_c^1, R_d^1, R^2, R_a^2, R_b^2, R_h^4,$
$R_i^4, R^6, R^7, R^8, R^a, R^b, R^c, R^d, R^e, A, A^2, A^8, A^9,$
$A^{10}, A^{11}, A^{12}, A^{13}, A^{14}, X^1, X^2$ and $X^3$ are each as defined above, $R'_C$ is amino or a group of the formula:

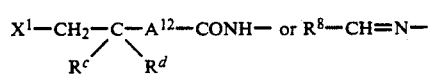

wherein $R^8, R^c, R^d, A^{12}$ and $X^1$ are each as defined above, $R''_C$ is amino or a group of the formula:

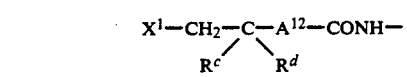

wherein $R^c, R^d, A^{12}$ and $X^1$ are each as defined above, $R'_D$ and $R^{g'}$ are each a protected amino group,
$R^{c'}$ and $R^{d'}$ are combined to form a protected oxo group,
$R^{f'}$ is trihalomethyl,
$R^i$ is a protected carboxy group,
$A^{15}$ is lower alkylene,
$A^{16}$ is lower alkylene having a group of the formula:
$=N\sim OR_f^4$, wherein $R_f^4$ is lower alkenyl substituted by carboxy or a protected carboxy group,
$X^4$ is halogen, and
$X^5$ is hydrogen or halogen.

In the above and subsequent description of the present specification, suitable examples and illustration of the various definitions to be included within the scope thereof are explained in detail as follows.

The term "lower" in the present specification is intended to mean a group having 1 to 7 carbon atoms, unless otherwise indicated.

Suitable "lower alkyl" group may include straight or branched one such as methyl, ethyl, propyl, isopropyl, butyl, isobutyl, pentyl, isopentyl, neopentyl, hexyl and the like, in which the preferred one is $C_1$-$C_4$ alkyl.

Suitable "lower alkenyl" group may include straight or branched one such as vinyl, 1-propenyl, allyl, 1-(or 2- or 3-)butenyl, 1-(or 2- or 3- or 4-)pentenyl, 1-(or 2- or 3- or 4- or 5-)hexenyl, 2-methyl-2-propenyl, and the like, in which the preferred one is $C_2$-$C_5$alkenyl.

Suitable "lower alkynyl" group may include straight or branched one such as propargyl, 2-(or 3-)butynyl, 2-(or 3- or 4-)pentynyl, 2-(or 3- or 4- or 5-)hexynyl, and the like, in which the preferred one is $C_2$-$C_5$alkynyl.

Suitable "cyclo(lower)alkenyl" group may include $C_3$-$C_7$cycloalkenyl such as cyclopropenyl, cyclobutenyl, cyclopentenyl, cyclohexenyl, cycloheptenyl, and the like, in which the preferred one is $C_5$-$C_6$cycloalkenyl.

Suitable "protected amino" group may include an amino group substituted by a conventional amino-protective group which is used in penicillin and cephalosporin compounds, for example, acyl as mentioned below, ar(lower)alkyl such as mono-(or di or tri)phenyl(lower)alkyl (e.g. benzyl, benzhydryl, trityl, etc.), lower alkoxycarbonyl(lower)alkylidene or its enamine tautomer (e.g. 1-methoxycarbonyl-1-propen-2-yl, etc.), di(lower)alkylaminomethylene (e.g. dimethylaminomethylene, etc.), etc.

Suitable "acyl" may include an aliphatic acyl, an aromatic acyl, a heterocyclic acyl and an aliphatic acyl substituted with aromatic or heterocyclic group(s).

The aliphatic acyl may include saturated or unsaturated acyclic or cyclic ones, such as lower alkanoyl (e.g. formyl, acetyl, propionyl, butyryl, isobutyryl, valeryl, isovaleryl, pivaloyl, hexanoyl, etc.), lower alkanesulfonyl (e.g. mesyl, ethanesulfonyl, propanesulfonyl, etc.), lower alkoxycarbonyl (e.g. methoxycarbonyl, ethoxycarbonyl, propoxycarbonyl, butoxycarbonyl, tert-butoxycarbonyl, isobutoxycarbonyl, etc.), lower alkenoyl (e.g. acryloyl, methacryloyl, crotonoyl, etc.), ($C_3$-$C_7$)-cycloalkanecarbonyl (e.g. cyclohexanecarbonyl, etc.), amidino, and the like.

The aromatic acyl may include aroyl (e.g. benzoyl, phthaloyl, toluoyl, xyloyl, etc.), arenesulfonyl (e.g. benzenesulfonyl, tosyl, etc.), arylcarbamoyl (e.g. phenylcarbamoyl, tolylcarbamoyl, naphthylcarbamoyl, etc.).

The heterocyclic acyl may include heterocyclecarbonyl (e.g. furoyl, thenoyl, nicotinoyl, isonicotinoyl, thiazolylcarbonyl, thiadiazolylcarbonyl, tetrazolylcarbonyl, etc.), and the like.

The aliphatic acyl substituted with aromatic group(s) may include ar(lower)alkanoyl such as phenyl(lower)alkanoyl (e.g. phenylacetyl, phenylpropionyl, phenylhexanoyl, etc.), ar(lower)alkoxycarbonyl such as phenyl(lower)alkoxycarbonyl (e.g. benzyloxycarbonyl, phenethyloxycarbonyl, etc.), phenoxy(lower)alkanoyl (e.g. phenoxyacetyl, phenoxypropionyl, etc.); and the like.

The aliphatic acyl substituted with heterocyclic group(s) may include thienylacetyl, imidazolylacetyl, furylacetyl, tetrazolylacetyl, thiazolylacetyl, thiadiazolylacetyl, thienylpropionyl, thiadiazolylpropionyl, and the like.

These acyl groups may be further substituted with one or more suitable substituents such as lower alkyl (e.g. methyl, ethyl, propyl, isopropyl, butyl, pentyl, hexyl, etc.), halogen (e.g. chlorine, bromine, iodine, fluorine), lower alkoxy (e.g. methoxy, ethoxy, propoxy, isopropoxy, butoxy, pentyloxy, hexyloxy, etc.), lower alkylthio (e.g. methylthio, ethylthio, propylthio, isopropylthio, butylthio, pentylthio, hexylthio, etc.), nitro and the like, and preferable acyl having such substituent(s) may be mono (or di tri)halo(lower)alkanoyl (e.g. chloroacetyl, bromoacetyl, dichloroacetyl, trifluoroacetyl, etc.), mono (or di or tri)halo(lower)alkoxycarbonyl (e.g. chloromethoxycarbonyl, dichloromethoxycarbonyl, 2,2,2-tri-chloroethoxycarbonyl, etc.), nitro (or halo or lower alkoxy)phenyl(lower)alkoxycarbonyl (e.g. nitrobenzyloxycarbonyl, chlorobenzyloxycarbonyl, methoxybenzyloxycarbonyl, etc.), and the like.

Suitable "protected carboxy" group may include an esterified carboxy group which is conventionally used in penicillin or cephalosporin compounds at their 3rd or 4th position thereof.

Suitable "ester moiety" in "esterified carboxy group" may include lower alkyl ester (e.g. methyl ester, ethyl ester, propyl ester, isopropyl ester, butyl ester, isobutyl ester, t-butyl ester, pentyl ester, tertpentyl ester, hexyl ester, etc.), lower alkenyl ester (e.g. vinyl ester, allyl ester, etc.), lower alkynyl ester (e.g. ethynyl ester, propynyl ester, etc.), lower alkoxy(lower)alkyl ester (e.g. methoxymethyl ester, ethoxymethyl ester, isopropoxymethyl ester, 1-methoxyethyl ester, 1-ethoxyethyl ester, etc.), lower alkylthio(lower)alkyl ester (e.g. methylthiomethyl ester, ethylthiomethyl ester, ethylthioethyl ester isopropylthiomethyl ester, etc.), amino- and carboxy-substituted-lower alkyl ester (e.g. 2-amino-2-carboxyethyl ester, 3-amino-3-carboxypropyl ester, etc.), protected amino- and protected carboxy-substituted-lower alkyl ester such as lower alkoxycarbonylamino- and mono-(or di or tri)phenyl(lower)alkoxycarbonyl-substituted-lower alkyl ester (e.g. 2-tert-butoxycarbonylamino-2-benzhydryloxycarbonylethyl ester, 3-tert-butoxycarbonylamino-3-benzhydryloxycarbonylpropyl ester, etc.), mono(or di or tri)halo(lower)alkyl ester (e.g. 2-iodoethyl ester, 2,2,2-trichloroethyl ester, etc.), lower alkanoyloxy(lower)alkyl ester (e.g. acetoxymethyl ester, propionyloxymethyl ester, butyryloxymethyl ester, isobutyryloxymethyl ester, valeryloxymethyl ester, pivaloyloxymethyl ester, hexanoyloxymethyl ester, 2-acetoxyethyl ester, 2-propionyloxyethyl ester, 1-acetoxypropyl ester, etc.), lower alkanesulfonyl(lower)alkyl ester (e.g. mesylmethyl ester, 2-mesylethyl ester, etc.), ar(lower)alkyl ester which may have one or more substituent(s) such as mono(or di or tri)phenyl(lower)alkyl ester which may have one or more suitable substituent(s) (e.g. benzyl ester, 4-methoxybenzyl ester, 4-nitrobenzyl ester, phenethyl ester, benzhydryl ester, trityl ester, bis(methoxyphenyl)methyl ester, 3,4-dimethoxybenzyl ester, 4-hydroxy-3,5-di-t-butylbenzyl ester, etc.), aryl ester which may have one or more suitable substituents (e.g. phenyl ester, tolyl ester, t-butylphenyl ester, xylyl ester, mesityl ester, cumenyl ester, salicyl ester, etc.), heterocyclic ester (e.g. phthalidyl ester, etc.), carboxy(lower)alkyl ester (e.g. carboxymethyl ester, 1- or 2-carboxyethyl ester, 1- or 2- or 3-carboxybutyl ester, etc.), protected carboxy(lower)alkyl ester such as lower alkoxycarbonyl(lower)alkyl ester (e.g. methoxycarbonylmethyl ester, ethoxycarbonylmethyl ester, tert-butoxycarbonylmethyl ester, 1- or 2-tert-butoxycarbonylethyl ester, 1- or 2- or 3-pentyloxycarbonylpropyl ester, etc.), and the like.

Suitable "protected phosphono group" may include O,O-di(lower)alkylphosphono such as O,O-dimethylphosphono, O,O-diethylphosphono, O,O-dipropylphosphono, and the like.

Suitable "lower alkylene" group may include straight or branched one such as methylene, ethylene, trimethylene, propylene, tetramethylene, hexamethylene, and the like, in which the preferred one is $C_1$-$C_2$alkylene and the most preferred one is methylene.

Suitable "heterocyclic" group in the "heterocyclic group which may have suitable substituent(s)" as the substituent of the lower alkyl for $R^4$ may include saturated or unsaturated, monocyclic or polycyclic heterocyclic group containing at least one hetero-atom such as an oxygen, sulfur, nitrogen atom, and the like. And, especially preferable heterocyclic group may be heterocyclic group such as unsaturated 3 to 8-membered(more preferably 5 or 6-membered)heteromonocyclic group containing 1 to 4 nitrogen atom(s), for example, pyrrolyl, pyrrolinyl, imidazolyl, pyrazolyl, pyridyl and its N-oxide, dihydropyridyl, pyrimidinyl, pyrazinyl, pyridazinyl, triazolyl (e.g. 4H-1,2,4-triazolyl, 1H-1,2,3-triazolyl, 2H-1,2,3-triazolyl, etc.), tetrazolyl (e.g. 1H-tetrazolyl, 2H-tetrazolyl, etc.) etc.;

saturated 3 to 8-membered(more preferably 5 or 6-membered)heteromonocyclic group containing 1 to 4 nitrogen atom(s), for example, pyrrolidinyl, imidazolidinyl, piperidino, piperazinyl, etc.;

unsaturated condensed heterocyclic group containing 1 to 4 nitrogen atom(s), for example, indolyl, isoindolyl, indolizinyl, benzimidazolyl, quinolyl, isoquinolyl, indazolyl, benzotriazolyl, etc.;

unsaturated 3 to 8-membered(more preferably 5 or 6-membered)heteromonocyclic group containing 1 to 2 oxygen atom(s) and 1 to 3 nitrogen atom(s), for example, oxazolyl, isoxazolyl, oxadiazolyl (e.g. 1,2,4-oxadiazolyl, 1,3,4-oxadiazolyl, 1,2,5-oxadiazolyl, etc.), etc.;

saturated 3 to 8-membered(more preferably 5 or 6-membered)heteromonocyclic group containing 1 to 2 oxygen atom(s) and 1 to 3 nitrogen atom(s), for example, morpholinyl, sydnonyl, etc.;

unsaturated condensed heterocyclic group containing 1 to 2 oxygen atom(s) and 1 to 3 nitrogen atom(s), for example, benzoxazolyl, benzoxadiazolyl, etc.;

unsaturated 3 to 8-membered(more preferably 5 or 6-membered)heteromonocyclic group containing 1 to 2 sulfur atom(s) and 1 to 3 nitrogen atom(s), for example, thiazolyl, isothiazolyl, thiadiazolyl (e.g. 1,2,3-thiadiazolyl, 1,2,4-thiadiazolyl, 1,3,4-thiadiazolyl, 1,2,5-thiadiazolyl, etc.), dihydrothiazinyl, etc.;

saturated 3 to 8-membered (more preferably 5 or 6-membered) heteromonocyclic group containing 1 to 2 sulfur atom(s) and 1 to 3 nitrogen atom(s), for example, thiazolidinyl, etc.;

unsaturated 3 to 8-membered (more preferably 5 or 6-membered) heteromonocyclic group containing 1 to 2 sulfur atom(s), for example, thienyl, dihydrodithiinyl, etc.;

unsaturated condensed heterocyclic group containing 1 to 2 sulfur atom(s) and 1 to 3 nitrogen atom(s), for example, benzothiazolyl, benzothiadiazolyl, etc.;

unsaturated 3 to 8-membered (more preferably 5 or 6-membered) heteromonocyclic group containing an oxygen atom, for example, furyl, etc.;

unsaturated 3 to 8-membered (more preferably 5 or 6-membered) heteromonocyclic group containing an oxygen atom and 1 to 2 sulfur atom(s), for example, dihydrooxathiinyl, etc.;

unsaturated condensed heterocyclic group containing 1 to 2 sulfur atom(s), for example, benzothienyl, benzodithiinyl, etc.;

unsaturated condensed heterocyclic group containing an oxygen atom and 1 to 2 sulfur atom(s), for example, benzoxathiinyl, etc. and the like.

Thus defined heterocyclic group may optionally be substituted by one to ten, same or different, suitable substituent(s) such as: lower alkyl (e.g. methyl, ethyl, etc.); lower alkoxy (e.g. methoxy, ethoxy, propoxy, etc.); lower alkylthio (e.g. methylthio, ethylthio, etc.); lower alkylamino (e.g. methylamino, etc.); cyclo(lower)alkyl (e.g. cyclopentyl, cyclohexyl, etc.); cyclo(lower)alkenyl (e.g. cyclohexenyl; cyclohexadienyl, etc.); hydroxy; halogen (e.g. chloro, bromo, etc.); amino; protected amino as aforementioned; cyano; nitro; carboxy; protected carboxy as aforementioned; sulfo; sulfamoyl; imino; oxo; amino(lower)alkyl (e.g. aminomethyl, aminoethyl, etc.); and the like.

Suitable "heterocyclic" group in "amino-substituted-heterocyclic group which may have halogen" for $R^1$ and $R_b^1$, and "protected amino-substituted-heterocyclic group which may have halogen" for $R^1$ and $R_a^1$ may include thiazolyl, thiadiazolyl (e.g. 1,2,3-thiadiazolyl, 1,2,4-thiadiazolyl, 1,3,4-thiadiazolyl, 1,2,5-thiadiazolyl, etc.), oxadiazolyl (e.g. 1,2,3-oxadiazolyl, 1,2,4-oxadiazolyl, 1,3,4-oxadiazolyl, 1,2,5-oxadiazolyl, etc.), pyridyl, pyrimidinyl, tetrazolyl (e.g. 1H-tetrazolyl, 2H-tetrazolyl, etc.), and the like.

Suitable "trihalomethyl" group may include trichloromethyl, and the like.

Suitable "lower alkoxycarbonyl(lower)alkyl" group may include ethoxycarbonylmethyl, propoxycarbonylmethyl, 1- or 2-ethoxycarbonylethyl, and the like.

Suitable "lower alkoxycarbonyl" group may include ethoxycarbonyl, propoxycarbonyl, and the like.

Suitable "halogen" may include chloro, bromo, iodo, and the like.

Suitable "aryl" group may include phenyl, tolyl, xylyl, naphthyl, and the like.

Suitable "protected oxo" group may include bis(substituted-oxy) such as di(lower)alkoxy (e.g. dimethoxy, diethoxy, dipropoxy, etc.), lower alkylenedioxy (e.g. ethylenedioxy, trimethylenedioxy, propylenedioxy, tetramethylenedioxy, hexamethylenedioxy, etc.), and the like.

Suitable "aryl which may have suitable substituent(s)" may include the same as those exemplified for "aryl" and those substituted by hydroxy, lower alkyl (e.g. methyl, ethyl, propyl, tert-butyl, etc.), and the like.

Suitable "lower alkoxycarbonyl substituted by a protected carboxy group" may include lower alkoxycarbonyl(lower)alkoxycarbonyl such as methoxycarbonylmethoxycarbonyl, ethoxycarbonylmethoxycarbonyl, tert-butoxycarbonylmethoxycarbonyl, 1- or 2-tert-butoxycarbonylethoxycarbonyl, 1- or 2- or 3-pentyloxycarbonylpropoxycarbonyl, and the like.

Suitable "lower alkoxycarbonyl substituted by carboxy" may include carboxy(lower)alkoxycarbonyl such as carboxymethoxycarbonyl, 1- or 2-carboxyethoxycarbonyl, 1- or 2- or 3-carboxypropoxycarbonyl, and the like.

Particularly, the preferred embodiments of the terms "R¹", "R²" and "A" of the object compounds (I) are as follows.

The formula: R¹—A— is a group of the formula:

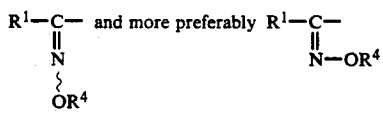

in which

R¹ is aminothiazolyl which may have halogen (more preferably 2-aminothiazol-4-yl, 2-aminothiazol-5-yl, 2-amino-5-halothiazol-4-yl, or 4-aminothiazol-2-yl), aminothiadiazolyl (more preferably 5-amino-1,2,4-thiadiazol-3-yl), aminooxadiazolyl (more preferably 5-amino-1,2,4-oxadiazol-3-yl), aminopyridyl (more preferably 6-aminopyridin-2-yl), aminopyrimidinyl (more preferably 4-aminopyrimidin-2-yl), acylaminothiazolyl which may have halogen [more preferably 2-loweralkanamidothiazol-4-yl (e.g. 2-formamidothiazol-4-yl, etc.), 4-loweralkoxycarbonylaminothiazol-2-yl (e.g. 4-tert-butoxycarbonylaminothiazol-2-yl, etc.)], di(lower)alkylaminomethyleneaminothiadiazolyl [more preferably 5-di(lower)alkylaminomethyleneamino-1,2,4-thiadiazol-3-yl (e.g. 5-dimethylaminomethyleneamino-1,2,4-thiadiazol-3-yl, etc.)], di(lower)alkylaminomethyleneaminooxadiazolyl [more preferably 5-di(lower)alkylaminomethyleneamino-1,2,4-oxadiazol-3-yl (e.g. 5-dimethylaminomethyleneamino-1,2,4-oxadiazol-3-yl, etc.)] or acylaminopyridyl [more preferably 6-lower alkanamidopyridin-2-yl (e.g. 6-formamidopyridin-2-yl, etc.)], R⁴ is cyclo(lower)alkenyl (e.g. cyclopentenyl, cyclohexenyl, etc.), lower alkynyl (e.g. propargyl, etc.), lower alkenyl (e.g. allyl, etc.), carboxy(lower)alkenyl (e.g. 3-carboxyallyl, etc.), esterified carboxy(lower)alkenyl [more preferably lower alkoxycarbonyl(lower)alkenyl (e.g. 3-tert-butoxycarbonylallyl, etc.)], lower alkyl (e.g. methyl, ethyl, propyl, isopropyl, butyl, pentyl, hexyl, etc.), carboxy(lower)alkyl (e.g. carboxymethyl, 1-carboxyethyl, 2-carboxyethyl, 3-carboxypropyl, 1-carboxy-1-methylethyl, etc.), esterified carboxy(lower)alkyl [more preferably lower alkoxycarbonyl(lower)alkyl (e.g. methoxycarbonylmethyl, ethoxycarbonylmethyl, tert-butoxycarbonylmethyl, 1-tert-butoxycarbonylethyl, 3-tert-butoxycarbonylpropyl, 1-tert-butoxycarbonyl-1-methylethyl, etc.), lower alkanoyloxy(lower)alkoxycarbonyl(lower)alkyl (e.g. acetoxymethoxycarbonylmethyl, pivaloyloxymethoxycarbonylmethyl, hexanoyloxymethoxycarbonylmethyl, etc.), mono- or di- or triphenyl(lower)alkoxycarbonyl(lower)alkyl which may have nitro (e.g. p-nitrobenzyloxycarbonylmethyl, benzyloxycarbonylmethyl, benzhydryloxycarbonylmethyl, tryloxycarbonylmethyl, 1- or 2-benzyloxycarbonylethyl, 1- or 2-benzhydryloxycarbonylethyl, 1- or 2- or 3-benzhydryloxycarbonylpropyl, etc.), mono- or di- or trihalo(lower)alkoxycarbonyl(lower)alkyl (e.g. chloromethoxycarbonylmethyl, bromomethoxycarbonylethyl, dichloromethoxycarbonylmethyl, trichloroethoxycarbonylmethyl, trichloroethoxycarbonylpropyl, etc.), amino-and carboxy-substituted-loweralkoxycarbonyl(lower)alkyl (e.g. 2-amino-2-carboxyethoxycarbonylmethyl, etc.), lower alkoxycarbonylamino- and mono- or di- or triphenyl (lower)alkoxycarbonyl-substituted-lower alkoxycarbonyl(lower)alkyl (e.g. 2-tert-butoxycarbonylamino-2-benzhydryloxycarbonylethoxycarbonylmethyl, etc.)], amino-and carboxy-substituted-lower alkyl (e.g. 3-amino-3-carboxypropyl, etc.), acylamino- and esterified carboxy-substituted-lower alkyl [more preferably lower alkoxycarbonylamino-and mono- or di- or triphenyl(lower)alkoxycarbonyl-substituted-lower alkyl (e.g. 3-tertbutoxycarbonylamino-3-benzhydryloxycarbonylpropyl, etc.)], cyano(lower)alkyl (e.g. cyanomethyl, cyanoethyl, etc.), phosphono(lower)alkyl (more preferably phosphonomethyl, phosphonoethyl, etc.), esterified phosphono(lower)alkyl [more preferably O,O-dialkylphosphono(lower)alkyl (e.g. O,O-dimethylphosphonomethyl, O,O-diethylphosphonomethyl, etc.)] or pyridyl(lower)alkyl (e.g. 2- or 3-pyridylmethyl, etc.); or the formula: R¹—A is one, in which R¹ is aminothiazolyl (more preferably 2-aminothiazol-4-yl), aminothiadiazolyl (more preferably 5-amino-1,2,4-thiadiazol-3-yl, 5-amino-1,3,4-thiadiazol-2-yl), aminooxadiazolyl (more preferably 5-amino-1,2,4-oxadiazol-3-yl), aminotetrazolyl (more preferably 5-amino-2H-tetrazol-2-yl), acylaminothiazolyl [more preferably 2-lower alkanamidothiazol-4-yl (e.g. 2-formamidothiazol-4-yl, etc.), 2-lower alkanesulfonamidothiazol-4-yl (e.g. 2-methanesulfonamidothiazol-4-yl, etc.), 2-trihalo(lower)alkanamidothiazol-4-yl (e.g. 2-trifluoroacetamidothiazol-4-yl, etc.) or 2-amidinothiazol-4-yl], mono- or di- or triphenyl(lower)alkylaminothiadiazolyl (more preferably 5-tritylamino-1,2,4-thiadiazol-3-yl, 5-tritylamino-1,3,4-thiadiazol-2-yl, etc.), mono- or di- or triphenyl(lower)alkylaminotetrazolyl (more preferably 5-tritylamino-2H-tetrazol-2-yl), or a group of the formula:

wherein R³ is lower alkyl (e.g. methyl, ethyl, propyl, isopropyl, butyl, pentyl, hexyl, etc.), A is methylene, aminomethylene, acylaminomethylene [more preferably lower alkoxycarbonylaminomethylene (e.g. tert-butoxycarbonylaminomethylene, etc.)], hydroxymethylene or carbonyl.

The term "R²" is carboxy or esterified carboxy group [more preferably mono- or di- or triphenyl(lower)alkoxycarbonyl (e.g. benzhydryloxycarbonyl, etc.), lower alkanoyloxy(lower)alkoxycarbonyl (e.g. acetoxymethoxycarbonyl, propionyloxymethoxycarbonyl, isobutyryloxymethoxycarbonyl, pivaloyloxymethoxycarbonyl, hexanoyloxymethoxycarbonyl, 1-acetoxypropoxycarbonyl, etc.), amino-and carboxy-substituted lower alkoxycarbonyl (e.g. 2-amino-2-carboxyethoxycarbonyl, etc.), lower alkoxycarbonylamino-and mono or di- or triphenyl(lower)alkoxycarbonyl-substituted-(lower)alkoxycarbonyl (e.g. 2-tert-butoxycarbonylamino-2-benzhydryloxycarbonylethoxycarbonyl, etc.), phthalidyl (e.g. phthalid-3-yl, etc.), carboxy(-lower)alkoxycarbonyl (e.g. carboxymethoxycarbonyl, 1- or 2-carboxyethoxycarbonyl, etc.), lower alkoxycarbonyl(lower)alkoxycarbonyl (e.g. methoxycarbonylmethoxycarbonyl, tert-butoxycarbonylmethoxycarbonyl, tert-butoxycarbonylethoxycarbonyl, etc.)].

Suitable intramolecular or intermolecular quaternary salt of the object compounds (I) may include 7-[2-(2-aminothiazol-4-yl)-2-{(1-methyl-3-pyridinio)methoxyimino}acetamido]-3-vinyl-3-cephem-4-carboxylate, 7-[2-(2-aminothiazol-4-yl)-2-{(1-methyl-2-pyridinio)methoxyimino}acetamido]-3-vinyl-3-cephem-4-carboxylate, 1-methyl-3-[1-(2-aminothiazol-4-yl)-1-{N-(4-benzhydryloxycarbonyl-3-vinyl-3-cephem-7-yl)carbamoyl} methyleneaminooxymethyl]pyridinium methylsulfate, 1-methyl-2-[1-(2-aminothiazol-4-yl)-1-{N-(4-benzhydryloxycarbonyl-3-vinyl-3-cephem-7-yl)carbamoyl} methyleneaminooxymethyl]pyridinium methylsulfate.

The processes 1 to 15 for the preparation of the object compounds (I) of the present invention are explained in detail in the following.

(1) Process 1

The compounds (I) or a salt thereof can be prepared by reacting the compound (II) or its reactive derivative at the amino group or a salt thereof with the compound (III) or its reactive derivative at the carboxy group or a salt thereof.

Suitable salts of the starting compounds (II) and (III) may include the same ones as illustrated for the compounds (I).

Suitable reactive derivative at the amino group of the compound (II) may include a conventional one, for example, a silyl derivative formed by the reaction of the compound (II) with a silyl compound such as bis(trimethylsilyl)acetamide, trimethylsilylacetamide, etc.; isocyanate; isothiocyanate; Schiff's base or its tautomeric enamine type isomer formed by the reaction of the amino group with a carbonyl compound such as an aldehyde compound (e.g. acetaldehyde, isopentaldehyde, benzaldehyde, salicylaldehyde, phenylacetaldehyde, p-nitrobenzaldehyde, m-chlorobenzaldehyde, p-chlorobenzaldehyde, hydroxynaphthoaldehyde, furfural, thiophenecarboaldehyde, etc.) or a ketone compound (e.g. acetone, methyl ethyl ketone, methyl isobutyl ketone, acetylacetone, ethyl acetoacetate, etc.), and the like.

Suitable reactive derivative of the compound (III) may include, for example, an acid halide, an acid anhydride, an activated amide, an activated ester, and the like, and preferably an acid chloride and acid bromide; a mixed acid anhydride with an acid such as substituted phosphoric acid (e.g. dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, sulfuric acid, alkyl carbonate (e.g. methyl carbonate, ethyl carbonate, propyl carbonate, etc.), aliphatic carboxylic acid (e.g. pivalic acid, pentanoic acid, isopentanoic acid, 2-ethylbutyric acid, trichloroacetic acid, etc.), aromatic carboxylic acid (e.g. benzoic acid, etc.); a symmetrical acid anhydride; an activated acid amide with a heterocyclic compound containing imino function such as imidazole, 4-substituted imidazole, dimethylpyrazole, triazole or tetrazole; an activated ester (e.g. p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyridyl ester, piperidinyl ester, 8-quinolyl thioester, or an ester with a N-hydroxy compound such as N,N-dimethylhydroxylamine, 1-hydroxy-2-(1H)-pyridone, N-hydroxysuccinimide, N-hydroxyphthalimide, 1-hydroxybenzotriazole, 1-hydroxy-6-chlorobenzotriazole, etc.), and the like.

The suitable reactive derivative can optionally be selected from the above according to the kinds of the compounds (II) and (III) to be used practically.

This reaction can be carried out in the presence of an organic or inorganic base such as alkali metal (e.g. lithium, sodium, potassium etc.), alkaline earth metal (e.g. calcium, etc.), alkali metal hydride (e.g. sodium hydride, etc.), alkaline earth metal hydride (e.g. calcium hydride, etc.), alkali metal hydroxide (e.g. sodium hydroxide, potassium hydroxide, etc.), alkali metal carbonate (e.g. sodium carbonate, potassium carbonate, etc.), alkali metal bicarbonate (e.g. sodium bicarbonate, potassium bicarbonate, etc.), alkali metal alkoxide (e.g. sodium methoxide, sodium ethoxide, potassium tert-butoxide, etc.), alkali metal alkanoic acid (e.g. sodium acetate, etc.), trialkylamine (e.g. triethylamine, etc.), pyridine compound (e.g. pyridine, lutidine, picoline, etc.), quinoline, and the like.

In case that the compound (III) is used in a form of the free acid or a salt in this reaction, the reaction is preferably carried out in the presence of a condensing agent such as a carbodiimide compound [e.g. N,N'-dicyclohexylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, etc.], a ketenimine compound (e.g. N,N'-carbonylbis(2-methylimidazole), pentamethyleneketene-N-cyclohexylimine, diphenylketene-N-cyclohexylimine, etc.); an olefinic or acetylenic ether compounds (e.g. ethoxyacetylene, β-chlorovinylethyl ether), a sulfonic acid ester of N-hydroxybenzotriazole derivative [e.g. 1-(4-chlorobenzenesulfonyloxy)-6-chloro-1H-benzotriazole etc.], a combination of trialkylphosphite or triphenylphosphine and carbon tetrachloride, disulfide or diazenedicarboxylate (e.g. diethyl diazenedicarboxylate, etc.), a phosphorus compound (e.g. ethyl polyphosphate, isopropyl polyphosphate, phosphoryl chloride, phosphorus trichloride, etc.), thionyl chloride, oxalyl chloride, N-ethylbenzisoxazolium salt, N-ethyl-5-phenylisoxazolium-3-sulfonate, a reagent (referred to as so-called "Vilsmeier reagent") formed by the reaction of an amide compound such as N,N-di(lower)alkylformamide (e.g. dimethylformamide, etc.), N-methylformamide or the like with a halogen compound such as thionyl chloride, phosphoryl chloride, phosgene or the like.

The reaction is usually carried out in a conventional solvent which does not adversely influence the reaction such as water, acetone, dioxane, acetonitrile, chloroform, benzene, methylene chloride, ethylene chloride, tetrahydrofuran, ethyl acetate, N,N-dimethylformamide, pyridine, hexamethylphosphoramide, etc., or a mixture thereof.

Among these solvents, hydrophilic solvents may be used in a mixture with water.

The reaction temperature is not critical and the reaction is usually carried out under cooling to warming.

The present invention includes, within the scope thereof, in case that the reaction is carried out in the presence of Vilsmeier reagent mentioned above, the amino group for $R^1$ in the starting compound (III) is occasionally transformed into a (N,N-(lower)alkylaminomethylene)amino group during the reaction.

(2) Process 2

The compound (I-b) or a salt thereof can be prepared by subjecting the compound (I-a) or a salt thereof to removal reaction of the amino-protective group in $R_a{}^1$.

Suitable method for this removal reaction may include conventional one such as hydrolysis, reduction, combined methods comprising iminohalogenation and then iminoetherification, followed by hydrolysis, if necessary, and the like.

(i) For hydrolysis:

Hydrolysis is preferably carried out in the presence of an acid.

Suitable acid may be an inorganic acid (e.g. hydrochloric acid, hydrobromic acid, sulfuric acid, etc.), an organic acid (e.g. formic acid, acetic acid, trifluoroacetic acid, propionic acid, methanesulfonic acid, benzenesulfonic acid, p-toluenesulfonic acid, etc.), an acidic ion-exchange resin and the like. In case that the organic acid such as trifluoroacetic acid and p-toluenesulfonic acid is used in this reaction, the reaction is preferably carried out in the presence of cation trapping agents (e.g. anisole, etc.).

The acid suitable for this hydrolysis can be selected according to the kinds of the protective group to be removed, for example, this hydrolysis can preferably be applied to the amino-protective group for $R_a{}^1$ such as substituted or unsubstituted lower alkoxycarbonyl, substituted or unsubstituted lower alkanoyl.

The hydrolysis is usually carried out in a conventional solvent which does not adversely influence the reaction such as water, methanol, ethanol, propanol, tert-butyl alcohol, tetrahydrofuran, N,N-dimethylformamide, dioxane or a mixture thereof, and further the above-mentioned acids can also be used as a solvent when they are in liquid.

The reaction temperature of this hydrolysis is not critical, and the reaction is usually carried out under cooling to at somewhat elevated temperature.

(ii) For Reduction:

Reduction is carried out in a conventional manner, including chemical reduction and catalytic reduction.

Suitable reducing agents to be used in chemical reduction are a combination of a metal (e.g. tin, zinc, iron, etc.) or metallic compound (e.g. chromium chloride, chromium acetate, etc.) and an organic or inorganic acid (e.g. formic acid, acetic acid, propionic acid, trifluoroacetic acid, p-toluenesulfonic acid, ammonium chloride, hydrochloric acid, hydrobromic acid, sodium biphosphate, etc.).

Suitable catalysts to be used in catalytic reduction are conventional ones such as platinum catalysts (e.g. platinum plate, spongy platinum, platinum black, colloidal platinum, platinum oxide, platinum wire, etc.), palladium catalysts (e.g. spongy palladium, palladium black, palladium oxide, palladium on carbon, colloidal palladium, palladium on barium sulfate, palladium on barium carbonate, etc.), nickel catalysts (e.g. reduced nickel, nickel oxide, Raney nickel, etc.), cobalt catalysts (e.g. reduced cobalt, Raney cobalt, etc.), iron catalysts (e.g. reduced iron, Raney iron, etc.), copper catalysts (e.g. reduced copper, Raney copper, Ullman copper, etc.) and the like.

The reduction manner can be selected according to the kinds of the protective group to be removed, for example, the chemical reduction can preferably be applied to the amino-protective group for $R_a{}^1$ such as halo(lower)alkoxycarbonyl and the like, and catalytic reduction can preferably be applied to that such as substituted or unsubstituted ar(lower)alkoxycarbonyl, and the like.

The reduction is usually carried out in a conventional solvent which does not adversely influence the reaction such as water, methanol, ethanol, propanol, N,N-dimethylformamide, or a mixture thereof. Additionally, in case that the above-mentioned acids to be used in chemical reduction are in liquid, they can also be used as a solvent. Further, a suitable solvent to be used in catalytic reduction may be the above-mentioned solvent, and other conventional solvent such as diethyl ether, dioxane, tetrahydrofuran, etc., or a mixture thereof.

The reaction temperature of this reduction is not critical and the reaction is usually carried out under cooling to warming.

(iii) For combined methods comprising iminohalogenation (the first step) and then iminoetherification (the 2nd step), followed by hydrolysis (the last step), if necessary:

The first and second steps of this method are preferably carried out in an anhydrous solvent. Suitable solvent for the first step (i.e. iminohalogenation) is an aprotic solvent such as methylene chloride, chloroform, diethyl ether, tetrahydrofuran, dioxane, etc., and for the second step (i.e. iminoetherification) is usually the same as those in the above first step. These two steps are usually conducted under cooling to at ambient temperature. These two steps and the last step (i.e. hydrolysis step) are most preferably conducted in one-batch system.

Suitable iminohalogenating agents include a halogenating agent such as phosphorus halo compound (e.g. phosphorus trichloride, phosphorus pentachloride, phosphorus tribromide, phosphorus pentabromide, phosphorus oxychloride, etc.), thionyl chloride, phosgene, and the like.

Suitable iminoetherifying agent may be an alcohol such as an alkanol (e.g. methanol, ethanol, propanol, isopropanol, butanol, etc.) or the corresponding alkanol having alkoxy (e.g. 2-methoxyethanol, 2-ethoxyethanol, etc.), and alkoxide of metal such as alkali metal, alkaline earth metal (e.g. sodium methoxide, potassium ethoxide, magnesium ethoxide, lithium methoxide, etc.), and the like.

Thus obtained reaction product is, if necessary, hydrolyzed in a conventional manner. The hydrolysis is preferably carried out at ambient temperature to under cooling, and proceeds simply pouring the reaction mixture into water or a hydrophilic solvent such as alcohol (e.g. methanol, ethanol, etc.) moistened or admixed with water, and if necessary, with addition of an acid or base.

Suitable acid may include the same ones as those given in the explanation of Hydrolysis mentioned in the above item (i), and suitable base may include the same ones as those given in the explanation of Process 1.

The methods thus explained may be selected depending upon the kind of the protective groups to be removed.

The present invention includes, within the scope of the invention cases that the protected amino group and/or the protected carboxy group in $R^2$ and A are transformed into free amino group and/or free carboxy group, respectively during the reaction.

(3) Process 3

The compound (I-d) or a salt thereof can be prepared by subjecting the compound (I-c) or a salt thereof to removal reaction of the carboxy-protective group for $R_a^2$.

This reaction is carried out by a conventional method such as hydrolysis, reduction, and the like.

The method of hydrolysis and reduction, and the reaction conditions (e.g. reaction temperature, solvent, etc.) are substantially the same as those illustrated for the removal reaction of the amino-protective group of the compound (I-a) in Process 2, and therefore are to be referred to said explanation.

The present invention includes, within the scope of the invention, cases that the protected amino group in $R^1$ and A and/or the protected carboxy group in A are transformed into free amino group(s) and/or a free carboxy group, respectively during the reaction.

(4) Process 4

The compound (I-c) or a salt thereof can be prepared by introducing a carboxy-protective group into the compound (I-d) or a salt thereof.

The introducing agent of a carboxy-protective group to be used in this reaction may include a conventional esterifying agent such as an alcohol or its reactive equivalent (e.g. halide, sulfonate, sulfate, diazo compound, etc.), and the like.

The reaction can also be carried out in the presence of a base, and suitable examples thereof are the same as those given in the explanation of Process 1, and can preferably be carried out in the presence of metal iodide (e.g. sodium iodide, etc.).

This reaction is usually carried out in a conventional solvent which does not adversely influence the reaction such as N,N-dimethylformamide, tetrahydrofuran, dioxane, methanol, ethanol, etc., or a mixture thereof.

The reaction temperature is not critical, and the reaction is usually carried out under cooling to at somewhat elevated temperature.

In case that the alcohol is used as the introducing agent of a carboxy-protective group, the reaction can be carried out in the presence of a condensing agent as illustrated in Process 1.

The present invention includes, within the scope thereof, the case that the carboxy-protective group is occasionally introduced into the carboxy group in A of the compound (I-d) during the reaction.

(5) Process 5

The compound (I-e) or a salt thereof can be prepared by reacting the compound (IV) or a salt thereof with the compound (V).

Suitable salts of the starting compound (IV) may include the same salts with a base for the compounds (I).

This reaction is usually carried out in a conventional solvent which does not adversely influence the reaction such as ethyl acetate, methylene chloride, chloroform, carbon tetrachloride, tetrahydrofuran, dioxane, water, etc., or a mixture thereof.

The reaction temperature is not critical and the reaction is usually carried out under cooling to warming.

(6) Process 6

The compound (I-g) or a salt thereof can be prepared by subjecting the compound (I-f) or a salt thereof to removal reaction of the carboxy-protective group or the phosphono-protective group in $A^1$.

This reaction is carried out by a conventional method such as hydrolysis, reduction, and the like.

The method of hydrolysis and reduction, and the reaction conditions (e.g. reaction temperature, solvent, etc.) are substantially the same as those illustrated for the removal reaction of the amino-protective group of the compound (I-a) in Process 2, and therefore are to be referred to said explanation.

Further, for removal reaction of the phosphono-protective group, the reaction can also be carried out by reacting the compound (I-f) with trialkylsilyl halide such as trimethylsilyl chloride, trimethylsilyl bromide, trimethylsilyl iodide, and the like.

The present invention includes, within the scope thereof, cases that the protected amino group in $R^1$ and $R^2$, and/or the protected carboxy group in $R^2$ are transformed into free amino group and/or free carboxy group, respectively during the reaction.

(7) Process 7

The compound (I) or a salt thereof can be prepared by reacting the compound (VI) or a salt thereof with formaldehyde.

Suitable salts of the compound (VI) may include the same ones as exemplified for the compounds (I).

This reaction is usually carried out in a conventional solvent which does not adversely influence the reaction such as tetrahydrofuran, dioxane, etc., or a mixture thereof.

The reaction temperature is not critical and the reaction is usually carried out under cooling to somewhat elevated temperature.

(8) Process 8

The compound (I-i) or a salt thereof can be prepared by subjecting the compound (I-h) or a salt thereof to removal reaction of the amino- and carboxy-protective groups in $R_b^2$.

This reaction is carried out by a conventional method such as hydrolysis, reduction, and the like.

The method of hydrolysis and reduction, and the reaction conditions (e.g. reaction temperature, solvent, etc.) are substantially the same as those illustrated for removal reaction of the amino-protective group of the compound (I-a) in Process 2, and therefore are to be referred to said explanation.

In this reaction, the amino- and carboxy-protective groups can be removed separately or at a time.

The present invention includes, within the scope thereof, cases that the protected amino group in $R^1$ and A and/or the protected carboxy group in A are transformed into free amino group and/or free carboxy group, respectively during the reaction.

(9) Process 9

The compound (I-k) or a salt thereof can be prepared by subjecting the compound (I-j) or a salt thereof to removal reaction of the amino- and carboxy-protective groups in $A^3$.

This reaction is carried out by a conventional method such as hydrolysis, reduction, and the like.

The method of hydrolysis and reduction, and the reaction conditions (e.g. reaction temperature, solvent, etc.) are substantially the same as those illustrated for removal reaction of the amino-protective group of the compound (I-a) in Process 2, and therefore are to be referred to said explanation.

In this reaction, the amino- and carboxy-protective groups can be removed separately or at a time.

The present invention includes, within the scope thereof, cases that the protected amino group in $R^1$ and $R^2$ and/or the protected carboxy group in $R^2$ are transformed into free amino group and/or free carboxy group, respectively during the reaction.

(10) Process 10

The compound (I-f) or a salt thereof can be prepared by introducing a carboxy-protective group or a phosphono-protective group into the compound (I-g) or a salt thereof.

This reaction is carried out by substantially the same method as that illustrated for introducing the carboxy-protective group into the compound (I-d) in Process 4, and therefore, the reaction conditions (e.g. reaction temperature, solvent, etc.) are to be referred to said explanation.

The present invention includes, within the scope thereof, case that the carboxy group for $R^2$ is transformed into the protected carboxy group during the reaction.

(11) Process 11

The compound (I-m) or a salt thereof can be prepared by reacting the compound (I-l) or a salt thereof with the compound (VPP).

This reaction is usually carried out in a conventional solvent which does not adversely influence the reaction such as tetrahydrofuran, dioxane, water, etc., or a mixture thereof.

The reaction temperature is not critical, and the reaction is usually carried out at ambient temperature to under heating.

(12) Process 12

The compound (I-o) or a salt thereof can be prepared by reacting the compound (I-n) or a salt thereof with a base.

Suitable base used in this Process may include the same ones as those exemplified in Process 1.

This reaction is usually carried out in a conventional solvent which does not adversely influence the reaction such as water, methanol, ethanol, etc., or a mixture thereof.

The reaction temperature is not critical, and the reaction is usually carried out under cooling to warming.

(13) Process 13

The compound (I-q) or a salt thereof can be prepared by subjecting the compound (I-p) or a salt thereof to removal reaction of the amino-protective group in $A^8$.

This reaction is carried out by a conventional method such as hydrolysis, reduction, and the like.

The method of hydrolysis and reduction, and the reaction conditions (e.g. reaction temperature, solvent, etc.) are substantially the same as those illustrated for removal reaction of the amino-protective group of the compound (I-a) in Process 2, and therefore are to be referred to said explanation.

The present invention includes, within the scope thereof, cases that the protected amino group in $R^1$ and $R^2$ and/or the protected carboxy group in $R^2$ are transformed into free amino group and/or free carboxy group, respectively during the reaction.

(14) Process 14

The compound (I-s) or a salt thereof can be prepared by inducing the compound (I-r) or a salt thereof.

The reduction can be carried out by a conventional method such as reduction using a reducing agent, catalytic reduction, and the like.

Suitable reducing agent may include a conventional one used for conversion of a carbonyl group to a hydroxymethyl group such as metal borohydride, for example, alkali borohydride (e.g. sodium borohydride, potassium borohydride, sodium cyanoborohydride, etc.), lithium aluminum hydride, etc.; diborane; and the like.

The catalyst to be used in the catalytic reduction may include the same ones as exemplified for the reduction in Process 2.

This reaction is usually carried out in a conventional solvent which does not adversely influence the reaction such as water, methanol, ethanol, tetrahydrofuran, dioxide; etc., or a mixture thereof.

The reaction temperature is not critical and the reaction is usually carried out under cooling to warming.

(15) Process 15

The compound (I-t) or a salt thereof can be prepared by reacting the compound (I-r) or a salt thereof with the compound (VIII) or a salt thereof.

Suitable salts of the compound (VIII) may include the same acid addition salts as exemplified for the compounds (I).

In this reaction, when the compound (VIII) is used in a salt form, this reaction can also be carried out in the presence of a base as exemplified in Process 1.

This reaction is usually carried out in a conventional solvent which does not adversely influence the reaction such as water, methanol, ethanol, propanol, dioxane, tetrahydrofuran, etc., or a mixture thereof.

The reaction temperature is not critical and the reaction is usually carried out under cooling to warming.

The object compound (I) obtained according to the Processes 1 to 15 as explained above can be isolated and purified in a conventional manner, for example, extraction, precipitation, fractional crystallization, recrystallization, chromatography, and the like.

Process ① to 15 for the preparation of the starting compounds are explained in detail in the following.

Process ①-(1)

The compound ((①- b) or a salt thereof can be prepared by reacting the compound ((①)-a) or a salt thereof with the halogenating agent.

Suitable salts of the compounds ((①)-a) and ((①)-b) may include the same salt with a base as exemplified for the compounds (I).

Suitable halogenating agent used in this reaction may include one which can be applied to conversion of a hydroxy group to halo group such as phosphorus halide (e.g. phosphorus trichloride, phosphorus pentachloride, phosphorus oxychloride, phosphorus tribromide, phosphorus pentabromide, etc.), thionyl halide (e.g. thionyl chloride, etc.), phosgene, and the like.

This reaction is preferably carried out in the presence of a base such as an organic base given in the explanation of Process 1.

This reaction is usually carried out in a conventional solvent which does not adversely influence the reaction such as methylene chloride, chloroform, ethylene chloride, tetrahydrofuran, dioxane, N,N-dimethylformamide, etc., or a mixture thereof.

The reaction temperature is not critical and the reaction is usually carried out under cooling to warming.

Process ①-(2)

The compound (①-c) or a salt thereof can be prepared by reacting the compound (①-b) or a salt thereof with a trisubstituted phosphine (IX) of the formula: $P(R^7)_3$, wherein $R^7$ is as defined above.

Suitable salts of the compound (①-c) may include the same salt with a base as exemplified for the compounds (I).

This reaction is preferably carried out in the presence of metal halide such as alkali metal halide (e.g. sodium iodide, potassium iodide, sodium bromide, etc.), and the like, and in such a case, the halogen for $X^2$ of the compound (①-b) can be replaced with the halo moiety of such metal halide in the object compound (①-c) during the reaction.

This reaction is usually carried out in a conventional solvent which does not adversely influence the reaction such as N,N-dimethylformamide, dimethylsulfoxide, methylene chloride, tetrahydrofuran, ethyl acetate, etc., or a mixture thereof.

The reaction temperature is not critical and the reaction is usually carried out under cooling to warming.

Process ①-(3)

The compound (①-d) or a salt thereof can be prepared by reacting the compound (①-c) or a salt thereof with a base.

Suitable salts of the compound (①-d) may include the same salt with a base as exemplified for the compounds (I).

Suitable base used in this process are the same as those given in the explanation of Process 1.

This reaction is usually carried out in a conventional solvent which does not adversely influence the reaction such as acetone, tetrahydrofuran, water, etc., or a mixture thereof.

The reaction temperature is not critical and the reaction is usually carried out under cooling to at somewhat elevated temperature.

Process ①-(4)

The compound (①-f) or a salt thereof can be prepared by reacting the compound (①-e) or its reactive derivative at the amino group or a salt thereof with the compound (III) or its reactive derivative at the carboxy group or a salt thereof.

Suitable salts of the compound (①-e) may include the same ones as exemplified for the compounds (I), and suitable salts of the compounds (①-f) may include the same salt with a base as exemplified for the compounds (I).

Suitable reactive derivative of the compounds (①-e) may include the same ones as exemplified for the compounds (II) in Process 1, respectively.

The reaction is substantially the same method as Process 1, and accordingly, the method, reaction conditions (e.g. reaction temperature, solvent, base, etc.) are to be referred to said explanation.

Process ②-(1)

The compound (②-b) or a salt thereof can be prepared by reacting the compound (②-a) or a salt thereof with formaldehyde.

Suitable salts of the compounds (②-a) and (②-b) may include the same ones as exemplified for the compounds (I).

This reaction can be carried out by substantially the same method as that illustrated for Process 7, and therefore reaction conditions (e.g. reaction temperature, solvent, etc.) are to be referred to said explanation.

Process ②-(2)

The compound (②-d) or a salt thereof can be prepared by subjecting the compound (②-c) or a salt thereof to removal reaction of the carboxy-protective group.

Suitable salts of the compound (②-c) may include the same acid addition salts as exemplified for the compounds (I), and suitable salts of the compound (②-d) may include the same ones as exemplified for the same compounds.

This reaction is carried out by a conventional method such as hydrolysis, and the like.

The hydrolysis is carried out by substantially the same method as that illustrated for Process 2, and therefore the method of hydrolysis and the reaction conditions (e.g. reaction temperature, solvent, etc.) are referred to said explanation.

Process (②-(3)

The compound (②-f) or a salt thereof can be prepared by reacting the compound (②-e) or its reactive derivative at the amino group or a salt thereof with the compound (X) or its reaction derivative at the carboxy group or a salt thereof.

Suitable salts of the compound (②-e) may include the same ones as exemplified for the compounds (I), and suitable salts of the compounds (②-f) and (X) may include the same salts with a base as exemplified for the compounds (I).

Suitable reactive derivative at the amino group of the compound (②-e) and that at the carboxy group of the compound (X) may include the same ones as exemplified for the compounds (II) and (III) in Process 1.

The reaction is substantially the same method as Process 1, and accordingly, the method, reaction conditions (e.g. reaction temperature, solvent, base, etc.) are to be referred to said explanation.

Process ②-(4)

The compound (②-h) or a salt thereof can be prepared by subjecting the compound (②-g) or a salt thereof to removal reaction of the oxo-protective group.

Suitable salts of the compounds (②-g) and (②-h) may include the same salt with a base as exemplified for the compounds (I).

This reaction is carried out by a conventional method such as hydrolysis, and the like.

The method of hydrolysis, and the reaction conditions (e.g. reaction temperature, solvent, etc.) are substantially the same as those illustrated for Process 2, and therefore are to be referred to said explanation.

Process ③-(1)

The compound (③-b) or a salt thereof can be prepared by reacting the compound (③-a) or a reactive derivative at the carboxy group or a salt thereof with lower alkanol substituted by protected amino and protected carboxy groups (XI).

Suitable salts of the compounds (③-a) and (③-b) may include the same ones as exemplified for the compounds (I).

Suitable reaction derivative at the carboxy group of the compound (③-a) may include the same ones as the compound (III) in Process 1.

This reaction is carried out by substantially the same method as that illustrated for Process 4, and therefore, the reaction conditions (e.g. reaction temperature, solvent, etc.) are to be referred to said explanation.

Process ③-(2)

The compound (③-c) or a salt thereof can be prepared by subjecting the compound (③-b) or a salt thereof to removal reaction of the amino-protective group in $R_D'$.

Suitable salt of the compound (③-c) may include the same ones as exemplified for the compounds (I).

This reaction is carried out by substantially the same method as that illustrated for Process 2, and therefore, the reaction conditions (e.g. reaction temperature, solvent, etc.) are to be referred to said explanation.

Process ④-(1)

Step 1

The compound (④-b) or a salt thereof can be prepared by reacting the compound (④-a) or a salt thereof with hydroxylamine or a salt thereof.

Suitable salt of hydroxylamine may include the same acid addition salt as exemplified for the compounds (I).

Suitable salts of the compounds (④-a) and (④-b) may include the same salt with a base as exemplified for the compounds (I).

In case that the salt of hydroxylamine is used as the reagent, the reaction can usually be carried out in the presence of a base such as those illustrated in Process 1.

The reaction is usually carried out in a conventional solvent which does not adversely influence the reaction such as methanol, ethanol, etc., or a mixture thereof.

The reaction temperature is not critical and the reaction is usually carried out under cooling to warming.

Step 2

The compound (④-c) or a salt thereof can be prepared by reacting the compound (④-b) or a salt thereof with the compound (XII) or its reactive derivative at the carboxy group or a salt thereof.

Suitable salt of the compounds (④-c) and (XII) may include the same salt with a base as exemplified for the compounds (I).

Suitable reactive derivative at the carboxy group of the compound (XII) may include the same ones as illustrated for the compound (III) in Process 1.

This reaction is carried out by substantially the same method as Process 1, and therefore, the reaction conditions (e.g. reaction temperature, solvent, etc.) are to be referred to said explanation.

Process ④-(2)

The compound (④-d) or a salt thereof can be prepared by reacting the compound (④-c) or a salt thereof with ammonia.

Suitable salts of the compound (④-d) may include the same ones as exemplified for the compounds (I).

This reaction can be carried out in the absence of or in the presence of a solvent which does not adversely influence the reaction such as dioxane, etc., and the reaction is usually carried out in the absence of a solvent.

The reaction temperature is not critical and the reaction is usually carried out under cooling to warming.

In case that the compound (④-d) is one of the geometrical isomers such as anti isomer, it can be transformed into the other isomer such as syn isomer in a conventional manner, for example, by treating an acid such as those illustrated in Process 2.

Process ④-(3)

The compound (④-f) or a salt thereof can be prepared by reacting the compound (④-e) or a salt thereof with the compound (XIII) or a salt thereof.

Suitable salts of the compounds (④-e), (④-f) and (XIII) may include the same salt with a base as exemplified for the compounds (I).

This reaction is usually carried out in a conventional solvent which does not adversely influence the reaction such as diethyl ether, diisopropyl ether, etc., or a mixture thereof.

The reaction temperature is not critical and the reaction is usually carried out under cooling to warming.

Process ④-(4)

The compound (④-g) or a salt thereof can be prepared by subjecting the compound (④-f) or a salt thereof to azidation (the first step) and then, subjecting the resultant compound to a thermal degradation reaction (the second step), followed by treating the resultant compound with the alcohol (the last step).

Suitable salts of the compound (④-g) may include the same salt with a base as exemplified for the compounds (I).

(i) As to the first step:

Suitable azidating agent may include hydrazoic acid or its reactive derivative such as sodium azide, potassium azide, calcium azide, diphenylphosphorous azide and the like.

This reaction is usually carried out in a conventional solvent which does not adversely influence the reaction such as alcohol mentioned below, tetrahydrofuran, dichloromethane, diethyl ether, or a mixture thereof, and the like.

The reaction temperature is not critical and the reaction is usually carried out under cooling to at ambient temperature.

(ii) As to the second step:

This reaction can be carried out by heating the resulting compound obtained in the first step. This reaction is usually carried out in a conventional solvent as mentioned in the first step.

(iii) As to the last step:

This reaction can be carried out by adding alcohol.

Suitable alcohol may include lower alkanol (e.g. methanol, ethanol, propanol, butanol, tert-butanol, etc.), ar(lower)alkanol (e.g. benzyl alcohol, benzhydryl alcohol, etc.), and the like.

The reaction temperature is not critical and the reaction is usually carried out under cooling to warming.

A chain of these steps mentioned above can also be carried out by one pot.

Process ④-(5)

The compound (④-h) or a salt thereof can be prepared by reacting the compound (④-g) or a salt thereof with an oxidizing agent.

Suitable salts of the compound (④-h) may include the same salt with a base as exemplified for the compounds (I).

Suitable oxidizing agents may include one which is applied for the transformation of so-called activated methylene group into carbonyl group such as selenium dioxide or the like.

The present reaction is usually carried out in a conventional solvent which does not adversely influence the reaction such as tetrahydrofuran, dioxane, etc., or a mixture thereof, The reaction temperature is not critical and the reaction is preferably carried out under warming to heating.

Process ④-(6)

The compound (④-i) or a salt thereof can be prepared by reacting the compound (④-h) or a salt thereof with the compound (VIII) or a salt thereof.

Suitable salts of the compound (④-i) may include the same salt with a base as exemplified for the compounds (I), and suitable salts of the compound (VIII) may include the same acid addition salt as exemplified for the same compounds.

This reaction is carried out by substantially the same method as that of Process 15, and therefore the reaction conditions (e.g. reaction temperature, solvent, base, etc.) are to be referred to said explanation.

Process ④-(7)

The compound (④-k) or a salt thereof can be prepared by subjecting the compound (④-j) or a salt thereof to removal reaction of the carboxy-protective group for $R^j$.

Suitable salts of the compound (④-k) may include the same ones as exemplified for the compounds (I), and suitable salts of the compound (④-j) may include the same acid addition salts as exemplified for the same compounds.

This reaction is carried out by a conventional method such as hydrolysis, reduction, and the like.

The method of hydrolysis and reduction, and the reaction conditions (e.g. reaction temperature, solvent, etc.) are substantially the same as those illustrated for Process 2, and therefore are to be referred to said explanation.

Process ⑤

The compound (⑤-b) or a salt thereof can be prepared by reacting the compound (⑤-a) or a salt thereof with the compound (XV) or a salt thereof.

Suitable salts of the compounds (⑤-a), (⑤-b) and (XV) may include the same ones as exemplified for the compounds (I).

This reaction is carried out by substantially the same method as that of Process 15, and therefore the reaction conditions (e.g. reaction temperature, solvent, base, etc.) are to be referred to said explanation.

Process ⑥

The compound (⑥-b) or a salt thereof can be prepared by reacting the compound (⑥-a) or a salt thereof with the compound (XVI) or a salt thereof.

Suitable salts of the compounds (⑥-a), (⑥-b) and (XVI) may include the same ones as exemplified for the compounds (I).

This reaction is carried out by substantially the same method as that of Process 15, and therefore the reaction conditions (e.g. reaction temperature, solvent, base, etc.) are to be referred to said explanation.

Process ⑦-(1)

The compound (⑦-b) can be prepared by reacting the compound (⑦-a) or a reactive derivative at the hydroxy group with N-hydroxyphthalimide or a salt thereof.

Suitable salts of N-hydroxyphthalimide may include the alkali metal salt as exemplified for the compounds (I).

Suitable reactive derivative at the hydroxy group may include halide such as chloride, bromide, and the like.

This reaction is preferably carried out in the presence of a base as exemplified in Process 1.

In case that the compound (⑦-a) is used in a free form, the reaction can usually be carried out in the presence of a condensing agent as exemplified in Process 1.

This reaction is usually carried out in a conventional solvent which does not adversely influence the reaction such as tetrahydrofuran, N,N-dimethylformamide, acetonitrile, etc., or a mixture thereof.

The reaction temperature is not critical and the reaction is usually carried out under cooling to heating.

Process ⑦-(2)

The compound (⑦-c) or a salt thereof can be prepared by subjecting the compound (⑦-b) to removal reaction of the phthaloyl group.

Suitable salt of the compound (⑦-c) may include the same acid addition salt as exemplified for the compounds (I).

This reaction is carried out by a conventional method such as hydrolysis, and the like.

The method of hydrolysis, and the reaction conditions (e.g. reaction temperature, solvent, etc.) are substantially the same as those illustrated for Process 2, and therefore are to be referred to said explanation.

Process ⑧

The compound (⑧-b) or a salt thereof can be prepared by subjecting the compound (⑧-a) to removal reaction of the acyl group.

Suitable salts of the compound (⑧-b) may include the same acid addition salts as exemplified for the compounds (I).

This reaction is usually carried out by combined methods comprising iminohalogenation and the iminoetherification, followed by hydrolysis, if necessary.

These combined methods and reaction conditions (e.g. reaction temperature, solvent, etc.) are substantially the same as those illustrated for Process 2, and therefore are to be referred to said explanation.

Process ⑨

Step 1:

The compound (⑨-b) or a salt thereof can be prepared by subjecting the compound (⑨-a) or a salt thereof to removal reaction of the acyl group.

Suitable salts of the compound (⑨-a) may include the same salt with a base as exemplified for the compounds (I), and suitable salts of the compound ((9)-b) may include the same ones as exemplified for the same compounds (I).

This reaction can be carried out by combined methods comprising iminohalogenation and then iminoetherification, followed by hydrolysis, if necessary.

The combined methods and the reaction conditions (e.g. reaction temperature, solvent, etc.) are substantially the same as those illustrated for Process 2, and therefore are to be referred to said explanation.

Step 2:

The compound ((9)-c) or a salt thereof can be prepared by reacting the compound ((9)-b) or a salt thereof with the compound (XVII) of the formula: $R^8$—CHO, wherein $R^8$ is as defined above.

Suitable salts of the compound ((9)-c) may include the same salt with a base as exemplified for the compounds (I).

This reaction is preferably carried out in the presence of a dehydrating agent such as molecular sieve, and the like.

This reaction is usually carried out in a conventional solvent which does not adversely influence the reaction such as N,N-dimethylformamide, etc.

The reaction temperature is not critical and the reaction is usually carried out at ambient temperature to under heating.

Process (10)

The compound ((10)-b) or a salt thereof can be prepared by reducing the compound ((10)-a) or a salt thereof.

Suitable salts of the compounds ((10)-a) and ((10)-b) may include the same ones as exemplified for the compounds (I).

This reaction is carried out by a conventional method such as catalytic reduction, using a reducing agent, and the like.

The method of catalytic reduction and the reaction conditions (e.g. reaction temperature, solvent, etc.) are substantially the same as those illustrated for Process 2, and therefore are to be referred to said explanation.

Further, suitable reducing agent may include borane, diborane, and the like.

Process (11)-(1)

The compound ((11)-b) or a salt thereof can be prepared by reducing the compound ((11)-a).

Suitable salts of the compound ((11)-b) may include the same acid addition salt as exemplified for the compounds (I).

The reduction can be carried out by a conventional method such as chemical reduction, catalytic reduction, and the like.

The method of chemical reduction and catalytic reduction, and the reaction conditions (e.g. reaction temperature, solvent, etc.) are substantially the same as those illustrated for Process 2, and therefore are to be referred to said explanation.

Process (11)-(2)

The compound ((11)-c) can be prepared by introducing an amino-protective group into the compound ((11)-b) or a salt thereof.

The introducing agent of an amino-protective group to be used in this reaction may include a conventional acylating agent such as the corresponding acid to the acyl group as aforementioned or its reactive derivative (e.g. acid halide, acid anhydride, etc.), 2-lower alkoxycarbonyloxyimino-2-phenylacetonitrile (e.g. 2-tert-butoxycarbonyloxyimino-2-phenylacetonitrile, etc.), alkyl ketone substituted by lower alkoxycarbonyl (e.g. lower alkyl acetoacetate, for example, methyl acetoacetate, etc., etc.), and the like.

This reaction is usually carried out in a conventional solvent which does not adversely influence the reaction such as water, methanol, ethanol, propanol, tetrahydrofuran, dioxane, etc., or a mixture thereof.

This reaction is preferably carried out in the presence of a base, and suitable examples thereof are the same as those given in the explanation of Process 1.

The reaction temperature is not critical and the reaction is usually carried out under cooling to warming.

Process (11)-(3)

The compound ((11)-f) or a salt thereof can be prepared by subjecting the compound ((11)-c) to removal reaction of the carboxy-protective group for $R^i$.

Suitable salts of the compound ((11)-f) may include the same salt with a base as exemplified for the compounds (I).

The reaction can be carried out by a conventional method such as hydrolysis, reduction, and the like.

The method of hydrolysis and reduction, and the reaction conditions (e.g. reaction temperature, solvent, etc.) are substantially the same as those illustrated for Process 2, and therefore are to be referred to said explanation.

Additionally, hydrolysis can be carried out in the presence of a base, and suitable examples thereof are the same as those in the explanation of Process 1.

Process (11)-(4)

The compound ((11)-e) or a salt thereof can be prepared by subjecting the compound ((11)-d) or a salt thereof to removal reaction of the carboxy-protective group.

Suitable salts of the compound ((11)-e) may include the same ones as exemplified for the compounds (I), and suitable salts of the compound ((11)-d) may include the same acid addition salt for the same compounds.

The reaction is carried out by a conventional method such as hydrolysis, reduction, and the like.

The method of hydrolysis and reduction, and the reaction conditions (e.g. reaction temperature, solvent, etc.) are substantially the same as those illustrated for the removal reaction of the amino-protective group in Process 2, and therefore are to be referred to said explanation. Additionally, hydrolysis can be carried out in the presence of a base, and suitable examples thereof are the same as those in the explanation of Process 1.

Process (11)-(5)

The compound ((11)-f) or a salt thereof can be prepared by introducing an amino-protective group into the compound ((11)-e) or a salt thereof.

This reaction is substantially the same as Process 11-(2), and therefore, the reaction method and reaction conditions (e.g. reaction temperature, solvent, etc.) are to be referred to said explanation.

Process (11)-(6)

The compound ((11)-f) or a salt thereof can be prepared by introducing an amino-protective group into the compound ((11)-g) or a salt thereof.

Suitable salts of the compound ( ⑪ -g) may include the same ones as exemplified for the compounds (I).

This reaction is carried out by substantially the same method as that of Process ⑪ -(2), and therefore the reaction conditions (e.g. reaction temperature, solvent, base, etc.) are to be referred to said explanation.

Process ⑫ -(1)

The compound ( ⑫ -c) can be prepared by reacting the compound ( ⑫ -a) with the compound ( ⑫ -b) or a reactive derivative thereof.

Suitable reactive derivative of the compound ( ⑫ -b) may include halide such as chloride, bromide, iodide, and the like.

This reaction is preferably carried out in the presence of a base as exemplified in Process 1 and in a conventional solvent such as those exemplified in Process 1.

The reaction temperature is not critical and the reaction is usually carried out from at ambient temperature to under heating.

Process ⑫ -(2)

The compound ( ⑫ -d) can be prepared by reacting the compound ( ⑫ -c) with a halogenating agent.

Suitable halogenating agent may include halogen such as chlorine, bromine, etc.; hypohalogenous acid or its alkyl ester such as hypochlorous acid, tert-butyl hypochlorite, etc., N-haloamide such as N-bromoacetamide, N-iodoacetamide, N-bromosuccinimide, N-chlorosuccinimide, N-chlorophthalimide, etc.; a cuprous halogenide such as cuprous chloride, cuprous bromide, etc.; pyridinium hydrobromide perbromide, dioxane dibromide, etc., sulfuryl chloride, and the like.

The reaction is usually carried out in a conventional solvent which does not adversely influence the reaction, for example, water, methanol, ethanol, alkanoic acid (e.g. acetic acid, etc.), chloroform, methylene chloride, carbon tetrachloride, dioxane, acetonitrile, tetrahydrofuran, dimethylformamide and the like.

The reaction temperature is not critical and the reaction is usually carried out from at ambient temperature to under heating.

In this reaction, in case that the alkanoic acid is used as the solvent, the carboxy-protective group in $R^i$ is frequently removed at the same time.

Process ⑫ -(3)

The compound ( ⑫ -e) or a salt thereof can be prepared by subjecting the compound (⑪ -d) to removal reaction of the carboxy-protective group for $R^i$.

This reaction is substantially the same as Process 2, and therefore, the reaction method, reaction conditions (e.g. reaction temperature, solvent, etc.) are to be referred to said explanation.

Process ⑫ -(4)

The compound ( ⑫ -f) or a salt thereof can be prepared by reacting the compound (⑪ -d) or ( ⑫ -e) or a salt thereof with the compound (V).

This reaction is substantially the same as Process 5, and therefore, the reaction method, reaction conditions (e.g. reaction temperature, solvent, etc.) are to be referred to said explanation.

Process ⑬

The compound ( ⑬ -c) or a salt thereof can be prepared by reacting the compound (⑬ -a) or its reactive derivative at the amino group or a salt thereof with the compound ( ⑬ -b) or its reactive derivative at the carboxy group or a salt thereof.

This reaction is substantially the same as Process 1, and therefore, each of the reactive derivative of the compounds ( ⑬ -a) and ( ⑬ -b) is the same as that of the compounds (II) and (III), respectively, and further the reaction method, the halogenating agent and reaction conditions (e.g. reaction temperature, solvent, etc.) are to be referred to said explanation.

Process ⑭ -(1)

The compound ( ⑭ -b) of a salt thereof can be prepared by reacting the compound ( ⑬ -a) or its reactive derivative at the amino group or a salt thereof with the compound ( ⑭ -a).

Suitable reactive derivative of the compound ( ⑬ -a) may include the same as those exemplified for the compound (II) in Process 1.

This reaction is usually carried out in the presence of a base as exemplified in Process 1 in a conventional solvent which does not adversely influence the reaction such as water, N,N-dimethylformamide, and the like.

The reaction temperature is not critical, and the reaction is usually carried out from under cooling to warming.

Process ⑭ -(2)

The compound ( ⑭ -c) of a salt thereof can be prepared by reacting the compound ( ⑭ -b) or a salt thereof with a halogenating agent.

This reaction is substantially the same as Process ①-(1), and therefore, the reaction method, the halogenating agent and reaction conditions (e.g. reaction temperature, solvent, etc.) are to be referred to said explanation.

Process ⑮

The compound ( ⑮ -b) can be prepared by introducing the carboxy-protective group into the compound ( ⑮ -a) or a salt thereof.

This reaction is substantially the same as Process 2, and therefore, the reaction method, reaction conditions (e.g. reaction temperature, solvent, etc.) are to be referred to said explanation.

The starting compounds thus prepared can be isolated in a conventional manner as mentioned for the object compounds of the present invention.

It is to be noted that, in the aforementioned reactions in Processes 1 to 15 and ① to ⑮ or the post-treatment of the reaction mixture therein, in case that the starting or object compounds possess an optical and/or geometrical isomer(s), it may occasionally be transformed into the other optical and/or geometrical isomer(s), and such cases are also included within the scope of the present invention.

In case that the object compounds (I) have a free carboxy group or free amino group at the 4th or 7th position thereof, it may be transformed into its pharmaceutically acceptable salts by a conventional method.

The object compounds (I) and the pharmaceutically acceptable salts thereof of the present invention are novel and exhibit high antimicrobial activity, inhibiting the growth of a wide variety of pathogenic microorganisms including Gram-positive and Gram-negative microorganisms and are useful as antimicrobial agents, especially for oral administration as shown in the following data.

Now in order to show the utility of the object compounds (I), the test data on the antimicrobial activity of some representative compounds (I) of this invention are shown in the following.

(1) Test 1: In Vitro Antimicrobial Activities

Test Compounds

No. 1—7-[2-(3-Methanesulfonamidophenyl)-D-glycinamido]-3-vinyl-3-cephem-4-carboxylic acid (hereinafter referred to as Compound A)

No. 2—7-[2-(2-Aminothiazol-4-yl)acetamido]-3-vinyl-3-cephem-4-carboxylic acid (hereinafter referred to as Compound B)

No. 3—7-[2-(2-Aminothiazol-4-yl)glycolamido]-3-vinyl-3-cephem-4-carboxylic acid (hereinafter referred to as Compound C)

No. 4—7-[2-(2-Formamidothiazol-5-yl)acetamido]-3-vinyl-3-cephem-4-carboxylic acid (hereinafter referred to as Compound D)

No. 5—7-[2-(2-Aminothiazol-5-yl)glycolamido]-3-vinyl-3-cephem-4-carboxylic acid (hereinafter referred to as Compound E)

No. 6—7-[2-(2-Methanesulfonamidothiazol-5-yl)acetamido]-3-vinyl-3-cephem-4-carboxylic acid (hereinafter referred to as Compound F)

No. 7—7-[2-(2-Guanidinothiazol-4-yl)acetamido]-3-vinyl-3-cephem-4-carboxylic acid hydrobromide (hereinafter referred to as Compound G)

No. 8—7-[2-(2-Aminothiazol-4-yl)acetamido]-3-vinyl-3-cephem-4-carboxylic acid (hereinafter referred to as Compound H)

No. 9—7-[2-(2-Aminothiazol-4-yl)-2-methoxyiminoacetamido]-3-vinyl-3-cephem-4-carboxylic acid (syn isomer) (hereinafter referred to as Compound I)

No. 10—7-[2-(2-Aminothiazol-4-yl)-2-ethoxyiminoacetamido]-3-vinyl-3-cephem-4-carboxylic acid (syn isomer) (hereinafter referred to as Compound J)

No. 11—7-[2-(2-Aminothiazol-4-yl)-2-hexyloxyiminoacetamido]-3-vinyl-3-cephem-4-carboxylic acid (syn isomer) (hereinafter referred to as Compound K)

No. 12—7-[2-(2-Aminothiazol-4-yl)-2-(L-2-amino-2-carboxyethoxycarbonylmethoxyimino)acetamido]-3-vinyl-3-cephem-4-carboxylic acid (syn isomer) (hereinafter referred to as Compound L)

No. 13—7-[2-(2-Aminothiazol-4-yl)-2-carboxymethoxyiminoacetamido]-3-vinyl-3-cephem-4-carboxylic acid (syn isomer) (hereinafter referred to as Compound M)

No. 14—7-[2-(2-Amino-5-chlorothiazol-4-yl)-2-carboxymethoxyiminoacetamido]-3-vinyl-3-cephem-4-carboxylic acid (syn isomer) (hereinafter referred to as Compound N)

No. 15—7-[2-(2-Aminothiazol-4-yl)-2-(trans-3-carboxyallyloxyimino)acetamido]-3-vinyl-3-cephem-4-carboxylic acid (syn isomer) (hereinafter referred to as Compound O)

No. 16—7-[2-(2-Aminothiazol-4-yl)-2-(3-carboxypropoxyimino)acetamido]-3-vinyl-3-cephem-4-carboxylic acid (syn isomer) (hereinafter referred to as Compound P)

Test Method

In vitro Antimicrobial activity was determined by the two-fold agar-plate dilution method as described below.

One loopful of an overnight culture of each test strain in Tripticase-soy broth (approximately $10^8$ viable cells per ml) was streaked on heart infusion agar (HI-agar) containing graded concentrations of antimicrobial agents, and the minimal inhibitory concentration (MIC) was expressed in term of $\mu g/ml$ after incubation at 37° C. for 20 hours.

Test Resuts 1
MIC ($\mu g/ml$)

| Test Compounds | Microorganisms | |
|---|---|---|
| | Staphylococcus aureus 209P JC-1 | Batilus subtilis ATCC 6633 |
| A | 1.56 | 0.10 |
| B | 1.56 | 1.56 |
| C | 1.56 | 0.78 |
| D | 0.39 | 0.20 |
| E | 0.78 | 0.05 |
| F | 1.56 | 0.39 |
| G | 0.39 | 0.10 |
| H | 0.78 | 0.39 |
| J | 1.56 | 0.78 |
| K | 1.56 | 0.78 |

Test Resuts 2
MIC ($\mu g/ml$)

| Test Compounds | Microorganisms | |
|---|---|---|
| | Proteus mirabilis 1 | Proteus mirabilis 18 |
| I | 0.05 | <0.025 |
| L | 0.05 | 0.05 |
| M | <0.025 | <0.025 |
| N | 0.20 | 0.05 |
| O | 0.10 | 0.10 |
| P | 0.10 | 0.05 |

Test Resuts 3
MIC ($\mu g/ml$)

| Test Compounds | Microorganisms Proteus vulgaris 2 |
|---|---|
| N | 0.05 |
| O | <0.025 |
| P | <0.025 |

(2) Test 2: Determination of Serum Levels after Oral Administration of Anti-Microbial Agents in Rats Test Compound Compound A Test Animal 6 weeks old male rats, SD strain, each weighing 160–230 g.

Test Method

The test compound A (100 mg/kg) was given orally to rats which had been fasted overnight. At specified intervals, the rats were anethetized with chloroform and blood samples were collected from the heart. The anti-microbial levels in each serum sample were determined by the disc method using standard solutions prepared with serum from rats.

| Test Results | | | | |
|---|---|---|---|---|
| | Mean Serum Level (µg/ml) | | | |
| Compound | 1 hour | 2 hours | 4 hours | 6 hours |
| A | 38.5 | 34.9 | 31.0 | 28.8 |

(3) Test 3: Protecting Effect in Experimental Mice Infection

Test Compound

Compound A

Test Animal 4-weeks old male mice, ICR strain, each weighing 20.0±1.5 g.

Test Method $1.3 \times 10^4$ cells of pathogenic microorganisms, suspended in 2.5% mucin, were intraperitoneally injected.

One hour after the injection, Compound A was orally given. These mice were observed for survival or death for 4 days, and the $ED_{50}$ values were calculated by the probit method.

Test Results

| Test Results | |
|---|---|
| Injected Pathogenic Microorganisms | $ED_{50}$ value: mg/mouse Compound A |
| *Escherichia coli* 29 | 0.480 |

For therapeutic administration, the object compounds (I) and the pharmaceutically acceptable salts thereof of the present invention are used in the form of conventional pharmaceutical preparation which contains said compound, as active ingredients, in admixture with pharmaceutically acceptable carriers such as an organic or inorganic solid or liquid excipient which is suitable for oral, parenteral and external administration. The pharmaceutical preparations may be in solid form such as tablet, granule, powder, capsule, or liquid form such as solution, suspension, syrup, emulsion, lemonade and the like.

If needed, there may be included in the above preparations auxiliary substances, stabilizing agents, wetting agents and other commonly used additives such as lactose, magnesium stearate, terra alba, sucrose, corn syrup, corn starch, talc, stearic acid, gelatin, agar, pectin, peanut oil, olive oil, cacao butter, ethylene glycol and the like.

While the dosage of the compounds (I) may vary from and also depend upon the age, conditions of the patient, a kind of diseases, a kind of the compounds (I) to be applied, etc. In general, amounts between 1 mg and about 4,000 mg or even more per day may be administered to a patient. An average single dose of about 50 mg, 100 mg, 250 mg, 500 mg, 1000 mg, 2000 mg of the object compounds (I) of the present invention may be used in treating diseases infected by pathogenic microorganisms.

The following examples are given for the purpose of illustrating the present invention.

PREPARATION OF THE STARTING COMPOUNDS

Preparation 1

To a solution of ethyl 2-(2-formamidothiazol-4-yl)-2-methoxyiminoacetate (syn isomer) (19 g) in methanol (200 ml) were added 50% formic acid (200 ml) and zinc (29 g), and the mixture was stirred at 5° to 10° C. for 6 hours. After filtration, the reaction mixture was evaporated, followed by dissolving the residue in water (150 ml). The resultant aqueous solution was adjusted to pH 6.5 with 4N aqueous solution of sodium hydroxide, followed by addition of ethanol (150 ml), 2-tert-butoxycarbonyloxyimino-2-phenylacetonitrile (18.2 g) and triethylamine (8.0 g). After stirring at ambient temperature for 24 hours, the reaction mixture was filtered, followed by removal of the organic solvent. The remained aqueous solution was washed with ethyl acetate, adjusted to pH 4 with 10% hydrochloric acid and then extracted with ethyl acetate. The extract was washed with an aqueous solution of sodium chloride, dried over anhydrous magnesium sulfate and evaporated to dryness under reduced pressure to give a residue, which was washed with diethyl ether to obtain N-tert-butoxycarbonyl-2-(2-formamidothiazol-4-yl)glycine (3.3 g).

IR (Nujol): 3250, 3180, 1720, 1700, 1670, 1640, 1540, 1510 cm$^{-1}$

NMR δppm (DMSO-d$_6$): 1.40 (9H, s), 5.18 (1H, d, J=8 Hz), 7.17 (1H, s), 8.42 (1H, s)

Preparation 2

A mixture of 2-(2-aminothiazol-4-yl)glycine ethyl ester (24.2 g) and 2N aqueous solution of sodium hydroxide (7.2 g) in methanol (240 ml) was stirred at ambient temperature for an hour. After adjusting to pH 7 with conc. hydrochloric acid, water (250 ml), and then 2-tert-butoxycarbonyloxyimino-2-phenylacetonitrile (29.5 g) and triethylamine (18.2 g) were added thereto. After stirring at ambient temperature for an hour, the reaction mixture was evaporated. The resultant aqueous solution was washed twice with ethyl acetate, followed by adding ethyl acetate and adjusting to pH 7 with 10% hydrochloric acid. After removal of the insoluble substance by filtration, the aqueous layer was separated out, adjusted to pH 4 with 10% hydrochloric acid and treated with activated charcoal. To the filtrate was added sodium chloride, followed by stirring under ice-cooling. The precipitated solid was collected by filtration and dried to give N-tert-butoxycarbonyl-2-(2-aminothiazol-4-yl)glycine (10.2 g).

NMR δppm (D$_2$O-NaHCO$_3$): 1.40 (9H, s), 4.90 (1H, s), 6.53 (1H, s)

Preparation 3

To a solution of N-tert-butoxycarbonyl-2-(2-aminothiazol-4-yl)glycine (5.5 g) and bis(trimethylsilyl)acetamide (10.6 g) in ethyl acetate (55 ml) was added trifluoroacetic anhydride (12.6 g) at −20° C., and the mixture was stirred at −15° to −5° C. for an hour. After addition of ethyl acetate (100 ml) and water, the mixture was stirred for a while. To the separated ethyl acetate solution was added water (80 ml), followed by adjusting to pH 7 with a saturated aqueous solution of sodium bicarbonate. After separating out the aqueous layer, thereto was added ethyl acetate, followed by adjusting to pH 2 with 10% hydrochloric acid. The ethyl acetate layer was separated out, washed with an aqueous solution of sodium chloride, dried over anhydrous magnesium sulfate and then evaporated to give N-tert-butoxycarbonyl-2-[2-(2,2,2-trifluoroacetamido)thiazol-4-yl]glycine (3,4 g).

IR (Nujol): 3350, 1720, 1680, 1580, 1520 cm$^{-1}$

NMR δppm (DMSO-d$_6$): 1.40 (9H, s), 5.27 (1H, d, J=8 Hz), 7.27 (1H, s)

Preparation 4

Formic acid (8.4 g) was added to acetic anhydride (18.7 g) under ice-cooling with stirring, and the stirring was continued at 45° to 50° C. for an hour. To the resultant solution was added 2-(2-aminothiazol-5-yl)acetic acid (5.8 g) at ambient temperature, and the mixture was stirred for 35 minutes. After the reaction mixture was evaporated to dryness, the residual product was treated with diisopropyl ether and then collected by filtration to give 2-(2-formamidothiazol-5-yl)acetic acid (5.87 g), mp 229° C. (dec.).

IR (Nujol): 3200, 1670, 1560, 1530 cm$^{-1}$

N.M.R. δppm (DMSO-d$_6$): 3.82 (2H, s), 7.29 (1H, s), 8.47 (1H, s), 12.37 (1H, broad s)

Preparation 5

To a solution of N,N-dimethylformamide ((8.8 g) and tetrahydrofuran (230 ml) was added dropwise phosphorus oxychloride (18.5 g) at −5° to 0° C., and the mixture was stirred for a while. To this solution was added 2-(2-formamidothiazol-4-yl)-2-methoxyiminoacetic acid (syn isomer) (25.2 g) at 3° C., followed by stirring at the same temperature for 40 minutes to prepare the activated acid solution.

On the other hand, a mixture of benzhydryl 7-amino-3-chloromethyl-3-cephem-4-carboxylate hydrochloride (45.1 g) and trimethylsilylacetamide (104.8 g) in ethyl acetate (400 ml) was stirred at ambient temperature for 20 minutes. To the resultant solution was added the activated acid solution prepared before at −40° C. with stirring, and the stirring was continued at −50° to −10° C. for 1.8 hours. After addition of water (200 ml), the organic layer was separated out. The remained aqueous solution was extracted with ethyl acetate, and this extract and the organic layer were combined and washed with a saturated aqueous solution of sodium bicarbonate and an aqueous solution of sodium chloride, followed by drying over anhydrous magnesium sulfate. After concentration, the precipitated substance was collected by filtration to give benzhydryl 7-[2-(2-formamidothiazol-4-yl)-2-methoxyiminoacetamido]-3-chloromethyl-3-cephem-4-carboxylate (syn isomer) (45.2 g). The filtrate was evaporated to dryness and the residue was washed with diethyl ether to recover the same product (7.9 g). Total yield: 53.1 g.

IR (Nujol): 3250, 3160, 3110, 1780, 1720, 1690, 1660, 1630, 1565, 1540 cm$^{-1}$ N.M.R. δppm (DMSO-d$_6$): 3.70 (2H, broad s), 3.93 (3H, s), 4.47 (2H, broad s), 5.30 (1H, d, J=5 Hz), 6.03 (1H, dd, J=5 Hz, 8 Hz), 7.05 (1H, s), 7.17–7.73 (11H, m), 8.62 (1H, s), 9.90 (1H, d, J=8 Hz)

Preparation 6

To a solution of benzhydryl 7-[2-(2-formamidothiazol-4-yl)-2-methoxyiminoacetamido]-3-chloromethyl-3-cephem-4-carboxylate (syn isomer) (25.0 g) in ethyl acetate (300 ml) was added a solution of triphenylphosphine (21.0 g) in tetrahydrofuran (170 ml), and the mixture was heated under reflux for 10 hours. The precipitated substance was collected by filtration to give [7-(2-(2formamidothiazol-4-yl)-2-methoxyiminoacetamido)-4-benzhydryloxycarbonyl-3-cephem-3-yl]methyl-triphenylphosphonium chloride (syn isomer) (17.7 g). The remained filtrate was heated under reflux for 10 hours. Similarly, the precipitated substance was collected by filtration to recover the same product (9.75 g). Further, this operation was repeated once to recover the same product (3.3 g). Total yield: 30.75 g.

I.R. (Nujol): 1780, 1720, 1680, 1590, 1540 cm$^{-1}$

Preparation 7

7-{2-(2-Formamidothiazol-4-yl)-2-methoxyiminoacetamido}-4-benzhydryloxycarbonyl-3-cephem-3-yl]meethyltriphenylphosphonium chloride (syn isomer) (5.33 g) was dissolved in a mixture of acetone (60 ml) and water (10 ml), and the solution was adjusted to pH 11 with 2N aqueous solution of sodium hydroxide, followed by extraction three times with ethyl acetate (100 ml). The extract was washed with an aqueous solution of sodium chloride, dried over anhydrous magnesium sulfate and then evaporated to dryness to give ea residue, which was pulverized with diethyl ether to obtain benzhydryl 7-[2-(2-formamidothiazol-4-yl)-2-methoxyiminoacetamido]-3-triphenylphosphoranylidenemethyl-3-cephem-4-carboxylate (syn isomer) (3.7 g).

I.R. (Nujol): 3300–3170, 1730, 1670, 1580, 1540 cm$^{-1}$

Preparation 8

To a suspension of L-serine (50 g) in water (500 ml) and dioxane (500 ml) were added triethylamine (140 ml) and 2-tert-butoxycarbonyloxyimino-2-phenylacetonitrile (138 g), and the mixture was stirred at ambient temperature for 24 hours. After removal of the dioxane, the remained aqueous solution was adjusted to pH 8.0 with an aqueous sodium bicarbonate and then washed four times with ethyl acetate (200 ml). The aqueous solution was adjusted to pH 2.0 with conc. hydrochloric acid and then extracted twice with ethyl acetate (300 ml). The combined ethyl acetate solution was washed with an aqueous sodium chloride, dried over anhydrous magnesium sulfate and then concentrated under reduced pressure. To the concentrate was added dropwise a solution of diazodiphenylmethane in ethyl acetate till the starting compound was disappeared on thin layer chromatography. Removal of the solvent gave a residue, which was pulverized with diisopropyl ether to obtain N-tert-butoxycarbonyl-L-serine benzhydryl ester (109 g).

I.R. (Nujol): 3250, 1746, 1677 cm$^{-1}$

N.M.R. δppm (DMSO-d$_6$): 1.37 (9H, s), 3.73 (2H, t, J=12.0 Hz), 4.20 (1H, m), 4.93 (1H, t, J=12 Hz), 6.82 (1H, s), 7.40 (10H, broad s)

Preparation 9

A mixture of DL-homoserine (50 g), triethylamine (140 ml), 2-tert-butoxycarbonyloxyimino-2-phenylacetonitrile (103.3 g), water (500 ml) and dioxane (500 ml) was stirred at ambient temperature for 24 hours. After removal of the dioxane, the remained aqueous solution was adjusted to pH 8.5–9.0 with 10% aqueous sodium hydroxide and then washed with ethyl acetate (500 ml×5). The resultant aqueous solution was adjusted to pH 2.0 with conc. hydrochloric acid and then extracted with ethyl acetate, followed by washing with an aqueous sodium chloride and drying over anhydrous magnesium sulfate. To this solution was added dropwise a solution of diazodiphenylmethane in ethyl acetate till the starting compound was disappeared on thin layer chromatography. Removal of the solvent gave a residue, which was pulverized with diisopropyl ether to obtain N-tert-butoxycarbonyl-DL-homoserine benzhydryl ester (117.0 g), mp 125°–129° C.

IR (Nujol): 3500, 3320, 1735, 1687 cm$^{-1}$

NMR δppm (CDCl$_3$): 1.43 (9H, s), 1.8–2.5 (2H, m), 3.6 (2H, m), 4.58 (1H, m), 5.5 (1H, d, J=8 Hz), 6.92 (1H, s), 7.3 (10H, s)

Preparation 10

A solution of 7-(2-phenylacetamido)-3vinyl-3-cephem-4-carboxylic acid (15.3 g), N-tert-butoxycarbonyl L-serine benzhydryl ester (15 g), triphenylphosphine (15.9 g) and diethyl diazenedicarboxylate (10.6 g) in tetrahydrofuran (450 ml) was heated under reflux for 3 hours. The reaction mixture was concentrated under reduced pressure to give a residue, which was dissolved in ethyl acetate (30 ml), and washed with an aqueous sodium bicarbonate and an aqueous sodium chloride, followed by drying over anhydrous magnesium sulfate. Removal of the solvent gave a residue, which was chromatographed on silica gel (400 ml) eluting with methylene chloride, and fractions containing a desired compound were collected. Removal of the solvent gave a residue, which was pulverized with diisopropyl ether to obtain L-2-benzhydryloxycarbonyl-2-tert-butoxycarbonylaminoethyl 7-(2-phenylacetamido)-3-vinyl-3-cephem-4-carboxylate (17.2 g).

IR (Nujol): 3350, 1767, 1735, 1718, 1678, 1653 cm$^{-1}$

NMR δppm (DMSO-d$_6$): 1.40 (9H, s), 3.53, 4.00 (2H, ABq, J=18 Hz), 3.57 (2H, s), 4.55 (3H, m), 5.13 (1H, d, J=5 Hz), 5.35 (1H, d, J=11 Hz), 5.61 (1H, dd, J=5 Hz), 5.68 (1H, d, J=18 Hz), 6.86 (1H, s), 6.92 (1H, dd, J=11 Hz, 18 Hz), 7.37 (5H, s), 7.57 (10H, broad s), 9.20 (1H, d, J=8 Hz)

Preparation 11

A mixture of phosphorus pentachloride (4.5 g), pyridine (1.8 ml) and methylene chloride (50 ml) was stirred at ambient temperature for half an hour. To the resultant suspension was added L-2-benzhydryloxycarbonyl-2-tert-butoxycarbonylaminoethyl 7-(2-phenylacetamido)-3-vinyl-3-cephem-4-carboxylate (10 g) at 5° C., and the mixture was stirred at the same temperature for half an hour. After the reaction mixture was poured into methanol (60 ml) at −30° C., the mixture was stirred at −20° C. for half an hour, followed by addition of water (50 ml), and then adjusting to pH 6.0 with 5% aqueous sodium hydroxide. After evaporation, the residue was extracted with methylene chloride. The extract was washed with an aqueous sodium chloride and then dried over anhydrous magnesium sulfate, followed by treating with an activated charcoal. The filtrate was evaporated under reduced pressure, and thereto was added benzene, followed by azeotropically removing the pyridine by evaporation. The residue was pulverized with a mixed solvent of petroleum ether and diisopropyl ether to obtain L-2-benzhydryloxycarbonyl-2-tert-butoxycarbonylaminoethyl 7-amino-3-vinyl-3-cephem-4-carboxylate (7.5 g).

IR (Nujol): 3350, 1773, 1737, 1709, 1693 cm$^{-1}$

NMR δppm (DMSO-d$_6$): 1.37 (9H, s), 3.47, 3.93 (2H, ABq, J=18 Hz), 4.52 (3H, m), 4.68, 5.02 (2H, ABq, J=5 Hz), 5.30 (1H, d, J=11 Hz), 5.58 (1H, d, J=18 Hz), 6.80 (1H, s), 6.82 (1H, dd, J=11 Hz, 18 Hz), 7.37 (10H, s)

Preparation 12

A suspension of (2-formamidothiazol-5-yl)glyoxylic acid (2.4 g) and methoxylamine hydrochloride (5.0 g) in water (144 ml) was adjusted to pH 4.9–5.0 with a saturated aqueous sodium bicarbonate and the mixture was stirred at ambient temperature for 4.7 hours. After water was added thereto in order to dissolve the insoluble material therein, the aqueous solution was concentrated to a volume of 100 ml. The precipitated material was collected by filtration, washed with water, followed by dissolving in a mixture of tetrahydrofuran and water. This solution was poured into a mixture of ethyl acetate and water, and the organic layer was separated out. After the aqueous solution was extracted with ethyl acetate, the combined ethyl acetate solution was washed with an aqueous sodium chloride and then dried over anhydrous magnesium sulfate. Removal of the solvent gave 2-(2-formamidothiazol-5-yl)-2-methoxyiminoacetic acid (anti isomer) (0.9 g), mp 159° C. (dec.). The filtrate obtained above was further concentrated to a volume of 70 ml, and the precipitated material was collected by filtration to recover the same product (0.23 g). Total yield: 1.13 g.

IR (Nujol): 3180, 1700, 1560, 1460 cm$^{-1}$

NMR δppm (DMSO-d$_6$): 4.14 (3H, s), 8.30 (1H, s), 8.57 (1H, s)

Further, to the filtrate was added ethyl acetate, and the mixture was adjusted to pH 1.5 with 10% hydrochloric acid, followed by separating out the ethyl acetate layer. After the remained aqueous solution was extracted with ethyl acetate, the combined ethyl acetate solution was washed with an aqueous sodium chloride and then dried over anhydrous magnesium sulfate. Removal of the solvent gave 2-(2-formamidothiazol-5-yl)-2-methoxyiminoacetic acid (syn isomer) (0.87 g), mp 183° C. (dec).

IR (Nujol): 1720, 1650, 1535, 1465 cm$^{-1}$

NMR δppm (DMSO-d$_6$): 3.92 (3H, s), 7.58 (1H, s), 8.57 (1H, s)

Preparation 13

To a solution of bromoacetyl bromide (20 g) in tetrahydrofuran (200 ml) were added N-tert-butoxycarbonyl-L-serine benzhydryl ester (10.84 g) and N,N-dimethylaniline (6.8 ml), and the mixture was stirred at 20° to 23° C. for 80 minutes. After adjusting to pH 5.0 with 10% aqueous sodium hydroxide and 5% aqueous sodium bicarbonate, the tetrahydrofuran was removed by evaporation. The residue was dissolved in a mixture of ethyl acetate (200 ml) and water (100 ml), and then washed with 5% hydrochloric acid and an aqueous sodium chloride, followed by drying over anhydrous magnesium sulfate. Removal of the solvent gave a residue, which was pulverized with diisopropyl ether to obtain L-2-benzhydryloxycarbonyl-2-tert-butoxycarbonylaminoethyl 2-bromoacetate (21.3 g), mp 92°–94° C.

IR (Nujol): 3350, 1735, 1727, 1704, 1160 cm$^{-1}$

NMR δppm (DMSO-d$_6$): 1.40 (9H, s), 4.03 (2H, s), 4.67 (3H, m), 6.85 (1H, s), 7.37 (10H, s)

Preparation 14

A mixture of L-2-benzhydryloxycarbonyl-2-tert-butoxycarbonylaminoethyl 2-bromoacetate (20 g), N-hydroxyphthalimide (6.7 g), triethylamine (8.5 ml) and N,N-dimethylformamide (80 ml) was stirred at 10° to 15° C. for half an hour. The reaction mixture was poured into 5% aqueous sodium chloride (1.5 l), and the precipitated material was collected by filtration and then washed with water, followed by dissolving in ethyl acetate (300 ml). The solution was washed twice with an aqueous sodium chloride and dried over anhydrous magnesium sulfate, followed by evaporation to give a residue, which was pulverized with diisopropyl ether to obtain L-2-benzhydryloxycarbonyl-2-tert-butoxycarbonylaminoethyl 2-phthalimidooxyacetate (24.5 g), mp 45°-50° C.

IR (Nujol): 3420, 1740, 1720 (shoulder) cm$^{-1}$

NMR δppm (DMSO—d$_6$): 1.38 (9H, s), 4.55 (3H, broad s), 4.89 (2H, broad s), 6.93 (1H, s), 7.47 (10H, broad s), 8.00 (4H, s)

Preparation 15

To a solution of N-hydroxyphthalimide (4.3 g), N-tert-butoxycarbonyl-DL-homoserine benzhydryl ester (10 g) and triphenylphosphine in tetrahydrofuran (100 ml) was added dropwise a diethyl diazenedicarboxylate (4.6 g) at ambient temperature with stirring, and the stirring was continued at 32° to 35° C. for 3 hours. Removal of the solvent gave a residue, which was chromatographed on silica gel eluting with a mixed solvent of benzene and acetone. Fractions containing a desired compound were collected and then evaporated to obtain benzhydryl DL-2-tert-butoxycarbonylamino-4-phthalimidooxybutyrate (10 g), mp 162°-163° C.

IR (Nujol): 3360, 1740, 1722, 1681 cm$^{-1}$

NMR δppm (CDCl$_3$): 1.45 (9H, s), 2.37 (2H, q, J=6 Hz), 4.26 (2H, t, J=6 Hz), 4.58 (1H, m), 5.73 (1H, d, J=8 Hz), 6.90 (1H, s), 7.3 (10H, s), 7.77 (4H, s)

Preparation 16

To a solution of L-2-benzhydryloxycarbonyl-2-tert-butoxycarbonylaminoethyl 2-phthalimidooxyacetate (20 g) in methylene chloride (100 ml) was added a solution of hydrazine monohydrate (3.5 g) in methanol under ice-cooling, and the mixture was stirred below 15° C. for an hour. The precipitated material was collected by filtration and washed with methylene chloride. The washings and the above obtained methylene chloride solution were combined, adjusted to pH 7.0 with 5% hydrochloric acid, and washed with an aqueous sodium chloride, followed by drying over anhydrous magnesium sulfate. Removal of the solvent gave a residue, which was chromatographed on silica gel (200 ml) eluting with a mixed solvent of benzene and ethyl acetate, and fractions containing a desired compound were collected. Removal of the solvent gave a residue, which was pulverized with diisopropyl ether to obtain L-2-benzhydryloxycarbonyl-2-tert-butoxycarbonylaminoethyl 2-aminooxyacetate (10.5 g), mp 90°-92° C.

IR (Nujol): 3400, 1745, 1720 cm$^{-1}$

NMR δppm (DMSO—d$_6$): 1.38 (9H, s), 4.10 (2H, s), 4.45 (3H, broad s), 6.30 (2H, s), 6.84 (1H, s), 7.37 (10H, s)

Preparation 17

A solution of benzhydryl DL-2-tert-butoxycarbonylamino-4-phthalimidooxybutyrate (7.0 g) in methylene chloride (100 ml) was added dropwise to a solution of hydrazine monohydrate (2.0 g) in methanol (6 ml) at ambient temperature, and the mixture was stirred for half an hour. The precipitated material was collected by filtration and then washed with methylene chloride (30 ml). After the filtrate and washings were combined, thereto was added water, followed by adjusting to pH 7.0 with conc. hydrochloric acid. The separated methylene chloride solution was washed with water and an aqueous sodium chloride, followed by drying over anhydrous magnesium sulfate. Removal of the solvent gave a residue which was pulverized with diisopropyl ether to obtain benzhydryl DL-2-tert-butoxycarbonylamino-4-aminooxybutyrate (5.0 g), mp 92°-93° C.

IR (Nujol): 3340, 3305, 1730, 1695 cm$^{-1}$

NMR δppm (DMSO—d$_6$): 1.38 (9H, s), 1.95 (2H, m), 3.58 (2H, t, J=6 Hz), 4.18 (1H, m), 5.92 (2H, s), 6.82 (1H, s), 7.37 (10H, s)

Preparation 18

To a suspension of (2-formamidothiazol-4-yl)-glyoxylic acid (3.6 g) in pyridine (3.7 ml) and water (33 ml) was added a solution of L-2-benzhydryloxycarbonyl-2-tert-butoxycarbonylaminoethyl 2-aminooxyacetate (10.5 g) in tetrahydrofuran (30 ml), and the mixture was stirred at ambient temperature for 5 hours. Water was added to the reaction mixture, followed by adjusting to pH 1.6 with conc. hydrochloric acid. After extraction with ethyl acetate, the extract was washed with an aqueous sodium chloride, and then dried over anhydrous magnesium sulfate. Removal of the solvent gave a residue, which was pulverized with diisopropyl ether to obtain 2-(2-formamidothiazol-4-yl)-2-(L-2-benzhydryloxycarbonyl-2-tert-butoxycarbonylaminoethoxycarbonylmethoxyimino)acetic acid (syn isomer) (11.7 g), mp 110°-113° C.

IR (Nujol): 3330, 3180, 1756 (shoulder), 1743, 1715, 1703 cm$^{-1}$

NMR δppm (DMSO—d$_6$): 1.38 (9H, s), 4.47 (3H, broad s), 4.70 (2H, broad s), 6.85 (1H, s), 7.40 (10H, broad s), 7.55 (1H, s), 8.55 (1H, s), 12.70 (1H, broad s)

Preparation 19

To a suspension of 2-(2-formamidothiazol-4-yl)-glyoxylic acid (3.40 g) in pyridine (3.6 ml) and water (32 ml) was added a solution of benzhydryl DL-2-tert-butoxycarbonylamino-4-aminooxybutyrate (7.0 g) in tetrahydrofuran (30 ml) at ambient temperature, and the mixture was stirred for 3 hours. The reaction mixture was poured into ethyl acetate (200 ml), and the separated ethyl acetate layer was washed with dilute hydrochloric acid and an aqueous sodium chloride, followed by drying over anhydrous magnesium sulfate. Removal of the solvent gave a 2-(2-formamidothiazol-4-yl)-2-(DL-3-benzhydryloxycarbonyl-3-tert-butoxycarbonylaminopropoxyimino)acetic acid (syn isomer) (9.0 g), mp 61°-65° C.

IR (Nujol): 3150, 1740, 1695 cm$^{-1}$

NMR δppm (DMSO—d$_6$): 1.4 (9H, s), 2.1 (2H, m), 4.2 (3H, m), 6.82 (1H, s), 7.33 (10H, s), 7.53 (1H, s), 8.53 (1H, s)

Preparation 20

Vilsmeir reagent, which was prepared from N,N-dimethylformamide (0.48 g) and phosphorus oxychloride (1.0 g), was suspended in ethyl acetate (20 ml), and thereto was added 4-bromo-2-methoxyiminoacetoacetic acid (syn isomer) (1.34 g) under ice-cooling, followed by stirring at the same temperature for half an hour to prepare the activated acid solution. This solution was added to a solution of benzhydryl 7-amino-3-vinyl-3-cephem-4-carboxylate hydrochloride (2.15 g) and trimethylsilylacetamide (3.93 g) in ethyl acetate (30 ml) at −20° C., and the mixture was stirred at −20° to 0° C. for 1.5 hours. To the reaction mixture were added ethyl acetate (100 ml) and water (100 ml), and the separated ethyl acetate solution was washed with a saturated aqueous sodium bicarbonate and an aqueous sodium chloride, followed by drying over anhydrous magnesium sulfate. Removal of the solvent gave a residue, which was washed with diethyl ether to obtain benzhydryl 7-(4-bromo-2-methoxyiminoacetoacetamido)-3-vinyl-3-cephem-4-carboxylate (syn isomer) (2.5 g).

IR (Nujol): 3280, 1770, 1710, 1700, 1660, 1600, 1560 cm$^{-1}$

NMR δppm (DMSO—d$_6$): 3.78 (2H, q, J=18 Hz), 4.07 (3H, s), 4.63 (2H, s), 5.27 (1H, d, J=5 Hz), 5.30 (1H, d, J=11 Hz), 5.63 (1H, d, J=17 Hz), 5.93 (1H, dd, J=5 Hz, 8 Hz), 6.78 (1H, dd, J=11 Hz, 17 Hz), 6.98 (1H, s), 7.17–7.67 (10H, m), 9.57 (1H, d, J=8 Hz)

Preparation 21

To a solution of benzhydryl 7-amino-3-vinyl-3-cephem-4-carboxylate hydrochloride (6.4 g) and trimethylsilylacetamide (9.8 g) in ethyl acetate (80 ml) was added 4-bromo-3,3-diethoxy-2-methoxyiminobutyryl chloride (syn isomer) (5.0 g) at −20° C. with stirring, and the stirring was continued at −20° to −5° C. for an hour. To the reaction mixture were added ethyl acetate and water, and the separated ethyl acetate solution was washed with a saturated aqueous sodium bicarbonate and an aqueous sodium chloride, followed by drying over anhydrous magnesium sulfate. Removal of the solvent gave benzhydryl 7-(4-bromo-3,3-diethoxy-2-methoxyiminobutyramido)-3-vinyl-3-cephem-4-carboxylate (syn isomer) (10.1 g).

IR (Nujol): 1780, 1720, 1610, 1510 cm$^{-1}$

NMR δppm (DMSO—d$_6$): 1.13 (3H, t, J=7 Hz), 3.60 (2H, q, J=7 Hz), 3.76 (2H, m), 3.83 (3H, s), 5.22 (1H, d, J=5 Hz), 5.24 (1H, d, J=11 Hz), 5.60 (1H, d, J=17 Hz), 5.82 (1H, dd, J=5 Hz, 8 Hz), 6.70 (1H, dd, J=11 Hz), 17 Hz), 6.93 (1H, s), 7.17–7.60 (10H, m), 9.00 (1H, d, J=8 Hz)

Preparation 22

To a solution of benzhydryl 7-(4-bromo-3,3-diethoxy-2-methoxyiminobutyramido)-3-vinyl-3-cephem-4-carboxylate (syn isomer) (6.5 g) in methylene chloride (60 ml) was added conc. hydrochloric acid (6 ml) at 3° to 5° C., and the mixture was stirred from under ice-cooling to at ambient temperature for 8 hours. After methylene chloride (100 ml) was added to the reaction mixture, it was washed with water and then dried over anhydrous magnesium sulfate. Removal of the solvent gave a residue, which was washed with diethyl ether to obtain benzhydryl 7-(4-bromo-2-methoxyiminoacetoacetamido)-3-vinyl-3-cephem-4-carboxylate (syn isomer) (3.5 g).

IR (Nujol): 3280, 1770, 1710, 1700, 1660, 1600, 1560 cm$^{-1}$

NMR δppm (DMSO—d$_6$): 3.78 (2H, q, J=18 Hz), 4.07 (3H, s), 4.63 (2H, s), 5.27 (1H, d, J=5 Hz), 5.30 (1H, d, J=11 Hz), 5.63 (1H, d, J=17 Hz), 5.93 (1H, dd, J=5 Hz), 8 Hz), 6.78 (1H, dd, J=11 Hz, 17 Hz), 6.98 (1H, s), 7.17–7.67 (10H, m), 9.57 (1H, d, J=8 Hz)

Preparation 23

To a solution of benzhydryl 7-(4-bromo-3,3-diethoxy-2-methoxyiminobutyramido)-3-vinyl-3-cephem-4-carboxylate (syn isomer) (3.36 g) and anisole (2.1 g) in methylene chloride (20 ml) was added trifluoroacetic acid (8.0 g) under ice-cooling with stirring, and the stirring was continued at ambient temperature for an hour. After removal of the solvent, the residue was dissolved in a mixture of ethyl acetate and water. To the separated ethyl acetate solution was added water, followed by adjusting to pH 7 with a saturated aqueous sodium bicarbonate. To the separated aqueous solution was added ethyl acetate, followed by adjusting to pH 2 with 10% hydrochloric acid. The ethyl acetate layer was separated out, washed with an aqueous sodium chloride and then dried over anhydrous magnesium sulfate. Removal of the solvent gave 7-(4-bromo-2-methoxyiminoacetoacetamido)-3-vinyl-3-cephem-4-carboxylate acid (syn isomer) (1.6 g).

IR (Nujol): 3300–3200, 1780, 1700, 1675 (shoulder), 1540 cm$^{-1}$

Preparation 24

To a suspension of hydroxylamine hydrochloride (22.3 g) in ethanol (25 ml) was added a phenolphthalein indicator (0.3 ml), and thereto was added dropwise a solution of potassium hydroxide (23.1 g) in ethanol (185 ml) little by little until dark red color of the mixture changed into pale red, followed by stirring for an hour. After removal of the potassium chloride by filtration, to the filtrate was added ethyl 2-cyano-2-methoxyiminoacetate (50 g), followed by stirring at 20° to 30° C. for 3 days. Removal of the solvent gave ethyl 3-amino-3-hydroxyimino-2-methoxyiminopropionate, which was dissolved in dioxane (200 ml) and then evaporated. The residue was dissolved in dioxane (130 ml), and thereto were added pyridine (75.8 g) and then trichloroacetyl chloride (87.3 g) under ice-cooling below 10° C., followed by stirring at the same temperature for an hour and allowing to stand overnight. After removal of the insoluble materials by filtration, the filtrate was evaporated to dryness. To the residue were added diethyl ether and water, and the separated organic solution was washed with dilute hydrochloric acid and an aqueous solution of sodium chloride, followed by drying over anhydrous magnesium sulfate. Removal of the solvent gave an oil, which was chromatographed on silica gel eluting with a mixed solvent of benzene and n-hexane (3:1 by volume), and fractions containing a desired compound were collected. Removal of the solvent gave ethyl 2-(5-trichloromethyl-1,2,4-oxadiazol-3-yl)-2-methoxyiminoacetate (anti isomer) (22.6 g).

IR (Film): 1730, 1600, 1565 cm$^{-1}$

NMR δppm (CDCl$_3$): 1.37 (3H, t, J=7 Hz), 4.22 (3H, s), 4.42 (2H, q, J=7 Hz)

Preparation 25

To a solution of ethyl 2-(5-trichloromethyl-1,2,4-oxadiazol-3-yl)-2-methoxyiminoacetate (anti isomer) (9 g) in dioxane (90 ml) was added conc. hydrochloric acid (3.5 ml), and the mixture was heated under reflux for 50 minutes. After removal of the solvent, the residue was dissolved in ethyl acetate, washed with an aqueous sodium chloride, and then dried over anhydrous magnesium sulfate. Removal of the solvent gave a residue, which was chromatographed on silica gel eluting with a mixed solvent of benzene and n-hexane (1:1 by volume). Fractions containing a desired compound were collected and evaporated to obtain ethyl 2-(5-trichloromethyl-1,2,4-oxadiazol-3-yl)-2-methoxyiminoacetate (syn isomer) (3.7 g). The starting compound (1.7 g) was recovered from the subsequent fractions.

IR (Film): 1740, 1600, 1570, 1495 cm$^{-1}$

NMR δppm (CDCl$_3$): 1.38 (3H, t, J=7 Hz), 4.17 (3H, s), 4.45 (2H, q, J=7 Hz)

Preparation 26

To ethyl 2-(5-trichloromethyl-1,2,4-oxadiazol-3-yl)-2-methoxyiminoacetate (syn isomer) (3.4 g) was added liquid ammonia (17 ml). After giving homogenous solution, it was poured into a petri dish, followed by removing liquid ammonia by ventilation. To the residue were added water and ethyl acetate, and the separated ethyl acetate solution was washed with an aqueous sodium chloride and dried over anhydrous magnesium sulfate. Removal of the solvent gave a residue, which was washed with diisopropyl ether to obtain ethyl 2-(5-trichloromethyl-1,2,4-oxadiazol-3-yl)-2-methoxyiminoacetate (syn isomer) (1.75 g). mp 143°–146° C.

IR (Nujol): 3440, 3310, 3240, 3180, 1720, 1660, 1600, 1505 cm$^{-1}$

NMR $\delta$ppm DMSO—$d_6$: 1.25 (3H, t, J=7 Hz), 4.00 (3H, s), 4.32 (2H, q, J=7 Hz), 8.17 (2H, s)

Preparation 27

Ethyl 2-(5-amino-1,2,4-oxadiazol-3-yl)-2-methoxyiminoacetate (syn isomer) (2.5 g) was added to 1N aqueous sodium hydroxide (14 ml), and the solution was stirred at ambient temperature for an hour. The reaction mixture was adjusted to pH 1.8 with 10% hydrochloric acid, salted out with sodium chloride, and then extracted with a mixture of ethyl acetate and tetrahydrofuran. After drying over anhydrous magnesium sulfate, the extract was evaporated to dryness to give a residue, which was washed with diisopropyl ether to obtain 2-(5-amino-1,2,4-oxadiazol-3-yl)-2-methoxyiminoacetate acid (syn isomer) (2.0 g).

IR (Nujol): 3420, 3330, 3250, 3180, 1720, 1665, 1600, 1500 cm$^{-1}$

NMR $\delta$ppm (DMSO—$d_6$): 4.00 (3H, s), 8.15 (2H, s)

Preparation 28

N-(2-Pyridylmethoxy)phthalimide (50 g) was suspended in ethanol (500 ml), and thereto was added hydrazine monohydrate (20.8 g) at 60° C., followed by stirring at the same temperature for an hour. To the reaction mixture was added conc. hydrochloric acid (60 ml) dissolved in water (450 ml) under cooling, and the precipitated materials were removed by filtration. The ethanol was removed by evaporation from the filtrate, and the precipitated materials therein were further removed by filtration. The filtrate was added ethanol (500 ml) and then adjusted to pH 7.0 with 4N aqueous sodium hydroxide. Thereto was added (2-formamidothiazol-4-yl)glyoxylic acid (30.3 g), followed by adjusting to pH 4.5 with 10% hydrochloric acid and stirring for 1.5 hours. During the stirring, the pH value of the mixture was kept at 4 to 4.5 with 4N aqueous sodium hydroxide. After the reaction mixture was adjusted to pH 7.5 with 4N aqueous sodium hydroxide, the ethanol was removed by evaporation. The resultant aqueous solution was adjusted to pH 3.0 with 10% hydrochloric acid, and the precipitated crystals were collected by filtration to obtain 2-(2-formamidothiazol-4-yl)-2-(2-pyridylmethoxyimino)acetic acid (syn isomer) (35.4 g).

IR (Nujol): 3100, 1680, 1610, 1560, 1540 cm$^{-1}$

NMR $\delta$ppm (NaHCO$_3$—D$_2$O): 5.3 (2H, s), 7.47 (1H, s), 7.17–8.07 (3H, m), 8.47 (1H, s), 8.33–8.67 (1H, m)

Preparation 29

2-(2-Formamidothiazol-4-yl)-2-(3-pyridylmethoxyimino)acetic acid (syn isomer) (8.0 g) was obtained by reacting (2-formamidothiazol-4-yl)glyoxylic acid (8.8 g) with 3-pyridylmethoxyamine, which was prepared from N-(3-pyridylmethoxy)phthalimide (14.5 g) and hydrazine monohydrate (6.3 g), according to a similar manner to that of Preparation 28.

IR (Nujol): 3400, 3050, 1670, 1550 cm$^{-1}$

NMR $\delta$ppm (NaHCO$_3$-D$_2$O): 5.28 (2H, s), 7.44 (1H, s), 7.24–7.50 (1H, m), 7.82 (1H, m), 8.46 (1H, s), 8.14–8.66 (2H, m)

Preparation 30

2-(2-Formamidothiazol-4-yl)-2-(4-pyridylmethoxyimino)acetic acid (syn isomer) (10.5 g) was obtained by reacting (2-formamidothiazol-4-yl)glyoxylic acid (10.3 g) with 4-pyridylmethoxyamine, which was prepared from N-(4-pyridylmethoxy)phthalimide (17.0 g) and hydrazine monohydrate (6.0 g), according to a similar manner to that of Preparation 28.

IR (Nujol): 3500, 1650, 1560, 1500 cm$^{-1}$

NMR $\delta$ppm (NaHCO$_3$-D$_2$O): 5.22 (2H, s), 7.38 (1H, s), 7.27–7.47 (2H, m), 8.42 (1H, s), 8.33–8.55 (2H, m)

Preparation 31

To a solution of sodium 7-(5-amino-5-carboxypentamido)-3-hydroxymethyl-3-cephem-4-carboxylate (118.6 g) in water (1000 ml) and acetone (600 ml) was added dropwise benzoyl chloride (42.1 g) under ice-cooling with stirring at 10° C. while the reaction mixture was continually adjusted to pH 6.5 to 7.5 with 20% aqueous sodium carbonate. After the stirring was continued at the same temperature for an hour, the reaction mixture was adjusted to pH 6.0 with conc. hydrochloric acid, followed by removing the acetone and washing with ethyl acetate (500 ml). To this aqueous solution was added ethyl acetate (300 ml), and thereto was added a solution of diphenyldiazomethane in ethyl acetate till the starting compound was disappeared on a thin layer chromatography, followed by adjusting to pH 3.0 with conc. hydrochloric acid. The ethyl acetate layer was separated, washed with an aqueous sodium chloride and then dried over magnesium sulfate, followed by evaporation under reduced pressure. After the residue was dissolved in acetone (400 ml), the solution was added dropwise to diisopropyl ether (4000 ml). The precipitated crystals were collected by filtration and then dried to obtain benzhydryl 7-(5-benzamido-5-benzhydryloxycarbonylpentanamido)-3-hydroxymethyl-3-cephem-4-carboxylate (224.8 g), mp 100°–110° C.

IR (Nujol): 3270, 1770, 1730, 1660, 1640 cm$^{-1}$

NMR $\delta$ppm (DMSO—$d_6$): 1.3–2.7 (6H, m), 3.38 (1H, s), 3.63 (2H, m), 4.27 (2H, d, J=5 Hz), 4.67 (1H, m), 5.15 (1H, d, J=5 Hz), 5.77 (1H, dd, J=5 Hz, 8 Hz), 6.87 (1H, s), 6.95 (1H, s), 7.43 (25H, m), 7.97 (1H, m), 8.87 (1H, m)

Preparation 32

To a solution of benzhydryl 7-(5-benzamido-5-benzhydryloxycarbonylpentanamido)-3-hydroxymethyl-3-cephem-4-carboxylate (100 g) in methylene chloride (600 ml) was added at a time phosphorus pentachloride (25.6 g) at −30° C., followed by adding dropwise pyridine (9.8 g) at the same temperature. After the reaction mixture was stirred at −20° C. for an hour, it was poured into a mixture of methylene chloride (500 ml) and water (300 ml). The separated organic layer was washed with an aqueous sodium chloride, dried over magnesium sulfate and then evaporated to dryness to obtain benzhydryl 7-(5-benzamido-5-benzhydryloxycarbonylpentanamido)-3-chloromethyl-3-cephem-4-carboxylate (114.5 g), mp 90°–110° C. (dec.).

IR (Nujol): 1780, 1725, 1640 cm$^{-1}$

NMR δppm (DMSO—d₆): 1.3–2.5 (6H, m), 3.67 (2H, m), 4.43 (2H, m), 4.67 (1H, m), 5.22 (1H, d, J=5 Hz), 5.83 (1H, m), 6.83 (1H, s), 7.00 (1H, s), 7.4 (25H, m), 7.92 (1H, m), 8.90 (1H, m)

Preparation 33

To a solution of benzhydryl 7-(5-benzamido-5-benzhydryloxycarbonylpentanamido)-3-chloromethyl-3-cephem-4-carboxylate (102 g) in N,N-dimethylformamide (150 ml) were added triphenylphosphine (48.5 g) and sodium iodide (18.4 g), and the mixture was stirred at ambient temperature for 1.5 hours. The reaction mixture was added dropwise to isopropyl alcohol (5000 ml), and the precipitated material was collected by filtration and washed with diisopropyl ether to obtain [7-(5-benzamido-5-benzhydryloxycarbonylpentanamido)-4-benzhydryloxycarbonyl-3-cephem-3-yl]methyl-triphenylphosphonium iodide (123.5 g), mp 165°–175° C. (dec.).

IR (Nujol): 1780, 1730, 1710, 1650 cm⁻¹

NMR δppm (DMSO—d₆): 1.3–2.6 (6H, m), 4.33 (2H, m), 4.67 (2H, m), 5.13 (1H, m), 5.33 (1H, d, J=5 Hz), 5.75 (1H, m), 6.33 (1H, s), 6.83 (1H, s), 7.0–8.3 (41H, m), 8.92 (1H, m)

Preparation 34

To a solution of [7-(5-benzamido-5-benzhydryloxycarbonylpentanamido)-4-benzhydryloxycarbonyl-3-cephem-3-yl)methyltriphenyl-phosphonium iodide (123.5 g) in methylene chloride (1000 ml) was added 36% aqueous formaldehyde (300 ml), followed by adjusting to pH 9.0 with 20% aqueous sodium bicarbonate. After the mixture was stirred at 25° C. for 2 hours, it was adjusted to pH 5.0 with conc. hydrochloric acid. The separated organic solution was concentrated, and to the concentrate was added ethyl acetate. The precipitated crystals were collected by filtration and then dried to obtain 7-(5-benzamido-5-benzhydryloxycarbonylpentanamido)-3-vinyl-3-cephem-4-carboxylate (63.5 g), mp 180°–184° C. (dec.).

IR (Nujol): 3300, 1770, 1730, 1710, 1650 cm⁻¹

NMR δppm (DMSO—d₆): 1.3–2.6 (6H, m), 3.72 (2H, m), 4.67 (2H, m), 5.1–5.6 (2H, m), 5.7–5.9 (21H, m), 6.83 (1H, dd, J=12 Hz, 18 Hz), 6.86 (1H, s), 7.0 (1H, s), 7.42 (25H, m), 7.98 (1H, m), 8.92 (1H, m)

Preparation 35

To a suspension of phosphorus pentachloride (15.5 g) in methylene chloride (200 ml) was added dropwise pyridine (5.9 g) at 5° to 10° C. with stirring, and the stirring was continued at 5° C. for 20 minutes. Thereto was added at a time benzhydryl 7-(5-benzamido-5-benzhydryloxycarbonylpentanamido)-3-vinyl-3-cephem-4-carboxylate (20 g) at 5° C., and the mixture was stirred at the same temperature for 2 hours. To the reaction mixture was added gradually methanol (120 ml) at −40° C., followed by stirring at −20° to −10° C. for an hour. Removal of the solvent gave a residue, to which ethyl acetate (300 ml) and water (50 ml) were added. The mixture was stirred under ice-cooling for a while, and the precipitated crystals were collected by filtration and then washed with isopropyl alcohol to obtain benzhydryl 7-amino-3-vinyl-3-cephem-4-carboxylate hydrochloride (8.4 g), mp 180°–195° C. (dec.).

IR (Nujol): 1760, 1705, 1580 cm⁻¹

NMR δppm (DMSO—d₆): 3.88 (2H, q, J=18 Hz), 5.1–5.4 (2H, m), 5.58 (1H, d, J=6 Hz), 5.93 (1H, m), 6.97 (1H, s), 7.0 (1H, dd, J=12 Hz, 18 Hz), 7.42 (10H, m), 9.17 (2H, m)

Preparation 36

To a suspension of benzhydryl 7-amino-3-vinyl-3-cephem-4-carboxylate hydrochloride (48 g) in methanol (250 ml) and anisole (70 ml) was added p-toluenesulfonic acid (85 g), and the mixture was stirred at 50° C. for 2 hours. The reaction mixture was poured into 10% aqueous sodium carbonate (600 ml) and ethyl acetate (700 ml), followed by adjusting to pH 7.5 with 20% aqueous sodium carbonate. The separated aqueous solution was washed with ethyl acetate (500 ml) and then adjusted to pH 2.5 with conc. hydrochloric acid, followed by stirring under ice-cooling for an hour. The precipitated crystals were collected by filtration and washed with acetone to obtain 7-amino-3-vinyl-3-cephem-4-carboxylic acid (15.4 g), mp 200° to 230° C. (dec.).

IR (Nujol): 1800, 1605 cm⁻¹

NMR δppm (D₂O—NaHCO₃): 3.67 (2H, s), 4.8–5.8 (5H, m), 6.88 (1H, dd, J=12 Hz, 18 Hz)

Preparation 37

To a suspension of phosphorus pentachloride (27.0 g) in methylene chloride (200 ml) was added dropwise pyridine (10.3 g) at 0° C., followed by stirring at 5° C. for 20 minutes. Thereto was added at a time benzhydryl 7-(5-benzamido-5-benzhydryloxycarbonylpentanamido)-3-hydroxymethyl-3-cephem-4-carboxylate (21.0 g) at −40° C., followed by stirring at −30° C. for an hour and at −10° C. for addition an hour. To the reaction mixture was added at a time at −40° C. methanol (100 ml), which was pre-cooled to −40° C., followed by stirring at −10° C. for an hour. Removal of the solvent gave a residue, to which methylene chloride (100 ml), water (30 ml) and diisopropyl ether (100 ml) were added in turn, and the mixture was stirred under ice-cooling for a while. The precipitated crystals were collected by filtration and suspended in ethyl acetate (300 ml), followed by adjusting to pH 8.0 with an aqueous sodium bicarbonate. The separated organic solution was washed with an aqueous sodium chloride and then dried over magnesium sulfate. Removal of the solvent gave benzhydryl 7-amino-3-chloromethyl-3-cephem-4-carboxylate (2.8 g), mp 135°–140° C. (dec.).

IR (Nujol): 3400, 1760, 1725, 1650 cm⁻¹

NMR δppm (DMSO—d₆): 3.60 (2H, q, J=17 Hz), 4.38 (2H, s), 4.85 (1H, d, J=5 Hz), 5.05 (1H, d, J=5 Hz), 6.95 (1H, s), 7.4 (10H, m), 8.8 (2H, m)

Preparation 38

To a solution of benzhydryl 7-amino-3-chloromethyl-3-cephem-4-carboxylate (8.0 g) in N,N-dimethylformamide (40 ml) were added molecular sieve (10 g) and benzaldehyde (2.1 g), followed by stirring at 40° C. for 40 minutes. Thereto were added sodium iodide (2.9 g) and triphenylphosphine (10.1 g), followed by stirring at 40° C. for an hour. The reaction mixture was added dropwise to a mixture of diisopropyl ether (200 ml) and ethyl acetate (100 ml), and the precipitated crystals were collected by filtration and then dried to obtain [4-benzhydryloxycarbonyl-7-benzylideneamino-3-cephem-3-yl]methyl-triphenyl-phosphonium iodide (16.9 g), mp 150°–158° C. (dec.).

IR (Nujol): 1780, 1705, 1635 cm⁻¹

NMR δppm (DMSO—d₆): 3.67 (2H, m), 5.2 (2H, m), 5.58 (1H, d, J=5 Hz), 5.82 (1H, d, J=5 Hz), 6.30 (1H, s), 7.2–8.3 (30H, m), 8.70 (1H, s)

Preparation 39

To a solution of [4-benzhydryloxycarbonyl-7-benzylidene-amino-3-cephem-3-yl]methyl-triphenylphosphonium iodide (16.9 g) in methylene chloride (200 ml) and water (100 ml) was added 36% aqueous formaldehyde (48 ml), followed by adjusting to pH 9.0 with sodium carbonate. After the mixture was stirred at ambient temperature for an hour, the separated organic solution was washed with an aqueous sodium chloride and then dried over magnesium sulfate. Removal of the solvent gave benzhydryl 7-benzylidene-amino-3-vinyl-3-cephem-4-carboxylate (8.6 g), mp 124°–132° C.

IR (Nujol): 1770, 1710, 1630 cm$^{-1}$

NMR δppm (DMSO—d$_6$): 3.75 (2H, q, J=18 Hz), 5.1–5.8 (4H, m), 6.75 (1H, dd, J=10 Hz, 18 Hz), 6.93 (1H, s), 7.1–8.0 (15H, m), 8.58 (1H, s)

Preparation 40

To a suspension of benzhydryl 7-benzylideneamino-3-vinyl-3-cephem-4-carboxylate (8.6 g) in anisole (10 ml) was added dropwise trifluoroacetic acid (10 ml) at −20° C., and the reaction temperature was gradually raised to ambient temperature with stirring, followed by stirring at ambient temperature for half an hour. The reaction mixture was poured into a mixture of ethyl acetate (100 ml) and a saturated aqueous sodium bicarbonate (100 ml), and then the mixture was adjusted to pH 7.5 with 20% aqueous sodium carbonate. The separated aqueous solution was washed with ethyl acetate (100 ml) and adjusted to pH 7.2 with conc. hydrochloric acid, followed by subjecting to column chromatography on alumina (10 ml). Elution was carried out with 15% aqueous sodium chloride, and fractions containing a desired compound were collected and then adjusted to pH 3.3 with conc. hydrochloric acid. The precipitated crystals were collected by filtration, washed with acetone and dried to obtain 7-amino-3-vinyl-3-cephem-4-carboxylate acid (2.0 g), mp 200°–230° C. (dec.).

IR (Nujol): 1800, 1605 cm$^{-1}$

NMR δppm (D$_2$O—NaHCO$_3$): 3.67 (2H, s), 4.8–5.8 (5H, m), 6.88 (1H, dd, J=12 Hz, 18 Hz)

Preparation 41

To a solution of N-hydroxyphthalimide (70.08 g) in acetonitrile (300 ml) were added triethylamine (48 g) and tert-butyl-4-bromocrotonate (96.0 g) with stirring, and the mixture was refluxed under heating for 1.5 hours. The reaction mixture was poured into water (600 ml), followed by extraction with ethyl acetate. The extract was washed with a saturated aqueous sodium chloride, dried over magnesium sulfate and then evaporated to dryness under reduced pressure to give a residue, which was pulverized with n-hexane. The resultant substance was subjected to column chromatography on silica gel eluting with a mixed solvent of n-hexane, ethyl acetate and diisopropyl ether (5:0.5:4.5 by volume), and the fractions containing a desired compound were collected. Removal of the solvent gave a residue, which was pulverized with n-hexane and collected by filtration to obtain tert-butyl 4-phthalimidooxycrotonate (41.7 g).

NMR δppm (DMSO—d$_6$): 1.45 (9H, s), 4.90 (2H, m), 6.09 (1H, m), 6.66–7.19 (1H, m), 7.86 (4H, s)

Preparation 42

To a solution of tert-butyl 4-phthalimidooxycrotonate (20.0 g) in methylene chloride (140 ml) was added a solution of hydrazine monohydrate (5.0 g) in methanol (10 ml) with stirring, and the stirring was continued at ambient temperature for 15 minutes. The insoluble substance was collected by filtration and washed with methylene chloride. The washings and the filtrate were combined and then extracted three times with 5% hydrochloric acid. After the combined extracts were washed with diethyl ether, thereto was added methylene chloride, followed by adjusting to pH 7.5 with 28% aqueous ammonium hydroxide. The separated methylene chloride solution was washed with a saturated aqueous sodium chloride and then dried over magnesium sulfate. Removal of the solvent gave an oil of tert-butyl 4-aminooxycrotonate (11.03 g).

IR (Film): 3340, 3250, 2980, 2940, 1720, 1660 cm$^{-1}$

NMR δppm (DMSO—d$_6$): 1.43 (9H, s), 4.18 (2H, m), 5.85 (1H, m), 6.14 (2H, broad s), 6.52–7.06 (1H, m)

Preparation 43

To tert-butyl 4-aminooxycrotonate (10.0 g) were added ethanol (150 ml) and water (150 ml), followed by gradually adding (2-formamidothiazol-4-yl)glyoxylic acid (110 g) with stirring. During the addition, the mixture was adjusted to pH 5 to 5.5 with 10% aqueous sodium hydroxide, and the stirring was continued at ambient temperature for 2 hours. After removal of the ethanol, to the remaining aqueous solution was added ethyl acetate, followed by adjusting to pH 7.5 with 10% aqueous sodium hydroxide. The aqueous layer was separated and washed with ethyl acetate. Thereto was further added ethyl acetate, followed by adjusting to pH 2.0 with 10% hydrochloric acid. The separated organic layer was washed with a saturated aqueous sodium chloride and then dried over magnesium sulfate. Removal of the solvent gave a residue, which was pulverized with n-hexane and tetrahydrofuran, and collected by filtration. To this substance were added ethanol (50 ml) and water (30 ml), followed by adjusting to pH 7.5 with 10% aqueous sodium hydroxide. The precipitated substance was collected by filtration, washed with a mixed solvent of water and ethanol (1:1 by volume), followed by addition of water and ethyl acetate, and adjusting to pH 2.0 with 10% hydrochloric acid. The organic layer was separated, washed with a saturated aqueous sodium chloride and then dried over magnesium sulfate. Removal of the solvent gave a residue, which was pulverized with n-hexane and tetrahydrofuran to obtain 2-(trans-3-tert-butoxycarbonylallyloxyimino)-2-(2-formamidothiazol-4-yl)acetic acid (syn isomer) (12.01 g).

IR (Nujol): 3150, 1720, 1650 cm$^{-1}$

NMR δppm (DMSO—d$_6$): 1.47 (9H, s), 4.89 (2H, m), 5.96 (1H, m), 6.69–7.16 (1H, m), 7.60 (1H, s), 8.57 (1H, s), 12.72 (1H, broad s)

Preparation 44

To a solution of 2-(trans-3-tert-butoxycarbonylallyloxyimino)-2-(2-formamidothiazol-4-yl)acetic acid (syn isomer) (8.0 g) in ethyl acetate (60 ml) and ethanol (60 ml) was added 10% palladium on carbon (4.0 g) moistened in water (3 ml) in a stream of nitrogen atmosphere, followed by subjecting to catalytic reduction under atmospheric pressure for 4 hours. After the catalyst was removed by filtration, the filtrate was evaporated. To the residue were added water and ethyl acetate, followed by adjusting to pH 7.5 with a saturated aqueous sodium bicarbonate. The separated aqueous layer was washed with ethyl acetate, and thereto was added ethyl acetate, followed by adjusting to pH 2.0 with 10% hydrochloric acid. The separated organic layer was washed with a saturated aqueous sodium chloride and then dried over magnesium sulfate. Removal of the solvent gave a residue, which was crystallized from n-hexane and collected by filtration to obtain 2-(3-tert-butoxycarbonylpropoxyimino)-2-(2-formamidothiazol-4yl)acetic acid (syn isomer) (1.80 g).

NMR δppm (DMSO—d$_6$): 1.44 (9H, s), 1.03 (2H, m), 2.33 (2H, t, J=6.0 Hz), 4.20 (2H, t, J=6.0 Hz), 7.61 (1H, s), 8.61 (1H, s), 12.63 (1H, broad s)

Preparation 45

Ethyl (2-formamido-5-chlorothiazol-4-yl)glyoxylate (14.5 g) was added to a solution of 1N aqueous potassium hydroxide (110 ml) at ambient temperature, and the mixture was stirred for 10 minutes to prepare the solution of potassium (2-formamido-5-chlorothiazol-4-yl) glyoxylate. After this solution was adjusted to pH 2 with 10% hydrochloric acid under ice-cooling, thereto were added pyridine (20 ml) and a solution of tert-butyl 2-aminooxyacetate (10.3 g) in tetrahydrofuran (50 ml), followed by stirring at ambient temperature for 5 hours. After the reaction mixture was washed with ethyl acetate, the remaining aqueous solution was adjusted to pH 1.5 with 10% hydrochloric acid and extracted with ethyl acetate. The extract was washed with an aqueous sodium chloride and then dried over magnesium sulfate. Removal of the solvent gave 2-tert-butoxycarbonylmethoxyimino-2-(2-formamido-5-chlorothiazol-4yl)acetic acid (syn isomer) (8.5 g).

IR (Nujol): 3150, 1725, 1690, 1650, 1560, 1530 cm$^{-1}$
NMR δppm (DMSO—d$_6$); 1.47 (9H, s), 4.75 (2H, s), 8.7 (1H, s), 12.8 (1H, s)

Preparation 46

1N Aqueous sodium hydroxide (49 ml) was added to a suspension of S-methyl (6-formamidopyridin-2-yl)thioglyoxylate (10 g) in methanol (100 ml), and the mixture was stirred at ambient temperature for 50 minutes to prepare the solution of sodium (6-formamidopyridin-2-yl)glyoxylate. To this solution was added tert-butyl 2-aminooxyacetate (7.2 g) and the mixture was adjusted to pH 3 to 4 with 6N hydrochloric acid, followed by stirring at ambient temperature for 4 hours. The reaction mixture was neutralized with an aqueous sodium bicarbonate and concentrated to half of the original volume under reduced pressure, followed by washing with ethyl acetate and adjusting to pH 1.5 with 10% hydrochloric acid.

The resultant aqueous solution was extracted three times with ethyl acetate, and the combined extracts were washed with a saturated aqueous sodium chloride and dried over magnesium sulfate. Removal of the solvent gave 2-tert-butoxycarbonylmethoxyimino-2-(6-formamidopyridin-2-yl)acetic acid (syn isomer) (11.9 g), mp 162°-168° C.

IR (Nujol): 3180, 1741, 1673 cm$^{-1}$
NMR δppm (DMSO—d$_6$): 1.47 (9H, s), 4.73 (2H, s), 7.3–8.3 (3H, m), 9.17 (1H, broad s), 10.7 (1H, d, J=6 Hz)

Preparation 47

2-(5-Amino-1,2,4-thiadiazol-3-yl)-2-tert-butoxycarbonylmethoxyiminoacetic acid (syn isomer), mp 150°-155° C. (dec.), was obtained by reacting S-methyl (5-formamido-1,2,4-thiadiazol-3-yl)thioglyoxylate with aqueous sodium hydroxide and then tert-butyl 2-aminooxyacetate according to a similar manner to that of Preparation 46.

IR (Nujol): 3420, 3230, 3100, 1725, 1610, 1530 cm$^{-1}$
NMR δppm (DMSO—d$_6$): 1.45 (9H, s), 4.70 (2H, s), 8.12 (2H, broad s)

Preparation 48

To an aqueous solution (27 ml) of sodium hydroxide (2.1 g) were added ethyl 2-(5-tritylamino-2H-tetrazol-2-yl)acetate (14.2 g), methanol (50 ml) and tetrahydrofuran (100 ml), and the mixture was stirred at 40° C. for 2 hours. After the organic solvent was removed by evaporation, to the residue were added water (50 ml) and ethyl acetate (50 ml), followed by separating out the aqueous layer. Thereto was added ethyl acetate (100 ml) and then adjusted to pH 1.5 with 10% hydrochloric acid. The aqueous solution was washed with an aqueous sodium chloride (50 ml) and dried over magnesium sulfate. Removal of the solvent gave a residue, which was pulverized with diisopropyl ether to obtain 2-(5-tritylamino-2H, tetrazol-2-yl)acetic acid (9.0 g).

IR (Nujol): 3350, 1860, 1730, 1570, 1530 cm$^{-1}$
NMR δppm (DMSO—d$_6$): 5.15 (2H, s), 7.0–7.58 (15 H, m), 7.83 (1H, s)

Preparation 49

Vilsmeier reagent was prepared from phosphorus oxychloride (14.8 g) and N,N-dimethylformamide (7.07 g) in ethyl acetate (50 ml) in a conventional manner. 2-(tert-Butoxycarbonylmethoxyimino)-2-(formamidothiazol-4-yl)acetic acid (syn isomer) (29 g) was added to the stirred suspension of Vilsmeier reagent in ethyl acetate (250 ml) under ice-cooling and stirred for 30 minutes at same temperature to prepare an activated acid solution. On the other hand, benzhydryl 7-amino-3-chloromethyl-3-cephem-4-carboxylate monohydrochloride (36.1 g) was dissolved in a solution of trimethylsilylacetamide (63 g) in ethyl acetate (400 ml). To this solution was added the above activated acid solution at −12° C. and the mixture was stirred for an hour at −20° to 0° C. Water was added to the reaction mixture at 0° C. The organic layer was separated, washed with a saturated aqueous sodium bicarbonate and an aqueous sodium chloride. The solution was dried over magnesium sulfate and evaporated under reduced pressure. The residue was pulverized with diethyl ether to give benzhydryl 7-[(2-tert-butoxycarbonylmethoxyimino-2-(2-formamidothiazol-4-yl)acetamido]3-chloromethyl-3-cephem-4-carboxylate (syn isomer) (49.7 g).

IR (Nujol): 3200, 1780, 1720, 1680, 1540 cm$^{-1}$
NMR δppm (DMSO—d$_6$): 1.42 (9H, s), 3.66 (2H, q, J=18 Hz), 4.43 (2H, s), 4.64 (2H, s), 5.27 (1H, d, J=5 Hz), 5.98 (1H, d d, J=5 Hz, 8 Hz), 6.96 (1H, s), 7.00–7.60 (11H, m), 8.50 (1H, s), 9.64 (1H, d, J=8 Hz), 12.58 (1H, broad s)

Preparation 50

Sodium iodide (4.5 g) was added to a solution of benzhydryl 7-[2-tert-butoxycarbonylmethoxyimino-2-(2-formamidothiazol-4-yl)acetamido]-3-chloromethyl-3-cephem-4-carboxylate (7.6 g) in acetone (70 ml) and the mixture was stirred for 2.5 hours at ambient temperature. The reaction mixture was poured into a mixture of ethyl acetate (200 ml) and an aqueous sodium chloride (100 ml), and the organic layer was separated out, washed with 10% aqueous sodium thiosulfate and an aqueous sodium chloride. The solution was dried over magnesium sulfate and evaporated to give a residue. This residue and triphenylphosphine (5.2 g) were dissolved in ethyl acetate (100 ml) and stirred for an hour. The precipitates were collected by filtration, washed with ethyl acetate and dried to give [4-benzhydryloxycarbonyl-{7-(2-tert-butoxycarbonylmethoxyimino)-2-(2-formamidothiazol-4-yl)acetamido}-3-cephem-3-ylmethyl]-triphenyl-phosphonium iodide (6.5 g).

IR (Nujol): 1788, 1710, 1680, 1530 cm$^{-1}$

Preparation 51

2-(4-Aminopyrimidin-2-yl)-2-tert-butoxycarbonylmethoxyiminoacetic acid (syn isomer) (9.7 g) was obtained by reacting S-methyl (4-formamidopyrimidin-2-yl)thioglyoxylate (20.0 g) with 1N aqueous sodium hydroxide (80 ml) and then tert-butyl 2-aminooxyacetate (15 g) according to a similar manner to that of Preparation 46.

IR (Nujol): 3200, 1750, 1718, 1693 cm$^{-1}$

Preparation 52

A solution of ethyl 3-amino-3-thioxopropionate (73.5 g) in diethyl ether (100 ml) was added to a solution of bromopiruvic acid (88.5 g) in diethyl ether (300 ml) and stirred for 15 hours at ambient temperature. The precipitates were collected by filtration and added to a mixture of water (500 ml) and diethyl ether (300 ml) and then adjusted to pH 7.5 with 20% aqueous sodium carbonate. The separated aqueous solution was adjusted to pH 1.0 with conc. hydrochloric acid and extracted with diethyl ether. The diethyl ether layer was dried over magnesium sulfate and evaporated. The residue was washed with diisopropyl ether to give ethyl 2-(4-carboxythiazol-2-yl)acetate (57.1 g).

IR (Nujol): 3100, 2870–2400, 1730, 1670 cm$^{-1}$
NMR δppm (DMSO—d6): 1.28 (3H, t, J=7 Hz), 4.23 (2H, q, J=7 Hz), 4.30 (2H, s), 8.50 (1H, s)

Preparation 53

Triethylamine (10.1 g) was added to a solution of ethyl 2-(4-carboxythiazol-2-yl)acetate (21.5 g) in tert-butanol (200 ml) and diphenylphosphorous azide (27.5 g) and the mixture was refluxed and stirred for 2 hours. After removing the solvent from the reaction mixture, the residue was dissolved in ethyl acetate (500 ml). The ethyl acetate was washed with water, a saturated aqueous sodium bicarbonate and an aqueous sodium chloride, and then dried over magnesium sulfate. The solvent was removed by evaporation, and the residue was washed with diisopropyl ether and collected by filtration to give ethyl 2-(4-tert-butoxycarbonylaminothiazol-2-yl)acetate (19.1 g).

IR (Nujol): 3180, 1730, 1710, 1530 cm$^{-1}$
NMR δppm (DMSO—d6): 1.23 (3H, t, J=7 Hz), 1.50 (9H, s), 4.07 (2H, s), 4.15 (2H, q, J=7 Hz), 7.15 (1H, s), 10.00 (1H, s)

Preparation 54

Ethyl 2-(4-tert-butoxycarbonylaminothiazol-2-yl)acetate (5.1 g) was added to a solution of selenium dioxide (2.96 g) in dioxane (60 ml) and water (2 ml) at 110° C. and stirred for 4.5 hours at 110° C. The mixture was evaporated and the residue was dissolved in ethyl acetate and water. The separated ethyl acetate layer was washed with an aqueous sodium chloride and dried over magnesium sulfate. After removing the solvent, the residue was subjected to column chromatography on silica gel and eluted with methylene chloride. The fraction containing an object compound was evaporated to give ethyl (4-tert-butoxycarbonylaminothiazol-2-yl)glyoxylate (4.2 g).

IR (Film): 3250, 3150, 1720, 1680 cm$^{-1}$
NMR δppm (CDCl$_3$): 1.42 (3H, t, J=7 Hz), 1.52 (9H, s), 4.44 (2H, q, J=7 Hz), 7.89 (1H, s), 8.28 (1H, s)

Preparation 55

A solution of sodium hydroxide (2.05 g) in water (30 was added to a solution of ethyl (4-tert-butoxycarbonylaminothiazol-2-yl)glyoxylate (7.7 g) in methanol (20 ml) and stirred for 1 hour at ambient temperature. The mixture was adjusted to pH 7.0 with 10% hydrochloric acid and washed with diethyl ether. The separated aqueous layer was adjusted to pH 2.0 with 10% hydrochloric acid and extracted with diethyl ether. The diethyl ether layer was washed with an aqueous sodium chloride and dried over magnesium sulfate. The solvent was removed by evaporation, and the resultant (4-tert-butoxycarbonylaminothiazol-2-yl)glyoxylic acid was dissolved in methanol (20 ml). On the other hand, a solution of 1N-sodium methylate in methanol (25 ml) was added to a solution of methoxylamine hydrochloride (2.35 g) in methanol (20 ml) and phenolphtharain indicator (2–3 drops), and stirred for 30 minutes. The insoluble material was filtered off, and the filtrate was added to the above solution and stirred for 2 hours at ambient temperature. The diisopropyl ether was added to the reaction mixture and the precipitates were collected by filtration to give 2-methoxyimino-2-(4-tert-butoxycarbonylaminothiazol-2-yl)acetic acid (syn isomer) (3.6 g).

IR (Nujol): 3250, 3150, 1730, 1640, 1630 cm$^{-1}$
NMR δppm (DMSO—d6): 1.45 (9H, s), 7.37 (1H, s), 10.33 (1H, s)

Preparation 56

To a suspension of tert-butyl 2-hydroxyimino-3-oxobutyrate (56.4 g) and potassium carbonate (62.4 g) in ethyl acetate (300 ml) and N,N-dimethylformamide (60 ml) was added benzyl chloroacetate (60 g), and the mixture was stirred at 40° C. for 7 hours. The reaction mixture was poured into ice-water (1000 ml), and the separated organic layer was washed twice with a saturated aqueous solution of sodium chloride and then dried over magnesium sulfate. Removal of the solvent gave tert-butyl 2-benzyloxycarbonylmethoxyimino-3-oxobutyrate (96.3 g) as an oil.

IR (Film): 2980, 1740, 1695, 1610 cm$^{-1}$
NMR δppm (CDCl$_3$): 1.50 (9H, s), 2.28 (3H, s), 4.78 (2H, s), 5.18 (2H, s), 7.28 (5H, s)

Preparation 57

Ethyl 2-(2,2,2-trichloroethoxycarbonylmethoxyimino)-3-oxobutyrate (66.7 g) was prepared by reacting ethyl 2-hydroxyimino-3-oxobutyrate (45.2 g) with 2,2,2-trichloroethyl chloroacetate (31.4 g) in the presence of potassium carbonate (41.5 g) according to a similar manner of that of Preparation 56.

IR (Film): 1750 (broad), 1610 cm$^{-1}$
NMR δppm (CDCl$_3$): 1.33 (3H, t, J=7 Hz), 2.37 (3H, s), 4.37 (2H, q, J=7 Hz), 4.83 (2H, s), 4.93 (2H, s)

Preparation 58

To a solution of tert-butyl 2-benzyloxycarbonylmethoxyimino-3-oxobutyrate (32.3 g) in acetic acid (32 ml) was slowly added bromine (16 g) at 45° to 48° C. with stirring, and the stirring was continued at the same temperature for 30 minutes. After the reaction mixture was concentrated under reduced pressure, the residue was dissolved in ethyl acetate, followed by washing six times with a saturated aqueous sodium chloride. The solution was evaporated under reduced pressure to give 2-benzyloxycarbonylmethoxyimino-4-bromo-3-oxobutyric acid (35. g).

IR (Nujol): 2950, 1740 (broad), 1602 cm$^{-1}$

NMR δppm (CDCl$_3$): 4.02 (2H, s), 4.82 (2H, s) 5.16 (2H, s), 7.32 (5H, s)

Preparation 59

2-Benzyloxycarbonylmethoxyimino-4-chloro-3-oxobutyric acid (3.8 g) was prepared by reacting tert-butyl 2-benzyloxycarbonylmethoxyimino-3-oxobutyrate (5.0 g) with sulfuryl chloride (1.25 ml) in acetic acid (5 ml) according to a similar manner to that of Preparation 58.

IR (Film): 3200, 1730 (broad), 1610 cm$^{-1}$

NMR δppm (CDCl$_3$): 4.03 (2H, s), 4.83 (2H, s), 5.23 (2H, s), 7.33 (5H, s)

Preparation 60

To a solution of tert-butyl 2-benzyloxycarbonylmethoxyimino-3-oxobutyrate (2.0 g) in dry tetrahydrofuran (20 ml) were added boron trifluoride diethyl etherate (3.0 ml) and pyridinium hydrobromide perbromide (3.0 g) at ambient temperature, followed by stirring for 6 hours. The reaction mixture was poured into water (50 ml) and then extracted twice with ethyl acetate (70 ml). The combined extracts were washed with 10% hydrochloric acid and then a saturated aqueous sodium chloride, followed by drying over magnesium sulfate. Removal of the solvent gave 2-benzyloxycarbonylmethoxyimino-4-bromo-3-oxobutyric acid (2.0 g).

IR (Nujol): 2950, 1740 (broad), 1602 cm$^{-1}$

Preparation 61

A mixture of ethyl 2-(2,2,2-trichloroethoxycarbonylmethoxyimino)-3-oxobutyrate (20 g) and sulfuryl chloride (7.7 g) in acetic acid (20 ml) was stirred at 40° C. for 7 hours. After the reaction mixture was added to a mixture of water (100 ml) and methylene chloride (100 ml) with stirring, the separated organic layer was washed with 5% aqueous sodium bicarbonate and water, followed by drying over magnesium sulfate. Removal of the solvent gave ethyl 2-(2,2,2-trichloroethoxycarbonylmethoxyimino)-4-chloro-3-oxobutyrate (22 g).

IR (Film): 1750 (broad), 1610 cm$^{-1}$

NMR δppm (CCl$_4$): 1.36 (3H, t, J=7 Hz), 4.32 (2H, q, J=7 Hz), 4.46 (2H, s), 4.79 (2H, s), 4.90 (2H, s)

Preparation 62

Vilsmeir reagent prepared from N,N-dimethylformamide (0.67 ml) and phosphorus oxychloride (0.79 ml) was suspended in dry tetrahydrofuran (25 ml). Thereto was added 2-benzyloxycarbonylmethoxyimino-4-bromo-3-oxobutyric acid (2.8 g) at 0° C. with stirring, and the stirring was continued at 0° to 5° C. for an hour to prepare the activated acid solution. This activated acid solution was added at a time to a solution of benzhydryl 7-amino-3-vinyl-3-cephem-4-carboxylate hydrochloride (2.2 g) and trimethylsilylacetamide (7.0 g) in methylene chloride (30 ml) at −35° C., and the mixture was stirred at −10° to −5° C. for 30 minutes. The reaction mixture was poured into ethyl acetate (200 ml), and the separated organic solution was washed with a saturated aqueous sodium bicarbonate and a saturated aqueous sodium chloride, followed by drying over magnesium sulfate. Removal of the solvent gave benzhydryl 7-(2-benzyloxycarbonylmethoxyimino-4-bromo-3-oxobutyramido)-3-vinyl-3-cephem-4-carboxylate (2.8 g).

IR (Nujol): 3270, 1773, 1715, 1660 cm$^{-1}$

NMR δppm (DMSO—d$_6$): 3.56, 3.96 (2H, ABq, J=18 Hz), 4.57 (2H, s), 5.03 (2H, s), 5.23 (2H, s), 5.30 (1H, d, J=5 Hz), 5.55 (1H, d, J=18 Hz), 5.61 (1H, d, J=11 Hz), 5.90 (1H, dd, J=5, 8 Hz), 6.83 (1H, dd, J=11, 18 Hz), 7.0 (1H, s), 7.4 (10H, m), 9.6 (1H, d, J=8 Hz)

Preparation 63

A mixture of ethyl 2-(2,2,2-trichloroethoxycarbonylmethoxyimino)-4-chloro-3-oxobutyrate (20 g), thiourea (3.9 g) and sodium acetate (4.2 g) in ethanol (50 ml) and water (50 ml) was stirred at 40° C. for 5 hours. After removal of the solvent from the reaction mixture, the residue was triturated with diisopropyl ether. The precipitates were collected by filtration and washed with diisopropyl ether to give ethyl 2-(2-aminothiazol-4-yl)-2-(2,2,2-trichloroethoxycarbonylmethoxyimino)acetate (syn isomer) (10.6 g), mp 138°–141° C.

IR (Nujol): 3400, 1750, 1710, 1620, 1540 cm$^{-1}$

NMR δppm (DMSO—d$_6$): 1.27 (3H, t, J=7 Hz), 4.32 (2H, q, J=7 Hz), 4.93 (2H, s), 4.97 (2H, s), 6.93 (1H, s), 7.27 (2H, broad s)

Preparation 64

A solution of hydrazine hydrate (8.0 g) in methanol (16 ml) was added to a suspension of benzyl 2-phthalimidoxyacetate (46.0 g) in tetrahydrofuran (150 ml), and the mixture was stirred at ambient temperature for 30 minutes. To the reaction mixture was added 20% hydrochloric acid under ice-cooling, followed by stirring at the same temperature for 10 minutes. The insoluble substance was filtered off to give a solution containing benzyl 2-aminooxyacetate. To this solution were added (2-formamidothiazol-4-yl)glyoxylic acid (24.7 g) and pyridine (24.8 ml), and the mixture was stirred at ambient temperature for 3 hours. The reaction mixture was adjusted to pH 7.5 with 10% aqueous sodium hydroxide and then washed with ethyl acetate. The resultant aqueous solution was acidified to pH 2.0 with 10% hydrochloric acid, followed by extraction with ethyl acetate. The extract was washed with an aqueous sodium chloride and then dried over magnesium sulfate. The solution was evaporated and the residue was pulverized with diisopropyl ether to give 2-benzyloxycarbonylmethoxyimino-2-(2-formamidothiazol-4-yl)acetic acid (syn isomer) (37 g), mp 152° C. (dec.).

IR (Nujol): 3350, 1730, 1700 cm$^{-1}$

NMR δppm (DMSO—d$_6$): 4.87 (2H, s), 5.20 (2H, s), 7.30 (5H, s), 7.52 (1H, s), 8.53 (1H, s), 12.57 (1H, broad s)

Preparation 65

Vilsmeier reagent was prepared from phosphorus oxychloride (8.4 g) and N,N-dimethylformamide (4.0 g) in a usual manner. 2-tert-Butoxycarbonylmethoxyimino-2-(2-formamidothiazol-4-yl)acetic acid (syn isomer) (16.5 g) was added to a stirred suspension of the Vilsmeier reagent obtained above in tetrahydrofuran (100 ml) under ice-cooling, and the mixture was stirred at the same temperature for 30 minutes to prepare the activated acid solution.

On the other hand, 7-amino-3-hydroxymethyl-3-cephem-4-carboxylic acid (11.5 g) was dissolved in a solution of sodium bicarbonate (8.4 g) in water (50 ml) and acetone (50 ml). To this solution was added dropwise the activated acid solution obtained above at 3° to 8° C. while keeping the pH value of the mixture to 7–8 with 20% aqueous sodium carbonate, and the mixture was stirred at the same temperature for an hour. The reaction mixture was adjusted to pH 6.0 with 10% hydrochloric acid and then washed with ethyl acetate to give an aqueous solution containing 7-[2-tert-butoxycarbonylmethoxyimino-2-(2-formamidothiazol-4-yl)acetamido]-3-hydroxymethyl-3-cephem-4-carboxylic acid (syn isomer). To this aqueous solution was added a solution of diphenyldiazomethane in ethyl acetate (1 mmol/ml) (100 ml), and the mixture was acidified to pH 2.5 with 10% hydrochloric acid. After stirring at ambient temperature for 2 hours, the solution was extracted with a mixture of ethyl acetate and tetrahydrofuran (1:1). The extract was washed with a saturated aqueous sodium bicarbonate and an aqueous sodium chloride, followed by drying over magnesium sulfate. The solution was evaporated and the residue was pulverized with diethyl ether to give benzhydryl 7-[2-tert-butoxycarbonylmethoxyimino-2-(2-formamidothiazol-4-yl)acetamido]-3-hydroxymethyl-3-cephem-4-carboxylate (syn isomer) (18.5 g).

IR (Nujol): 3200, 1785, 1720, 1680 cm$^{-1}$

NMR δppm (DMSO—$d_6$): 1.47 (9H, s), 3.68 (2H, s), 4.35 (2H, d, J=5 Hz), 4.7 (2H, s), 5.27 (1H, d, J=5 Hz), 5.97 (1H, dd, J=5, 8 Hz), 6.97 (1H, s), 7.2–7.77 (11H, m), 8.58 (1H, s), 9.67 (1H, d, J=8 Hz), 12.70 (1H, s)

Preparation 66

Pyridine (0.45 g) was added to a solution of benzhydryl 7-[2-tert-butoxycarbonylmethoxyimino)-2-(2-formamidothiazol-4-yl)acetamido]-3-hydroxymethyl-3-cephem-4-carboxylate (syn isomer) (2.1 g) and phosphorus pentachloride (1.1 g) in methylene chloride (20 ml) at −20° C., and the mixture was stirred at −20° to −5° C. for 2 hours. The reaction mixture was washed with 10% hydrochloric acid and an aqueous sodium chloride, followed by drying over magnesium sulfate. The solution was evaporated to give benzhydryl 7-[2-tert-butoxycarbonylmethoxyimino)-2-(2-formamidothiazol-4-yl)acetamido]-3-chloromethyl-3-cephem-4-carboxylate (syn isomer) (2.1 g).

IR (Nujol): 3200, 1780, 1720, 1680, 1540 cm$^{-1}$

NMR δppm (DMSO—$d_6$): 1.42 (9H, s), 3.66 (2H, q, J=18 Hz), 4.43 (2H, s), 4.64 (2H, s), 5.27 (1H, d, J=5 Hz), 5.98 (1H, dd, J=5, 8 Hz), 6.96 (1H, s), 7.00–7.60 (11H, m), 8.50 (1H, s), 9.64 (1H, d, J=8 Hz), 12.58 (1H, broad s)

Preparation 67

7-Amino-3-hydroxymethyl-3-cephem-4-carboxylic acid (9.21 g) was suspended in water (200 ml) and neutralized to pH 7.5 with dicyclohexylamine (7 g). To the resultant solution was added dropwise salicylaldehyde (5.42 g). After stirring at ambient temperature for 2 hours, the precipitates were collected by filtration and dried to give 7-salicylideneamino-3-hydroxymethyl-3-cephem-4-carboxylic acid dicyclohexylamine salt (17.4 g).

IR (Nujol): 3300, 1780, 1640, 1560 cm$^{-1}$

NMR δppm (DMSO—$d_6$): 0.9–2.2 (22H, m), 3.5(2H, broad s), 4.2 (2H, m), 5.15 (1H, d, J=5 Hz), 5.5 (1H, d, J=5 Hz), 6.8–7.8 (4H, m), 8.8 (1H, s)

Preparation 68

7-Benzylideneamino-3-hydroxymethyl-3-cephem-4-carboxylic acid dicyclohexylamine salt (15 g) was obtained by reacting 7-amino-3-hydroxymethyl-3-cephem-4-carboxylic acid (10 g) with benzaldehyde (4.2 g) and dicyclohexylamine (7.25 g) in water (200 ml) according to a similar manner to that of Preparation 67.

IR (Nujol): 3300, 1780, 1650, 1560 cm$^{-1}$

NMR δppm (DMSO—$d_6$): 0.9–2.2 (22H, m), 3.5 (2H, broad s), 4.15 (2H, ABq, J=14 Hz), 5.15 (1H, d, J=5 Hz), 5.5 (1H, d, J=5 Hz), 7.3–8.1 (5H, m), 8.55 (1H, s)

Preparation 69

To a suspension of 7-salicylideneamino-3-hydroxymethyl-3-cephem-4-carboxylic acid dicyclohexylamine salt (3 g) in ethyl acetate (60 ml) was added dropwise an ethyl acetate solution of p-toluenesulfonic acid (1.1 g) with stirring, and the reaction mixture was stirred for an hour at ambient temperature. After the precipitate was filtered off, the filtrate was treated with a solution of excess diphenyldiazomethane in ethyl acetate for an hour. The solvent was distilled off, and the residue was pulverized with diisopropyl ether, collected by filtration and dried to give benzhydryl 7-salicylideneamino-3-hydroxymethyl-3-cephem-4-carboxylate (2.66 g).

IR (Nujol): 3470, 1760, 1700, 1620 cm$^{-1}$

NMR δppm (DMSO—$d_6$): 3.7 (2H, s), 4.3 (2H, s), 5.15 (1H, broad), 3.8 (1H, d, J=5 Hz), 5.71 (1H, d, J=5 Hz), 6.96 (1H, s), 7.0–7.7 (14H, m), 8.8 (1H, s)

Preparation 70

Benzhydryl 7-salicylideneamino-3-hydroxymethyl-3-cephem-4-carboxylate (1.01 g) was dissolved in methylene chloride (10 ml) and cooled to −30° C. To this solution was added phosphorus pentachloride (0.46 g), followed by addition of pyridine (0.18 ml). The reaction mixture was stirred for an hour at −30° to −20° C. and poured into ice-water. The separated organic layer was washed with water and an aqueous sodium chloride, followed by drying over magnesium sulfate. The solvent was evaporated in vacuo to give benzhydryl 7-salicylideneamino-3-chloromethyl-3-cephem-4-carboxylate (0.9 g).

IR (Nujol): 1775, 1710, 1605, 1560(s) cm$^{-1}$

NMR δppm (DMSO—$d_6$): 3.85 (2H, ABq, J=18 Hz), 4.55 (2H, s), 5.40 (1H, s), 5.50 (1H, d, J=5 Hz), 5.85 (1H, d, J=5 Hz), 7.05 (1H, s), 7.2–7.8 (14H, m), 8.95 (1H, s)

Preparation 71

To a cooled solution of benzhydryl 7-salicylideneamino-3-chloromethyl-3-cephem-4-carboxylate (4 g) in dimethylformamide (10 ml) were added triphenylphosphine (2.2 g) and sodium iodide with stirring. After stirring for 2 hours at ambient temperature, the reaction mixture was poured into isopropyl alcohol (250 ml), and the precipitated solids (6.7 g) were collected by filtration. To a stirred solution of the above solids in methylene chloride (10 ml) and water (5 ml) was added 36% formaldehyde solution (17.4 ml). Then the reaction mixture was adjusted to pH 9.0 with a saturated aqueous sodium bicarbonate. After stirring for an hour at ambient temperature, the separated organic layer was washed with water and an aqueous sodium chloride, followed by drying over magnesium sulfate. The solution was evaporated under reduced pressure to give benzhydryl 7-salicylideneamino-3-vinyl-3-cephem-4-carboxylate (3 g).

IR (Nujol): 1770, 1710, 1620, 1580(s) cm$^{-1}$

NMR δppm (DMSO—$d_6$): 3.85 (2H, ABq, J=18 Hz), 5.30 (1H, d, J=11 Hz), 5.42 (1H, d,J=5 Hz), 5.65 (1H, d, J=18 Hz), 5.75 (1H, d,J=5 Hz), 6.90 (1H, dd, J=11, 18 Hz), 7.05 (1H, s), 7.2–7.9 (14H, m), 8.95 (1H, s)

Preparation 72

To a solution of benzhydryl 7-salicylideneamino-3-vinyl-3-cephem-4-carboxylate (1.6 g) in methylene chloride (20 ml) and anisole (5 ml) was added dropwise trifluoroacetic acid (6 ml) with stirring, and the stirring was continued at ambient temperature for an hour. The reaction mixture was poured into diisopropyl ether, and the precipitates were collected by filtration and then suspended in water, followed by adjusting to pH 3.5 with a saturated aqueous sodium bicarbonate. The solid was collected by filtration to give 7-amino-3-vinyl-3-cephem-4-carboxylic acid (0.4 g).

IR (Nujol): 1800, 1605 cm$^{-1}$

Preparation 73

To a suspension of tert-butyl 2-hydroxyimino-3-oxobutyrate (46.8 g) and potassium carbonate (51.8 g) in ethyl acetate (70 ml) and N,N-dimethylformamide (70 ml) was added 2,2,2-trichloroethyl chloroacetate (56.5 g), and the mixture was stirred at 45° to 48° C. for 3.5 hours. After the insoluble inorganic substance was filtered off, to the filtrate were added water and ethyl acetate. The separated ethyl acetate solution was washed with water and a saturated aqueous sodium chloride, followed by drying over magnesium sulfate. Removal of the solvent gave tert-butyl 2-(2,2,2-trichloroethoxycarbonylmethoxyimino)-3-oxobutyrate (84.9 g).

IR (Film): 1760 (broad), 1700, 1615 cm$^{-1}$

NMR δppm (CDCl$_3$): 1.52 (9H, s), 2.35 (3H, s), 4.85 (2H, s), 4.95 (2H, s)

Preparation 74

To a solution of tert-butyl 2-(2,2,2-trichloroethoxycarbonylmethoxyimino)-3-oxobutyrate (29.5 g) in acetic acid (59 ml) was added bromine (23.2 g) at 52° C., and the mixture was stirred at 52° to 68° C. for 15 minutes. After removal of the acetic acid from the reaction mixture under reduced pressure, the residual oil was dissolved in ethyl acetate (400 ml). The solution was washed with 10% hydrochloric acid (20 ml) and a saturated aqueous sodium chloride, followed by drying over magnesium sulfate. Removal of the solvent gave 4-bromo-2-(2,2,2-trichloroethoxycarbonylmethoxyimino)-3-oxobutyric acid (30.7 g).

IR (Nujol): 1740 (broad), 1609 cm$^{-1}$

NMR δppm (CCl$_4$): 4.27 (2H, s), 4.78 (2H, s), 4.98 (2H, s)

Preparation 75

4-Chloro-2-(2,2,2-trichloroethoxycarbonylmethoxyimino)-3-oxobutyric acid (4.70 g) was prepared by reacting tert-butyl 2-(2,2,2-trichloroethoxycarbonylmethoxyimino)-3-oxobutyrate (5.0 g) with sulfuryl chloride (2.83 ml) according to a similar manner to that of Preparation 74.

IR (Film): 1740 (broad), 1710 cm$^{-1}$

NMR δppm (CCl$_4$): 4.50 (2H, s), 4.77 (2H, s), 4.93 (2H, s)

Preparation 76

To a solution of 4-bromo-2-(2,2,2-trichloroethoxycarbonylmethoxyimino)-3-oxobutyric acid (20 g) in tetrahydrofuran (50 ml) was added a solution of thiourea (3.9 g) and sodium acetate (4.2 g) in water (50 ml), and the mixture was stirred at 40° C. for 2.5 hours. The reaction mixture was concentrated under reduced pressure to half of the original volume, which was adjusted to pH 7.5 with a saturated aqueous sodium bicarbonate and then washed with ethyl acetate. After the aqueous solution was further adjusted to pH 2.0 with 10% hydrochloric acid, the water was removed by decantation. The residual substance was dissolved in tetrahydrofuran (200 ml), followed by drying over magnesium sulfate. Removal of the solvent gave an oil, which was triturated with diisopropyl ether to give 2-(2-aminothiazol-4-yl)-2-(2,2,2-trichloroethoxycarbonylmethoxyimino)acetic acid (syn isomer) (3.5 g).

IR (Nujol): 3200 (broad), 1762, 1610 (broad) cm$^{-1}$

NMR δppm (DMSO—$d_6$): 4.88 (2H, s), 4.96 (2H, s), 6.84 (1H, s), 7.2 (2H, broad s)

Preparation 77

2-(2-Aminothiazol-4-yl)-2-benzyloxycarbonylmethoxyiminoacetic acid (syn isomer) (1.7 g) was prepared by reacting 4-bromo-2-benzyloxycarbonylmethoxyimino-3-oxobutyric acid (10 g) with thiourea (2.6 g) in the presence of sodium acetate (2.75 g) according to a similar manner to that of Preparation 63.

IR (Nujol): 1730, 1610 (broad) cm$^{-1}$

NMR δppm (DMSO—$d_6$): 4.78 (2H, s), 5.18 (2H, s), 6.86 (1H, s), 7.48 (2H, broad s), 7.56 (5H, s)

Preparation 78

Vilsmeier reagent prepared from phosphorus oxychloride (7.1 ml) and N,N-dimethylformamide (6.0 ml) was suspended in dry tetrahydrofuran (25 ml). To this suspension was added 4-bromo-2-(2,2,2-trichloroethoxycarbonylmethoxyimino)-3-oxobutyric acid (25 g), and the mixture was stirred at 5° C. for an hour to prepare the activated acid solution. This solution was added at a time to a solution of benzhydryl 7-amino-3-vinyl-3-cephem-4-carboxylate hydrochloride (16.2 g) and trimethylsilylacetamide (40 g) in ethyl acetate (140 ml) at −30° C., and the mixture was stirred at −15° to −5° C. for an hour. The reaction mixture was extracted with ethyl acetate, and the extract was washed with a saturated aqueous sodium bicarbonate and a saturated aqueous sodium chloride, followed by drying over magnesium sulfate. Removal of the solvent gave benzhydryl 7-[4-bromo-2-(2,2,2-trichloroethoxycarbonylmethoxyimino)-3-oxobutyramido]-3-vinyl-3-cephem-4-carboxylate (26.0 g).

IR (CHCl$_3$): 3400 (broad), 1775, 1713, 1690 cm$^{-1}$

NMR δppm (DMSO—$d_6$): 3.48, 3.88 (2H, ABq, J=18 Hz), 4.8–5.5 (8H, m), 5.5 (1H, d, J=18 Hz), 5.80 (1H, dd, J=5, 8 Hz), 6.83 (1H, dd, J=11, 18 Hz), 6.85 (1H, s), 7.3 (10H, m), 9.4 (1H, d, J=8 Hz)

Preparation 79

To a solution of sodium 7-(5-amino-5-carboxypentanamido)-3-hydroxymethyl-3-cephem-4-carboxylate (10 g) in water (50 ml) and acetone (30 ml) was added ethyl chloroformate (7.14 g), and the mixture was stirred at 7°–8° C. for 45 minutes while maintaining the pH value at 7.8–8 with 40% aqueous potassium carbonate. To the solution was added diphenyldiazomethane (14.7 g) in ethyl acetate (122 ml), and the mixture was stirred at ambient temperature for an hour while maintaining the pH value at 2.5 with 6N hydrochloric acid. The organic layer was separated, washed with an aqueous sodium chloride. The solution was evaporated to give a residue, which was dissolved in acetone (30 ml). To diisopropyl ether (300 ml) was added the resultant acetone solution, and the precipitates were collected by filtration to give benzhydryl 7-(5-benzhydryloxycarbonyl-5-ethoxycarbonylaminopentanamido)-3-hydroxymethyl-3-cephem-4-carboxylate (18.15 g).

IR (Nujol): 3300, 1780, 1720, 1670 cm$^{-1}$

NMR δppm (DMSO—d$_6$/D$_2$O): 1.15 (3H, t, J=7 Hz), 1.43-2.37 (6H, m), 3.4-3.73 (3H, m), 4.03 (2H, q, J=7 Hz), 4.27 (3H, m), 5.13 (1H, d, J=5 Hz), 5.71 (1H, dd, J=8, 5 Hz), 6.83 (1H, s), 6.97 (1H, s), 7.17-7.7 (21H, m), 8.85 (1H, d, J=8 Hz)

Preparation 80

Benzhydryl 7-[5-benzhydryloxycarbonyl-5-(3-phenylureido)pentanamido]-3-hydroxymethyl-3-cephem-4-carboxylate (18.06 g) was prepared by reacting sodium 7-(5-amino-5-carboxypentanamido)-3-hydroxymethyl-3-cephem-4-carboxylate (10 g) with phenyl isocyanate (15.1 g) and diphenyldiazomethane (14.7 g) according to a similar manner to that of Preparation 79.

NMR δppm (DMSO—d$_6$): 1.28-2.40 (6H, m), 3.59 (2H, s), 4.21 (2H, q, J=14 Hz), 4.26-4.55 (1H, m), 5.1 (1H, d, J=5 Hz), 5.68 (1H, dd, J=5, 8 Hz), 6.61 (1H, d, J=7 Hz), 6.81 (1H, s), 6.90 (1H, s), 7.01-7.77 (25H, m), 8.59 (1H, s), 8.82 (1H, d, J=8 Hz)

Preparation 81

Benzhydryl 7-(5-benzhydryloxycarbonyl-5-phthalimidopentanamido)-3-hydroxymethyl-3-cephem-4-carboxylate (21.04 g) was prepared by reacting sodium 7-(5-amino-5-carboxypentanamido)-3-hydroxymethyl-3-cephem-4-carboxylate (10 g) with N-propionyloxyphthalimide (6.65 g) and diphenyldiazomethane (14.7 g) according to a similar manner to that of Preparation 79.

IR (Nujol): 3350, 1780, 1715 cm$^{-1}$

NNR δppm (DMSO—d$_6$): 1.4-2.53 (6H, m), 3.35 (1H, bs), 3.60 (2H, bs), 4.25 (2H, m), 4.83-5.13 (1H, m), 5.08 (1H, d, J=5 Hz), 5.68 (1H, d d, J=5 Hz, 8 Hz), 6.83 (1H, s), 6.90 (1H, s), 7.07-7.67 (20H, m), 7.9 (4H, s), 8.82 (1H, d, J=8 Hz)

Preparation 82

Benzhydryl 7-(5-benzhydryloxycarbonyl-5-acetamidopentanamido)-3-hydroxymethyl-3-cephem-4-carboxylate (3.94 g) was prepared by reacting sodium 7-(5-amino-5-carboxypentanamido)-3-hydroxymethyl-3-cephem-4-carboxylate (10 g) with acetyl chloride (9.93 g) and diphenyldiazomethane (14.7 g) according to a similar manner to that of Preparation 79.

IR (Nujol): 3280, 1780, 1720, 1655 cm$^{-1}$

NMR δppm (DMSO—d$_6$): 1.4-2.36 (6H, m), 1.90 (3H, s), 3.62 (2H, s), 4.25 (2H, s), 4.28-4.52 (1H, m), 5.1 (1H, d, J=5 Hz), 5.71 (1H, dd, J=5, 8 Hz), 6.79 (1H, s), 6.92 (1H, s), 7.0-7.74 (21H, m), 8.83 (1H, d, J=8 Hz)

Preparation 83

Benzhydryl 7-(5-benzhydryloxycarbonyl-5-isobutoxycarbonylaminopentanamido)-3-hydroxymethyl-3-cephem-4-carboxylate (17.45 g) was prepared by reacting sodium 7-(5-amino-5-carboxypentanamido)-3-hydroxymethyl-3-cephem-4-carboxylate (10 g) with isobutyl chloroformate (8.98 g) and diphenyldiazomethane (14.7 g) according to a similar manner to that of Preparation 79.

IR (Nujol): 3300, 1780, 1720, 1670 cm$^{-1}$

NMR δppm (DMSO—d$_6$/D$_2$O): 0.87 (6H, d, J=6 Hz), 1.33-2.5 (6H, m), 3.33 (1H, m), 3.62 (3H, m), 3.77 (2H, d, J=6 Hz), 4.23 (3H, m), 5.12 (1H, d, J=5 Hz), 5.72 (1H, d d, J=8 Hz, 5 Hz), 6.82 (1H, s), 6.93 (1H, s), 7.12-7.83 (21H, m), 8.83 (1H, d, J=8 Hz)

Preparation 84

To a solution of benzhydryl 7-(5-benzhydryloxycarbonyl-5-ethoxycarbonylaminopentanamido)-3-hydroxymethyl-3-cephem-4-carboxylate (18 g) in ethylene chloride (180 ml) were added phosphorus pentachloride (4.82 g) and pyridine (1.83 g) at −30° to −35° C. After stirring for 30 minutes, to the solution was added water (180 ml), and the organic layer was separated and washed with an aqueous sodium chloride. The solution was evaporated, and the residue was dissolved in N,N-dimethylformamide (39 ml). To the solution was added triphenylphosphine (6.66 g) and sodium iodide (3.81 g) at ambient temperature. After stirring for an hour, the mixture was added to diisopropyl alcohol (1000 ml) at 0°-5° and allowed to stand for an hour. The precipitates were collected by filtration, washed with diisopropyl alcohol, and then dissolved in ethylene chloride (160 ml). To the solution were added water (35.3 ml) and 36% aqueous formaldehyde, and the mixture was stirred at ambient temperature for 70 minutes while maintaining the pH value at 9.0 with 40% aqueous potassium carbonate. The organic layer was separated, washed with an aqueous sodium chloride and dried over magnesium sulfate. The solution was evaporated, and the residue was dissolved in acetone (30 ml). To diisopropyl ether (300 ml) was added the acetone solution. The precipitates were collected by filtration and washed with diisopropyl ether to afford benzhydryl 7-(5-benzhydryloxycarbonyl-5-ethoxycarbonylaminopentanamido)-3-vinyl-3-cephem-4-carboxylate (9.82 g).

IR (Nujol): 1780, 1715, 1680 cm$^{-1}$

NMR δppm (DMSO—d$_6$/D$_2$O): 1.17 (3H, t, J=7 Hz), 1.43-2.47 (6H, m), 3.4-3.9 (3H, m), 4.03 (2H, q, J=7 Hz), 5.22 (1H, d, J=5 Hz), 5.39 (1H, d, J=11 Hz), 5.65 (1H, d, J=18 Hz), 5.78 (1H, d d, J=8, 5 Hz), 6.82 (1H, d d, J=18, 11 Hz), 6.83 (1H, s), 7.00 (1H, s), 7.17-7.9 (21H, m), 8.90 (1H, d, J=8 Hz)

Preparation 85

Benzhydryl 7-[5-benzhydryloxycarbonyl-5-(5-phenylureido)pentanamido]-3-vinyl-3-cephem-4-carboxylate (9.34 g) was prepared by reacting benzhydryl 7-[5-benzhydryloxycarbonyl-5-(3-phenylureido)pentanamido]-3-hydroxymethyl-3-cephem-4-carboxylate (18 g) with phosphorus pentachloride (4.54 g), pyridine (1.72 g, triphenylphosphine (6.29 g), sodium iodide (3.6 g) and 30% aqueous formaldehyde (33.4 ml) according to a similar manner to that of Preparation 84.

IR (Nujol): 3330, 3250, 1780, 1725, 1700, 1650 cm$^{-1}$

NMR δppm (DMSO—d$_6$): 1.36-2.5 (6H, m), 3.76 (2H, ABq, J=18 Hz), 4.28-4.62 (1H, m), 5.24 (1H, d, J=5 Hz), 5.38 (1H, d, J=11 Hz), 5.55 (1H, d, J=17 Hz), 6.78 (1H, d d, J=5 Hz, 8 Hz), 6.65 (1H, d, J=8 Hz), 6.90 (1H, d d, J=11 Hz, 17 Hz), 6.86 (1H, s), 7.00 (1H, s), 7.18-7.69 (25H, m), 8.63 (1H, s), 8.94 (1H, d, J=8 Hz)

Preparation 86

Benzhydryl 7-(5-benzhydryloxycarbonyl-5-phthalimidopentanamido)-3-vinyl-3-cephem-4-carboxylate (13.35 g) was prepared by reacting benzhydryl 7-(5-benzhydryloxycarbonyl-5-phthalimidopentanamido)-3-hydroxymethyl-3-cephem-4-carboxylate (20 g) with phosphorus pentachloride (4.98 g), pyridine (20.8 g), triphenylphosphine (6.9 g), sodium iodide (3.94 g) and 30% aqueous formaldehyde (36.6 ml) according to a similar manner to that of Preparation 84.

IR (Nujol): 3300, 1780, 1720 cm$^{-1}$

NMR δppm (DMSO—d$_6$): 1.34–2.5 (6H, m), 3.62 (1H, broad s), 3.72 (2H, m), 5.0–5.24 (1H, m), 5.2 (1H, d, J=5 Hz), 5.37 (1H, d, J=11 Hz), 5.53 (1H, d, J=17 Hz), 5.75 (1H, d d, J=5, 8 Hz), 6.78 (1H, d d, J=11, 17 Hz), 6.87 (1H, s,), 7.0 (1H, s), 7.17–7.83 (20H, m), 7.94 (4H, s), 8.92 (1H, d, J=8 Hz)

Preparation 87

To a solution of phosphorus pentachloride (7.87 g) in ethylene chloride (47.75 ml) was added pyridine (2.99 g) at 5° to 6° C. After stirring for 30 minutes, to the mixture was added benzhydryl 7-(5-benzhydryloxycarbonyl-5-ethoxycarbonylaminopentanamido)-3-vinyl-3-cephem-4-carboxylate (9.75 g). After stirring for 2 hours at 5° to 6° C. and cooling to −30° to −20° C., the mixture was treated with 2-methoxyethanol (7.67 ml) for 1.5 hours and then with water (10 ml) for an hour. The precipitates were collected by filtration and washed with ethyl acetate and diisopropyl alcohol to give benzhydryl 7-amino-3-vinyl-3-cephem-4-carboxylate hydrochloride (1.99 g).

IR (Nujol): 1760, 1705, 1580 cm$^{-1}$

Preparation 88

Benzhydryl 7-amino-3-vinyl-3-cephem-4-carboxylate hydrochloride (3.45 g) was prepared by reacting benzhydryl 7-[5-benzhydryloxycarbonyl-5-(3-phenylureido)pentanamido]-3-vinyl-3-cephem-4-carboxylate (9.25 g) with phosphorus pentachloride (7.04 g), pyridine (2.77 g) and 2-methoxyethanol (6.88 g) according to a similar manner to that of Preparation 87.

IR (Nujol): 1760, 1705, 1580 cm$^{-1}$

Preparation 89

Benzhydryl 7-amino-3-vinyl-3-cephem-4-carboxylate hydrochloride (1.2 g) was prepared by reacting benzhydryl 7-(5-benzhydryloxycarbonyl-5-phthalimidopentanamido)-3-vinyl-3-cephem-4-carboxylate (13.3 g) with phosphorus pentachloride (5 g), pyridine (1.96 g) and 2-methoxyethanol (9.74 g) according to a similar manner to that of Preparation 87.

IR (Nujol): 1760, 1705, 1580 cm$^{-1}$

PREPARATION OF THE OBJECT COMPOUNDS

Example 1

To a solution of N-tert-butoxycarbonyl-2-(3-methanesulfonamidophenyl)-D-glycine (4.13 g) and triethylamine (1.2 g) in tetrahydrofuran (40 ml) was added dropwise a solution of ethyl chloroformate (1.3 g) in tetrahydrofuran (4 ml) at −5° to −4° C. over a period of 5 minutes, followed by stirring at −5° to 2° C. for an hour to give a solution of the activated acid.

On the other hand, benzhydryl 7-amino-3-vinyl-3-cephem-4-carboxylate hydrochloride (4.3 g) and trimethylsilylacetamide (7.9 g) were added to ethyl acetate (50 ml), and the mixture was stirred for 5 minutes. To the resultant solution was added the solution of the activated acid prepared above, and the mixture was stirred at −30° to 0° C. for 2 hours. After addition of ethyl acetate (150 ml) and water, the organic layer was separated out. The remaining aqueous solution was extracted with ethyl acetate, and the combined ethyl acetate solution was washed with a saturated aqueous solution of sodium bicarbonate and an aqueous solution of sodium chloride, dried over anhydrous magnesium sulfate, and then evaporated. The residue was washed with diethyl ether and collected by filtration to give benzhydryl 7-[N-tert-butoxycarbonyl-2-(3-methanesulfonamidophenyl)-D-glycinamido]-3-vinyl-3-cephem-4-carboxylate (5.3 g). The washings of diethyl ether were evaporated to dryness to recover the same compound (0.7 g). Total yield is 6.0 g.

I.R. (Nujol): 3340, 3280, 3250, 1790, 1710, 1690, 1670, 1520 cm$^{-1}$

NMR δppm (DMSO—d$_6$): 1.37 (9H, s), 2.97 (3H, s), 3.65 (2H, q, J=16 Hz), 5.12 (1H, d, J=5 Hz), 5.15 (1H, s), 5.25 (1H, d, J=10 Hz), 5.58 (1H, d, J=17 Hz), 5.78 (1H, dd, J=5 Hz, 8 Hz), 6.70 (1H, dd, J=10 Hz, 17 Hz), 6.93 (1H, s), 7.00–7.60 (14H, m), 9.20 (1H, d, J=8 Hz), 9.70 (1H, s)

Example 2

To a suspension of 2-(3-methanesulfonamidophenyl)-D-glycine (2.44 g) in methylene chloride (25 ml) was blown hydrogen chloride gas at 5° to 10° C. over a period of 5 minutes. After addition of phosphorus pentoxide (3.1 g), the mixture was stirred at 0° to 10° C. for 5 hours. The precipitated solid therein was collected by filtration, washed with methylene chloride (5 ml) and then dried to give the residue (2.7 g). This residue was added to a solution of 7-amino-3-vinyl-3-cephem-4-carboxylate acid (1.8 g) and trimethylsilylacetamide (6.3 g) in methylene chloride (30 ml) at −15° C. with stirring, and the stirring was continued at −5° to 0° C. for 3 hours. To the reaction mixture was added water (30 ml) and shaken for a while. After separating out the aqueous layer, it was adjusted to pH 5 with 20% aqueous solution of sodium carbonate and evaporated to dryness under reduced pressure to give the solid, which was chromatographed on a nonionic adsorption resin "Diaion HP-20" (120 ml). After washing with water, elution was carried out with 30% isopropyl alcohol, and the fractions containing the desired compound were collected and evaporated under reduced pressure. The residue obtained was lyophilized to give 7-[2-(3-methanesulfonamidophenyl)-D-glycinamido]-3-vinyl-3-cephem-4-carboxylate acid (0.47 g).

I.R. (Nujol): 3350–3150, 1760, 1685, 1605 cm$^{-1}$

Example 3

To a suspension of benzhydryl 7-[N-tert-butoxycarbonyl-2-(3-methanesulfonamidophenyl)-D-glycinamido]-3-vinyl-3-cephem-4-carboxylate (5.0 g) in methylene chloride (50 ml) were added anisole (6.0 g) and trifluoroacetic acid (16.0 g) under ice-cooling, and the mixture was stirred at ambient temperature for an hour. After removal of the solvent, to the residue were added ice-water and ethyl acetate, followed by adjusting to pH 7.5 with an aqueous solution of sodium carbonate. The aqueous layer was separated out, washed with ethyl acetate and then adjusted to pH 2.5 with 10% hydrochloric acid. After washing with ethyl acetate, the aqueous solution was adjusted to pH 6 with an aqueous solution of sodium bicarbonate, followed by removing the organic solvent therefrom completely. The resultant aqueous solution was adjusted to pH 3.6 with 10% hydrochloric acid and then subjected to column chromatography using non-ionic adsorption resin "Diaion HP-20" (Trade Mark, manufactured by Mitsubishi Chemical Industries Ltd.) (120 ml). After washing it with water (240 ml), elution was carried out with 30% isopropyl alcohol (180 ml) and the eluate was evaporated and lyophilized to give 7-[2-(3-methanesulfonamidophenyl)-D-glycinamido]-3-vinyl-3-cephem-4-carboxylic acid (1.4 g).

I.R. (Nujol): 3300–3150, 1760, 1685, 1605 cm$^{-1}$

NMR δppm (D$_2$O): 3.08 (3H, s), 3.47 (2H, s), 4.73 (1H, d, J=4 Hz), 5.10 (1H, d, J=4 Hz), 5.32 (1H, s), 5.33 (1H, d, J=17 Hz), 5.63 (1H, d, J=4 Hz), 6.73 (1H, dd, J=11 Hz, 17 Hz), 7.33 (4H, s)

Example 4

(1) To a solution of 7-[2-(3-methanesulfonamidophenyl)-D-glycinamido]-3-vinyl-3-cephem-4-carboxylic acid (3.6 g) in water (50 ml) was added sodium bicarbonate (0.668 g) and the solution was filtered. The filtrate was lyophilized to give sodium 7-[2-(3-methanesulfonamidophenyl)-D-glycinamido]-3-vinyl-3-cephem-4-carboxylate (3.69 g).

(2) To the compound (1.5 g) obtained above in N,N-dimethylformamide (15 ml) was added a solution of iodomethyl pivalate (0.76 g) in N,N-dimethylformamide (2 ml) under ice-cooling, and the mixture was stirred at the same temperature for 10 minutes. After addition of ethyl acetate (80 ml), the reaction mixture was washed twice with water (80 ml), three times with 5% aqueous solution of sodium bicarbonate (80 ml) and three times with an aqueous solution of sodium chloride in turn, and then dried over anhydrous magnesium sulfate. Removal of the solvent gave a residue, which was pulverized with diisopropyl ether to give pivaloyloxymethyl 7-[2-(3-methanesulfonamidophenyl)-D-glycinamido]-3-vinyl-3-cephem-4-carboxylate (0.61 g).

I.R. (Nujol): 1773, 1745, 1670 cm$^{-1}$

Example 5

To a solution of diketene (1.26 g) in carbon tetrachloride (12 ml) was added a solution of bromine (2.40 g) in carbon tetrachloride (3 ml) at −30° to −25° C., and the mixture was stirred at the same temperature for half an hour to prepare a solution of 4-bromoacetoacetyl bromide. This solution was added dropwise to a solution of benzhydryl 7-amino-3-vinyl-3-cephem-4-carboxylate hydrochloride (6.43 g) and trimethylsilylacetamide (7.82 g) in ethyl acetate (129 ml) at −30° C. with stirring, and the stirring was continued at −30° to −10° C. for 2 hours. To the reaction mixture was added water at −20° C. and ethyl acetate, followed by separating out the organic layer, which was washed with water, an aqueous solution of sodium bicarbonate and a saturated aqueous solution of sodium chloride in turn, dried over anhydrous magnesium sulfate and then evaporated. The residue obtained was dissolved in a mixture of ethanol (100 ml) and tetrahydrofuran (100 ml), and to this solution was added thiourea (3.42 g), followed by stirring at ambient temperature for an hour. After evaporation of the reaction mixture, to the residue were added water and ethyl acetate, and then adjusted to pH 7 with sodium bicarbonate. The separated ethyl acetate layer was washed with an aqueous solution of sodium chloride, dried over anhydrous magnesium sulfate and then evaporated under reduced pressure to give benzhydryl 7-[2-(2-aminothiazol-4yl)acetamido]-3-vinyl-3-cephem-4-carboxylate (6.89 g).

IR (Nujol): 1760, 1740, 1650, 1610 cm$^{-1}$

NMR δppm (DMSO—d$_6$): 3.47 (2H, broad s), 3.80 (2H, m), 5.27 (1H, d, J=5 Hz), 5.35 (1H, d, J=11 Hz), 5.68 (1H, d, J=18 Hz), 5.87 (1H, dd, J=5 Hz, 8 Hz), 6.33 (1H, s), 6.85 (1H, dd, J=11 Hz, 18 Hz), 6.93 (2H, m), 7.02 (1H, s), 7.43 (10H, s), 9.00 (1H, d, J=8 Hz)

Example 6

Pivaloyloxymethyl 7-[2-(2-aminothiazol-4-yl)acetamido]-3-vinyl-3-cephem-4-carboxylate was obtained according to the similar manner to that of Example 5.

IR (Nujol): 1770, 1750, 1650 cm$^{-1}$

Example 7

To a solution of benzhydryl 7-amino-3-vinyl-3-cephem-4-carboxylate hydrochloride (1.9 g) and trimethylsilylacetamide (4.6 g) in ethyl acetate (30 ml) was added at −30° C. a solution of the activated acid, which was prepared by stirring a mixture of 2-(2-formamidothiazol-4-yl)-2-methoxyiminoacetic acid (syn isomer) (1.1 g), phosphorus oxychloride (0.81 g), N,N-dimethylformamide (0.39 g) and ethyl acetate (20 ml) for half an hour under ice-cooling, and the mixture was stirred at −30° to −10° C. for an hour. After addition of ethyl acetate (100 ml) and water (50 ml), the organic layer was separated out, washed with a saturated aqueous solution of sodium bicarbonate and an aqueous solution of sodium chloride, dried over anhydrous magnesium sulfate and then evaporated to dryness to give benzhydryl 7-[2-(2-formamidothiazol-4-yl)-2-methoxyiminoacetamido]-3-vinyl-3-cephem-4-carboxylate (syn isomer) (2.4 g).

IR (Nujol): 3250, 1780, 1710, 1700, 1660, 1540 cm$^{-1}$

NMR δppm (DMSO—d$_6$): 3.78 (2H, m), 3.95 (3H, s), 5.30 (1H, d, J=11 Hz), 5.32 (1H, d, J=5 Hz), 5.66 (1H, d, J=17 Hz), 5.96 (1H, dd, J=5 Hz, 8 Hz), 6.82 (1H, dd, J=11 Hz, 17 Hz), 7.00 (1H, s), 7.17–7.73 (11H, m), 8.57 (1H, s), 9.80 (1H, d, J=8 Hz), 12.7 (1H, broad s)

Example 8

Benzhydryl 7-[2-(2-formamidothiazol-4-yl)-2-allyloxyiminoacetamido]-3-vinyl-3-cephem-4-carboxylate (syn isomer) (3.1 g) was obtained by reacting benzhydryl 7-amino-3-vinyl-3-cephem -4-carboxylate hydrochloride (2.15 g) with 2-(2-formamidothiazol-4yl)-2-allyloxyiminoacetic acid (syn isomer) (1.53 g) according to the similar manner to that of Example 7.

IR (Nujol): 3250, 1760, 1710, 1690, 1660, 1530 cm$^{-1}$

NMR δppm (DMSO—d$_6$): 3.75 (2H, q, J=18 Hz), 4.65 (2H, d, J=5 Hz), 5.00–6.3 (7H, m), 6.77 (1H, dd, J=11 Hz, 18 Hz), 6.97 (1H, s), 7.17–7.63 (11H, m), 8.53 (1H, s), 9.78 (1H, d, J=8 Hz), 12.7 (1H, broad s)

Example 9

Benzhydryl 7-[2-(2-formamidothiazol-4-yl)-2-propargyloxyiminoacetamido]-3-vinyl-3-cephem-4-carboxylate (syn isomer) (1.3 g) was obtained by reacting benzhydryl 7-amino-3-vinyl-3-cephem-4-carboxylate hydrochloride (1.0 g) with 2-(2-formamidothiazol-4-yl)-2-propargyloxyiminoacetic acid (syn isomer) (0.71 g) according to the similar manner to that of Example 7.

IR (Nujol): 3250, 1780, 1720, 1690, 1660, 1550 cm$^{-1}$

NMR δppm (DMSO—d$_6$): 3.38 (1H, m), 3.82 (2H, q, J=18 Hz), 4.82 (2H, m), 5.35 (1H, d, J=5 Hz), 5.35 (1H, d, J=11 Hz), 5.55 (1H, d, J=18 Hz), 5.98 (1H, dd, J=5 Hz, 8 Hz), 6.85 (1H, dd, J=11 Hz, 18 Hz), 7.02 (1H, s), 7.17-7.82 (10H, m), 7.55 (1H, s), 8.62 (1H, s), 9.80 (1H, d, J=8 Hz), 12.60 (1H, broad s)

Example 10

Benzhydryl 7-[(2-formamidothiazol-4-yl)glyoxylamido]-3-vinyl-3-cephem-4-carboxylate (6.1 g) was obtained by reacting benzhydryl 7-amino-3-vinyl-3-cephem-4-carboxylate hydrochloride (6.0 g) with (2-formamidothiazol-4-yl)glyoxylic acid (3.93 g) according to the similar manner to that of Example 7, mp 141°-144° C. (dec.).

IR (Nujol): 3150, 1780, 1720, 1695, 1670, 1620, 1520 cm$^{-1}$

NMR δppm (DMSO—d$_6$): 3.78 (2H, q, J=18 Hz), 5.35 (1H, d, J=5 Hz), 5.33 (1H, d, J=11 Hz), 5.68 (1H, d, J=17 Hz), 5.93 (1H, dd, J=5 Hz, 8 Hz), 6.87 (1H, dd, J=11 Hz, 17 Hz), 7.00 (1H, s), 7.20–7.67 (10H, m), 8.50 (1H, s), 8.63 (1H, s), 9.97 (1H, d, J=8 Hz), 12.82 (1H, broad s)

The compounds described in the following Examples 11 to 20 were obtained by reacting the 7-amino-3-vinyl-cephalosporanic acid derivatives with the corresponding acid according to the similar manner to that of Example 7.

Example 11

7-[2-(2-Aminothiazol-4-yl)acetamido]-3-vinyl-3-cephem-4-carboxylic acid

IR (Nujol): 3260, 1760, 1650 cm$^{-1}$

Example 12

7-[2-(2-Aminothiazol-4-yl)-2-methoxyiminoacetamido]-3-vinyl-3-cephem-4-carboxylic acid hydrochloride (syn isomer)

IR (Nujol): 3260, 1775, 1720, 1660, 1645, 1600, 1550 cm$^{-1}$

Example 13

7-[2-(2-Aminothiazol-4-yl)-2-allyloxyiminoacetamido]-3-vinyl-3-cephem-4-carboxylic acid (syn isomer)

IR (Nujol): 3250, 1770, 1655, 1605, 1545 cm$^{-1}$

Example 14

7-[2-(2-Aminothiazol-4-yl)-2-propargyloxyiminoacetamido]-3-vinyl-3-cephem-4-carboxylic acid (syn isomer)

IR (Nujol): 3250, 1760, 1680, 1620, 1530 cm$^{-1}$

Example 15

7-[(2-Aminothiazol-4-yl)glyoxylamido]-3-vinyl-3-cephem-4-carboxylic acid

IR (Nujol): 3300, 3200–3100, 1780, 1660, 1610, 1520 cm$^{-1}$

Example 16

Pivaloyloxymethyl 7-[2-(2-aminothiazol-4-yl)acetamido]-3-vinyl-3-cephem-4-carboxylate IR (Nujol): 1770, 1750, 1650 cm$^{-1}$

Example 17

Pivaloyloxymethyl 7-[2-(2-aminothiazol-4-yl)-2-propargyloxyiminoacetamido]-3-vinyl-3-cephem-4-carboxylate (syn isomer)

IR (Nujol): 1770, 1740, 1670 cm$^{-1}$

Example 18

Pivaloyloxymethyl 7-[2-(2-aminothiazol-4-yl)glyoxylamido]-3-vinyl-3-cephem-4-carboxylate IR (Nujol): 1775, 1745, 1660 cm$^{-1}$

Example 19

Hexanoyloxymethyl 7-[2-(2-aminothiazol-4-yl)-2-propargyloxyiminoacetamido]-3-vinyl-3-cephem-4-carboxylate (syn isomer)

IR (Nujol): 1770, 1650 cm$^{-1}$

Example 20

Hexanoyloxymethyl 7-[(2-aminothiazol-4-yl)glyoxylamido]-3-vinyl-3-cephem-4-carboxylate IR (Nujol): 1770, 1660 cm$^{-1}$

Example 21

To a solution of benzhydryl 7-[2-(2-aminothiazol-4-yl)acetamido]-3-vinyl-3-cephem-4-carboxylate (6.79 g) in methylene chloride (68 ml) were added trifluoroacetic acid (29.1 g) and anisole (11.02 g) at 0° C., and the mixture was stirred at ambient temperature for 65 minutes. After the reaction mixture was evaporated, to the residue were added ethyl acetate and water, followed by adjusting to pH 7 with an aqueous solution of sodium bicarbonate. The separated aqueous solution was adjusted to pH 3.0 with 10% hydrochloric acid, and the precipitated substance was collected by filtration to give 7-[2-(2-aminothiazol-4yl)acetamido]-3-vinyl-3-cephem-4-carboxylic acid (1.88 g), mp 104°-116° C. (dec.).

IR (Nujol): 3260, 1760, 1650 cm$^{-1}$

NMR δppm (DMSO—d$_6$): 3.47 (2H, s), 3.77 (2H, q, J=18 Hz), 5.18 (1H, d, J=5 Hz), 5.35 (1H, d, J=11 Hz), 5.62 (1H, d, J=18 Hz), 5.73 (1H, dd, J=5 Hz, 8 Hz), 6.33 (1H, s), 6.75–7.15 (2H, m), 6.98 (1H, dd, J=11 Hz, 18 Hz), 8.95 (1H, d, J=8 Hz)

Example 22

To a suspension of benzhydryl 7-[2-(2-formamidothiazol-4-yl)-2-methoxyiminoacetamido]-3-vinyl-3-cephem-4-carboxylate (syn isomer) (2.3 g) in methylene chloride (40 ml) were added anisole (3.3 g) and trifluoroacetic acid (8.7 g) under ice-cooling with stirring, and the stirring was continued at ambient temperature for 75 minutes. After evaporation of the reaction mixture, to the residue was added water and ethyl acetate, followed by adjusting to pH 7 with a saturated aqueous solution of sodium bicarbonate. To the separated aqueous solution was added ethyl acetate, followed by adjusting to pH 2 with 10% hydrochloric acid. The ethyl acetate layer was separated out, washed with an aqueous solution of sodium chloride, dried over anhydrous magnesium sulfate and then evaporated to dryness to give a residue, which was washed with diethyl ether to obtain 7-[2-(2-formamidothiazol-4-yl)-2-methoxyiminoacetamido]-3-vinyl-3-cephem-4-carboxylic acid (syn isomer) (1.45 g).

IR (Nujol): 3250, 1770, 1690, 1650, 1540 cm$^{-1}$

NMR δppm (DMSO—d$_6$): 3.70 (2H, q, J=17 Hz), 3.88 (3H, s), 5.20 (1H, d, J=5 Hz), 5.30 (1H, d, J=11 Hz), 5.55 (1H, d, J=18 Hz), 5.82 (1H, dd, J=5 Hz, 8

Hz), 6.93 (1H, dd, J=11 Hz, 18 Hz), 7.45 (1H, s), 8.52 (1H, s), 9.73 (1H, d, J=8 Hz)

Example 23

7-[2-(2-Formamidothiazol-4-yl)-2-allyloxyiminoacetamido]-3-vinyl-3-cephem-4-carboxylic acid (syn isomer) (1.7 g) was obtained by reacting benzhydryl 7-[2-(2-formamidothiazol-4-yl)-2-allyloxyiminoacetamido]-3-vinyl-3-cephem-4-carboxylate (syn isomer) (3.0 g) with trifluoroacetic acid (10.8 g) in the presence of anisole (4.0 g) according to the similar manner to that of Example 22.

IR (Nujol): 3250, 1770, 1680 (shoulder), 1650, 1530 cm$^{-1}$

NMR δppm (DMSO—d$_6$): 3.67 (2H, q, J=18 Hz), 4.60 (2H, d, J=4 Hz), 4.83–6.33 (7H, m), 6.90 (1H, dd, J=11 Hz, 18 Hz), 7.38 (1H, s), 8.48 (1H, s), 9.70 (1H, d, J=8 Hz), 12.62 (1H, broad s)

Example 24

7-[2-(2-Formamidothiazol-4-yl)-2-propargyloxyiminoacetamido]-3-vinyl-3-cephem-4-carboxylic acid (syn isomer) (0.77 g) was obtained by reacting benzhydryl 7-[2-(2-formamidothiazol-4-yl)-2-propargyloxyiminoacetamido]-3-vinyl-3-cephem-4-carboxylate (syn isomer) (1.2 g) with trifluoroacetic acid (4.4 g) in the presence of anisol (1.7 g) according to the similar manner to that of Example 22.

IR (Nujol): 3250, 1780, 1680, 1660, 1550 cm$^{-1}$

NMR δppm (DMSO—d$_6$): 3.52 (1H, m), 3.77 (2H, q, J=18 Hz), 4.80 (2H, s), 5.27 (1H, d, J=5 Hz), 5.37 (1H, d, J=11 Hz), 5.62 (1H, d, J=18 Hz), 5.87 (1H, dd, J=5 Hz, 8 Hz), 7.00 (1H, dd, J=11 Hz, 18 Hz), 7.50 (1H, s), 8.57 (1H, s), 9.83 (1H, d, J=8 Hz), 12.77 (1H, broad s)

Example 25

7-[(2-Formamidothiazol-4-yl)glyoxylamido]-3-vinyl-3-cephem-4-carboxylic acid (3.0 g) was obtained by reacting benzhydryl 7-[(2-formamidothiazol-4-yl)glyoxylamido]-3-vinyl-3-cephem-4-carboxylate (6.0 g) with trifluoroacetic acid (23.7 g) in the presence of anisole (9.0 g) according to the similar manner to that of Example 22.

NMR δppm (DMSO—d$_6$): 3.75 (2H, q, J=17 Hz), 5.27 (1H, d, J=5 Hz), 5.37 (1H, d, J=11 Hz), 5.63 (1H, d, J=17 Hz), 5.83 (1H, dd, J=5 Hz, 8 Hz), 7.00 (1H, dd, J=11 Hz, 17 Hz), 8.50 (1H, s), 8.65 (1H, s), 9.93 (1H, d, J=8 Hz), 12.8 (1H, broad s)

The compounds described in the following Examples 26 to 29 were obtained by reacting benzhydryl ester of the corresponding cephalosporanic acid derivatives with trifluoroacetic acid in the presence of anisole according to the similar manner to that of Example 22.

Example 26

7-[2-(2-Aminothiazol-4-yl)-2-methoxyiminoacetamido]-3-vinyl-3-cephem-4-carboxylic acid hydrochloride (syn isomer)

IR (Nujol): 3260, 1775, 1720, 1660, 1645, 1600, 1550 cm$^{-1}$

Example 27

7-[2-(2-Aminothiazol-4-yl)-2-allyloxyiminoacetamido]-3-vinyl-3-cephem-4-carboxylic acid (syn isomer)

IR (Nujol): 3250, 1770, 1655, 1605, 1545 cm$^{-1}$

Example 28

7-[2-(2-Aminothiazol-4-yl)-2-propargyloxyiminoacetamido]-3-vinyl-3-cephem-4-carboxylic acid (syn isomer)

IR (Nujol): 3250, 1760, 1680, 1620, 1530 cm$^{-1}$

Example 29

7-[(2-Aminothiazol-4-yl)glyoxylamido]-3-vinyl-3-cephem-4-carboxylic acid

IR (Nujol): 3300, 3200–3100, 1780, 1660, 1610, 1520 cm$^{-1}$

Example 30

To a solution of 7-[2-(2-formamidothiazol-4-yl)-2-methoxyiminoacetamido]-3-vinyl-3-cephem-4-carboxylic acid (syn isomer) (1.4 g) in methanol (30 ml) and tetrahydrofuran (20 ml) was added conc. hydrochloric acid (1.0 ml), and the mixture was stirred at ambient temperature for 2.7 hours. After evaporation of the reaction mixture, the residue was washed with tetrahydrofuran to give 7-[2-(2-aminothiazol-4-yl)-2-methoxyiminoacetamido]-3-vinyl-3-cephem-4-carboxylic acid hydrochloride (syn isomer) (1.2 g).

IR (Nujol): 3260, 1775, 1720, 1660, 1645, 1600, 1550 cm$^{-1}$

NMR δppm (DMSO—d$_6$): 3.75 (2H, q, J=18 Hz), 4.00 (3H, s), 5.25 (1H, d, J=5 Hz), 5.35 (1H, d, J=11 Hz), 5.60 (1H, d, J=18 Hz), 5.80 (1H, dd, J=5 Hz, 8 Hz), 6.98 (1H, dd, J=11 Hz, 18 Hz), 7.02 (1H, s), 9.87 (1H, d, J=8 Hz).

Example 31

A mixture of 7-[2-(2-formamidothiazol-4-yl)-2-allyloxyiminoacetamido]-3-vinyl-3-cephem-4-carboxylic acid (syn isomer) (1.6 g) and conc. hydrochloric acid (1.5 ml) in methanol (30 ml) was stirred at ambient temperature for 2 hours. After evaporation of the reaction mixture, thereto was added a saturated aqueous solution of sodium bicarbonate, followed by removing the insoluble substance by filtration. The filtrate was adjusted to pH 3 with 10% hydrochloric acid, and the precipitated solid was collected by filtration and washed with water to give 7-[2-(2-aminothiazol-4-yl)-2-allyloxyiminoacetamido]-3-vinyl-3-cephem-4-carboxylic acid (syn isomer) (1.25 g).

IR (Nujol): 3250, 1770, 1655, 1605, 1545 cm$^{-1}$

NMR δppm (DMSO—d$_6$): 3.75 (2H, q, J=18 Hz), 4.67 (2H, m), 5.00–6.5 (7H, m), 6.80 (1H, s), 7.00 (1H, dd, J=11 Hz, 18 Hz), 9.67 (1H, d, J=8 Hz)

Example 32

7-[2-(2-Aminothiazol-4-yl)-2-propargyloxyiminoacetamido]-3-vinyl-3-cephem-4-carboxylic acid (syn isomer) (0.5 g) was obtained by reacting 7-[2-(2-formamidothiazol-4-yl)-2-propargyloxyiminoacetamido]-3vinyl-3-cephem-4-carboxylic acid (syn isomer) with conc. hydrochloric acid (0.5 ml) in a mixture of methanol (14 ml) and tetrahydrofuran (4 ml) according to the similar manner to that of Example 31.

IR (Nujol): 3250, 1760, 1680, 1620, 1530 cm$^{-1}$

NMR δppm (DMSO—d$_6$): 3.43 (1H, m), 3.68 (2H, q, J=18 Hz), 4.7 (2H, m), 5.17 (1H, d, J=4 Hz), 5.28 (1H, d, J=12 Hz), 5.53 (1H, d, J=18 Hz), 5.73 (1H, dd, J=4 Hz, 8 Hz), 6.83 (1H, s), 6.92 (1H, dd, J=12 Hz, 18 Hz), 9.67 (1H, d, J=8 Hz)

Example 33

7-[(2-Aminothiazol-4-yl)glyoxylamido]-3-vinyl-3-cephem-4-carboxylic acid (0.76 g) was obtained by reacting 7-[(2-formamidothiazol-4-yl)glyoxylamido]-3-vinyl-3-cephem-4-carboxylic acid (1.23 g) with conc. hydrochloric acid (1.25 ml) in a mixture of methanol (25 ml) and tetrahydrofuran (10 ml) according to the similar manner to that of Example 31.

IR (Nujol): 3300, 3200–3100, 1780, 1660, 1610, 1520 cm$^{-1}$

NMR δppm (DMSO—d$_6$): 3.80 (2H, q, J=17 Hz), 5.28 (1H, d, J=5 Hz), 5.42 (1H, d, J=11 Hz), 5.63 (1H, d, J=18 Hz), 5.82 (1H, dd, J=5 Hz, 8 Hz), 7.05 (1H, dd, J=11 Hz, 18 Hz), 7.92 (1H, s), 9.58 (1H, d, J=8 Hz)

The compounds described in the following Examples 34 to 38 were obtained by reacting the corresponding cephalosporanic acid derivatives having formamido group with conc. hydrochloric acid according to the similar manner to that of Example 31.

Example 34

Pivaloyloxymethyl 7-[2-(2-aminothiazol-4-yl)acetamido]-3-vinyl-3-cephem-4-carboxylate IR (Nujol): 1770, 1750, 1650 cm$^{-1}$

Example 35

Pivaloyloxymethyl 7-[2-(2-aminothiazol-4-yl)-2-propargyloxyiminoacetamido]-3-vinyl-3-cephem-4-carboxylate (syn isomer)

IR (Nujol): 1770, 1740, 1670 cm$^{-1}$

Example 36

Pivaloyloxymethyl 7-[(2-aminothiazol-4-yl)glyoxylamido]-3-vinyl-3-cephem-4-carboxylate IR (Nujol): 1775, 1745, 1660 cm$^{-1}$

Example 37

Hexanoyloxymethyl 7-[2-(2-aminothiazol-4-yl)-2-propargyloxyiminoacetamido]-3-vinyl-3-cephem-4-carboxylate (syn isomer)

IR (Nujol): 1770, 1650 cm$^{-1}$

Example 38

Hexanoyloxymethyl 7-[(2-aminothiazol-4-yl)glyoxylamido]-3-vinyl-3-cephem-4-carboxylate IR (Nujol): 1770, 1660 cm$^{-1}$

Example 39

Sodium 7-[2-(2-aminothiazol-4-yl)acetamido]-3-vinyl-3-cephem-4-carboxylate (1.36 g), which was prepared from 7-[2-(2-aminothiazol-4-yl)acetamido]-3-vinyl-3-cephem-4-carboxylic acid (1.33 g) and sodium bicarbonate (0.304 g), was dissolved in N,N-dimethylformamide (14 ml). To this solution was added iodomethyl pivalate (0.932 g) in N,N-dimethylformamide (3 ml) under ice-cooling, followed by stirring at the same temperature for 10 minutes. After addition of ethyl acetate (80 ml), the reaction mixture was washed twice with water, three times with 5% aqueous solution of sodium bicarbonate and twice with an aqueous solution of sodium chloride in turn, dried over anhydrous magnesium sulfate, and then evaporated to dryness under reduced pressure to give a residue, which was pulverized with diisopropyl ether to obtain pivaloyloxymethyl 7-[2-(2-aminothiazol-4-yl)acetamido]-3-vinyl-3-cephem-4-carboxylate (1.0 g), mp 128°–132° C. (dec.)

IR (Nujol): 1770, 1750, 1650 cm$^{-1}$

NMR δppm (DMSO—d$_6$): 1.18 (9H, s), 3.42 (2H, s), 3.80 (2H, q, J=17 Hz), 5.18 (1H, d, J=5 Hz), 5.40 (1H, d, J=11 Hz), 5.68 (1H, d, J=17 Hz), 5.77 (1H, dd, J=5 Hz, 8 Hz), 5.87 (2H, s), 6.30 (1H, s), 6.87 (2H, broad s), 6.88 (1H, dd, J=11 Hz, 17 Hz), 8.93 (1H, d, J=8 Hz)

Example 40

Privaloyloxymethyl 7-[2-(2-aminothiazol-4-yl)-2-propargyloxyiminoacetamido]-3-vinyl-3-cephem-4-carboxylate (syn isomer) (1.64 g) was obtained by reacting sodium 7-[2-(2-aminothiazol-4-yl)-2-propargyloxyiminoacetamido]-3-vinyl-3-cephem-4-carboxylate (syn isomer) (2 g) with iodomethyl pivalate (1.21 g) according to the similar manner to that of Example 39, mp 163°–185° C. (dec.).

IR (Nujol): 1770, 1740, 1670 cm$^{-1}$

NMR δppm (DMSO—d$_6$): 1.22 (9H, s), 3.5 (1H, s), 3.85 (2H, q, J=18 Hz), 4.75 (1H, s), 5.35 (1H, d, J=5 Hz), 5.45 (1H, d, J=11 Hz), 5.70 (1H, d, J=18 Hz), 5.85 (1H, dd, J=5 Hz, 8 Hz), 5.92 (2H, s), 6.87 (1H, s), 6.88 (1H, dd, J=11 Hz, 18 Hz), 7.32 (2H, m), 9.73 (1H, d, J=8 Hz)

Example 41

Privaloyloxymethyl 7-[(2-aminothiazol-4-yl)glyoxylamido]-3-vinyl-3-cephem-4-carboxylate (0.94 g) was obtained by reacting sodium 7-[(2-aminothiazol-4-yl)glyoxylamido]-3-vinyl-3-cephem-4-carboxylate (1.05 g) with iodomethyl pivalate (0.63 g) according to the similar manner to that of Example 39, mp 108°–115° C.

IR (Nujol): 1775, 1745, 1660 cm$^{-1}$

NMR δppm (DMSO—d$_6$): 1.12 (9H, s), 3.75 (2H, m), 5.22 (1H, d, J=5 Hz), 5.38 (1H, d, J=11 Hz), 5.67 (1H, d, J=18 Hz), 5.78 (1H, dd, J=5 Hz, 8 Hz), 5.83 (2H, s), 6.85 (1H, dd, J=11 Hz, 18 Hz), 7.35 (2H, broad s), 7.83 (1H, s), 9.80 (1H, d, J=8 Hz)

Example 42

To a solution of sodium 7-[2-(2-aminothiazol-4-yl)-2-propargyloxyiminoacetamido]-3-vinyl-3-cephem-4-carboxylate (syn isomer) (2 g) in N,N-dimethylformamide (20 ml) was added a solution of iodomethyl hexanoate (1.28 g) in N,N-dimethylformamide (4 ml) under ice-cooling, and the mixture was stirred at the same temperature for 15 minutes. To the reaction mixture was added ethyl acetate (80 ml), followed by washing twice with water, three times with 5% aqueous solution of sodium bicarbonate and twice with a saturated aqueous solution of sodium chloride. The resultant solution was dried over anhydrous magnesium sulfate and then evaporated to give a residue, which was pulverized with diisopropyl ether to obtain hexanoyloxymethyl 7-[2-(2-aminothiazol-4-yl)-2-propargyloxyiminoacetamido]-3-vinyl-3-cephem-4-carboxylate (syn isomer) (1.85 g), mp 98°–109° C. (dec.).

IR (Nujol): 1770, 1650 cm$^{-1}$

NMR δppm (DMSO—d$_6$): 0.87 (3H, t, J=8 Hz), 1.38 (6H, m), 2.53 (2H, m), 3.47 (1H, s), 3.80 (2H, q, J=18 Hz), 4.72 (2H, s), 5.27 (1H, d, J=5 Hz), 5.42 (1H, d, J=11 Hz), 5.70 (1H, d, J=18 Hz), 5.88 (3H, m), 6.80 (1H, s), 6.80 (1H, dd, J=11 Hz, 18 Hz), 7.25 (2H, broad s), 9.70 (1H, d, J=8 Hz)

Example 43

Hexanoyloxymethyl 7-[(2-aminothiazol-4-yl)glyoxylamido]-3-vinyl-3-cephem-4-carboxylate (0.96 g) was obtained by reacting sodium 7-[(2-aminothiazol-4-yl)glyoxylamido]-3-vinyl-3-cephem-4-carboxylate (1.05 g) with iodomethyl hexanoate (0.666 g) according to the similar manner to that of Example 42, mp 89°–94° C.

IR (Nujol): 1770, 1660 cm$^{-1}$

NMR δppm (DMSO—d$_6$), 0.82 (3H, s), 1.30 (6H, m), 2.30 (2H, t, J=6 Hz), 3.77 (2H, m), 5.22 (1H, d, J=5 Hz), 5.37 (1H, d, J=11 Hz), 5.68 (1H, d, J=18 Hz), 5.77 (1H, dd, J=5 Hz, 8 Hz), 5.83 (2H, s), 6.88 (1H, dd, J=11 Hz, 18 Hz), 7.37 (2H, m), 7.83 (1H, s), 9.78 (1H, d, J=8 Hz)

Example 44

To a solution of benzhydryl 7-amino-3-vinyl-3-cephem-4-carboxylate hydrochloride (4.3 g) and 2,6-lutidine (1.08 g) in methylene chloride (60 ml) were added N-tert-butoxycarbonyl-2-(2-formamidothiazol-4-yl)glycine (3.0 g) and N,N'-dicyclohexylcarbodiimide (2.06 g) under ice-cooling with stirring, and the stirring was continued at the same temperature for an hour and at ambient temperature for additional 3.5 hours. After addition of methylene chloride (100 ml), the reaction mixture was washed with diluted hydrochloric acid, followed by removal of the precipitated substance by filtration. The filtrate was washed with a saturated aqueous solution of sodium bicarbonate and an aqueous solution of sodium chloride, dried over anhydrous magnesium sulfate and then evaporated to give a residue, which was pulverized with diethyl ether to obtain benzhydryl 7-[N-tert-butoxycarbonyl-2-(2-formamidothiazol-4-yl)glycinamido]-3-vinyl-3-cephem-4-carboxylate (5.7 g).

IR (Nujol): 3280, 1780, 1720, 1660, 1630, 1540 cm$^{-1}$

NMR δppm (DMSO—d$_6$): 1.39 (9H, s), 3.65 (2H, q, J=17 Hz), 5.10 (1H, d, J=5 Hz), 5.19 (1H, s), 5.22 (1H, d, J=11 Hz), 5.59 (1H, d, J=18 Hz), 5.74 (1H, dd, J=4 Hz, 8 Hz), 6.68 (1H, dd, J=11 Hz), 18 Hz), 6.93 (1H, s), 7.00–7.70 (12H, m), 9.24 (1H, d, J=8 Hz)

Example 45

Benzhydryl 7-[N-tert-butoxycarbonyl-2-{2-(2,2,2-trifluoroacetamido)thiazol-4-yl}glycinamido]-3-vinyl-3-cephem-4-carboxylate (4.1 g) was obtained by reacting benzhydryl 7-amino-3-vinyl-3-cephem-4-carboxylate (3.4 g) with N-tert-butoxycarbonyl-2-[2-(2,2,2-trifluoroacetamido)thiazol-4-yl]glycine (3.3 g) according to the similar manner to that of Example 44.

IR (Nujol): 3270, 1780, 1720, 1670, 1560 cm$^{-1}$

NMR δppm (DMSO—d$_6$): 1.43 (9H, s), 3.77 (2H, m), 5.15–6.00 (5H, m), 6.82 (1H, dd, J=11 Hz, 18 Hz), 7.00 (1H, s), 7.10–7.70 (11H, m), 9.27 (1H, d, J=8 Hz)

Example 46

To a suspension of benzhydryl 7-[N-tert-butoxycarbonyl-2-(2-aminothiazol-4-yl)glycinamido]-3-vinyl-3-cephem-4-carboxylate (3.9 g) in methylene chloride (20 ml) were added trifluoroacetic acid (13.7 g) and anisole (3.8 g) under ice-cooling, and the mixture was stirred at ambient temperature for an hour. After evaporation of the reaction mixture, to the residue were added water (100 ml) and ethyl acetate, followed by adjusting to pH 7 with 2N aqueous solution of sodium bicarbonate. The precipitated solid was removed by filtration and the aqueous layer was separated out. Thereto was added ethyl acetate, followed by adjusting to pH 5 with 10% hydrochloric acid. After separating out the aqueous layer, the organic solvent was completely removed therefrom by evaporation, and then the resultant aqueous solution was adjusted to pH 4 with 10% hydrochloric acid under cooling, followed by subjecting to column chromatography on a nonionic adsorption resin "Diaion HP-20" (120 ml). After washing with water (270 ml), elution was carried out with 10% isopropyl alcohol and then 30% isopropyl alcohol, and the fractions containing the desired compound were collected and evaporated under reduced pressure to give a residue, which was lyophilized to obtain 7-[2-(2-aminothiazol-4-yl)glycinamido]-3-vinyl-3-cephem-4-carboxylic acid (0.8 g).

IR (Nujol): 3400–3100, 1760, 1670, 1610, 1520 cm$^{-1}$

NMR δppm (D$_2$O+NaHCO$_3$): 3.68 (2H, broad s), 5.08 (1H, s), 5.08 (1H, d, J=5 Hz), 5.25 (1H, d, J=11 Hz), 5.40 (1H, d, J=18 Hz), 5.70 (1H, d, J=5 Hz), 6.73 (1H, s), 6.80 (1H, dd, J=11 Hz, 18 Hz)

Example 47

A mixture of benzhydryl 7-[N-tert-butoxycarbonyl-2-(2-formamidothiazol-4-yl)glycinamido]-3-vinyl-3-cephem-4-carboxylate (5.6 g) and conc. hydrochloric acid (2.6 ml) in methanol (60 ml) and tetrahydrofuran (15 ml) was stirred at ambient temperature for 2.5 hours. The precipitated substance in the reaction mixture was collected by filtration, and washed with a mixture of methanol and water (1:2 by volume) and then water, followed by drying to give benzhydryl 7-[N-tert-butoxycarbonyl-2-(2-aminothiazol-4-yl)glycinamido]-3-vinyl-3-cephem-4-carboxylate (0.4 g).

IR (Nujol): 3300, 1770, 1710, 1650, 1620, 1570, 1510 cm$^{-1}$

NMR δppm (DMSO—d$_6$): 1.40 (9H, s), 3.67 (2H, broad s), 5.00–6.00 (5H, m), 6.47 (1H, s), 6.97 (1H, s), 6.67–7.67 (12H, m), 9.00 (1H, m)

Example 48

A mixture of benzhydryl 7-[N-tert-butoxycarbonyl-2-{2-(2,2,2-trifluoroacetamido)thiazol-4-yl}glycinamido]-3-vinyl-3-cephem-4-carboxylate (2.5 g) and sodium acetate (2.8 g) in tetrahydrofuran (20 ml), acetone (20 ml) and water (40 ml) was stirred at ambient temperature for 2 hours. After the reaction mixture was evaporated, the residue was extracted with ethyl acetate. The extract was washed with an aqueous solution of sodium chloride, dried over anhydrous magnesium sulfate and then evaporated to give a residue, which was subjected to column chromatography on silica gel (50 g). Elution was carried out with methylene chloride and then a mixture of methylene chloride and diethyl ether (9:1 by volume), and the fractions containing the desired compound were collected and evaporated to give benzhydryl 7-[N-tert-butoxycarbonyl-2-(2-aminothiazol-4-yl)glycinamido]-3-vinyl-3-cephem-4-carboxylate (1.0 g).

IR (Nujol): 3300, 1770, 1710, 1650, 1620, 1570, 1510 cm$^{-1}$

Example 49

To a solution of 7-[(2-aminothiazol-4-yl)glyoxylamido]-3-vinyl-3-cephem-4-carboxylic acid (2.35 g) in methanol (100 ml) was added sodium borohydride (0.34 g) at 5°–10° C., and the mixture was stirred at the same temperature for 5 minutes. After the reaction mixture was adjusted to pH 5 with 10% hydrochloric acid, the methanol was removed by evaporation, and the remained aqueous solution was adjusted to pH 5 with 10% hydrochloric acid, which was subjected to column chromatography on a nonionic adsorption resin "Diaion HP-20" (70 ml). After washing with water (140 ml), elution was carried out with 30% isopropyl alcohol (140 ml), and the fractions containing the desired compound were collected. After removal of the isopropyl alcohol therefrom, the remained aqueous solution was lyophilized to give 7-[2-(2-aminothiazol-4-yl)-DL-glycolamido]-3-vinyl-3-cephem-4-carboxylic acid (2.01 g).

IR (Nujol): 1755, 1650 cm$^{-1}$

NMR δppm (DMSO—d$_6$): 3.48 (2H, m), 3.83 (1H, broad s), 4.83 (1H, s), 4.98 (1H, d, J=5 Hz), 5.2 (1H, d, J=11 Hz), 5.47 (1H, d, J=18 Hz), 5.5, 5.53 (1H, dd, J=5 Hz, 8 Hz), 6.37 (1H, s), 6.85 (2H, m), 7.07 (1H, dd, J=11 Hz, 18 Hz), 8.17, 8.27 (1H, d, J=8 Hz)

Example 50

7-[2-(2-Aminothiazol-4-yl)glycinamido]-3-vinyl-3-cephem-4-carboxylic acid was obtained by reacting 7-amino-3-vinyl-3-cephem-4-carboxylic acid with 2-(2-aminothiazol-4-yl)glycine according to the similar manner to that of Example 2.

IR (Nujol): 3400–3100, 1760, 1670, 1610, 1520 cm$^{-1}$

Example 51

A mixture of 2-(2-methanesulfonamidothiazol-4-yl)acetic acid (2.6 g), N,N-dimethylformamide (0.88 g) and phosphorus oxychloride (1.85 g) in ethyl acetate (10 ml) and tetrahydrofuran (20 ml) was stirred under ice-cooling for 30 minutes. This solution was added to a solution of benzhydryl 7-amino-3-vinyl-3-cephem-4-carboxylate hydrochloride (4.3 g) and trimethylsilylacetamide (7.9 g) in ethyl acetate (50 ml) at −20° C. with stirring, and the stirring was continued at −20° to 0° C. for 2 hours. After addition of water, tetrahydrofuran and ethyl acetate, the reaction mixture was adjusted to pH 7 with a saturated aqueous solution of sodium bicarbonate. The precipitated substance was collected by filtration to give benzhydryl 7-[2-(2-methanesulfonamidothiazol-4-yl)acetamido]-3-vinyl-3-cephem-4-carboxylates (3.6 g). After addition of ethyl acetate tetrahydrofuran to the filtrate, the organic layer was separated out, washed with an aqueous solution of sodium chloride and then dried over anhydrous magnesium sulfate, followed by evaporation to recover the same product (0.9 g). Total yield: 4.5 g.

I.R. (Nujol): 3250, 1760, 1700, 1650, 1610, 1600 cm$^{-1}$

N.M.R. δppm (DMSO—d$_6$): 2.88 (3H, s), 3.75 (2H, q, J=17 Hz), 5.20 (1H, d, J=5 Hz), 5.23 (1H, d, J=11 Hz), 5.62 (1H, d, J=17 Hz), 5.77 (1H, dd, J=5 Hz, 8 Hz), 6.51 (1H, s), 6.74 (1H, dd, J=11 Hz, 17 Hz), 6.94 (1H, s), 7.10–7.54 (10H, m), 9.22 (1H, d, J=8 Hz)

Example 52

Benzhydryl 7-[2-(2-formamidothiazol-5-yl)acetamido]-3-vinyl-3-cephem-4-carboxylate (11.48 g), mp 173° C. (dec.) was obtained by reacting benzhydryl 7-amino-3-vinyl-3-cephem-4-carboxylate hydrochloride (10.3 g) with the activated acid, which was prepared from 2-(2-formamidothiazol-5-yl)acetic acid (5.4 g), N,N-dimethylformamide (2.56 g) and phosphorus oxychloride (5.34 g), in a conventional manner according to the similar manner to that of Example 51.

I.R. (Nujol): 3270, 1770, 1715, 1680 cm$^{-1}$

N.M.R. δppm (DMSO—d$_6$): 3.78 (2H, s), 3.79 (2H, q, J=18 Hz), 5.24 (1H, d, J=5 Hz), 5.3–6.0 (3H, m), 6.5–7.1 (1H, m), 6.97 (1H, s), 7.2–7.7 (11H, m), 8.46 (1H, s), 9.23 (1H, d, J=8 Hz)

Example 53

The activated acid, which was prepared from 2-tert-butoxycarbonylmethoxyimino-2-(2-formamidothiazol-4-yl)acetic acid (syn isomer) (13.8 g), N,N-dimethylformamide (3.66 g) and phosphorus oxychloride (7.7 g) in tetrahydrofuran (80 ml) in a conventional manner, was added to a solution of benzhydryl 7-amino-3-vinyl-3-cephem-4-carboxylate hydrochloride (15 g) and trimethylsilylacetamide (32 g) in ethyl acetate (150 ml) at −20° C. with stirring, and the stirring was continued at the same temperature for half an hour. After addition of water (100 ml), the ethyl acetate layer was separated out, and washed with an aqueous solution of sodium chloride, an aqueous solution of sodium bicarbonate and then an aqueous solution of sodium chloride in turn, followed by drying over anhydrous magnesium sulfate. Removal of the solvent gave an oil, which was pulverized with diisopropyl ether and washed with the same to obtain benzhydryl 7-[2-tert-butoxycarbonylmethoxyimino-2-(2-formamidothiazol-4-yl)acetamido]-3-vinyl-3-cephem-4-carboxylate (syn isomer) (23.1 ) g), mp 101° C. (dec.).

I.R. (Nujol): 3250, 1780, 1720, 1680, 1540 cm$^{-1}$

N.M.R. δppm (DMSO—d$_6$): 1.45 (9H, s), 3.77 (2H, q, J=18 Hz), 4.64 (2H, s), 5.32 (1H, d, J=5 Hz), 5.2–6.0 (2H, m), 5.97 (1H, dd, J=5 Hz, 8 Hz), 6.5–7.6 (1H, m), 6.98 (1H, s), 7.2–7.8 (11H, m), 8.55 (1H, s), 9.68 (1H, d, J=8 Hz), 12.71 (1H, broad s)

Example 54

To a suspension of benzhydryl 7-amino-3-vinyl-3-cephem-4-carboxylate hydrochloride (4.3 g) in methylene chloride (100 ml) was added 2,6-lutidine (1.08 g) at 108° C., and the mixture was stirred for a while. To the resultant solution were added 2-(2-methanesulfonamidothiazol-5-yl)acetic acid (2.6 g) and dicyclohexylcarbodiimide (2.06 g) under ice-cooling with stirring, and the stirring was continued at the same temperature for an hour and then at ambient temperature for additional 3.5 hours. After addition of water, the precipitated substance was removed by filtration. The filtrate was washed with 10% hydrochloric acid, and the organic layer was separated out, and washed with a saturated aqueous solution of sodium bicarbonate and an aqueous solution of sodium chloride, followed by drying over anhydrous magnesium sulfate. Removal of the solvent gave a residue, which was washed with diethyl ether to obtain benzhydryl 7-[2-(2-methanesulfonamidothiazol-5-yl)acetamido]-3-vinyl-3-cephem-4-carboxylate (1.8 g). The same product (1.8 g) was recovered from the removed substance obtained above. Total yield: 3.6 g.

I.R. (Nujol): 3320, 1770, 1710, 1660, 1620, 1570, 1520 cm$^{-1}$

N.M.R. δppm (DMSO—d$_6$): 2.90 (3H, s), 3.67 (2H, m), 5.22 (1H, d, J=5 Hz), 5.30 (1H, d, J=11 Hz), 5.62 (1H, d, J=17 Hz), 5.77 (1H, dd, J=5 Hz, 8 Hz), 6.75 (1H, dd, J=11 Hz, 17 Hz), 6.95 (1H, s), 7.03 (1H, s), 7.17–7.60 (10H, m), 9.145 (1H, dd, J=5 Hz, 8 Hz)

The following compounds were obtained by reacting 7-amino-3-vinyl cephalosporanic acid derivatives with the corresponding acids according to the similar manner to that of Example 53.

Example 55

7-[2-(2-Aminothiazol-5-yl)acetamido]-3-vinyl-3-cephem-4-carboxylic acid

I.R. (Nujol): 3350, 3280, 1725, 1650, 1540 cm$^{-1}$

Example 56

Hexanoyloxymethyl 7-[2-(2-aminothiazol-4-yl)acetamido]-3-vinyl-3-cephem-4-carboxylate I.R. (Nujol): 3250, 1765, 1655 cm$^{-1}$

Example 57

Phthalid-3-yl 7-[2-(2-aminothiazol-4-yl)acetamido]-3-vinyl-3-cephem-4-carboxylate I.R. (Nujol): 3250, 1780, 1760, 1650 cm$^{-1}$

Example 58

7-[2-(2-Guanidinothiazol-4-yl)acetamido]-3-vinyl-3-cephem-4-carboxylic acid hydrobromide I.R. (Nujol): 3400–3100, 1760, 1680, 1660, 1620, 1540 cm$^{-1}$

Example 59

Phthalid-3-yl 7-[(2-aminothiazol-4-yl)glyoxylamido]-3-vinyl-3-cephem-4-carboxylate I.R. (Nujol): 3300, 1770, 1650 cm$^{-1}$

Example 60

Pivaloyloxymethyl 7-[2-(2-aminothiazol-4-yl)-2-methoxyiminoacetamido]-3-vinyl-3-cephem-4-carboxylate (syn isomer)

I.R. (Nujol): 3400–3100, 1770, 1745, 1670, 1610, 1530 cm$^{-1}$

Example 61

Phthalid-3-yl 7-[2-(2-aminothiazol-4-yl)-2-methoxyiminoacetamido]-3-vinyl-3-cephem-4-carboxylate (syn isomer)

I.R. (Nujol): 3300, 1775, 1670, 1610, 1530 cm$^{-1}$

Example 62

Benzhydryl 7-[2-(2-aminothiazol-4-yl)-2-tert-butoxycarbonylmethoxyiminoacetamido]-3-vinyl-3-cephem-4-carboxylate (syn isomer)

I.R. (Nujol): 3440, 3260, 3100, 1780, 1720, 1660, 1530 cm$^{-1}$

Example 63

A mixture of 7-[2-(2-formamidothiazol-5-yl)acetamido]-3-vinyl-3-cephem-4-carboxylic acid (4.67 g) and conc. hydrochloric acid (4.67 g) in methanol (93 ml) and tetrahydrofuran (46 ml) was stirred at 30° C. for 4 hours. After the organic solvent was removed by evaporation, to the residue was added water (70 ml), followed by adjusting to pH 6 to 7 with 10% aqueous solution of sodium hydroxide. After the insoluble substance was removed by filtration, the filtrate was adjusted to pH 3.0 with 10% hydrochloric acid under cooling, followed by stirring at the same temperature for 20 minutes. The precipitated substance was collected by filtration, washed with water and dried to give a residue, which was dissolved in an aqueous solution of sodium bicarbonate and then chromatographed on alumina (12 ml) using 5% aqueous sodium acetate as an eluant. The fractions containing the desired compound were collected and acidified to pH 3.1 with 10% hydrochloric acid, and the precipitated substance was collected by filtration and then dried to give 7-[2-(2-aminothiazol-5-yl)acetamido]-3-vinyl-3-cephem-4-carboxylic acid (1.53 g), mp>290° C.

I.R. (Nujol): 3550, 3280, 1725, 1650, 1540 cm$^{-1}$

N.M.R. δppm (DMSO—d$_6$): 3.53 (2H, s), 3.70 (2H, q, J=18 Hz), 5.12 (1H, d, J=5 Hz), 5.2–5.8 (2H, m), 5.67 (1H, dd, J=5 Hz, 8 Hz), 6.73 (1H, s), 6.7–7.4 (1H, m), 9.07 (1H, d, J=8 Hz)

Example 64

A mixture of benzhydryl 7-[2-tert-butoxycarbonylmethoxyimino-2-(2-formamidothiazol-4-yl)acetamido]-3-vinyl-3-cephem-4-carboxylate (syn isomer) (19.0 g)· and conc. hydrochloride acid (11.6 g) in methanol (380 ml) was stirred at ambient temperature for 15 minutes. After addition of water (200 ml), the reaction mixture was neutralized with sodium bicarbonate, followed by removing the methanol under reduced pressure. The resultant aqueous solution was extracted three times with ethyl acetate, and the combined extract was washed with water and an aqueous solution of sodium chloride, and then dried over anhydrous magnesium sulfate. Removal of the solvent gave an oil, which was pulverized with diisopropyl ether to obtain benzhydryl 7-[2-(2-aminothiazol-4-yl)-2-tert-butoxycarbonylmethoxyiminoacetamido]-3-vinyl-3-cephem-4-carboxylate (syn isomer) (15.3 g).

I.R. (Nujol): 3440, 3260, 3100, 1780, 1720, 1660, 1530 cm$^{-1}$

N.M.R. δppm DMSO—d$_6$): 1.44 (9H, s), 3.77 (2H, q, J=18 Hz), 4.58 (2H, s), 5.29 (1H, d, J=5 Hz), 5.1–5.9 (2H, m), 5.90 (1H, dd, J=5 Hz, 8 Hz), 6.5–7.8 (13H, m), 6.83 (1H, s), 6.93 (1H, s), 9.56 (1H, d, J=8 Hz)

The following compounds were obtained by reacting 7-acylamino-3-vinyl cephalosporanic acid derivatives having a formamido group with hydrochloric acid according to the similar manner to that of Example 64.

Example 65

Hexanoyloxymethyl 7-[2-(2-aminothiazol-4-yl)acetamido]-3-vinyl-3-cephem-4-carboxylate I.R. (Nujol): 3250, 1765, 1655 cm$^{-1}$

Example 66

Phthalid-3-yl 7-[2-(2-aminothiazol-4yl)acetamido]-3-vinyl-3-cephem-4-carboxylate I.R. (Nujol): 3250, 1780, 1760, 1650 cm$^{-1}$

Example 67

Phthalid-3-yl 7-[(2-aminothiazol-4-yl)glyoxylamido]-3-vinyl-3-cephem-4-carboxylate I.R. (Nujol): 3300, 1770, 1650 cm$^{-1}$

Example 68

Pivaloyloxymethyl 7-[2-(2-aminothiazol-4-yl)-2-methoxyiminoacetamido]-3-vinyl-3-cephem-4-carboxylate (syn isomer)

I.R. (Nujol): 3400–3100, 1770, 1745, 1670, 1610, 1530 cm$^{-1}$

Example 69

Phthalid-3-yl 7-[2-(2-aminothiazol-4-yl)-2-methoxyiminoacetamido]-3-vinyl-3-cephem-4-carboxylate (syn isomer)

I.R. (Nujol): 3300, 1775, 1670, 1610, 1530 cm$^{-1}$

Example 70

7-[2-(2-Aminothiazol-4-yl)-2-carboxymethoxyiminoacetamido]-3-vinyl-3-cephem-4-carboxylic acid (syn isomer)

I.R. (Nujol): 3350, 1770, 1680, 1640 cm$^{-1}$

Example 71

Pivaloyloxymethyl 7-[2-(2-aminothiazol-4-yl)-DL-glycolamido]-3-vinyl-3-cephem-4-carboxylate I.R. (Nujol): 3370, 1780, 1750, 1680, 1620 cm$^{-1}$

Example 72

Phthalid-3-yl 7-[2-(2-aminothiazol-4-yl)-DL-glycolamido]-3-vinyl-3-cephem-4-carboxylate I.R. (Nujol): 1770, 1740, 1660, 1610 cm$^{-1}$

Example 73

To a suspension of benzhydryl 7-[2-(2-methanesulfonamidothiazol-4-yl)acetamido]-3-vinyl-3-cephem-4-carboxylate (4.5 g) in methylene chloride (30 ml) and anisole (4.6 g) was added 2,2,2-trifluoroacetic acid (16.8 g) under ice-cooling, and the solution was stirred at ambient temperature for an hour. After evaporation of the reaction mixture, thereto were added water and ethyl acetate, followed by adjusting to pH 7 with 1N aqueous solution of sodium hydroxide. To the separated aqueous layer were added ethyl acetate and tetrahydrofuran, followed by adjusting to pH 2 with 10% hydrochloric acid. After the organic layer was separated out, it was washed with an aqueous solution of sodium chloride and then dried over anhydrous magnesium sulfate. Removal of the solvent gave a residue, which was washed with diethyl ether to obtain 7-[2-(2-methanesulfonamidothiazol-4-yl)acetamido]-3-vinyl-3-cephem-4-carboxylic acid (1.5 g).

I.R. (Nujol): 3260, 3140, 3080, 1770, 1700, 1660, 1610, 1540 cm$^{-1}$

N.M.R. $\delta$ppm (DMSO—d$_6$): 2.88 (3H, s), 3.53 (2H, s), 3.72 (2H, q, J=18 Hz), 5.13 (1H, d, J=5 Hz), 5.30 (1H, d, J=11 Hz), 5.57 (1H, d, J=18 Hz), 5.68 (1H, dd, J=5 Hz, 8 Hz), 6.50 (1H, s), 6.95 (1H, dd, J=11 Hz, 18 Hz), 9.07 (1H, d, J=8 Hz)

Example 74

7-[2-(2-Methanesulfonamidothiazol-5-yl)acetamido]-3-vinyl-3-cephem-4-carboxylic acid (2.1 g) was obtained by reacting benzhydryl 7-[2-(2-methanesulfonamidothiazol-5-yl)acetamido]-3-vinyl-3-cephem-4-carboxylate (3.6 g) with 2,2,2-trifluoroacetic acid (13.2 g) in the presence of anisole (3.7 g) according to the similar manner to that of Example 73.

I.R. (Nujol): 3250, 3110, 1770, 1705, 1660, 1560, 1530 cm$^{-1}$

N.M.R. $\delta$ppm (DMSO—d$_6$): 2.88 (3H, s), 3.58 (2H, s), 3.68 (2H, q, J=18 Hz), 5.13 (1H, d, J=5 Hz), 5.32 (1H, d, J=12 Hz), 5.56 (1H, d, J=18 Hz), 5.68 (1H, dd, J=5 Hz, 8 Hz), 6.95 (1H, dd, J=12 Hz, 18 Hz), 7.07 (1H, s), 9.20 (1H, d, J=8 Hz)

The following compounds were obtained by reacting 7-acylamino-3-vinyl cephalosporanic acid derivatives having benzhydryl ester with 2,2,2-trifluoroacetic acid in the presence of anisole according to the similar manner to that of Example 73.

Example 75

7-[2-(2-Aminothiazol-5-yl)acetamido]-3-vinyl-3-cephem-4-carboxylic acid

I.R. (Nujol): 3550, 3280, 1725, 1650, 1540 cm$^{-1}$

Example 76

7-[2-(2-Guanidinothiazol-4-yl)acetamido]-3-vinyl-3-cephem-4-carboxylic acid hydrobromide I.R. (Nujol): 3400–3100, 1760, 1680, 1660, 1620, 1540 cm$^{-1}$

Example 77

To a suspension of benzhydryl 7-[2-(2-formamidothiazol-5-yl)acetamido]-3-vinyl-3-cephem-4-carboxylate (11.48 g) in methylene chloride (57.4 ml) and anisole (15 ml) was added 2,2,2-trifluoroacetic acid (46 ml) under ice-cooling, and the mixture was stirred at 7° to 8° C. for 15 minutes. After the reaction mixture was poured into diisopropyl ether (600 ml), it was stirred under ice-cooling for 20 minutes, followed by collecting the insoluble substance by filtration and washing it with diisopropyl ether. This substance (11.4 g) was suspended in water (150 ml) adjusted to pH 6.5 with sodium bicarbonate and then treated with charcoal. The resultant filtrate was adjusted to pH 2.0 with 10% hydrochloric acid, and the precipitated substance was collected by filtration, washed with water and then dried to give 7-[2-(2-formamidothiazol-5-yl)acetamido]-3-vinyl-3-cephem-4-carboxylic acid (5.88 g), mp 200° C. (dec.).

I.R. (Nujol): 3260, 3220, 3050, 1780, 1750, 1670, 1540 cm$^{-1}$

N.M.R. $\delta$ppm (DMSO—d$_6$): 3.71 (2H, q, J=18 Hz), 3.76 (2H, s), 5.15 (1H, d, J=5 Hz), 5.3–6.9 (3H, m), 6.6–7.2 (1H, m), 7.29 (1H, s), 8.50 (1H, s), 9.24 (1H, d, J=8 Hz)

Example 78

(1) To a suspension of 7-[2-(2-aminothiazol-4-yl)-DL-glycolamido]-3-vinyl-3-cephem-4-carboxylic acid (6.2 g) in water (60 ml) was added sodium bicarbonate (1.36 g) with stirring, and the stirring was continued for a while. The resultant solution was lyophilized to prepare sodium 7-[2-(2-aminothiazol-4-yl)-DL-glycolamido]-3-vinyl-3-cephem-4-carboxylate (6.50 g).

(2) Thus prepared product (9.5 g) was suspended in N,N-dimethylformamide (95.0 ml), and the suspension was stirred under ice-cooling in a stream of nitrogen gas for 5 minutes. To the resultant solution was added dropwise a solution of iodomethyl pivalate (5.7 g) in N,N-dimethylformamide (10 ml) under ice-cooling, and the mixture was stirred at the same temperature for 10 minutes. After the reaction mixture was poured into a mixture of water and ethyl acetate, it was stirred for a while. The organic layer was separated out and the remainder aqueous solution as further extracted with ethyl acetate. This extract and the organic layer obtained above were combined, washed three times with a saturated aqueous solution of sodium chloride, dried over anhydrous magnesium sulfate and then evaporated. To the residue was added diisopropyl ether, and the suspension was stirred for a while. The insoluble substance was collected by decantation and this operation was repeated three times to obtain pivaloyloxymethyl 7-[2-(2-aminothiazol-4-yl)-DL-glycolamido]-3-vinyl-3-cephem-4-carboxylate (8.8 g), mp 90°-94° C.

I.R. (Nujol): 3370, 1780, 1750, 1680, 1620 cm$^{-1}$

N.M.R. δppm (DMSO-d$_6$): 1.18(9H, m), 3.77(2H, q, J=18.0Hz), 4.90(1H, m), 5.19 (1H, d, J=5.0Hz), 5.36(1H, d, J=12.0Hz), 5.50-6.22(4H, m), 6.43(1H, s), 6.84(1H, dd, J=12.0Hz, 18.0Hz), 8.36(d, J=8.0Hz) } (1H)
8.47(d, J=8.0Hz)

Example 79

Sodium 7-[2-(2-aminothiazol-4-yl)-2-methoxyiminoacetamido]-3-vinyl-3-cephem-4-carboxylate (syn isomer) (2.9 g), which was prepared from 7-[2-(2-aminothiazol-4-yl)-2-methoxyiminoacetamido]-3-vinyl-3-cephem-4-carboxylic acid and sodium bicarbonate in substantially the same manner as that of Example 78-(1), was dissolved in N,N-dimethylformamide (30 ml), and thereto was added dropwise a solution of iodomethyl pivalate (1.62 g) in N,N-dimethylformamide (5 ml) under ice-cooling with stirring, and the stirring was continued at the same temperature for 10 minutes. To the reaction mixture were added ethyl acetate (200 ml) and water (150 ml), followed by separating out the organic layer, which was washed with a saturated aqueous solution of sodium bicarbonate and an aqueous solution of sodium chloride, and then dried over anhydrous magnesium sulfate. Removal of the solvent gave an oil, which was pulverized with diisopropyl ether to obtain pivaloyloxymethyl 7-[2-(2-aminothiazol-4yl)-2-methoxyiminoacetamido]-3-vinyl-3-cephem-4-carboxylate (syn isomer) (2.1 g).

I.R. (Nujol): 3400-3100, 1770, 1745, 1670, 1610, 1530 cm$^{-1}$

N.M.R. δppm (DMSO—d$_6$): 1.18 (9H, s), 3.77 (2H, q, J=18 Hz), 3.84 (3H, s), 5.23 (1H, d, J=5 Hz), 5.38 (1H, d, J=11 Hz), 5.69 (1H, d, J=18 Hz), 5.64–6.00 (3H, m), 6.75 (1H, s), 6.82 (1H, dd, J=11 Hz, 18 Hz), 7.24 (2H, broad s), 9.60 (1H, d, J=8 Hz)

Example 80

To a solution of sodium 7-[2-(2-aminothiazol-4-yl)acetamido]-3-vinyl-3-cephem-4-carboxylate (2.0 g) in N,N-dimethylformamide (20 ml) were added iodomethyl hexanoate (3.4 g) and sodium iodide (3.1 g) in a stream of nitrogen, and the mixture was stirred at ambient temperature for 1.5 hours. After the reaction mixture was poured into a mixture of ethyl acetate (200 ml) and water (200 ml), the organic layer was separated out, washed with water and a saturated aqueous solution of sodium chloride, and then dried over anhydrous magnesium sulfate, followed by treating with charcoal. The filtrate was concentrated, and thereto was added diisopropyl ether, followed by collecting the precipitated substance by filtration to obtain hexanoyloxymethyl 7-[2-(2-aminothiazol-4-yl)acetamido]-3-vinyl-3-cephem-4-carboxylate (1.5 g).

I.R. (Nujol): 3250, 1765, 1655 cm$^{-1}$

N.M.R. (DMSO—d$_6$): 1.2 (10H, m), 2.41 (2H, m), 3.40 (2H, s), 3.75 (2H, q, J=16 Hz), 5.15 (1H, d, J=5 Hz), 5.58 (3H, m), 5.82 (2H, s), 6.23 (1H, s), 6.72 (1H, dd, J=12 Hz, 18 Hz), 6.90 (2H, m), 8.87 (1H, d, J=8 Hz)

Example 81

To a solution of 7-[(2-aminothiazol-4-yl)glyoxylamido]-3-vinyl-3-cephem-4-carboxylic acid (1.0 g) in N,N-dimethylformamide (10 ml) were added triethylamine (0.27 g), 3-bromophthalide (0.56 g) and sodium iodide (0.39 g) at 10° C. with stirring, and the stirring was continued at the same temperature for half an hour. After the reaction mixture was poured into water (50 ml), it was extracted with a mixture of tetrahydrofuran and ethyl acetate (1:1 by volume). The extract was washed with a saturated aqueous solution of sodium chloride and then dried over anhydrous magnesium sulfate, followed by evaporation to give an oil, which was pulverized with diisopropyl ether to obtain phthalid-3-yl 7-[(2-aminothiazol-4-yl)glyoxylamido]-3-vinyl-3-cephem-4-carboxylate (1.0 g).

I.R. (Nujol): 3300, 1770, 1650 cm$^{-1}$

Example 82

To a solution of sodium 7-[2-(2-aminothiazol-4-yl)-2-methoxyiminoacetamido]-3-vinyl-3-cephem-4-carboxylate (syn isomer) (2.16 g) in N,N-dimethylformamide (20 ml) were added 3-bromophthalide (1.3 g) and sodium iodide (1.35 g), and the mixture was stirred at ambient temperature for 40 minutes. Thereto were added ethyl acetate (100 ml) and water (50 ml), and the separated ethyl acetate layer was washed with a saturated aqueous solution of sodium bicarbonate and an aqueous solution of sodium chloride, and then dried over anhydrous magnesium sulfate. After removal of the solvent, the residue (2.6 g) was chromatographed on silica gel (50 g) using a mixture of benzene and ethyl acetate as an eluent. The fractions containing the desired compound were collected and evaporated to give phthalid-3-yl 7-[2-(2-aminothiazol-4-yl)-2-methoxyiminoacetamido]-3-vinyl-3-cephem-4-carboxylate (syn isomer) (1.4 g).

I.R. (Nujol): 3300, 1775, 1670, 1610, 1530 cm$^{-1}$

N.M.R. δppm (DMSO-d$_6$): 3.80(2H, m), 3.88(3H, s), 5.23(1H, d, J=4Hz), 5.20-6.00 (3H, m),
6.78(s) } (1H), 7.05(1H, dd, J=11Hz, 17(Hz),
6.82(s)
7.65(s) } (1H), 7.67-8.10
7.68(s)   (4H, m),
9.67(d, J=8Hz) } (1H)
9.70(d, J=8Hz)

Example 83

To a solution of 7-[2-(2-aminothiazol-4-yl)acetamido]-3-vinyl-3-cephem-4-carboxylic acid (2.0 g) in N,N-dimethylformamide (15 ml) were added triethylamine (0.55 g), 3-bromophthalide (1.2 g) and sodium iodide (0.82 g) in turn in a stream of nitrogen, and the mixture was stirred at ambient temperature for half an hour. After the reaction mixture was poured into a mixture of ethyl acetate (300 ml) and water (200 ml), the organic layer was separated out, washed with water and a saturated aqueous solution of sodium chloride, and then dried over anhydrous magnesium sulfate, followed by treating with charcoal. After the filtrate was concentrated and thereto was added diethyl ether. The precipitated substance was collected by filtration to obtain phthalid-3-yl 7-[2-(2-aminothiazol-4-yl)acetamido]-3-vinyl-3-cephem-4-carboxylate (1.5 g).

I.R. (Nujol): 3250, 1780, 1760, 1650 cm$^{-1}$

N.M.R. δppm (DMSO-d$_6$): 3.43(2H, s), 3.80(2H, m), 5.15(1H, d, J=5Hz), 5.6(3H, m), 6.23 (1H, s), 6.87(2H, m), 7.03(1H, dd, J=12Hz, 18Hz), 7.60(s) ⎫ 7.63(s) ⎬ (1H), 7.8(4H, m), 8.83(d, J=8Hz) ⎫ 8.86(d, J=8Hz) ⎬ (1H)

Example 84

Phthalid-3-yl 7-[2-(2-aminothiazol-4-yl)-DL-glycolamido]-3-vinyl-3-cephem-4-carboxylate was obtained according to the similar manner to that of Example 83.

I.R. (Nujol): 1770, 1740, 1660, 1610 cm$^{-1}$

Example 85

To a solution of phthalid-3-yl 7-[(2-aminothiazol-4-yl)glyoxylamido]-3-vinyl-3-cephem-4-carboxylate (0.3 g) in methanol (9.0 ml) and tetrahydrofuran (3.0 ml) was added sodium borohydride (0.012 g) under ice-cooling, and the mixture was stirred at the same temperature for 30 minutes. After removal of the solvent, the residue was dissolved in a mixture of water (15 ml), tetrahydrofuran (15 ml) and ethyl acetate (15 ml), followed by adjusting to pH 7.0 with 10% hydrochloric acid. The separated organic layer was washed twice with a saturated aqueous solution of sodium chloride and then dried over anhydrous magnesium sulfate. After removal of the solvent, the residue was chromatographed on silica gel using a mixture of ethyl acetate and chloroform (17:3 by volume) as an eluent. The fractions containing the desired compound were collected and evaporated to dryness to give a residue, which was pulverized with diisopropyl ether and washed with the same to obtain phthalid-3-yl 7-[2-(2-aminothiazol-4-yl)-DL-glycolamido]-3-vinyl-3-cephem-4-carboxylate (0.14 g), mp 118°–120° C. (dec.).

I.R. (Nujol): 1770, 1740, 1660, 1610 cm$^{-1}$

N.M.R. (DMSO—d$_6$): 3.80 (2H, m), 4.84 (1H, m), 5.14 (1H, d, J=4.0 Hz), 5.19–6.04 (3H, m), 6.38 (1H, s), 6.93 (1H, m), 7.54–8.04 (5H, m), 8.33 (1H, m)

Example 86

Pivaloyloxymethyl 7-[2-(2-aminothiazol-4-yl)-DL-glycolamido]-3-vinyl-3-cephem-4-carboxylate was obtained according to the similar manner to that of Example 85.

I.R. (Nujol): 3370, 1780, 1750, 1680, 1620 cm$^{-1}$

Example 87

A suspension of 7-amino-3-vinyl-3-cephem-4-carboxylic acid (1.95 g) and trimethylsilylacetamide (5.6 g) in ethyl acetate (20 ml) was stirred at 40° C. for a while to prepare the solution A.

On the other hand, to a solution of diketene (0.87 g) in carbon tetrachloride (9 ml) was added dropwise a solution of bromine (1.65 g) in carbon tetrachloride (2 ml) at −20° C., and the mixture was stirred at −10° C. for half an hour to prepare the solution B.

To the solution A was added the solution B at −20° to −10° C., and the mixture was stirred at the same temperature for half an hour. After ethyl acetate (80 ml) and water (80 ml) were added to the reaction mixture, the organic layer was separated out, washed with an aqueous solution of sodium chloride, and then dried over anhydrous magnesium sulfate, followed by evaporation under reduced pressure to give 7-(4-bromo-3-oxo-butyramido)-3-vinyl-3-cephem-4-carboxylic acid (3.2 g). This produce was dissolved in a mixture of tetrahydrofuran (50 ml) and ethanol (50 ml), and thereto was added 1-amidinothiourea (1.7 g), followed by stirring for 2 hours. The precipitated substance was collected by filtration and then dried to give 7-[2-(2-guanidinothiazol-4-yl)-acetamido]-3-vinyl-3-cephem-4-carboxylic acid hydrobromide (0.7 g).

I.R. (Nujol): 3400–3100, 1760, 1680, 1660, 1620, 1540 cm$^{-1}$

N.M.R. δppm (DMSO—d$_6$): 3.27–3.95 (4H, m), 5.1–5.91 (4H, m), 6.9 (1H, s), 7.1 (1H, dd, J=11 Hz, 17 Hz), 9.1 (1H, d, J=8 Hz)

The following compounds were obtained by reacting 7-amino-3-vinyl cephalosporanic acid derivatives with diketene, bromine and thiourea according to the similar manner to that of Example 87.

Example 88

Hexanoyloxymethyl 7-[2-(2-aminothiazol-4-yl)acetamido]-3-vinyl-3-cephem-4-carboxylate I.R. (Nujol): 3250, 1765, 1655 cm$^{-1}$

Example 89

Phthalid-3-yl 7-[2-(2-aminothiazol-4-yl)acetamido]-3-vinyl-3-cephem-4carboxylate I.R. (Nujol): 3250, 16780, 1760, 1650 cm$^{-1}$

Example 90

To a suspension of benzhydryl 7-[2-(2-aminothiazol-4-yl)-2-tert-butoxycarbonylmethoxyiminoacetamido]-3-vinyl-3-cephem-4-carboxylate (syn isomer) (15.0 g) in anisole (15 ml) was added 2,2,2-trifluoroacetic acid (60 ml) under ice-cooling with stirring, and the stirring was continued at 10° to 15° C. for 80 minutes. After the reaction mixture was poured into diisopropyl ether (600 ml), the insoluble substance was collected by filtration and then dried. This substance (11.2 g) was dissolved in an aqueous solution to sodium bicarbonate so as to adjust the resultant solution to pH 6.0, and then chromatographed on alumina (44.8 ml) using 5% aqueous sodium acetate as an eluent. The fractions containing the desired compound were collected and evaporated to dryness to give 7-[2-(2-aminothiazol-4-yl)-2-carboxymethoxyiminoacetamido]-3-vinyl-3-cephem-4-carboxylic acid (syn isomer) (3.55 g), mp>250° C.

I.R. (Nujol): 3350, 1770, 1680, 1640 cm$^{-1}$

N.M.R. δppm (DMSO—d$_6$); 3.70 (2H, q, J=18 Hz), 4.62 (2H, s), 5.21 (1H, d, J=5 Hz), 5.82 (1H, dd, J=5 Hz, 8 Hz), 5–6 (2H, m), 6.82 (1H, s), 7.22 (2H, broad s), 6.5–7.5 (1H, m), 9.50 (1H, d, J=8 Hz)

Example 91

A mixture of benzhydryl 7-[2-(2-formamidothiazol-4-yl)-2-methoxyiminoacetamido]-3-triphenylphosphoranylidenemethyl-3-cephem-4-carboxylate (syn isomer) (2.2 g), 36% aqueous formaldehyde (20 ml) and tetrahydrofuran (60 ml) were stirred at ambient temperature for 12.5 hours. After addition of ethyl acetate (100 ml) to the reaction mixture, the organic layer was separated out, washed with 10% hydrochloric acid and an aqueous solution of sodium chloride, and then dried over anhydrous magnesium sulfate. Removal of the solvent gave a residue, which was pulverized with diethyl ether, and chromatographed on silica gel using chloroform and then a mixture of chloroform and acetone (19:1 and 9:1 by volume) as an eluent. The fractions containing the desired compound were collected and evaporated to give benzhydryl 7-[2-(2-formamidothiazol-4-yl)-2-methoxyiminoacetamido]-3-vinyl-3-cephem-4-carboxylate (syn isomer) (0.25 g).

I.R. (Nujol): 3250, 1780, 1710, 1700, 1660, 1540 cm$^{-1}$

Example 92

[4-Benzhydryloxycarbonyl-7-{2-tert-butoxycarbonylmethoxyimino-2-(2-formamidothiazol-4-yl)acetamido}-3-cephem-3yl]methyl triphenyl-phosphonium iodide (syn isomer) (0.59 g) was dissolved in a mixture of methylene chloride (20 ml), water (10 ml) and 36% aqueous formaldehyde (1 ml), followed by adjusting to pH 8 with 20% aqueous sodium carbonate. After stirring for 3 hours at 30°–35° C., the reaction mixture was further adjusted to pH 2.0 with 10% hydrochloric acid and then extracted with methylene chloride. The extract was washed with an aqueous sodium chloride dried over magnesium sulfate and then evaporated. The residue (0.46 g) was chromatographed on silica gel using a mixed solvent of benzene and ethyl acetate (2:1 by volume) as an eluent to obtain benzhydryl 7-[2-tert-butoxycarbonylmethoxyimino-2-(2-formamidothiazol-4-yl)acetamido]-3-vinyl-3-cephem-4-carboxylate (syn isomer) (0.14 g).

I.R. (Nujol): 3250, 1780, 1720, 1680, 1540 cm$^{-1}$

The following compounds were obtained by reacting 7-acylamino-3-triphenylphosphoranylidenemethyl-cephalosporanic acid derivatives with an aqueous formaldehyde according to the similar manner to that of Examples 91 and 92.

Example 93

Benzhydryl 7-[2-(2-methanesulfonamidothiazol-4-yl)acetamido]-3-vinyl-3-cephem-4-carboxylate I.R. (Nujol): 3250, 1760, 1700, 1650, 1610, 1600 cm$^{-1}$

Example 94

Benzhydryl 7-[2-(2-formamidothiazol-5-yl)acetamido]-3-vinyl-3-cephem-4-carboxylate I.R. (Nujol): 3270, 1770, 1715, 1680 cm$^{-1}$

Example 95

Benzhydryl 7-[2-(2-methanesulfonamidothiazol-5-yl)acetamido]-3-vinyl-3-cephem-4-carboxylate I.R. (Nujol): 3320, 1770, 1710, 1660, 1620, 1570, 1520 cm$^{-1}$

Example 96

Pivaloyloxymethyl 7-[2-(2-aminothiazol-4-yl)-DL-glycolamido]-3-vinyl-3-cephem-4-carboxylate I.R. (Nujol): 3370, 1780, 1750, 1680, 1620 cm$^{-1}$

Example 97

Pivaloyloxymethyl 7-[2-(2-aminothiazol-4-yl)-2-methoxyiminoacetamido]-3-vinyl-3-cephem-4-carboxylate (syn isomer)

I.R. (Nujol): 3400–3100, 1770, 1745, 1670, 1610, 1530 cm$^{-1}$

Example 98

Hexanoyloxymethyl 7-[2-(2-aminothiazol-4-yl)acetamido]-3-vinyl-3-cephem-4-carboxylate I.R. (Nujol): 3250, 1765, 1655 cm$^{-1}$

Example 99

Phthalid-3-yl 7-[(2-aminothiazol-4-yl)glyoxylamido]-3-vinyl-3-cephem-4-carboxylate I.R. (Nujol): 3300, 1770, 1650 cm$^{-1}$

Example 100

Phthalid-3-yl 7-[2-(2-aminothiazol-4-yl)-2-methoxyiminoacetamido]-3-vinyl-3-cephem-4-carboxylate (syn isomer)

I.R. (Nujol): 3300, 1775, 1670, 1610, 1530 cm$^{-1}$

Example 101

Phthalid-3-yl 7-[2-(2-aminothiazol-4-yl)acetamido]-3-vinyl-3-cephem-4-carboxylate I.R. (Nujol): 3250, 1780, 1760, 1650 cm$^{-1}$

Example 102

Phthalid-3-yl 7-[2-(2-aminothiazol-4-yl)-DL-glycolamido]-3-vinyl-3-cephem-4-carboxylate I.R. (Nujol): 1770, 1740, 1660, 1610 cm$^{-1}$

Example 103

To a solution of benzhydryl 7-amino-3-vinyl-3-cephem-4-carboxylate (3.02 g) in methylene chloride (30 ml) were added a solution of 2-(2-formamidothiazol-4-yl)-2-(L-2-benzhydryloxycarbonyl-2-tert-butoxycarbonylaminoethoxycarbonylmethoxyimino)acetic acid (syn isomer) (5.5 g) and then N,N'-dicyclohexylcarbodimide (1.81 g), followed by stirring at ambient temperature for 2 hours. Diethyl ether (100 ml) was added to the reaction mixture, and the precipitated material was removed by filtration. After removing the solvent from the filtrate, the residue was dissolved in ethyl acetate, washed with 5% aqueous sodium bicarbonate and then an aqueous sodium chloride, followed by drying over anhydrous magnesium sulfate. Removal of the solvent gave a residue (10 g), which was chromatographed on silica gel (200 ml) eluting with a mixed solvent of diisopropyl ether and acetone. Fractions containing a desired compound were collected and evaporated to obtain benzhydryl 7-[2-(2-formamidothiazol-4-yl)-2-(L-2-benzhydryloxycarbonyl-2-tert-butoxycarbonylaminoethoxycarbonylmethoxyimino)acetamido]-3-vinyl-3-cephem-4-carboxylate (syn isomer) (5.9 g), mp 87°–94° C.

I.R. (Nujol): 3350, 1780, 1720, 1700 (broad) cm$^{-1}$

NMR δppm (DMSO—d$_6$): 1.33 (9H, s), 3.57, 3.96 (2H, ABq, J=18 Hz), 4.53 (3H, m), 4.73 (2H, broad s), 5.3 (1H, d, J=11 Hz), 5.33 (1H, d, J=5 Hz), 5.53 (1H, d, J=18 Hz), 6.00 (1H, dd, J=5 Hz, 8 Hz), 6.87 (1H, s), 7.00 (1H, s), 7.4 (20H, m), 7.50 (1H, s), 8.57 (1H, s), 9.80 (1H, d, J=8 Hz), 12.7 (1H, broad s)

Example 104

To a solution of benzhydryl 7-amino-3-vinyl-3-cephem-4-carboxylic (3.54 g) in methylene chloride (35 ml) were added a solution of 2-(2-formamidothiazol-4-yl)-2-(DL-3-benzhydryloxycarbonyl-3-tert-butoxycarbonylaminopropoxyimino)acetic acid (syn isomer) (6.0 g) in tetrahydrofuran (60 ml) and then N,N-dicyclohexylcarbodimide (2.2 g), followed by stirring at ambient temperature for 4 hours. The precipitated material was removed by filtration, and the filtrate was evaporated to dryness to give a residue, which was chromatographed on silica gel eluting with a mixed solvent of diisopropyl ether and acetone. Fractions containing a desired compound were collected and evaporated to obtain benzhydryl 7-[2-(2-formamidothiazol-4-yl)-2-(DL-3-benzhydryloxycarbonyl-3-tert-butoxycarbonylaminopropoxyimino)acetamido]-3-vinyl-3-cephem-4-carboxylate (syn isomer) (3.80 g), mp 153°–158° C.

I.R. (Nujol): 3200, 1780, 1700 (broad) cm$^{-1}$

NMR δppm (DMSO—d$_6$): 1.36 (9H, s), 2.1 (2H, m), 3.6 (2H, m), 4.2 (3H, m), 5.2–6.1 (4H, m), 6.8 (1H, s), 6.97 (1H, s), 6.8–7.2 (1H, m), 7.37 (20H, m), 7.43 (1H, s), 8.53 (1H, s), 9.75 (1H, d, J=8 Hz), 12.7 (1H, broad s)

Example 105

To a solution of N,N-dimethylformamide (1.10 ml) and tetrahydrofuran (6 ml) was added dropwise phosphorus oxychloride (1.30 ml), followed by stirring for 10 minutes. After addition of tetrahydrofuran (25 ml) and 2-(2-formamidothiazol-4-yl)-2-methoxyiminoacetic acid (syn isomer) (2.96 g), the mixture was stirred at 5° C. for 45 minutes to prepare the activated acid solution. This solution was added dropwise to a solution of L-2-benzhydryloxycarbonyl-2-tert-butoxycarbonylaminoethyl 7-amino-3-vinyl-3-cephem-4-carboxylate (5.0 g) and trimethylsilylacetamide (9.05 g) in methylene chloride (50 ml) at −30° C. in the course of 5 minutes, followed by stirring at −20° to −10° C. for half an hour. The reaction mixture was poured into a mixture of ethyl acetate (300 ml) and water (100 ml), and then adjusted to pH 7.5 with 10% aqueous sodium hydroxide and an aqueous sodium bicarbonate. The separated ethyl acetate solution was washed with an aqueous sodium chloride and then dried over anhydrous magnesium sulfate. Removal of the solvent gave crude product (7.5 g) of L-2-benzhydryloxycarbonyl-2-tert-butoxycarbonylaminoethyl 7-[2-(2-formamidothiazol-4-yl)-2-methoxyiminoacetamido]-3-vinyl-3-cephem-4-carboxylate (syn isomer).

I.R. (Nujol): 3280, 1782, 1709, 1689, 1656 cm$^{-1}$

NMR δppm (DMSO—d$_6$): 1.40 (9H, s), 3.73 (3H, m), 3.92 (3H, s), 4.56 (3H, m), 5.20 (1H, d, J=5 Hz), 5.33 (1H, d, J=11 Hz), 5.65 (1H, d, J=18 Hz), 5.75 (1H, dd, J=5 Hz, 8 Hz), 6.84 (1H, s), 6.93 (1H, dd, J=11 Hz, 18 Hz), 7.37 (10H, m), 7.43 (1H, s), 8.53 (1H, s), 9.73 (1H, d, J=8 Hz), 12.7 (1H, broad s)

Example 106

To a Vilsmeier reagent, which was prepared by N,N-dimethylformamide (1.44 ml) and phosphorus oxychloride (1.71 ml) in tetrahydrofuran (6 ml) in a conventional manner, was added (2-formamidothiazol-4-yl)glyoxylic acid (3.108 g), followed by stirring for a while. Thereto were added N,N-dimethylformamide (45 ml) and tetrahydrofuran (60 ml) to prepare the activated acid solution. This activated acid solution was added dropwise to a solution of L-2-benzhydryloxycarbonyl-2-tert-butoxycarbonylaminoethyl-7-amino-3-vinyl-3-cephem-4-carboxylate (4.5 g) and trimethylsilylacetamide (8.4 g) in methylene chloride (45 ml) at −30° C. in the course of 5 minutes. To the reaction mixture was added ethyl acetate (400 ml), followed by adjusting to pH 7.5 with an aqueous sodium bicarbonate. After washing with an aqueous sodium chloride, the solution was dried over anhydrous magnesium sulfate. Removal of the solvent gave crude product (8.0 g) of L-2-benzhydryloxycarbonyl-2-tert-butoxycarbonylaminoethyl 7-[(2-formamidothiazol-4-yl)glyoxylamido]-3-vinyl-3-cephem-4-carboxylate.

I.R. (Nujol): 1777, 1720, 1667 cm$^{-1}$

NMR δppm (DMSO—d$_6$): 1.37 (9H, s), 3.67 (2H, m), 4.43 (3H, broad s), 5.10 (1H, d, J=5 Hz), 5.20 (1H, d, J=11 Hz), 5.55 (1H, d, J=18 Hz), 5.58 (1H, dd, J=5 Hz, 8 Hz), 6.71 (1H, s), 7.23 (10H, m), 8.37 (1H, s), 8.47 (1H, s), 9.77 (1H, d, J=8 Hz), 12.7 (1H, broad s)

Example 107

Benzhydryl 7-[2-(2-formamidothiazol-5-yl)-2-methoxyiminoacetamido]-3-vinyl-3-cephem-4-carboxylate (syn isomer) (2.9 g), mp 208° C. (dec.), was obtained by reacting benzhydryl 7-amino-3-cephem-4-carboxylate hydrochloride (2.28 g) with 2-(2-formamidothiazol-5-yl)-2-methoxyiminoacetic acid (syn isomer) (1.4 g) according to a similar manner to those of Examples 105 and 106.

IR (Nujol): 3250, 1780, 1720, 1685, 1655, 1570 cm$^{-1}$

NMR δppm (DMSO—d$_6$): 3.82 (2H, q, J=18 Hz), 3.92 (3H, s), 5.30 (1H, d, J=11 Hz), 5.32 (1H, d, J=5 Hz), 5.67 (1H, d, J=17 Hz), 5.92 (1H, dd, J=5.8 Hz), 6.85 (1H, dd, J=11 Hz, 17 Hz), 7.00 (1H, s), 7.2–7.6 (10H, m), 7.61 (1H, s), 8.62 (1H, s), 9.98 (1H, d, J=8 Hz)

Example 108

Benzhydryl 7-[2-(2-formamidothiazol-5-yl)-2-methoxyiminoacetamido]-3-vinyl-3-cephem-4-carboxylate (anti isomer) (4.14 g) was obtained by reacting benzhydryl 7-amino-3-vinyl-3-cephem-4-carboxylate hydrochloride (3.26 g) with 2-(2-formamidothiazol-5-yl)-2-methoxyiminoacetic acid (anti isomer) (2.0 g) according to a similar manner to those of Examples 105 and 106.

I.R. (Nujol): 3250, 1780, 1720, 1685, 1660 cm$^{-1}$

NMR δppm (DMSO—d$_6$): 3.79 (2H, q, J=18 Hz), 4.12 (3H, s), 5.34 (1H, d, J=5 Hz), 5.31 (1H, d, J=11 Hz), 5.65 (1H, d, J=18 Hz), 5.83 (1H, dd, J=5 Hz, 8 Hz), 6.83 (1H, dd, J=11 Hz, 18 Hz), 7.00 (1H, s), 7.42 (10H, broad s), 8.26 (1H, s), 8.62 (1H, s), 9.55 (1H, d, J=8 Hz)

Example 109

Benzhydryl 7-[(2-formamidothiazol-5-yl)glyoxylamido]-3-vinyl-3-cephem-4-carboxylate (3.0 g), mp 178° C. (dec.), was obtained by reacting benzhydryl 7-amino-3-vinyl-3-cephem-4-carboxylate hydrochloride (2.68 g) with (2-formamidothiazol-5-yl)glyoxylic acid (1.5 g) according to a similar manner to those of Examples 105 and 106.

I.R. (Nujol): 3280, 1773, 1730, 1705, 1635, 1555 cm$^{-1}$

NMR δppm (DMSO—d$_6$): 3.80 (2H, q, J=17 Hz), 5.34 (1H, d, J=5 Hz), 5.35 (1H, d, J=11 Hz), 5.70 (1H, d, =17 Hz), 5.82 (1H, dd, J=5 Hz, 8 Hz), 6.89 (1H, dd, J=11 Hz, 17 Hz), 7.2–7.8 (10H, m), 6.99 (1H, s), 8.58 (1H, s), 8.68 (1H, s), 9.92 (1H, d, J=8 Hz), 12.98 (1H, broad s).

Example 110

Benzhydryl 7-[2-(2-formamidothiazol-4-yl)-2-ethoxyiminoacetamido]-3-vinyl-3-cephem-4-carboxylate (syn isomer) (25.0 g) was obtained by reacting benzhydryl 7-amino-3-vinyl-3-cephem-4-carboxylate hydrochloride (17.2 g) with 2-(2-formamidothiazol-4-yl)-2-ethoxyiminoacetic acid (syn isomer) (8.8 g) according to a similar manner to those of Examples 105 and 106.

I.R. (Nujol): 3260, 3150, 1770, 1720, 1700, 1660, 1620, 1560, 1540 cm$^{-1}$

NMR δppm (DMSO—d$_6$): 1.27 (3H, t, J=7 Hz), 3.79 (2H, q, J=17 Hz), 4.18 (2H, q, J=7 Hz), 5.32 (1H, d, J=5 Hz), 5.33 (1H, d, J=11 Hz), 5.65 (1H, d, J=17 Hz), 5.96 (1H, dd, J=5 Hz, 8 Hz), 6.78 (1H, dd, J=11 Hz, 17 Hz), 6.97 (1H, s), 7.17–7.67 (11H, m), 8.55 (1H, s), 9.73 (1H, d, J=8 Hz), 12.70 (1H, broad s)

Example 111

Benzhydryl 7-[2-(2-formamidothiazol-4-yl)-2-hexyloxyiminoacetamido]-3-vinyl-3-cephem-4-carboxylate (syn isomer) (5.7 g) was obtained by reacting benzhydryl 7-amino-3-vinyl-3-cephem-4-carboxylate hydrochloride (4.29 g) with 2-(2-formamidothiazol-4-yl)-2-hexyloxyiminoacetic acid (syn isomer) (3.29 g) according to a similar manner to those of Examples 105 and 106.

I.R. (Nujol): 3250, 1770, 1710, 1700, 1650, 1570, 1535 cm$^{-1}$

NMR δppm (DMSO—d$_6$): 0.87 (3H, t, J=6 Hz), 1.0–2.0 (8H, m), 3.75 (2H, ABq, J=18 Hz), 4.12 (2H, t, J=6 Hz), 5.28 (1H, d, J=5 Hz), 5.42 (1H, d, J=11 Hz), 5.62 (1H, d, J=17 Hz), 5.90 (1H, dd, J=5 Hz, 8 Hz), 6.77 (1H, dd, J=11 Hz, 17 Hz), 6.97 (1H, s), 7.12–7.75 (11H, m), 8.50 (1H, s), 9.52 (1H, d, J=8 Hz), 12.70 (1H, broad s)

The following compounds were obtained by reacting 7-amino-3-vinyl cephalosporanic acid derivatives with hydrochloride of the corresponding acid according to a similar manner to those of Examples 105 and 106.

Example 112

7-[2-(2-Aminothiazol-5-yl)-2-methoxyiminoacetamido]-3-vinyl-3-cephem-4-carboxylic acid (syn isomer), mp>250° C.

I.R. (Nujol): 3300, 1780, 1645, 1580, 1515 cm$^{-1}$

Example 113

7-[2-(2-Aminothiazol-5-yl)-2-methoxyiminoacetamido]-3-vinyl-3-cephem-4-carboxylic acid (anti isomer), mp>250° C.

I.R. (Nujol): 3320, 1775, 1655, 1575, 1515 cm$^{-1}$

Example 114

7-[(2-Aminothiazol-5-yl)glyoxylamido]-3-vinyl-3-cephem-4-carboxylic acid (anti isomer), mp>250° C.

I.R. (Nujol): 3300, 3180, 1770, 1690, 1620, 1510, 1460 cm$^{-1}$

Example 115

7-[2-(2-Aminothiazol-4-yl)-2-ethoxyiminoacetamido]-3-vinyl-3-cephem-4-carboxylic acid (syn isomer), I.R. (Nujol): 3300, 1770, 1660, 1545 cm$^{-1}$

Example 116

Pivaloyloxymethyl 7-[2-(2-aminothiazol-4-yl)-2-pivaloyloxymethoxycarbonylmethoxyimino)acetamido]-3-vinyl-3-cephem-4-carboxylate (syn isomer), mp 115° C. ((dec.).

IR (Nujol): 3400, 3260, 3100, 1780, 1750, 1660, 1530 cm$^{-1}$

Example 117

Pivaloyloxymethyl 7-[2-(2-aminothiazol-4-yl)-2-ethoxyiminoacetamido]-3-vinyl-3-cephem-4-carboxylate (syn isomer)

IR (Nujol): 3300, 1780, 1740, 1670, 1610, 1530 cm$^{-1}$

Example 118

7-[2-(2-Aminothiazol-4-yl)-2-hexyloxyiminoacetamido]-3-vinyl-3-cephem-4-carboxylate acid (syn isomer), mp 147°–155° C. ((dec.).

IR (Nujol): 3250, 1770, 1530 cm$^{-1}$

Example 119

Acetoxymethyl 7-[2-(2-aminothiazol-4-yl)-2-methoxyiminoacetamido]-3-vinyl-3-cephem-4-carboxylate (syn isomer), mp 78°–83° C.

IR (Nujol): 3300, 1765 (broad), 1660, 1610, 1535 cm$^{-1}$

Example 120

Propionyloxymethyl 7-[2-(2-aminothioazol-4-yl)-2-methoxyiminoacetamido]-3-vinyl-3-cephem-4-carboxylate (syn isomer), mp 79°–85° C.

IR (Nujol): 3350, 1770 (broad), 1650, 1620, 1530 cm$^{-1}$

Example 121

Isobutyryloxymethyl 7-[2-(2-aminothiazol-4-yl)-2-methoxyiminoacetamido]-3-vinyl-3-cephem-4-carboxylate (syn isomer), mp 92°–100° C. ((dec.).

IR (Nujol): 3400–3100, 1780–1740, 1670, 1610, 1530 cm$^{-1}$

Example 122

1-Acetoxypropyl 7-[2-(2-aminothiazol-4-yl)-2-methoxyiminoacetamido]-3-vinyl-3-cephem-4-carboxylate (syn isomer), mp 97°–101° C.

IR (Nujol): 3300, 1765, 1670, 1610 cm$^{-1}$

Example 123

L-2-Amino-2-carboxylic 7-[2-2-aminothiazol-4-yl)-2-methoxyiminoacetamido]-3-vinyl-3-cephem-4-carboxylate (syn isomer)

IR (Nujol): 3200, 1770, 1735, (shoulder), 1650 (broad) cm$^{-1}$

Example 124

L-2-Benzhydryloxycarbonyl-2-tert-butoxycarbonylaminoethyl 7-[(2-aminothiazol-4-yl)glyoxylamido]-3-vinyl-3-cephem-4-carboxylate IR (Nujol): 3340, 1775, 1720, 1660, 1614 cm−

Example 125

Benzhydryl 7-[(2-(2-aminothiazol-4-yl)-2-(L-2-benzhydryloxycarbonyl-2-tert-butoxycarbonylaminoethoxycarbonylmethoxyimino)acetamido]-3-vinyl-3-cephem-4-carboxylate (syn isomer), mp 124°–128° C.

IR (Nujol): 3360, 1750 (broad) cm$^{-1}$

Example 126

Benzhydryl 7-[2-(2-aminothiazol-4-yl)-2-(DL-3-benzhydryloxycarbonyl-3-tert-butoxycarbonylaminopropoxyimino)acetamido]-3-vinyl-3-cephem-4-carboxylate (syn isomer), mp 119°–122° C.
IR (Nujol): 3300, 1780, 1719, 1680 cm⁻¹

Example 127

To a suspension of 2-(5-amino-1,2,4-oxadiazol-3-yl)-2-methoxyiminoacetic acid (syn isomer) (2.23 g) in methylene chloride (70 ml) was added phosphorus oxychloride (7.2 g), followed by stirring at ambient temperature for 45 minutes. Thereto was added N,N-dimethylformamide (4.4 g) at −10° C., and the mixture was stirred at −10° C. to 0° C. for an hour to prepare the activated acid solution. This solution was added to a solution of benzhydryl 7-amino-3-vinyl-3-cephem-4-carboxylate hydrochloride (4.7 g) and trimethylsilylacetamide (8.6 g) in ethyl acetate (50 ml) at −20° C. and the mixture was stirred at −20° to 0° C. for an hour. After ethyl acetate (200 ml) and water (100 ml) were added to the reaction mixture, the ethyl acetate layer was separated out, washed with a saturated aqueous sodium bicarbonate and an aqueous sodium chloride, and then dried over anhydrous magnesium sulfate. Removal of the solvent gave a residue, which was chromatographed on silica gel eluting with a mixed solvent of ethyl acetate and benzene (6:4 by volume). Fractions containing a desired compound firstly eluted were collected and evaporated to obtain benzhydryl 7-[2-(5-amino-1,2,4-oxadiazol-3-yl)-2-methoxyiminoacetamido]-3-vinyl-3-cephem-4-carboxylate (syn isomer) (2.4 g).

IR (Nujol): 3250, 1770, 1710, 1670, 1600, 1550 cm⁻¹
NMR $\delta$ppm (DMSO—$d_6$): 3.77 (2H, q, J=17 Hz), 3.97 (3H, s), 5.28 (1H, d, J=5 Hz), 5.28 (1H, d, J=11 Hz), 5.65 (1H, d, J=17 Hz), 5.92 (1H, dd, J=5 Hz, 8 Hz), 6.78 (1H, dd, J=11 Hz, 17 Hz), 6.97 (1H, s), 7.17–7.67 (10H, m), 8.03 (2H, s), 9.77 (1H, d, J=8 Hz)

Fractions containing another desired compound secondly eluted were collected and evaporated to obtain benzhydryl-7-[2-[5-(N,N-dimethylaminomethylene)amino)-1,2,4-oxadiazol-3-yl]-2-methoxyiminoacetamido]-3-vinyl-3-cephem-4-carboxylate (syn isomer) (2.0 g).

IR (Nujol): 3200, 1780, 1720, 1680, 1640, 1540 cm⁻¹
NMR $\delta$ppm (DMSO—$d_6$): 3.07 (3H, s), 3.22 (3H, s), 3.68 (2H, m), 4.00 (3H, s), 5.30 (1H, d, J=5 Hz), 5.32 (1H, d, J=11 Hz), 5.67 (1H, d, J=17 Hz), 5.95 (1H, dd, J=5 Hz, 8 Hz), 6.80 (1H, dd, J=11 Hz, 17 Hz), 6.98 (1H, s), 7.20–7.67 (10H, m), 8.65 (1H, s), 9.83 (1H, d, J=8 Hz)

Example 128

Benzhydryl 7-[2-(5-amino-1,2,4-oxadiazol-3-yl)acetamdio]-3-vinyl-3-cephem-4-carboxylate (2.1 g) was obtained by reacting benzhydryl 7-amino-3-vinyl-3-cephem-4-carboxylate hydrochloride (4.3 g) with 2-(5-amino-1,2,4-oxadiazol-3-yl)acetic acid (1.72 g) according to a similar manner to that of Example 127.

IR (Nujol): 3380, 3250, 3180, 3130, 1770, 1710, 1650, 1540 cm⁻¹
NMR $\delta$ppm (DMSO—$d_6$): 3.35 (2H, s), 3.78 (2H, q, J=18 Hz), 5.23 (1H, d, J=5 Hz), 5.32 (1H, d, J=11 Hz), 5.65 (1H, d, J=17 Hz), 5.82 (1H, dd, J=5 Hz, 8 Hz), 6.80 (1H, dd, J=11 Hz, 17 Hz), 7.00 (1H, s), 7.20–7.67 (10H, m), 7.73 (2H, s), 9.18 (1H, d, J=8 Hz)

Example 129

To a solution of benzhydryl 7-[2-(2-formamidothiazol-4-yl)-2-(L-2-benzhydryloxycarbonyl-2-tert-butoxycarbonylaminoethoxycarbonylmethoxyimino)acetamido]-3-vinyl-3-cephem-4-carboxylate (syn isomer) (6.9 g) in methanol (140 ml) was added conc. hydrochloric acid (3.1 ml), and the mixture was stirred at 35° C. for 90 minutes. The reaction mixture was adjusted to pH 6.0 with 5% aqueous sodium bicarbonate and then diluted with water (200 ml). Removal of the methanol gave an aqueous solution, which was extracted with ethyl acetate. The extract was washed with an aqueous sodium chloride and then dried over anhydrous magnesium sulfate, followed by removal of the solvent. The residue was pulverized with diisopropyl ether and collected by filtration to obtain benzhydryl 7-[2-(2-aminothiazol-4-yl)-2-(L-2-benzhydryloxycarbonyl-2-tert-butoxycarbonylaminoethoxycarbonylmethoxyimino)acetamido]-3-vinyl-3-cephem-4-carboxylate (syn isomer) (5.5 g), mp 124°–128° C.

IR (Nujol): 3360, 1750 (broad) cm⁻¹
NMR $\delta$ppm (DMSO—$d_6$): 1.40 (9H, s), 3.57, 3.98 (2H, ABq, J=18 Hz), 4.50 (3H, m), 4.63 (2H, broad s), 5.30 (1H, d, J=11 Hz), 5.31 (1H, d, J=5 Hz), 5.67 (1H, d, J=18 Hz), 5.95 (1H, dd, J=5 Hz, 8 Hz), 6.86 (2H, s), 6.8–7.20 (1H, m), 7.00 (1H, s), 7.40 (10H, s), 9.65 (1H, d, J=8 Hz)

Example 130

To a solution of benzhydryl 7-[2-(2-formamidothiazol-4-yl)-2-(DL-3-benzhydryloxycarbonyl-3-tert-butoxycarbonylaminopropoxyimino)acetamido]-3-vinyl-3-cephem-4-carboxylate (syn isomer) (3.65 g) in methanol (109 ml) was added conc. hydrochloric acid (1.96 ml), and the mixture was stirred at 35° C. for 24 minutes. The reaction mixture was adjusted to pH 6.5 with 10% aqueous sodium hydroxide and 5% aqueous sodium bicarbonate, followed by removal of the methanol. The residue was dissolved in ethyl acetate, washed with an aqueous sodium chloride and then dried over anhydrous magnesium sulfate. Removal of the solvent gave a residue, which was pulverized with diisopropyl ether to obtain benzhydryl 7-[2-(2-aminothiazol-4-yl)-2-(DL-3-benzhydryloxycarbonyl-3-tert-butoxycarbonylaminopropoxyimino)acetamido]-3-vinyl-3-cephem-4-carboxylate (syn isomer) (3.5 g), mp 119°–122° C.

IR (Nujol): 3300, 1780, 1719, 1680 cm⁻¹
NMR $\delta$ppm (DMSO—$d_6$): 1.37 (9H, s), 2.1 (2H, m), 3.7 (3H, m), 4.2 (3H, m), 5.2–6.1 (4H, m), 6.8 (2H, s), 6.8–7.2 (1H, m), 6.97 (1H, s), 7.37 (20H, s), 9.67 (1H, d, J=8 Hz)

Example 131

To a solution of L-2-benzhydryloxycarbonyl-2-tert-butoxycarbonylaminoethyl 7-[2-(2-formamidothiazol-4-yl)-2-methoxyiminoacetamido]-3-vinyl-3-cephem-4-carboxylate (syn isomer) (6.8 g) in methanol (300 ml) was added conc. hydrochloric acid (3.8 ml), and the mixture was stirred at 35° C. for an hour. After addition of water (100 ml), the reaction mixture was adjusted to pH 5.5 with an aqueous sodium bicarbonate, followed by removal of the methanol. The residue was dissolved in ethyl acetate, washed with an aqueous sodium chloride and then dried over anhydrous magnesium sulfate, followed by treating with an activated charcoal. Removal of the solvent gave L-2-benzhydryloxycarbonyl-2-tert-butoxycarbonylaminoethyl 7-[2-(2-aminothiazol-4-yl)-2-methoxyiminoacetamido]-3-vinyl-3-cephem-4-carboxylate (syn isomer) (5.0 g). IR (Nujol): 3370, 1775, 1730, 1616 cm⁻¹

NMR $\delta$ppm (DMSO—$d_6$): 1.33 (9H, s), 3.83, 3.93 (2H, ABq, J=18 Hz), 3.80 (3H, s), 4.47 (3H, broad s), 5.12 (1H, d, J=5 Hz), 5.23 (1H, d, J=11 Hz), 5.60 (1H, dd, J=5 Hz, 8 Hz), 5.66 (1H, d, J=18 Hz), 6.70 (1H, s), 6.77 (1H, s), 6.8–7.2 (1H, m), 7.3 (10H, broad s), 9.57 (1H, d, J=8 Hz)

Example 132

To a solution of L-2-benzhydryloxycarbonyl-2-tert-butoxycarbonylaminoethyl 7-[(2-formamidothiazol-4-yl)glyoxylamido]-3-vinyl-3-cephem-4-carboxylate (8.7 g) in methanol (150 ml) was added conc. hydrochloric acid (4.7 g), and the mixture was stirred at 35° to 40° C. for 70 minutes. The reaction mixture was adjusted to pH 5.0 with 5% aqueous sodium hydroxide and 5% aqueous sodium bicarbonate, followed by adding dropwise to water (600 ml). The precipitated solid was collected by filtration, washed with water and then dried to give L-2-benzhydryloxycarbonyl-2-tert-butoxycarbonylaminoethyl 7-[(2-aminothiazol-4-yl)glyoxylamido]-3-vinyl-3-cephem-4-carboxylate (5.40 g).

IR (Nujol): 3340, 1775, 1720, 1660, 1614 cm$^{-1}$

NMR $\delta$ppm (DMSO—$d_6$): 1.37 (9H, s), 3.47, 3.97 (2H, ABq, J=18 Hz), 4.53 (3H, m), 5.18 (1H, d, J=5 Hz), 5.33 (1H, d, J=11 Hz), 5.65 (1H, dd, J=5 Hz, 8 Hz), 5.68 (1H, d, J=18 Hz), 6.82 (1H, s), 6.92 (1H, dd, J=11 Hz, 18 Hz), 7.37 (10H, s), 7.83 (1H, s), 9.80 (1H, d, J=8 Hz)

Example 133

A solution of 7-[2-(2-formamidothiazol-5-yl)-2-methoxyiminoacetamido]-3-vinyl-3-cephem-4-carboxylic acid (syn isomer) (1.9 g) and conc. hydrochloric acid (1.36 g) in methanol (190 ml) was stirred at ambient temperature for 1.3 hours. After the reaction mixture was evaporated to dryness, the residue was suspended in water (35 ml) and then adjusted to pH 7–8 with 10% aqueous sodium hydroxide, followed by adjusting to pH 3 with 10% hydrochloric acid. The precipitated solid was collected by filtration, washed with water and then dried to give 7-[2-(2-aminothiazol-5-yl)-2-methoxyiminoacetamdio]-3-vinyl-3-cephem-4-carboxylic acid (syn isomer) (1.3 g), mp >250° C.

IR (Nujol): 3300, 1780, 1645, 1580, 1515 cm$^{-1}$

NMR $\delta$ppm (DMSO—$d_6$): 3.76 (2H, q, J=20 Hz), 3.81 (3H, s), 5.23 (1H, d, J=5 Hz), 5.35 (1H, d, J=11 Hz), 5.60 (1H, d, J=18 Hz), 5.78 (1H, dd, J=5, 8 Hz), 6.98 (1H, dd, J=11, 18 Hz), 7.12 (1H, s), 7.60 (2H, broad s), 9.76 (1H, d, J=8 Hz)

Example 134

7-[2-(2-Aminothiazol-5-yl)-2-methoxyiminoacetamido]-2-vinyl-3-cephem-4-carboxylic acid (anti isomer) (1.27 g) was obtained by reacting 7-[2-(2-formamidothiazol-5-yl)-2-methoxyiminoacetamido]-3-vinyl-3-cephem-4-carboxylic acid (anti isomer) (2.1 g) with conc. hydrochloric acid (1.5 g) according to a similar manner to that of Example 133, mp >250° C.

IR (Nujol): 3320, 1775, 1655, 1575, 1515 cm$^{-1}$

NMR $\delta$ppm (DMSO—$d_6$): 3.76 (2H, q, J=20 Hz), 4.01 (3H, s), 5.23 (1H, d, J=5 Hz), 5.33 (1H, d, J=11 Hz), 5.58 (1H, d, J=18 Hz), 5.73 (1H, dd, J=5, 8 Hz), 6.98 (1H, dd, J=11, 18 Hz), 7.72 (2H, broad s), 7.79 (1H, s), 9.27 (1H, d, J=8 Hz)

Example 135

7-[(2-Aminothiazol-5-yl)glyoxylamido]-3-vinyl-3-cephem-4-carboxylic acid (1.1 g) was obtained by reacting 7-[(2-formamidothiazol-5-yl)glyoxylamido]-3-vinyl-3-cephem-4-carboxylic acid (1.73 g) with conc. hydrochloric acid (2.2 g) according to a similar manner to that of Example 133, mp >250° C.

IR (Nujol): 3300, 3180, 1770, 1690, 1620, 1510, 1460 cm$^{-1}$

NMR $\delta$ppm (DMSO—$d_6$): 3.75 (2H, q, J=18 Hz), 5.24 (1H, d, J=5 Hz), 5.35 (1H, d, J=11 Hz), 5.62 (1H, d, J=17 Hz), 5.73 (1H, dd, J=5, 8 Hz), 7.03 (1H, dd, J=11, 17 Hz), 8.28 (1H, s), 8.56 (2H, broad s), 9.54 (1H, d, J=8 Hz)

Example 136

7-[2-(2-Aminothiazol-4-yl)-2-ethoxyiminoacetamido]-3-vinyl-3-cephem-4-carboxylic acid (syn isomer) (12.2 g) was obtained by reacting 7-[2-(2-formamidothiazol-4-yl)-2-ethoxyiminoacetamido]-3-vinyl-3-cephem-4-carboxylic acid (syn isomer) (15.2 g) with conc. hydrochloric acid (14 ml) according to a similar manner to that of Example 133.

IR (Nujol): 3300, 1770, 1660, 1545 cm$^{-1}$

NMR $\delta$ppm (DMSO—$d_6$): 1.27 (3H, t, J=7 Hz), 3.77 (2H, q, J=18 Hz), 4.17 (2H, q, J=7 Hz), 5.23 (1H, d, J=5 Hz), 5.35 (1H, d, J=11 Hz), 5.62 (1H, d, J=17 Hz), 5.83 (1H, dd, J=5 Hz, 8 Hz), 6.78 (1H, s), 6.98 (1H, dd, J=11 Hz, 17 Hz), 9.63 (1H, d, J=8 Hz)

Example 137

7-[2-(2-Aminothiazol-4-yl)-2-hexyloxyiminoacetamido]-3-vinyl-3-cephem-4-carboxylic acid (syn isomer) (2.1 g) mp 147°–155° C. (dec.), was obtained by reacting 7-[2-(2-formamidothiazol-4-yl)-2-hexyloxyiminoacetamido]-3-vinyl-3-cephem-4-carboxylic acid (syn isomer) (3 g) with conc. hydrochloric acid (0.65 g) according to a similar manner to that of Example 133.

IR (Nujol): 3250, 1770, 1660, 1530 cm$^{-1}$

NMR $\delta$ppm (DMSO—$d_6$): 0.84 (3H, t, J=6 Hz), 1.03–2.0 (8 H, m), 3.70 (2H, ABq, J=18 Hz), 4.07 (2H, t, J=6 Hz), 5.20 (1H, d, J=5 Hz), 5.28 (1H, d, J=11 Hz), 5.55 (1H, d, J=17 Hz), 5.77 (1H, dd, J=5 Hz, 8 Hz), 6.70 (1H, s), 6.93 (1H, dd, J=11 Hz, 17 Hz), 9.58 (1H, d, J=8 Hz)

The following compounds were obtained by reacting 7-acylamino-3-vinyl cephalosporanic acid derivatives having formamido group with conc. hydrochloric acid according to a similar manner to that of Example 133.

Example 138

7-[2-(5-Amino-1,2,4-oxadiazol-3-yl)-2-methoxyiminoacetamido]-3-vinyl-3-cephem-4-carboxylic acid (syn isomer).

IR (Nujol): 3250, 1770, 1660, 1550 cm$^{-1}$

Example 139

7-[2-(5-Amino-1,2,4-oxadiazol-3-yl)acetamido]-3-vinyl-3-cephem-4-carboxylic acid IR (Nujol): 3500–3200, 1770, 1690, 1670, 1565 cm$^{-1}$

Example 140

L-2-Amino-2-carboxyethyl 7-[2-(2-aminothiazol-4-yl)-2-methoxyiminoacetamido]-3-vinyl-3-cephem-4-carboxylate (syn isomer)

IR (Nujol): 3200, 1770, 1735 (shoulder), 1650 (broad) cm$^{-1}$

Example 141

L-2-Amino-2-carboxyethyl 7-[2-(2-aminothiazol-4-yl)-DL-glycolamido]-3-vinyl-3-cephem-4-carboxylate IR (Nujol): 3300, 3180, 1760, 1720, 1628 cm$^{-1}$

Example 142

7-[2-(2-Aminothiazol-4-yl)-2-(L-amino-2-carboxyethoxycarbonylmethoxyimino)acetamido]-3-vinyl-3-cephem-4-carboxlic acid (syn isomer), mp 158° C. (dec.).

IR (Nujol): 3200 (broad), 1760 (broad) cm$^{-1}$

Example 143

7-[2-(2-Aminothiazol-4-yl)-2-(DL-3-amino-3-carboxypropoxyimino)acetamido]-3-vinyl-3-cephem-4-carboxylic acid (syn isomer), mp 145° C. (dec.).

IR (Nujol): 3220, 1766, 1612 cm$^{-1}$

Example 144

A solution of benzhydryl 7-[2-(2-formamidothiazol-5-yl)-2-methoxyiminoacetamido]-3-vinyl-3-cephem-4-carboxylate (syn isomer) (2.7 g) in anisole (3.5 ml) and trifluoroacetic acid (10.8 ml) was stirred under ice-cooling for 15 minutes. The reaction mixture was poured into diisopropyl ether (140 ml), followed by stirring for 10 minutes. The precipitated solid was collected by filtration, washed with diisopropyl ether and then dried to give 7-[2-(2-formamidothiazol-5-yl)2-methoxyiminoacetamido]-3-vinyl-3-cephem-4-carboxylic acid (syn isomer) (2.0 g), mp 147° C. (dec.).

IR (Nujol): 3250, 3090, 1770, 1660, 1530 cm$^{-1}$

NMR δppm (DMSO—d$_6$): 3.78 (2H, q, J=18 Hz), 3.92 (3H, s), 5.27 (1H, d, J=5 Hz), 5.35 (1H, d, J=11 Hz), 5.58 (1H, d, J=17 Hz), 5.82 (1H, dd, J=5,8 Hz), 6.97 (1H, dd, J=11, 17 Hz), 7.57 (1H, s), 8.57 (1H, s), 9.89 (1H, d, J=8 Hz)

Example 145

7-[2-(2-Formamidothiazol-5-yl)-2-methoxyiminoacetamido]-3-vinyl-3-cephem-4-carboxlic acid (anti isomer) (2.35 g), mp 165° C. (dec.) was obtained by reacting benzhydryl 7-[2-(2-formamidothiazol-5-yl)-2-methoxyiminoacetamido]-3-vinyl-3-cephem-4-carboxylate (anti isomer) (3.0 g) with trifluoroacetic acid (12 ml) in the presence of anisole (3.9 ml) according to a similar manner to that of Example 144.

IR (Nujol): 3260, 1780, 1730, 1690, 1670, 1575, 1520 cm$^{-1}$

NMR δppm (DMSO—d$_6$): 3.75 (2H, q, J=18 Hz), 4.14 (3H, s), 5.28 (1H, d, J=5 Hz), 5.35 (1H, d, J=11 Hz), 5.62 (1H, d, J=18 Hz), 5.77 (1H, dd, J=5, 8 Hz), 7.02 (1H, dd, J=11, 18 Hz), 8.23 (1H, s), 8.60 (1H, s), 9.48 (1H, d, J=8 Hz)

Example 146

7-[(2-Formamidothiazol-5-yl)glyoxylamido]-3-vinyl-3-cephem-4-carboxylic acid (2.1 g), mp 157° C. (dec.), was obtained by reacting benzhydryl 7-[(2-formamidothiazol-5-yl)glyoxylamido]-3-vinyl-3-cephem-4-carboxylate (2.9 g) with trifluoroacetic acid (11.6 ml) in the presence of anisole (3.8 ml) according to a similar manner to that of Example 144.

IR (Nujol): 3270, 1775, 1700, 1655, 1535, 1470 cm$^{-1}$

NMR δppm (DMSO—d$_6$): 3.73 (2H, q, J=18 Hz), 5.24 (1H, d, J=5 Hz), 5.34 (1H, d, J=11 Hz), 5.60 (1H, d, J=17 Hz), 5.73 (1H, dd, J=5, 8 Hz), 7.00 (1H, dd, J=11, 17 Hz), 8.57 (1H, s), 8.68 (1H, s), 9.87 (1H, d, J=8 Hz)

Example 147

7-[2-(2-Formamidothiazol-4-yl)-2-ethoxyiminoacetamido]-3-vinyl-3-cephem-4-carboxylic acid (syn isomer) (15.3 g) was obtained by reacting benzhydryl 7-[2-(2-formamidothiazol-4-yl)-2-ethoxyiminoacetamido]-3-vinyl-3-cephem-4-carboxylate ((syn isomer) (24.7 g) with trifluoroacetic acid (45.6 g) in the presence of anisole (17 g) according to a similar manner to that of Example 144

IR (Nujol): 3250, 1770, 1690, 1660, 1540 cm$^{-1}$

NMR δppm (DMSO—d$_6$): 1.30 (3H, t, J=7 Hz), 3.77 (2H, q, J=17 Hz), 4.22 (2H, q, J=7 Hz), 5.27 (1H, d, J=5 Hz), 5.36 (1H, d, J=11 Hz), 5.62 (1H, d, J=17 Hz), 5.88 (1H, dd, J=5 Hz, 8 Hz), 6.98 (1H, dd, J=11 Hz, 17 Hz), 7.43 (1H, s), 8.55 (1H, s), .70 (1H, d, J=8 Hz), 12.47 (1H, broad s)

Example 148

7-[2-(2-Formamidothiazol-4-yl)-2-hexyloxyiminoacetamido]-3-vinyl-3-cephem-4-carboxylic acid (syn isomer) (3.1 g) was obtained by reacting benzhydryl 7-[2-(2-formamidothiazol-4-yl)-2-hexyloxyiminoacetamido]-3-vinyl-3-cephem-4-carboxylate (syn isomer) (5.5 g) with trifluoroacetic acid (9.3 g) in the presence of anisole (3.5 g) according to a similar manner to that of Example 144.

IR (Nujol): 3250, 1780, 1700, 1685 (shoulder), 1650, 1570, 1550 cm$^{-1}$

NMR δppm (DMSO—d$_6$): 0.88 (3H, t, J=6 Hz), 1.07–2.0 (8H, m), 3.72 (2H, ABq, J=18 Hz), 4.13 (2H, t, J=6 Hz), 5.23 (1H, d, J=5 Hz), 5.37 (1H, d, J=11 Hz), 5.60 (1H, d, J=17 Hz), 5.83 (1H, dd, J=5 Hz, 8 Hz), 6.97 (1H, dd, J=11 Hz, 17 Hz), 7.40 (1H, s), 8.53 (1H, s), 9.63 (1H, d, J=8 Hz), 12.62 (1H, broad s)

The following compounds were obtained by reacting 7-acylamino-3-vinyl cephalosporanic acid derivatives having benzhydryloxycarbonyl with trifluoroacetic acid in the presence of anisole according to a similar manner to that of Example 144.

Example 149

7-[2-(2-Aminothiazol-5-yl)-2-methoxyiminoacetamido]-3-vinyl-3-cephem-4-carboxylic acid (syn isomer), mp >250° C.

IR (Nujol): 3300, 1780, 1645, 1580, 1515 cm$^{-1}$

Example 150

7-[2-(2-Aminothiazol-5-yl)-2-methoxyiminoacetamido]-3-vinyl-3-cephem-4-carboxylic acid (anti isomer), mp >250° C.

IR (Nujol): 3320, 1775, 1655, 1575, 15145 cm$^{-1}$

Example 151

7-[(2-Aminothiazol-5-yl)glyoxylamido]-3-vinyl-3-cephem-4-carboxylic acid, mp >250° C.

IR (Nujol): 3300, 3180, 1770, 1690, 1620, 1510, 1460 cm$^{-1}$

Example 152

7-[2-(2-Aminothiazol-4-yl)-2-ethoxyiminoacetamido]-3-vinyl-3-cephem-4-carboxylic acid (syn isomer).

IR (Nujol): 3300, 1770, 1660, 1545 cm$^{-1}$

Example 153

7-[2-(2-Aminothiazol-4-yl)-2-hexyloxyiminoacetamido]-3-vinyl-3-cephem-4-carboxylic acid (syn isomer), mp 147°–155° C. (dec.).

IR (Nujol): 3250, 1770, 1660, 1530 cm$^{-1}$

Example 154

To a suspension of benzhydryl 7-[2-(5-amino-1,2,4-oxadiazol-3-yl)-2-methoxyiminoacetamido]-3-vinyl-3-cephem-4-carboxylate (2.4 g) in methylene chloride (15 ml) and anisole (1.8 g) was added trifluoroacetic acid (4.9 g), and the mixture was stirred at ambient temperature for an hour. To the reaction mixture was added diisopropyl ether (150 ml), and the precipitated material was collected by filtration, followed by suspension in a mixture of ethyl acetate and water, and adjusting to pH 7 with 10% aqueous sodium hydroxide. To the separated aqueous solution was added ethyl acetate and saturated with sodium chloride. After adjusting to pH 1.5 with 10% hydrochloric acid, the ethyl acetate solution was separated, washed with a saturated aqueous sodium chloride and then dried over anhydrous magnesium sulfate. Removal of the solvent gave a residue, which was washed with diethyl ether to obtain 7-[2-(5-amino-1,2,4-oxadiazol-3-yl)-2-methoxyiminoacetamido]-3-vinyl-3-cephem-4-carboxylic acid (syn isomer) (1.6 g).

IR (Nujol): 3250, 1770, 1660, 1550 cm$^{-1}$

NMR δppm (DMSO—d$_6$): 3.77 (2H, q, J=17 Hz), 4.00 (3H, s), 5.23 (1H, d, J=5 Hz), 5.37 (1H, d, J=11 Hz), 5.62 (1H, d, J=17 Hz), 5.85 (1H, dd, J=5 Hz, 8 Hz), 7.00 (1H, dd, J=11 Hz, 17 Hz), 8.07 (2H, s), 9.78 (1H, d, J=8 Hz)

Example 155

7-[2-{N-(N,N-Dimethylaminomethylene)amino}-1,2,4-oxadiazol-3-yl]-2-methoxyiminoacetamido]-3-vinyl-3-cephem-4-carboxylic acid (syn isomer) (2.2 g) was obtained by reacting benzhydryl 7-[2-[5-{N-(N,N-dimethylaminomethylene)amino}-1,2,4-oxadiazol-3-yl]-2-methoxyiminoacetamido]-3-vinyl-3-cephem-4-carboxylate (syn isomer) (3.3 g) with trifluoroacetic acid (5.93 g) in the presence of anisole (2.2 g) according to a similar manner to that of Example 154.

IR (Nujol): 3200, 1770, 1700, 1660, 1640, 1530 cm$^{-1}$

NMR δppm (DMSO—d$_6$): 3.08 (3H, s), 3.23 (3H, s), 3.75 (2H, q, J=17 Hz), 4.00 (3H, s), 5.23 (1H, d, J=5 Hz), 5.37 (1H, d, J=11 Hz), 5.60 (1H, d, J=17 Hz), 5.85 (1H, dd, J=5 Hz, 8 Hz, 6.99 (1H, dd, J=11 Hz, 17 Hz), 8.65 (1H, s), 9.78 (1H, d, J=8 Hz)

Example 156

7-[2-(5-Amino-1,2,4-oxadiazol-3-yl)acetamido]-3-vinyl-3-cephem-4-carboxylic acid (0.55 g) was obtained by reacting benzhydryl 7-[2-(5-amino-1,2,4-oxadiazol-3-yl)acetamido]-3-vinyl-3-cephem-4-carboxylate (2.05 g) with trifluoroacetic acid (9.0 g) in the presence of anisole (2.5 g) according to a similar manner to that of Example 154.

IR (Nujol): 3500–3200, 1770, 1690, 1670, 1565 cm$^{-1}$

NMR δppm (DMSO—d$_6$): 3.50 (2H, s), 3.73 (2H, q, J=17 Hz), 5.18 (1H, d, J=5 Hz), 5.35 (1H, d, J=11 Hz), 5.62 (1H, d, J=18 Hz), 5.75 (1H, dd, J=5 Hz, 8 Hz), 7.02 (1H, dd, J=11 Hz, 18 Hz), 7.80 (2H, s), 9.22 (1H, d, J=8 Hz)

Example 157

(1) 7-[2-(2-Aminothiazol-4-yl)-2-carboxymethoxyiminoacetamido]-3-vinyl-3-cephem-4-carboxylic acid (syn isomer) (1.8 g) and sodium bicarbonate (667 mg) were dissolved in water (40 ml) and the solution was lyophilized and then dried to prepare disodium salts of 7-[2-(2-aminothiazol-4-yl)-2-carboxymethoxyiminoacetamido]-3-vinyl-3-cephem-4-carboxylic acid (syn isomer) (1.9 g).

IR (Nujol): 3300 (broad), 3180 (broad), 1750, 1660, 1535 cm$^{-1}$

NMR δppm (DMSO—d$_6$): 3.42 (2H, broad s), 4.37 (2H, broad s), 5.10 (1H, d, J=5 Hz), 4.6–5.9 (3H,m), 6.89 (1H,s), 6.6–7.3 (1H,m), 7.33 (2H, broad s) mp >250° C.

(2) To a solution of the above product (1.8 g) in N,N-dimethylformamide (18 ml) was added iodomethyl pivalate (1.84 g) in N,N-dimethylformamide (1.8 ml) under ice-cooling, followed by stirring at the same temperature for 15 minutes. After the reaction mixture was poured into a mixture of ice-water and ethyl acetate, the organic layer was separated out. The remained aqueous layer was extracted with ethyl acetate and the combined ethyl acetate solution was washed with an aqueous sodium bicarbonate and an aqueous sodium chloride, followed by drying over anhydrous magnesium sulfate. Removal of the solvent gave a residue, which was pulverized with diisopropyl ether, followed by collecting by filtration to obtain pivaloyloxymethyl 7-[2-(2-aminothiazol-4-yl)-2-(pivaloyloxymethoxycarbonylmethoxyimino)acetamido]-3-vinyl-3-cephem-4-carboxylate (syn isomer) (0.9 g), mp 115° C. (dec.).

IR (Nujol): 3400, 3260, 3100, 1780, 1750, 1660, 1530 cm$^{-1}$

NMR δppm (DMSO—d$_6$): 1.06 (18H, s), 3.77 (2H, q, J=18 Hz), 4.76 (2H, s), 5.25 (1H, d, J=5 Hz), 5.4–6.1 (7H, m), 6.5–7.2 (1H, m), 6.82 (1H, s), 7.24 (2H, broad s), 9.59 (1H, d, J=8 Hz)

Example 158

To a solution of sodium 7-[2-(2-aminothiazol-4-yl)-2-methoxyiminoacetamido]-3-vinyl-3-cephem-4-carboxylate (syn isomer) (2.2 g) in N,N-dimethylformamide (25 ml) was added dropwise a solution of iodomethyl acetate (1 g) in N,N-dimethylformamide (3 ml) below 5° C. in the course of 2 minutes, and the mixture was stirred at the same temperature for 15 minutes. The reaction mixture was poured into a mixture of water (100 ml) and ethyl acetate (50 ml), and the separated aqueous solution was extracted with ethyl acetate (30 ml). The combined ethyl acetate solution was washed twice with 5% aqueous sodium bicarbonate and twice with an aqueous sodium chloride, and then dried over anhydrous magnesium sulfate. Removal of the solvent gave a residue, which was pulverized with diisopropyl ether and collected by filtration to obtain acetoxymethyl 7-[2-(2-aminothiazol-4-yl)-2-methoxyiminoacetamido]-3-vinyl-3-cephem-4-carboxylate (syn isomer) (1.6 g), mp 78°–83° C.

IR (Nujol): 3300, 1765 (broad), 1660, 1610, 1535 cm$^{-1}$

NMR δppm (DMSO—d$_6$): 2.10 (3H, s), 3.77 (2H, ABq, J=18 Hz), 3.87 (3H, s), 5.25 (1H, d, J=5 Hz), 5.38 (1H, d, J=11 Hz), 5.67 (1H, d, J=17 Hz), 5.85 (3H, m), 6.77 (1H, s), 6.90 (1H, dd, J=11 Hz, 17 Hz), 9.80 (1H, d, J=8 Hz)

Example 159

Propionyloxymethyl 7-[2-(2-aminothiazol-4-yl)-2-methoxyiminoacetamido]-3-vinyl-3-cephem-4-carboxylate (syn isomer) (1.5 g), mp 79°-85° C., was obtained by reacting sodium 7-[2-(2-aminothiazol-4-yl)-2-methoxyiminoacetamido]-3-vinyl-3-cephem-4-carboxylate (syn isomer) (1.5 g) was iodomethyl propionate (0.82 g) according to a similar manner to that of Example 158.

IR (Nujol): 3350, 1770 (broad), 1650, 1620, 1530 cm$^{-1}$

NMR δppm (DMSO—d$_6$): 1.03 (3H, t, J=7 Hz), 2.40 (2H, q, J=7 Hz), 3.77 (2H, ABq, J=17 Hz), 3.85 (3H, s), 5.38 (3H, m), 6.75 (1H, s), 6.85 (1H, dd, J=11 Hz, 17 Hz), 9.62 (1H, d, J=8 Hz)

Example 160

Isobutyryloxymethyl 7-[2-(2-aminothiazol-4-yl)-2-methoxyiminoacetamido]-3-vinyl-3-cephem-4-carboxylate (syn isomer) (2.3 g), mp 92°-100° C. (dec.), was obtained by reacting sodium 7-[2-(2-aminothiazol-4-yl)-2-methoxyiminoacetamido]-3-vinyl-3-cephem-4-carboxylate (syn isomer) (3.0 g) with iodomethyl isobutyrate (1.7 g) according to a similar manner to that of Example 158.

IR (Nujol): 3400-3100, 1780-1740, 1670, 1610, 1530 cm$^{-1}$

NMR δppm (DMSO—d$_6$): 1.1 (6H, d, J=6 Hz), 2.3-2.9 (1H, m), 3.46-4.23 (2H, m), 3.85 (3H, s), 5.25 (1H, d, J=5 Hz), 5.38 (1H, d, J=11 Hz), 5.52-6.0 (2H, m), 5.87 (2H, s), 6.77 (1H, s), 6.85 (1H, dd, J=11 Hz, 17 Hz), 9.63 (1H, d, J=8 Hz)

Example 161

Pivaloyloxymethyl 7-[2-(2-aminothiazol-4-yl)-2-ethoxyiminoacetamido]-3-vinyl-3-cephem-4-carboxylate (syn isomer) (2.6 g) was obtained by reacting sodium 7-[2-(2-aminothiazol-4-yl)-2-ethoxyiminoacetamido]-3-vinyl-3-cephem-4-carboxylate (syn isomer) (3.56 g) with iodomethyl pivalate (1.94 g) according to a similar manner to that of Example 158.

IR (Nujol): 3300, 1780, 1740, 1670, 1610, 1530 cm$^{-1}$

NMR δppm (DMSO—d$_6$): 1.17 (9H, s), 1.23 (3H, t, J=6 Hz), 3.77 (2H, q, J=17 Hz), 4.12 (2H, q, J=6 Hz), 5.23 (1H, d, J=5 Hz), 5.38 (1H, d, J=11 Hz), 5.62 (1H, d, J=17 Hz), 5.73 (3H, m), 6.73 (1H, s), 6.83 (1H, dd, J=11 Hz, 17 Hz), 9.57 (1H, d, J=8 Hz)

Example 162

Hexanoyloxymethyl 7-[2-(2-aminothiazol-4-yl)-DL-glycolamido]-3-vinyl-3-cephem-4-carboxylate (1.86 g) was obtained by reacting sodium 7-[2-(2-aminothiazol-4-yl)-DL-glycolamido]-3-vinyl-3-cephem-4-carboxylate (2.0 g) with iodomethyl hexanoate (1.3 g) according to a similar manner to that of Example 158, mp 65°-70° C.

IR (Nujol): 3300, 1770, 1680, 1610 cm$^{-1}$

NMR δ ppm (DMSO-d$_6$): 0.61-1.80(9H, m), 2.37(2H, t, J=6.0Hz), 3.40(1H, m,) 3.78(2H, q, J=18.0Hz), 4.90(1H, d, J=4.0Hz), 5.23(1H, d, J=4.0Hz), 5.41 (1H, d, J=12.0Hz), 5.53-6.13(4H, m), 6.45(1H, s), 6.88(1H, dd, J=12.0Hz, 18.0Hz), 8.44(d, J=9.0Hz), ⎫
8.56(d, J=9.0Hz) ⎬ (1H)

The following compounds were obtained according to a similar manner to that of Example 158.

Example 163

L-2-Benzhydryloxycarbonyl-2-tert-butoxycarbonylaminoethyl 7-[2-(2-formamidothiazol-4-yl)-2-methoxyiminoacetamido]-3-vinyl-3-cephem-4-carboxylate (syn isomer)

IR (Nujol): 3280, 1782, 1709, 1689, 1656 cm$^{-1}$

Example 164

L-2-Benzhydryloxycarbonyl-2-tert-butoxycarbonylaminoethyl 7-[(2-formamidothiazol-4-yl)glyoxylamido]-3-vinyl-3-cephem-4-carboxylate (syn isomer)

IR (Nujol): 1777, 1720, 1667 cm$^{-1}$

Example 165

To a solution of sodium 7-[2-(2-aminothiazol-4-yl)-2-methoxyiminoacetamido]-3-vinyl-3-cephem-4-carboxylate (syn isomer) (2.0 g) in N,N-dimethylformamide (40 ml) was added sodium iodide (0.8 g) and 1-bromopropyl acetate (0.9 g) under ice-cooling with stirring, and the stirring was continued at the same temperature for half an hour. The reaction mixture was poured into a mixture of water and ethyl acetate, and the separated organic solvent was washed twice with a saturated aqueous sodium chloride and twice with water, followed by drying over anhydrous magnesium sulfate. Removal of the solvent gave a residue, which was pulverized with diisopropyl ether and them chromatographed on silica gel eluting with a mixed solvent of ethyl acetate and chloroform (4:6 to 6:4 by volume), and fraction containing a desired compound were collected. Removal of the solvent gave a residue, which was pulverized with diisopropyl ether and then collected by filtration to obtain 1-acetoxypropyl 7-[2-(2-aminothiazol-4-yl)-2-methoxyiminoacetamido]-3-vinyl-3-cephem-4-carboxylate (syn isomer) (0.62 g), mp 97°-101° C.

IR (Nujol): 3300, 1765, 1670, 1610 cm$^{-1}$

NMR δppm (DMSO—d$_6$): 0.95 (3H, m), 1.87 (2H, m), 2.07 (3H, s), 3.48-4.23 (2H, m), 3.85 (3H, s), 5.25 (1H, d, J=4.0 Hz), 5.25-5.98 (3H, m), 6.74 (1H, s), 6.53-7.38 (4H, m), 9.58 (1H, d, J=8.0 Hz)

Example 166

1-Acetoxypropyl 7-[2-(2-aminothiazol-4-yl)-DL-glycolamido]-3-vinyl-3-cephem-4-carboxylate (0.68 g) was obtained by reacting sodium 7-[2-(2-aminothiazol-4-yl)-DL-glycolamido]-3-vinyl-3-cephem-4-carboxylate (2.0 g) with 1-bromopropyl acetate (1.0 g) in the presence of sodium iodide (0.8 g) according to a similar manner to that of Example 165.

IR (Nujol): 3300, 1770, 1680, 1620 cm$^{-1}$

NMR δppm (DMSO—d$_6$): 0.71-1.12 (3H, m), 1.81 (2H, m), 2.05 (3H, s), 3.76 (2H, q, J=18.0 Hz), 4.91 (1H, m), 5.20 (1H, d, J=5.0 Hz), 5.23-5.96 (3H, m), 6.41-7.51 (3H, m), 8.53 (1H, m)

Example 167

To a solution of L-2-benzhydryloxycarbonyl-2-tert-butoxycarbonylaminoethyl 7-[(2-aminothiazol-4-yl)glyoxylamido]-3-vinyl-3-cephem-4-carboxylate (5.4 g) in methanol was added bit by bit sodium borohydride (0.417 g) at 5° C., and the mixture was stirred at the same temperature for 15 minutes. After adjusting the reaction mixture to pH 5.0 with conc. hydrochloric acid, it was concentrated to dryness under reduced pressure to give a residue which was chromatographed on silica gel (100 ml) eluting with a mixed solvent of benzene and acetone. Fractions containing a desired compound were collected and then evaporated to obtain L-2-benzhydryloxycarbonyl-2-tert-butoxycarbonylaminoethyl 7-[2-(2-aminothiazol-4-yl)-DL-glycolamido]-3-vinyl-3-cephem-4carboxylate (2.50 g).

IR (Nujol): 3340, 1774, 1715 cm$^{-1}$

| NMR δppm (DMSO-d$_6$): | 1.33(9H, s), 3.30(1H, s), 3.46, 3.90(2H, ABq, J=18Hz), 4.50 (3H, m), 4.83(s) ⎫ 4.92(s) ⎭ (1H), 5.1–6.0(3H, m), 5.11(1H, d, J=5Hz), 6.41(1H, s), 6.77(1H, s), 6.88(1H, dd, J=11Hz, 18Hz), 7.37(10H, s), 8.36(d, J=8Hz), ⎫ 8.46(d, J=8Hz) ⎭ (1H) |
|---|---|

Example 168

A solution of benzhydryl 7-(4-bromo-2-methoxyiminoacetoacetamido)-3-vinyl-3-cephem-4-carboxylate (syn isomer) (1.2 g), thiourea (0.5 g) and sodium acetate (trihydrate) (0.7 g) in water (20 ml) and tetrahydrofuran (20 ml) was stirred at 30° C. for 3.5 hours. The reaction mixture was extracted with ethyl acetate, and the extract was washed with water and dried over anhydrous magnesium sulfate. Removal of the solvent gave a residue, which was pulverized with diethyl ether to obtain benzhydryl 7-[2-(2-aminothiazol-4-yl)-2-methoxyiminoacetamido]-3-vinyl-3-cephem-4-carboxylate (syn isomer) (1.05 g).

IR (Nujol): 3230, 1780, 1710, 1650, 1620, 1580, 1540 cm$^{-1}$

NMR δppm (DMSO—d$_6$): 3.78 (2H, q, J=17 Hz), 3.87 (3H, s), 5.28 (1H, d, J=5 Hz), 5.32 (1H, d, J=11 Hz), 5.65 (1H, d, J=17 Hz), 5.72 (1H, dd, J=5 Hz, 8 Hz), 6.80 (1H, s), 6.80 (1H, dd, J=11 Hz, 17 Hz), 6.97 (1H, s), 7.20–7.67 (10H, m), 9.67 (1H, d, J=8 Hz)

Example 169

7-[2-(2-Aminothiazol-4-yl)-2-methoxyiminoacetamido]-3-vinyl-3-cephem-4-carboxylate acid (syn isomer) (0.8 g) was obtained by reacting 7-(4-bromo-2-methoxyiminoacetoacetamido)-3-vinyl-3-cephem-4-carboxylic acid (syn isomer) (1.5 g) with thiourea (0.8 g) according to a similar manner to that of Example 168.

IR (Nujol): 3400–3100, 1780, 1660, 1630, 1540 cm$^{-1}$

NMR δppm (DMSO—d$_6$): 3.72 (2H, q, J=18 Hz), 3.87 (3H, s), 5.20 (1H, d, J=5 Hz), 5.33 (1H, d, J=11 Hz), 5.58 (1H, d, J=18 Hz), 5.78 (1H, dd, J=5 Hz, 8 Hz), 6.77 (1H, s), 6.95 (1H, dd, J=11 Hz, 18 Hz), 9.62 (1H, d, J=8 Hz)

The following compounds were obtained by reacting the corresponding 7-acylamino-3-vinyl cephalosporanic acid derivatives with thiourea according to a similar manner to that of Example 168.

Example 170

L-2-Benzhydryloxycarbonyl-2-tert-butoxycarbonylaminoethyl 7-[2-(2-aminothiazol-4-yl)-2-methoxyiminoacetamido]-3-vinyl-3-cephem-4-carboxylate (syn isomer)

IR (Nujol): 3370, 1775, 1730, 1616 cm$^{-1}$

Example 171

7-[2-(2-Aminothiazol-4-yl)-2-ethoxyiminoacetamido]-3-vinyl-3-cephem-4-carboxylic acid (syn isomer)

IR (Nujol): 3300, 1770, 1660, 1545 cm$^{-1}$

Example 172

7-[2-(2-Aminothiazol-4-yl)-2-hexyloxyiminoacetamido]-3-vinyl-3-cephem-4-carboxylic acid (syn isomer), mp 147°–155° C. (dec).

IR (Nujol): 3250, 1770, 1660, 1530 cm$^{-1}$

Example 173

Pivaloyloxymethyl 7-[2-(2-aminothiazol-4-yl)-2-(pivaloyloxymethoxycarbonylmethoxyimino)acetamido]-3-vinyl-3-cephem-4-carboxylate (syn isomer), mp 115° C. (dec.).

IR (Nujol): 3400, 3260, 3100, 1780, 1750, 1660, 1530 cm$^{-1}$

Example 174

Acetoxymethyl 7-[2-(2-aminothiazol-4-yl)-2-methoxyiminoacetamido]-3-vinyl-3-cephem-4-carboxylate (syn isomer), mp 78°–83° C.

IR (Nujol): 3300, 1765 (broad), 1660, 1610, 1535 cm$^{-1}$

Example 175

Propionyloxymethyl 7-[2-(2-aminothiazol-4-yl)-2-methoxyiminoacetamido]-3-vinyl-3-cephem-4-carboxylate (syn isomer), mp 79°–85° C.

IR (Nujol): 3350, 1770 (broad), 1650, 1620, 1530 cm$^{-1}$

Example 176

Isobutyryloxymethyl 7-[2-(2-aminothiazol-4-yl)-2-methoxyiminoacetamido]-3-vinyl-3-cephem-4-carboxylate (syn isomer), mp 92°–100° C. (dec).

IR (Nujol): 3400–3100, 1780–1740, 1670, 1610, 1530 cm$^{-1}$

Example 177

Pivaloyloxymethyl 7-[2-(2-aminothiazol-4-yl)-2-ethoxyiminoacetamido]-3-vinyl-3-cephem-4-carboxylate (syn isomer)

IR (Nujol): 3300, 1780, 1740, 1670, 1610, 1530 cm$^{-1}$

Example 178

1-acetoxypropyl 7-[2-(2-aminothiazol-4-yl)-2-methoxyiminoacetamido]-3-vinyl-3-cephem-4-carboxylate (syn isomer), mp 97°–101° C.

IR (Nujol): 3300, 1765, 1670, 1610 cm$^{-1}$

Example 179

To a mixture of trifluoroacetic acid (28.8 ml) and anisole (4.8 ml) was added 1-2-benzhydryloxycarbonyl-2-tert-butoxycarbonylaminoethyl 7-[2-(2-aminothiazol-4-yl)-2-methoxyiminoacetamido]-3-vinyl-3-cephem-4- carboxylate (4.8 g) at 5° C., and the mixture was stirred at 0° to 5° C. for half an hour. The reaction mixture was added dropwise to diisopropyl ether (900 ml), and the precipitated material was collected by filtration, and thereto were added water (100 ml) and ethyl acetate (100 ml). The separated aqueous solution was washed with ethyl acetate (50 ml), followed by completely removing the ethyl acetate therein by evaporation. The resultant aqueous solution was adjusted to pH 3.0 with 5% aqueous sodium bicarbonate, followed by removal of the precipitated material. The aqueous solution was chromatographed on a nonionic adsorption resin, "Diaion HP-20" (Trade Mark, manufactured by Mitsubishi Chemical Industries, Ltd.) (100 ml). After washing with water (300 ml), elution was carried out with 30% aqueous isopropyl alcohol and fractions containing a desired compound were collected. Removal of the solvent gave a residue, which was lyophilized and then dried to obtain L-2-amino-2-carboxyethyl 7-[2-(2-aminothiazol-4-yl)-2-methoxyiminoacetamido]-3-vinyl-3-cephem-4-carboxylate (syn isomer) (1.5 g).

IR (Nujol): 3200, 1770, 1735 (shoulder), 1650 (broad) cm$^{-1}$

NMR δppm (DCl+D$_2$O): 3.73, 3.94 (2H, ABq, J=18 Hz), 4.13 (3H, s), 4.5–4.9 (3H, m), 5.30 (1H, d, J=5 Hz), 5.56 (1H, d, J=11 Hz), 5.77 (1H, d, J=18 Hz), 5.80 (1H, d, J=5 Hz), 7.11 (1H, dd, J=11 Hz, 18 Hz), 7.19 (1H, s)

Example 180

A solution of L-2-benzhydryloxycarbonyl-2-tert-butoxycarbonylaminoethyl 7-[2-(2-aminothiazol-4-yl)-DL-glycolamido]-3-vinyl-3-cephem-4-carboxylate (2.2 g) and anisole (5 ml) in trifluoroacetic acid (20 ml) was stirred at 5° C. for half an hour. The reaction mixture was added dropwise to diisopropyl ether (600 ml), and the precipitated material was collected by filtration and then washed with diisopropyl ether, followed by dissolving in water (50 ml). After adjusting to pH 3.5 with 5% aqueous sodium bicarbonate, the aqueous solution was chromatographed on a nonionic adsorption resin, "Diaion HP-20" (80 ml). After washing with water (240 ml), elution was carried out with 10% aqueous isopropyl alcohol, and fractions containing a desired compound were collected. Removal of the solvent gave a residue, which was lyophilized and then dried to obtain L-2-amino-2-carboxyethyl 7-[2-(2-aminothiazol-4-yl)-DL-glycolamido]-3-vinyl-3-cephem-4-carboxylate (1.1 g).

IR (Nujol): 3300, 3180, 1760, 1720, 1628 cm$^{-1}$

| NMR δ ppm (DMSO-d$_6$): | 3.55, 3.97(2H, ABq, J=18Hz), 4.3–4.83(3H, m), 4.88(1H, s), 5.18(1H, d, J=5Hz), 5.38(1H, d, J=11Hz), 5.62(1H, d, J=18Hz), 5.77(1H, m), 6.43(1H, s), 6.98 (1H, dd, J=11Hz, 18Hz), 8.4(d, J=8Hz), 8.47(d, J=8Hz) ⎫⎬⎭ (1H) |
|---|---|

Example 181

A mixture of benzhydryl 7-[2-(2-aminothiazol-4-yl)-2-(L-2-benzhydryloxycarbonyl-2-tert-butoxycarbonylaminoethoxycarbonylmethoxyimino)acetamido]-3-vinyl-3-cephem-4-carboxylate (syn isomer) (5.4 g), trifluoroacetic acid (21.6 ml) and anisole (5.4 ml) was stirred at 5° to 10° C. for 70 minutes. The reaction mixture was added dropwise to diisopropyl ether (1000 ml), followed by collecting the precipitated material. After washing with diisopropyl ether, said material was dissolved in a mixture of ethyl acetate (50 ml) and water (50 ml). The separated aqueous solution was washed with ethyl acetate, and the ethyl acetate therein was completely removed by evaporation. The resultant aqueous solution was adjusted to pH 3.0 with 5% sodium bicarbonate and then chromatographed on a nonionic adsorption resin, "Diaion HP-20" (100 ml). After washing with water (300 ml), elution was carried out 20% aqueous isopropyl alcohol, and fractions containing a desired compound were collected. Removal of the solvent gave a residue, which as lyophilized to obtain 7-[2-(2-aminothiazol-4-yl)-2-(L-2-amino-2-carboxyethoxycarbonylmethoxyimino)acetamido]-3-vinyl-3-cephem-4-carboxylic acid (syn isomer) (1.7 g), mp 158° C. (dec.).

IR (Nujol): 3200 (broad), 1760 (broad) cm$^{-1}$

NMR δppm (DMSO—d$_6$): 3.51, 3.75 (2H, Abq, J=18 Hz), 4.3–4.8 (5H, m), 5.13 (1H, d, J=5 Hz), 5.19 (1H, d, J=11 Hz), 5.44 (1H, d, J=18 Hz), 5.72 (1H, dd, J=5 Hz, 8 Hz), 6.79 (1H, s), 6.93 (1H, dd, J=11 Hz, 18 Hz), 9.66 (1H, d, J=8 Hz)

Example 182

A mixture of benzhydryl 7-[2-(2-aminothiazol-4-yl)-2-(DL-3-benzhydryloxycarbonyl-3-tert-butoxycarbonylaminopropoxyimino)acetamido]-3-vinyl-3-cephem-4-carboxylate (syn isomer) (3.3 g), trifluoroacetic acid (20 ml) and anisole (3.3 ml) was stirred at 5° to 10° C. for 1.5 hours. The reaction mixture was added dropwise to diisopropyl ether (300 ml), and the precipitated material was collected by filtration and then washed with diisopropyl ether, followed by dissolving in water (50 ml). The aqueous solution was washed with ethyl acetate (50 ml×2), and the ethyl acetate therein was completely removed by evaporation. The resultant aqueous solution was adjusted to pH 3.1 with 5% aqueous sodium bicarbonate and chromatographed on a nonionic adsorption resin, "Diaion HP-20" (100 ml). After washing with water (300 ml), elution was carried out with 20% aqueous isopropyl alcohol, and the fractions containing a desired compound were collected and then treated with an activated charcoal. Removal of the solvent gave a residue, which was lyophilized to obtain 7-[2-(2-aminothiazol-4-yl)-2-(DL-3-amino-3-carboxypropoxyimino)acetamido]-3-vinyl-3-cephem-4-carboxylic acid (syn isomer) (0.7 g), mp 145° C. (dec.).

IR (Nujol): 3120, 1766, 1612 cm$^{-1}$

NMR δppm (D$_2$O+DCl): 2.53 (2H, m), 3.82 (2H, broad s), 4.31 (1H, t, J=6 Hz), 4.57 (2H, t, J=6 Hz), 5.32 (1H, d, J=5 Hz), 5.53 (1H, d, J=11 Hz), 5.73 (1H, d, J=18 Hz), 5.82 (1H, d, J=5 Hz), 7.13 (1H, dd, J=11 Hz, 18 Hz), 7.25 (1H, s)

Example 183

To a suspension of Vilsmeier reagent, which was prepared from N,N-dimethylformamide (1.8 g) and phosphorus oxychloride (3.7 g), in tetrahydrofuran (60 ml) was added 2-(2-formamidothiazol-4-yl)-2-(2-pyridylmethoxyimino)acetic acid (syn isomer) (6.74 g) under ice-cooling with stirring, and the stirring was continued at the same temperature for 30 minutes to prepare the activated acid solution. This solution was added to a solution of benzhydryl 7-amino-3-vinyl-3-cephem-4-carboxylate hydrochloride (8.6 g) and trimethylsilylacetamide (15.7 g) in ethyl acetate (100 ml) at −20° C., and the mixture was stirred at −20° to −5° C.

for 2 hours. To the reaction mixture were added ethyl acetate and water, followed by separating the ethyl acetate layer. After the ethyl acetate solution was washed with a saturated aqueous sodium bicarbonate and an aqueous sodium chloride, it was dried over anhydrous magnesium sulfate. Removal of the solvent gave a residue, which was pulverized with diisopropyl ether to obtain benzhydryl 7-[2-(2-formamidothiazol-4-yl)-2-(2-pyridylmethoxyimino)acetamido]-3-vinyl-3-cephem-4-carboxylate (syn isomer) (13.6 g).

IR (Nujol): 3250, 1760, 1720, 1660, 1580, 1560, 1540 cm$^{-1}$

NMR δppm (DMSO—d$_6$): 3.77 (2H, q, J=18 Hz), 5.33 (4H, m), 5.63 (1H, d, J=17 Hz), 6.03 (1H, dd, J=5 Hz, 8 Hz), 6.80 (1H, dd, J=11 Hz, 17 Hz), 7.00 (1H, s), 7.13–8.00 (14H, m), 8.53 (1H, m), 8.53 (1H, s), 10.07 (1H, d, J=8 Hz), 12.7 (1H, s)

moval of the solvent, to the residue were added ethyl acetate and water, followed by adjusting to pH 7 with 20% aqueous sodium carbonate. The separated ethyl acetate solution was washed with an aqueous sodium chloride and then dried over anhydrous magnesium sulfate. Removal of the solvent gave benzhydryl 7-[2-(2-aminothiazol-4-yl)-2-(2-pyridylmethoxyimino)acetamido]-3-vinyl-3-cephem-4-carboxylate (syn isomer) (4.6 g).

IR (Nujol): 3240, 1775, 1720, 1670, 1610, 1590, 1540 cm$^{-1}$

NMR δppm (DMSO—d$_6$): 3.73 (2H, q, J=17 Hz), 5.28 (2H, s), 5.28 (2H, m), 5.63 (1H, d, J=17 Hz), 5.98 (1H, dd, J=5 Hz, 8 Hz), 6.82 (1H, dd, J=11 Hz, 17 Hz), 6.85 (1H, s), 7.00 (1H, s), 7.1–8.00 (13H, m), 8.53 (1H, dd, J=2 Hz, 6 Hz), 10.00 (1H, d, J=8 Hz)

Example 186

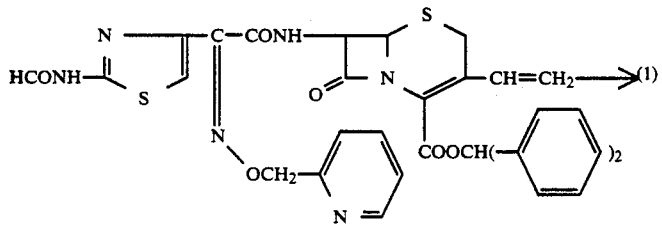

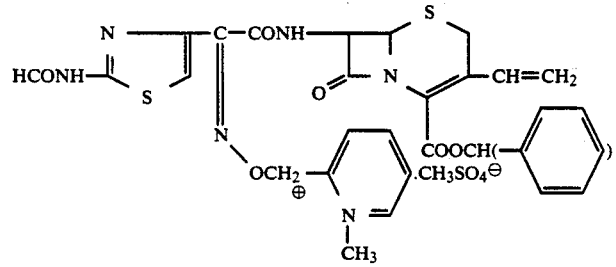

Example 184

Benzhydryl 7-[2-(2-formamidothiazol-4-yl)-2-(3-pyridylmethoxyimino)acetamido]-3-vinyl-3-cephem-4-carboxylate (syn isomer) (8.7 g) was obtained by reacting benzhydryl 7-amino-3-vinyl-3-cephem-4-carboxylate hydrochloride (8.6 g) with 2-(2-formamidothiazol-4-yl)-2-(3-pyridylmethoxyimino)acetic acid (syn isomer) (6.74 g) according to a similar manner to that of Example 183.

IR (Nujol): 3260, 1770, 1710, 1690, 1650, 1580, 1570, 1530 cm$^{-1}$

NMR δppm (DMSO—d$_6$): 3.75 (2H, q, J=18 Hz), 5.27 (2H, s), 5.30 (1H, d, J=5 Hz), 5.30 (1H, d, J=11 Hz), 5.67 (1H, d, J=17 Hz), 5.97 (1H, dd, J=5 Hz, 8 Hz), 6.78 (1H, dd, J=11 Hz, 17 Hz), 6.97 (1H, s), 7.20–7.67 (12H, m), 7.87 (1H, m), 8.53 (1H, s), 8.47–8.70 (2H, m), 9.88 (1H, d, J=8 Hz), 12.67 (1H, broad s)

Example 185

A mixture of benzhydryl 7-[2-(2-formamidothiazol-4-yl)-2-(2-pyridylmethoxyimino)acetamido]-3-vinyl-3-cephem-4-carboxylate (syn isomer) (5.45 g), conc. hydrochloric acid (5 ml) and methanol (150 ml) was stirred at ambient temperature for 1.5 hours. After re- Benzhydryl 7-[2-(2-formamidothiazol-4-yl)-2-(2-pyridylmethoxyimino)acetamido]-3-vinyl-3-cephem-4-carboxylate (syn isomer) (2.72 g) was added to a solution of dimethylsulfate (0.95 g) in tetrahydrofuran (120 ml), and the mixture was stirred at 43° to 46° C. for 25 hours. After removal of the solvent, the residue was dissolved in a mixture of water (30 ml), tetrahydrofuran (30 ml) and ethyl acetate (50 ml), followed by separating an aqueous layer. The remained organic solution was extracted with water, and ethanol was added to the combined aqueous solution. Removal of the solvent gave a residue, which was washed with a mixture of ethanol and diethyl ether to obtain 1-methyl-2-[1-(2-formamidothiazol-4-yl)-1-{N-(4-benzhydryloxycarbonyl-3-vinyl-3-cephem-7-yl)carbamoyl}-methyleneaminooxymethyl]pyridinium methylsulfate (syn isomer) (1.7 g).

IR (Nujol): 3180, 1770, 1710, 1670, 1625, 1540 cm$^{-1}$

NMR δppm (DMSO—d$_6$): 3.40 (3H, s), 3.73 (2H, m), 4.38 (3H, s), 5.33 (1H, d, J=5 Hz), 5.35 (1H, d, J=11 Hz), 5.65 (1H, d, J=17 Hz), 5.75 (2H, s), 6.02 (1H, dd, J=5 Hz, 8 Hz), 6.80 (1H, dd, J=11 Hz, 17 Hz), 6.98 (1H, s), 7.2–7.70 (10H, m), 7.57 (1H, s), 8.55 (1H, s), 7.93–8.63 (3H, m), 9.13 (1H, dd, J=2 Hz, 6 Hz), 10.00 (1H, d, J=8 Hz)

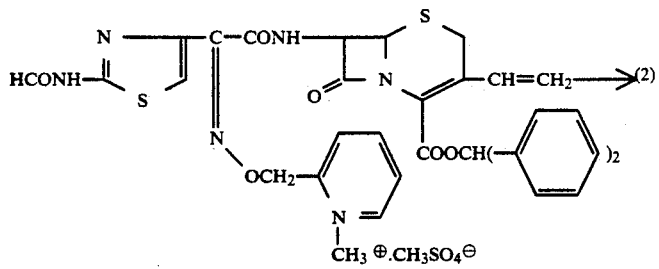

A solution of the object compound (1.6 g) obtained above and conc. hydrochloric acid (1 ml) in methanol (30 ml) and tetrahydrofuran (20 ml) was stirred at ambient temperature for 5 hours. After removal of the solvent, the residue was dissolved in tetrahydrofuran and ethanol, followed by concentration to give a residue, which was pulverized with diethyl ether to obtain hydrochloride of 1-methyl-2-[1-(2-aminothiazol-4-yl)-1-{N-(4-benzhydryloxycarbonyl-3-vinyl-3-cephem-7-yl)carbamoyl}methyleneaminooxymethyl]pyridinium methylsulfate (syn isomer) (1.5 g).

IR (Nujol): 1780, 1720, 1680, 1630, 1585, 1545, 1500 cm$^{-1}$

NMR δppm (DMSO—d$_6$): 3.43 (3H, s), 3.80 (2H, m), 4.40 (3H, s), 5.33 (1H, d, J=5 Hz), 5.33 (1H, d, J=11 Hz), 5.57 (1H, d, J=17 Hz), 5.73 (2H, s), 5.83 (1H, dd, J=5 Hz, 8 Hz), 6.82 (1H, dd, J=11 Hz, 17 Hz), 6.97 (1H, s), 7.07 (1H, s), 7.17–7.67 (10H, m), 7.93–8.80 (3H, m), 9.17 (1H, dd, J=2 Hz, 6 Hz), 10.08 (1H, d, J=8 Hz)

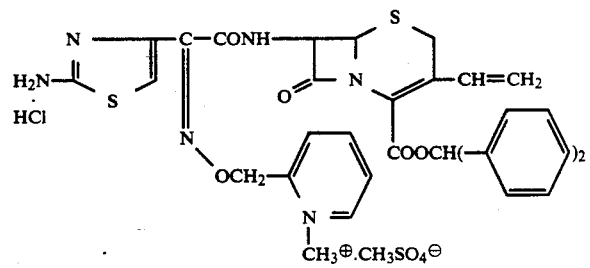

1-Methyl-3-[1-(2-formamidothiazol-4-yl)-1-{N-(4-benzhydryloxycarbonyl-3-vinyl-3-cephem-7yl)carbamoyl}methyleneaminooxymethyl]pyridinium methylsulfate (syn isomer) (2.6 g) was obtained by reacting benzhydryl 7-[2-(2-formamidothiazol-4-yl)-2-(3-pyridylmethoxyimino)acetamido]-3-vinyl-3-cephem-4-carboxylate (syn isomer) (3.4 g) with dimethylsulfate (1.26 g) according to a similar manner to that of Example 186-(1).

IR (Nujol): 1770, 1720, 1670, 1550 cm$^{-1}$

NMR δppm (DMSO—d$_6$): 3.42 (3H, s), 3.80 (2H, m), 4.40 (3H, s), 5.33 (1H, d, J=5 Hz), 5.38 (1H, d, J=11 Hz), 5.52 (2H, s), 5.70 (1H, d, J=17 Hz), 5.95 (1H, dd, J=5 Hz, 8 Hz), 6.82 (1H, dd, J=11 Hz, 17 Hz), 7.00 (1H, s), 7.13–7.67 (10H, m), 7.58 (1H, s), 8.17 (1H, m), 8.57 (1H, s), 8.67 (1H, m), 9.03 (1H, m), 9.03 (1H, s), 9.95 (1H, d, J=8 Hz)

Example 187

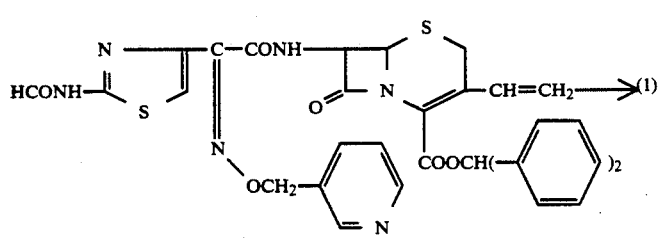

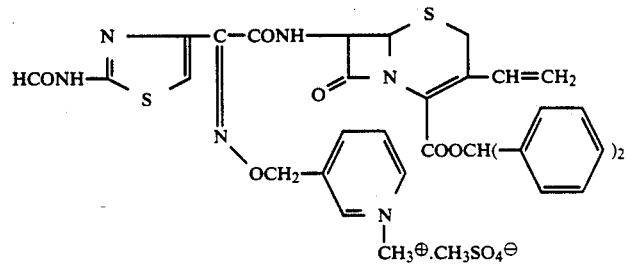

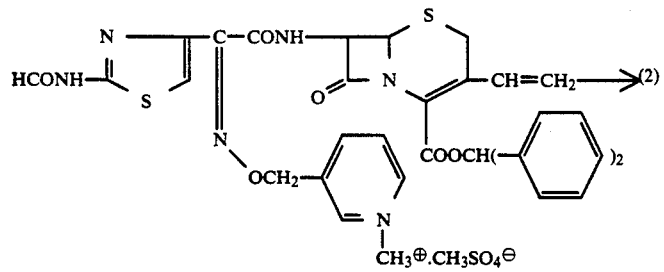

Hydrochloride of 1-methyl-3-[1-(2-aminothiazol-4-yl)-1-{N-(4-benzhydryloxycarbonyl-3-vinyl-4-cephem-7-yl)carbamoyl}methyleneaminooxymethyl]pyridinium methylsulfate (syn isomer) (1.1 g) was obtained by reacting the object compound (1.5 g) obtained above with conc. hydrochloric acid (1.2 ml) according to a similar manner to that of Example 186-(2).

IR (Nujol): 3400–3100, 1760, 1660, 1600, 1530 cm$^{-1}$

NMR δppm (DMSO—d$_6$): 3.40 (3H, s), 3.73 (2H, broad s), 4.45 (3H, s), 5.20 (1H, d, J=5 Hz), 5.38 (1H, d, J=11 Hz), 5.47 (2H, s), 5.63 (1H, d, J=17 Hz), 5.80 (1H, dd, J=5 Hz, 8 Hz), 6.7–7.7 (11H, m), 6.97 (1H, s), 7.12 (1H, s), 8.17 (1H, m), 8.7 (1H, m), 9.00 (1H, m), 9.17 (1H, broad s), 10.02 (1H, d, J=8 Hz)

Example 188

To a solution of benzhydryl 7-[2-(2-aminothiazol-4-yl)-2-(2-pyridylmethoxyimino)acetamido]-3-vinyl-3-cephem-4-carboxylates (syn isomer) (4.6 g) in methylene chloride (20 ml) and anisole (3.0 g) was added trifluoroacetic acid (11.2 g) under ice-cooling with stirring, and the stirring was continued at ambient temperature for 1.5 hours. The reaction mixture was added dropwise to diisopropyl ether (300 ml) and the precipitated crystals were collected by filtration, followed by suspending in water (70 ml). After adjusting to pH 7.5 with 1N aqueous sodium hydroxide, the resultant aqueous solution was washed with ethyl acetate. The aqueous solution was further adjusted to pH 3.4 with 10% hydrochloric acid, followed by collecting the precipitated crystals to obtain 7-[2-(2-aminothiazol-4-yl)-2-(2-pyridylmethoxyimino)acetamido]-3-vinyl-3-cephem-4-carboxylic acid (syn isomer) (1.8 g).

IR (Nujol): 3300, 1770, 1650, 1620 (shoulder), 1540 cm$^{-1}$

NMR δppm (DMSO—d$_6$): 3.70 (2H, q, J=18 Hz), 5.23 (1H, d, J=5 Hz), 5.30 (2H, s), 5.32 (1H, d, J=11 Hz), 5.60 (1H, d, J=17 Hz), 5.85 (1H, dd, J=5 Hz, 8 Hz), 6.82 (1H, dd, J=11 Hz, 17 Hz), 6.82 (1H, s), 7.00–8.10 (3H, m), 8.57 (1H, d, J=4 Hz), 9.97 (1H, d, J=8 Hz)

Example 189

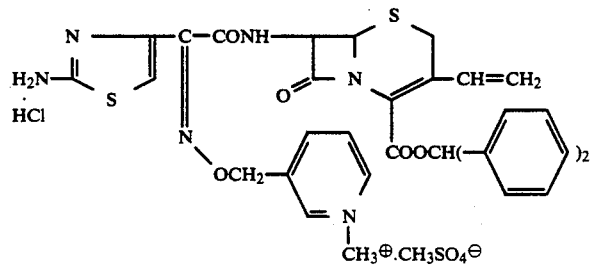

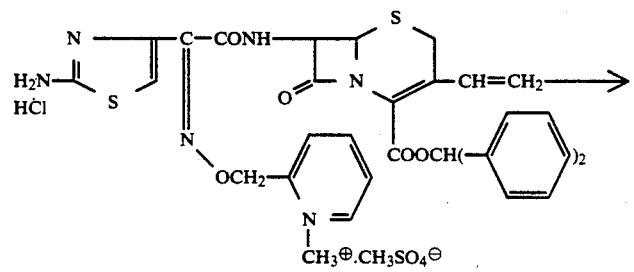

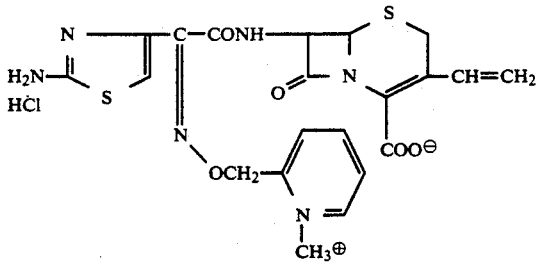

Hydrochloride of 1-methyl-2-[1-(2-aminothiazol-4-yl)-1-{N-(4-benzhydryloxycarbonyl-3-vinyl-3-cephem-7-yl)carbamoyl)methyleneaminooxymethyl]pyridinium methylsulfate (syn isomer) (2.6 g) was suspended in methylene chloride (20 ml) and anisole (1.4 g), and thereto was added trifluoroacetic acid (5.8 g) under ice-cooling with stirring, followed by stirring at ambient temperature for 1.5 hours. After the reaction mixture was added dropwise to diisopropyl ether (250 ml), the precipitated materials were collected by filtration and dissolved in water (20 ml). The aqueous solution was adjusted to pH 6.5 with 1N aqueous sodium hydroxide and washed with ethyl acetate, and then adjusted to pH 2 with 10% hydrochloric acid, followed by subjecting to column chromatography on nonionic adsorption resin "Diaion HP-20" (100 ml). After washing with water, elution was carried out with 30% aqueous isopropyl alcohol, and fractions containing a desired compound were collected and evaporated. The residue obtained was lyophilized to obtain hydrochloride of 7-[2-(2-aminothiazol-4-yl)-2-{(1-methyl-2-pyridinio)methoxyimino}acetamido]-3-vinyl-3-cephem-4-carboxylate (syn isomer) (1.2 g).

IR (Nujol): 1770, 1720, 1670, 1630, 1540 cm$^{-1}$

NMR δppm (D$_2$O): 3.60 (2H, broad s), 4.38 (3H, s), 5.22 (1H, d, J=5 Hz), 5.25 (1H, d, J=11 Hz), 5.40 (1H, d, J=17 Hz), 5.70 (2H, s), 5.82 (1H, d, J=5 Hz), 6.82 (1H, dd, J=11 Hz, 17 Hz), 7.03 (1H, s), 7.80–8.73 (3H, m), 8.87 (1H, dd, J=2 Hz, 6 Hz)

Example 190

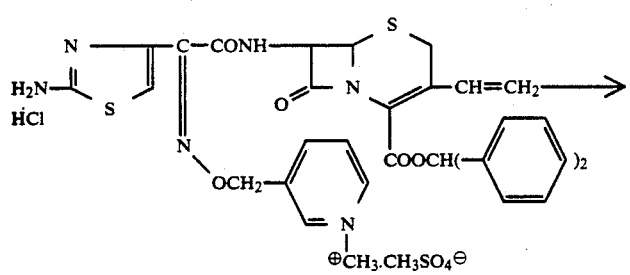

Hydrochloride of 7-[2-(2-aminothiazol-4-yl)-2-{(1-methyl-3-pyridinio)methoxyimino}acetamido]-3-vinyl-3-cephem-4-carboxylate (syn isomer) (0.4 g) was obtained by reacting hydrochloride of 1-methyl-3-[1-(2-aminothiazol-4-yl)-1-{N-(4-benzhydryloxycarbonyl-3-vinyl-3-cephem-7-yl)carbamoyl}methyleneaminooxymethyl]pyridinium methylsulfate (syn isomer) (1.0 g) with trifluoroacetic acid (2.8 g) in the presence of anisole (0.52 g) according to a similar manner to that of Example 189.

IR (Nujol): 3400–3100, 176, 1660, 1600, 1530 cm$^{-1}$

NMR δppm (D$_2$O): 3.67 (2H, broad s), 4.43 (3H, s), 5.25 (1H, d, J=5 Hz), 5.30 (1H, d, J=11 Hz), 5.43 (1H, d, J=17 Hz), 5.50 (2H, s), 5.80 (1H, d, J=5 Hz), 6.83 (1H, dd, J=11 Hz, 17 Hz), 7.02 (1H, s), 8.10 (1H, m), 8.78–8.90 (2H, m), 8.90 (1H, s).

Example 190

Benzhydryl 7-[2-(2-formamidothiazol-4-yl)-2-(1-tert-butoxycarbonyl-1-methylethoxyimino)acetamido]-3-vinyl-3-cephem-4-carboxylate (syn isomer) (4.93 g) was obtained by reacting benzhydryl 7-amino-3-vinyl-3-cephem-4-carboxylate hydrochloride (3.2 g) with 2-(2-formamidothiazol-4-yl)-2-(1-tert-butoxycarbonyl-1-methylethoxyimino)acetic acid (syn isomer) (2.9 g) according to a similar manner to that of Example 103.

IR (Nujol): 3150, 1780, 1720, 1690 cm$^{-1}$

NMR δppm (DMSO—d$_6$): 1.27–1.81 (15H, m), 3.81 (2H, q, J=18.0 Hz), 5.34 (1H, d, J=4.0 Hz), 5.22–6.18 (3H, m), 6.79 (1H, dd, J=12.0 Hz, 18.0 Hz), 7.00 (1H, s), 7.13–7.75 (11H, m), 8.54 (1H, s), 9.58 (1H, d, J=8.0 Hz)

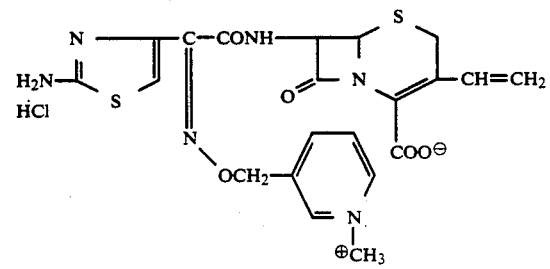

Example 192

Benzhydryl 7-[2-(2-formamidothiazol-4-yl)-2-(1tert-butoxycarbonylethoxyimino)acetamido]-3-vinyl-3-cephem-4-carboxylate (syn isomer) (5.62 g) was obtained by reacting benzhydryl 7-amino-3-vinyl-3-cephem-4-carboxylate hydrochloride (3.4 g) with 2-(2-formamidothiazol-4-yl)-2-(1-tert-butoxycarbonylethoxyimino)acetic acid (syn isomer) (3.0 g) according to a similar manner to that of Example 103.

IR (Nujol): 3250, 3150, 1780, 1720, 1680 cm$^{-1}$

| NMR $\delta$ppm (DMSO-$d_6$): | 1.23–1.72(12H, m), 3.78(2H, q, J=18.0Hz), 4.66(1H, q, J=8.0Hz), 5.33(1H, d, J=5.0Hz), 3.27–6.16(1H, m), 6.79(1H, dd, J=10.0Hz, 18.0Hz), 6.98(1H, s), 7.18–7.82(11H, m), 8.56 (1H, s), |
|---|---|
| | 9.59(d, J=8.0Hz) ⎫ |
| | 9.67(d, J=8.0Hz) ⎬ (1H) |

Example 193

Benzhydryl 7-[2-(2-formamidothiazol-4-yl)-2-ethoxycarbonylmethoxyiminoacetamido]-3-vinyl-3-cephem-4-carboxylate (syn isomer) (6.4 g) was obtained by reacting benzhydryl 7-amino-3-vinyl-3-cephem-4-carboxylate hydrochloride (4.29 g) with 2-(2-formamidothiazol-4-yl)-2-ethoxycarbonylmethoxyiminoacetic acid (syn isomer) (3.3 g) according to a similar manner to that of Example 103.

IR (Nujol): 3250, 1780, 1710, 1690, 1660, 1540 cm$^{-1}$

NMR $\delta$ppm (DMSO—$d_6$): 1.20 (3H, t, J=7 Hz), 3.77 (2H, m), 4.15 (2H, q, J=7 Hz), 4.75 (2H, s), 5.28 (1H, d, J=11 Hz), 5.30 (1H, d, J=5 Hz), 5.65 (1H, d, J=17 Hz), 5.97 (1H, dd, J=5 Hz, 8 Hz), 6.82 (1H, dd, J=11 Hz, 17 Hz), 6.97 (1H, s), 7.17–7.67 (11H, m), 8.55 (1H, s), 9.73 (1H, d, J=8 Hz), 12.67 (1H, broad s)

Example 194

7-[2-(2-Formamidothiazol-4-yl)-2-tert-butoxycarbonylmethoxyiminoacetamido]-3-vinyl-3-cephem-4-carboxylic acid (syn isomer) (2.7 g) was obtained by reacting 7-amino-3-vinyl-3-cephem-4-carboxylic acid (2.26 g) with 2-(2-formamidothiazol-4-yl)-2-tert-butoxycarbonylmethoxyiminoacetic acid (syn isomer) (3.29 g) according to a similar manner to that of Example 103.

IR (Nujol): 3230, 1780, 1720, 1680, 1542 cm$^{-1}$

NMR $\delta$ppm (DMSO—$d_6$): 1.45 (9H, s), 3.73 (2H, q, J=18 Hz), 4.63 (2H, s), 5.23 (1H, d, J=5 Hz), 5.30 (1H, d, J=11 Hz), 5.58 (1H, d, J=18 Hz), 5.58 (1H, dd, J=5 Hz, 8 Hz), 6.98 (1H, dd, J=11 Hz, 18 Hz), 7.46 (1H, s), 8.53 (1H, s), 9.63 (1H, d, J=8 Hz), 12.73 (1H, broad s)

Example 195

Benzhydryl 7-[2-(2-aminothiazol-4-yl)-2-(1-tert-butoxycarbonyl-1-methylethoxyimino)acetamido]-3-vinyl-3-cephem-4-carboxylate (syn isomer) (4.03 g) was obtained by reacting benzhydryl 7-[2-(2-formamidothiazol-4-yl)-2-(1-tert-butoxycarbonyl-1-methylethoxyimino)acetamido)-3-vinyl-3-cephem-4-carboxylate (syn isomer) (4.8 g) with conc. hydrochloric acid (1.4 g) according to a similar manner to that of Example 129.

IR (Nujol): 3260, 1780, 1720, 1680, 1620 cm$^{-1}$

NMR $\delta$ppm (DMSO—$d_6$): 1.21–1.70 (15H, m), 3.83 (2H, m), 5.30 (1H, d, J=4.0 Hz), 5.16–6.10 (2H, m), 6.94 (1H, dd, J=4.0 Hz, 8.0 Hz), 6.44–7.04 (1H, m), 6.74 (1H, s), 6.96 (1H, s), 7.07–7.66 (10H, m), 9.41 (1H, d, J=8.0 Hz)

Example 196

Benzhydryl 7-[2-(2-aminothiazol-4-yl)-2-(1-tert-butoxycarbonylethoxyimino)acetamido]-3-vinyl-3-cephem-4-carboxylate (syn isomer) (4.81 g) was obtained by reacting benzhydryl 7-[2-(2-formamidothiazol-4-yl)-2-(1-tert-butoxycarbonylethoxyimino)acetamido]-3-vinyl-3-cephem-4-carboxylate (syn isomer) (5.5 g) with conc. hydrochloric acid (1.6 g) according to a similar manner to that of Example 129.

IR (Nujol): 3250, 1780, 1720, 1680, 1640, 1620 cm$^{-1}$

| NMR $\delta$ppm (DMSO-$d_6$): | 1.27–1.50(12H, m), 3.78 (2H, m), 4.65(1H, q, J=7.0Hz), 5.18–5.86(3H, m), 5.93(1H, dd, J=5.0Hz, 8.0Hz), 6.80(1H, s), 6.96(1H, s), 7.07–7.67(10H, m), |
|---|---|
| | 9.44(d, J=8.0Hz) ⎫ |
| | 9.54(d, J=8.0Hz) ⎬ (1H) |

Example 197

Benzhydryl 7-[2-(2-aminothiazol-4-yl)-2-ethoxycarbonylmethoxyimino)acetamido]-3-vinyl-3-cephem-4-carboxylate (syn isomer) (5.45 g) was obtained by reacting benzhydryl 7-[2-(2-formamidothiazol-4-yl)-2-ethoxycarbonylmethoxyimino)acetamido]-3-vinyl-3-cephem-4-carboxylate (syn isomer) (6.2 g) with conc. hydrochloric acid (3.8 ml) according to a similar manner to that of Example 129.

IR (Nujol): 3250, 1780, 1720, 1662, 1620, 1535 cm$^{-1}$

NMR $\delta$ppm (DMSO—$d_6$): 1.2 (3H, t, J=7 Hz), 3.68 (2H, m), 4.15 (2H, q, J=7 Hz), 5.28 (1H, d, J=11 Hz), 5.65 (1H, d, J=17 Hz), 5.95 (1H, dd, J=5 Hz, 8 Hz), 6.82 (1H, dd, J=11 Hz, 17 Hz), 6.87 (1H, s), 7.00 (1H, s), 7.30–7.70 (10H, m), 9.65 (1H, d, J=8 Hz)

Example 198

7-[2-(2-Aminothiazol-4-yl)-2-tert-butoxycarbonylmethoxyiminoacetamido]-3-vinyl-3-cephem-4-carboxylic acid (syn isomer) (1.7 g) was obtained by reacting 7-[2-(2-formamidothiazol-4-yl)-2-tert-butoxycarbonylmethoxyiminoacetamido]-3-vinyl-3-cephem-4-carboxylic acid (syn isomer) (2.1 g) with conc. hydrochloric acid (1.2 ml) according to a similar manner to that of Example 129.

IR (Nujol): 3300, 1770, 1725, 1680, 1610, 1530 cm$^{-1}$

NMR $\delta$ppm (DMSO—$d_6$): 1.45 (9H, s), 3.72 (2H, q, J=18 Hz), 4.58 (2H, s), 5.22 (1H, d, J=5 Hz), 5.33 (1H, d, J=12 Hz), 5.58 (1H, d, J=18 Hz), 5.82 (1H, dd, J=5 Hz, 8 Hz), 6.82 (1H, s), 6.98 (1H, dd, J=12 Hz, 18 Hz), 9.52 (1H, d, J=8 Hz)

Example 199

To a mixture of benzhydryl 7-[2-(2-aminothiazol-4-yl)-2-(1-tert-butoxycarbonyl-1-methylethoxyimino)acetamido]-3-vinyl-3-cephem-4-carboxylic (syn isomer) (3.9 g) and anisole (3.9 ml) was added trifluoroacetic acid (15.6 ml) under ice-cooling, and the mixture was stirred at ambient temperature for an hour. To the reaction mixture was added diisopropyl ether and the precipitated crystals were collected by filtration and then washed with diisopropyl ether. To the crystals were added ethyl acetate and water, followed by adjusting to pH 7.5 with sodium bicarbonate. The separated aqueous solution was washed with ethyl acetate and then adjusted to pH 2.5 with 10% hydrochloric acid. The precipitated crystals were collected by filtration, washed with water and then dried to obtain 7-[2-(2-aminothiazol-4-yl)-2-(1-carboxy-1-methylethoxyimino)acetamido]-3-vinyl-3-cephem-4-carboxylic acid (syn isomer) (1.09 g), mp 173°-177° C. (dec.). The filtrate and the washings were combined and saturated with sodium chloride, followed by extraction with tetrahydrofuran. The extract was washed with a saturated aqueous sodium chloride, dried over anhydrous magnesium sulfate and then evaporated to dryness to give a residue, which was pulverized with diisopropyl ether and collected by filtration to recover the same object compound (0.59 g). Total yield: 1.68 g.

IR (Nujol): 3300, 3200, 1770, 1670, 1640 cm$^{-1}$

NMR δppm (DMSO—d$_6$): 1.49 (6H, s), 3.76 (2H, q, J=18.0 Hz), 5.24 (1H, d, J=4.0 Hz), 5.18–5.98 (3H, m), 6.79 (1H, s), 6.95 (1H, dd, J=12.0 Hz, 18.0 Hz), 9.41 (1H, d, J=8.0 Hz)

Example 200

7-[2-(2-Aminothiazol-4-yl)-2-(1-carboxyethoxyimino)acetamido]-3-vinyl-3-cephem-4-carboxylic acid (syn isomer) (0.73 g) was obtained by reacting benzhydryl 7-[2-(2-aminothiazol-4-yl)-2-(1-tert-butoxycarbonylethoxyimino)acetamido]-3-vinyl-3-cephem-4-carboxylate (syn isomer) (4.7 g) with trifluoroacetic acid (18.8 ml) in the presence of anisole (4.7 ml) according to a similar manner to that of Example 199.

IR (Nujol): 3260, 3160, 1770, 1670 cm$^{-1}$

| NMR δppm (DMSO-d$_6$): | 1.44(3H, d, J=7.0Hz), 3.73(2H, m), 4.66(1H, q, J=7.0Hz), 5.23(1H, d, J=5.0Hz), 5.33(1H, d, J=11.5Hz), 5.63–6.00(2H, m), 6.81 (1H, s), 6.97(1H, dd, J=11.5Hz, 18.0Hz), |
|---|---|
| | 9.44(d, J=8.0Hz) } (1H) 9.49(d, J=8.0Hz) |

Example 201

7-[2-(2-Aminothiazol-4-yl)-2-ethoxycarbonylmethoxyiminoacetamido]-3-vinyl-3-cephem-4-carboxylic acid (syn isomer) (3.2 g) was obtained by reacting benzhydryl 7-[2-(2-aminothiazol-4-yl)-2-ethoxyiminoacetamido]-3-vinyl-3-cephem-4-carboxylate (syn isomer) (5.2 g) with trifluoroacetic acid (12.8 g) in the presence of anisole (3.4 g) according to a similar manner to that of Example 144.

IR (Nujol): 3250, 1770, 1670, 1530 cm$^{-1}$

NMR δppm (DMSO—d$_6$): 1.22 (3H, t, J=7 Hz), 3.70 (2H, broad s), 4.17 (2H, q, J=7 Hz), 4.75 (2H, s), 5.23 (1H, d, J=5 Hz), 5.35 (1H, d, J=11 Hz), 5.58 (1H, d, J=17 Hz), 5.82 (1H, dd, J=5 Hz, 8 Hz), 6.88 (1H, s), 6.98 (1H, dd, J=11 Hz, 17 Hz), 9.63 (1H, d, J=8 Hz)

Example 202

Benzhydryl 7-amino-3-vinyl-3-cephem-4-carboxylate hydrochloride (2.3 g) was dissolved in dried ethyl acetate (50 ml) and trimethylsilylacetamide (4.9 g) at 40° C.

On the other hand, to a Vilsmeier reagent, which was prepared by reacting dried N,N-dimethylformamide (0.5 g) with phosphorus oxychloride (1.1 g) in dried ethyl acetate (2.0 ml) in a conventional manner, were added dried tetrahydrofuran (20 ml) and 2-(3-tert-butoxycarbonylpropoxyimino)-2-(2-formamidothiazol-4-yl)acetic acid (syn isomer) (2.1 g), followed by stirring at −3° to 3° C. for a while to prepare the activated acid solution.

This solution was added to the ethyl acetate solution obtained before at −10° C. with stirring, and the stirring was continued at −10° to −5° C. for half an hour. To the reaction mixture was added water, and the separated organic layer was washed with a saturated aqueous sodium bicarbonate and a saturated aqueous sodium chloride, followed by drying over magnesium sulfate. Removal of the solvent gave a residue, which was pulverized with diisopropyl ether to obtain benzhydryl 7-[2-(3-tert-butoxycarbonylpropoxyimino)-2-(2-formamidothiazol-4-yl)acetamido]-3-vinyl-3-cephem-4-carboxylate (syn isomer) (3.63 g).

IR (Nujol): 3280, 3150, 1780, 1720, 1660 cm$^{-1}$

NMR δppm (DMSO—d$_6$): 1.43 (9H, s), 1.97 (2H, m), 2.38 (2H, t, J=6.0 Hz), 3.79 (2H, q, J=18.0 Hz), 4.18 (2H, t, J=6.0 Hz), 5.33 (1H, d, J=11.0 Hz), 5.34 (1H, d, J=5.0 Hz), 5.67 (1H, d, J=17.0 Hz), 5.97 (1H, dd, J=5.0 Hz, 8.0 Hz), 6.82 (1H, dd, J=11.0 Hz, 17.0 Hz), 7.00 (1H, s), 7.19–7.73 (11H, m), 8.57 (1H, s), 9.77 (1H, d, J=8.0 Hz)

Example 203

Benzhydryl 7-amino-3-vinyl-3-cephem-4-carboxylate hydrochloride (10.6 g) was dissolved in methylene chloride (100 ml) and trimethylsilylacetamide (20.6 g) at 25° C.

On the other hand, to a suspension of 2-[5-amino-1,2,4-thiadiazol-3-yl)-2-methoxyiminoacetic acid (syn isomer) (4.0 g) in methylene chloride (100 ml) was added phosphorus oxychloride (12.1 g), followed by stirring at ambient temperature for 1.5 hours. Thereto was added N,N-dimethylformamide (8 ml) at −12° to −10° C., and the mixture was stirred at −10° to −8° C. for 45 minutes to prepare the activated acid solution.

The activated acid solution was added to the methylene chloride solution obtained before at −30° C. with stirring, and the stirring was continued at −15° C. for 45 minutes. The reaction mixture was poured into a saturated aqueous sodium bicarbonate (300 ml), followed by stirring for half an hour. During the stirring, the reaction mixture was adjusted to pH 7.5 with sodium bicarbonate. Thereto was added ethyl acetate (500 ml), and the insoluble substance was removed by filtration. The separated organic layer was washed with an aqueous sodium chloride and then dried over magnesium sulfate. Removal of the solvent gave a residue, which was pulverized with diethyl ether to obtain benzhydryl 7-[2-(5-amino-1,2,4-thiadiazol-3-yl)-2-methoxyiminoacetamido]-3-vinyl-3-cephem-4-carboxylate (syn isomer) (6.3 g).

IR (Nujol): 3300, 3175, 1770, 1720, 1670, 1610, 1510 cm$^{-1}$

NMR δppm (DMSO—d$_6$): 3.77 (2H, m), 3.93 (3H, s), 5.25 (1H, d, J=5 Hz), 5.27 (1H, d, J=11 Hz), 5.62 (1H, d, J=17 Hz), 5.92 (1H, dd, J=5 Hz, 8 Hz), 6.77 (1H, dd, J=11 Hz, 17 Hz), 6.97 (1H, s), 7.38 (10H, m), 9.62 (1H, d, J=8 Hz)

Example 204

Vilsmeier reagent, which was prepared from N,N-dimethylformamide (0.37 ml) and phosphorus oxychloride (0.44 ml) in a conventional manner, was suspended in dried tetrahydrofuran (20 ml). 2-(tert-Butoxycarbonylmethoxyimino)-2-(6-formamidopyridin-2-yl)a- cetic acid (syn isomer) (3.0 g) was added thereto under ice-cooling, with stirring, and the stirring was continued at the same temperature for an hour to prepare the activated acid solution. This solution was added at a time to a solution of benzhydryl 7-amino-3-vinyl-3-cephem-4-carboxylate (2.72 g) and trimethylsilylacetamide (5.5 g) in methylene chloride at −20° C. with stirring, and the stirring was continued at −20° to −10° C. for an hour. To the reaction mixture were added water (50 ml) and ethyl acetate (200 ml), and the separated organic layer was washed with 5% aqueous sodium bicarbonate and then a saturated aqueous sodium chloride, followed by drying over magnesium sulfate. Removal of the solvent gave benzhydryl 7-[2-(tert-butoxycarbonylmethoxyimino)-2-(6-formamidopyridin-2-yl)acetamido]-3-vinyl-3-cephem-4-carboxylate (syn isomer) (4.8 g), mp 154°-157° C.

IR (Nujol): 3240, 1777, 1745, 1715, 1689, 1667 cm$^{-1}$

NMR δppm (DMSO—d$_6$): 1.40 (9H, s), 3.50, 3.93 (2H, ABq, J=18 Hz), 4.60 (2H, s), 5.20 (1H, d, J=11 Hz), 5.25 (1H, d, J=5 Hz), 5.56 (1H, d, J=18 Hz), 5.95 (1H, dd, J=5 Hz, 8 Hz), 6.9 (1H, m), 6.9 (1H, s), 7.3 (10H, m), 7.3-8.3 (3H, m), 9.4 (1H, broad s), 9.53 (1H, d, J=8 Hz), 10.6 (1H, d, J=6 Hz)

Example 205

Benzhydryl 7-[2-(trans-3-tert-butoxycarbonylallyloxyimino)-2-(2-formamidothiazol-4-yl)acetamido]-3-vinyl-3-cephem-4-carboxylate (syn isomer) (4.83 g) was obtained by reacting benzhydryl 7-amino-3-vinyl-3-cephem-4-carboxylate hydrochloride (3.0 g) with 2-(trans-3-tert-butoxycarbonylallyloxyimino)-2-(2-formamidothiazol-4-yl)acetic acid (syn isomer) (2.7 g) according to similar manner to those of Examples 202 to 204.

IR (Nujol): 3250, 1780, 1710, 1660 cm$^{-1}$

NMR δppm (DMSO—d$_6$): 1.47 (9H, s), 3.79 (2H, q, J=18.0 Hz), 4.89 (2H, m), 5.34 (1H, d, J=11.0 Hz), 5.35 (1H, d, J=5.0 Hz), 5.68 (1H, d, J=18.0 Hz), 5.86-6.30 (2H, m), 6.52-7.22 (2H, m), 7.00 (1H, s), 7.21-7.74 (11H, m), 8.58 (1H, s), 9.91 (1H, d, J=8.0 Hz), 12.73 (1H, broad s)

Example 206

Benzhydryl 7-[2-(cyanomethoxyimino-2-(2-formamidothiazol-4-yl)acetamdio]-3-vinyl-3-cephem-4-carboxylate (syn isomer) (3.1 g) was obtained by reacting benzhydryl 7-amino-3-vinyl-3-cephem-4-carboxylate hydrochloride (2.5 g) with 2-cyanomethoxyimino-2-(2-formamidothiazol-4-yl)acetic acid (syn isomer) (1.6 g) according to similar manners to those of Examples 202 to 204.

IR (Nujol): 3180, 1770, 1720, 1680 cm$^{-1}$

NMR δppm (DMSO—d$_6$): 3.77 (2H, m), 5.03-6.10 (5H, m), 5.81 (1H, dd, J=5.0 Hz, 8.0 Hz), 6.43-7.13 (1H, m), 6.96 (1H, s), 7.35 (10H, s), 7.56 (1H, s), 8.53 (1H, s), 9.93 (1H, d, J=8.0 Hz)

Example 207

Benzhydryl 7-[2-tert-butoxycarbonylmethoxyimino-2-(5-chloro-2-formamidothiazol-4-yl)acetamido]-3-vinyl-3-cephem-4-carboxylate (syn isomer) (5.6 g) was obtained by reacting benzhydryl 7-amino-3-vinyl-3-cephem-4-carboxylate hydrochloride (3.43 g) with 2-tert-butoxycarbonylmethoxyimino-2-(5-chloro-2-formamidothiazol-4-yl)acetic acid (syn isomer) (3.2 g) according to similar manners to those of Examples 202 to 204.

IR (Nujol): 3200, 1780, 1720, 1680, 1606, 1540 cm$^{-1}$

NMR δppm (DMSO—d$_6$): 1.43 (9H, s), 3.77 (2H, m), 4.67 (2H, s), 5.30 (1H, d, J=5 Hz), 5.32 (1H, d, J=11 Hz), 5.65 (1H, d, J=18 Hz), 6.03 (1H, dd, J=5 Hz, 8 Hz), 6.83 (1H, dd, J=11 Hz, 18 Hz), 7.02 (1H, s), 7.23-7.8 (10H, m), 8.60 (1H, s), 9.73 (1H, d, J=8 Hz)

Example 208

Benzhydryl 7-[2-(6-formamidopyridin-2-yl)-2-methoxyiminoacetamido]-3-vinyl-3-cephem-4-carboxylate (syn isomer) (5.7 g), mp 154°-159° C., was obtained by reacting benzhydryl 7-amino-3-vinyl-3-cephem-4-carboxylate (3.8 g) with 2-(6-formamidopyridin-2-yl)-2-methoxyiminoacetic acid (syn isomer) (3.0 g) according to similar manners to those of Examples 202 to 204.

IR (Nujol): 3350, 1770, 1720, 1670, 1613 cm$^{-1}$

NMR δppm (DMSO—d$_6$): 3.78 (2H, m), 4.0 (3H, s), 5.30 (1H, d, J=11 Hz), 5.33 (1H, d, J=5 Hz), 5.63 (1H, d, J=18 Hz), 6.03 (1H, dd, J=5 Hz, 8 Hz), 6.83 (1H, dd, J=11 Hz, 18 Hz), 7.0 (1H, s), 7.4 (10H, m), 7.0-8.0 (3H, m), 9.3 (1H, broad s), 9.7 (1H, d, J=8 Hz), 10.7 (1H, d, J=5 Hz)

The following compounds were obtained by reacting 7-amino-3-vinylcephalosporanic acid derivatives with the corresponding acylating agents according to similar manners to those of Examples 202 to 204.

Example 209

Benzhydryl 7-[2-(2-aminothiazol-4-yl)-2-(3-tert-butoxycarbonylpropoxyimino)acetamido]-3-vinyl-3-cephem-4-carboxylate (syn isomer).

IR (Nujol): 3340, 3250, 1780, 1720, 1680, 1620 cm$^{-1}$

Example 210

Benzhydryl 7-[2-(2-aminothiazol-4-yl)-2-(trans-3-tert-butoxycarbonylallyloxyimino)acetamido]-3-vinyl-3-cephem-4-carboxylate (syn isomer)

IR (Nujol): 3250, 1770, 1700, 1670, 1610 cm$^{-1}$

Example 211

Benzhydryl 7-[2-(6-aminopyridin-2-yl)-2-tert-butoxycarbonylmethoxyiminoacetamido]-3-vinyl-3-cephem-4-carboxylate (syn isomer)

IR (Nujol): 3350, 1778, 1721, 1682, 1615 cm$^{-1}$

Example 212

Benzhydryl 7-[2-(2-aminothiazol-4-yl)-2-cyanomethoxyiminoacetamido]-3-vinyl-3-cephem-4-carboxylate (syn isomer)

IR (Nujol): 3430, 3250, 1780, 1720, 1680, 1660 cm$^{-1}$

Example 213

Benzhydryl 7-[2-(2-amino-5-chlorothiazol-4-yl)-2-tert-butoxycarbonylmethoxyiminoacetamido]-3-vinyl-3-cephem-4-carboxylate (syn isomer)

IR (Nujol): 3425, 3270, 1780, 1720, 1675, 1620, 1540 cm$^{-1}$

Example 214

Benzhydryl 7-[2-(6-aminopyridin-2-yl)-2-methoxyiminoacetamido]-3-vinyl-3-cephem-4-carboxylate (syn isomer)

IR (Nujol): 3250, 1775, 1720 (shoulder), 1680 (broad) cm$^{-1}$

Example 215

7-[2-(5-Amino-1,2,4-thiadiazol-3-yl)-2-methoxyiminoacetamido]-3-vinyl-3-cephem-4-carboxylic acid (syn isomer)

IR (Nujol): 3350, 3250, 1770, 1670, 1620, 1530 cm$^{-1}$

Example 216

7-[2-(2-Aminothiazol-4-yl)-2-cyanomethoxyiminoacetamido]-3-vinyl-3-cephem-4-carboxylic acid (syn isomer)

IR (Nujol): 3330, 2020, 1770, 1670, 1620 cm$^{-1}$

Example 217

7-[2-(6-Aminopyridin-2-yl)-2-methoxyiminoacetamido]-3-vinyl-3-cephem-4-carboxylate acid (syn isomer)

IR (Nujol): 3350, 3250, 1780 (broad), 1667 (broad) cm$^{-1}$

Example 218

Pivaloyloxymethyl 7-[2-(5-amino-1,2,4-thiadiazol-3-yl)-2-methoxyiminoacetamido]-3-vinyl-3-cephem-4-carboxylate (syn isomer)

IR (Nujol): 3400-3100, 1770, 1760, 1680, 1620, 1530 cm$^{-1}$

Example 219

Phosphorus oxychloride (4.1 g) was added to a suspension of 2-(5-amino-1,2,4-thiadiazol-3-yl)-2-tert-butoxycarbonylmethoxyiminoacetic acid (syn isomer) (2.0 g) in methylene chloride (26 ml), and the mixture was stirred at ambient temperature for 1.5 hours. Thereto was added N,N-dimethylformamide (4.0 ml) at −15° C., followed by stirring at −15° to −5° C. for 40 minutes to prepare the activated acid solution.

On the other hand, trimethylsilylacetamide (5.5 g) was added to a suspension of benzhydryl 7-amino-3-vinyl-3-cephem-4-carboxylate hydrochloride (2.6 g) in methylene chloride (26 ml), and the mixture was stirred at 35° to 40° C. for 10 minutes.

To this solution was added at a time the activated acid solution prepared before at −10° C., and the mixture was stirred at −10° to −5° C. for half an hour. To the reaction mixture were added a saturated aqueous sodium chloride (150 ml) and ethyl acetate (150 ml), followed by adjusting to pH 7.5 with a saturated aqueous sodium bicarbonate. The separated organic layer was washed with a saturated aqueous sodium chloride and then dried over magnesium sulfate. Removal of the solvent gave benzhydryl 7-[2-[5-{N-(N,N-dimethylaminomethylene)amino}-1,2,4-thiadiazol-3-yl]-2-tert-butoxycarbonylmethoxyiminoacetamido]-3-vinyl-3-cephem-4-carboxylate (syn isomer) (4.13 g).

IR (Nujol): 1770, 1710, 1620 cm$^{-1}$

NMR δppm (DMSO—d$_6$): 1.47 (9H, s), 3.09 (3H, s), 3.20 (3H, s), 3.82 (2H, m), 4.71 (2H, s), 5.17–6.17 (3H, m), 5.32 (1H, d, J=5.0 Hz), 6.80 (1H, dd, J=12.0 Hz, 18.0 Hz), 7.00 (1H, s), 7.43 (10H, s), 8.50 (1H, s), 9.69 (1H, d, =8.0 Hz)

Example 220

To a solution of benzhydryl 7-[2-tert-butoxycarbonylmethoxyimino-2-(2-formamidothiazol-4-yl)acetamido]-3-vinyl-3-cephem-4-carboxylate (syn isomer) (2.5 g) in anisole (2.5 ml) and methylene chloride (5.0 ml) was added trifluoroacetic acid (10.0 ml) under ice-cooling, and the mixture was stirred at ambient temperature for 2 hours. To the reaction mixture was added dropwise diisopropyl ether, and the precipitated crystals were collected by filtration, washed with diisopropyl ether to obtain 7-[2-carboxymethoxyimino-2-(2-formamidothiazol-4-yl)acetamido]-3-vinyl-3-cephem-4-carboxylic acid (syn isomer) (1.57 g).

IR (Nujol): 3130, 1770, 1670 cm$^{-1}$

NMR δppm (DMSO—d$_6$): 3.71 (2H, q, J=18.0 Hz), 4.66 (2H, s), 5.22 (1H, d, J=4.0 Hz), 5.22–5.85 (2H, m), 5.84 (1H, dd, J=4.0 Hz, 8.0 Hz), 6.93 (1H, dd, J=12.0 Hz, 18.0 Hz), 7.44 (1H, s), 8.50 (1H, s), 9.59 (1H, d, J=8.0 Hz), 12.30 (1H, broad s)

Example 221

To a solution of benzhydryl 7-[2-(2-aminothiazol-4-yl)-2-(trans-3-tert-butoxycarbonylallyloxyimino)acetamido]-3-vinyl-3-cephem-4-carboxylate (syn isomer) (4.4 g) and anisole (4.4 ml) in methylene chloride (9.0 ml) was added trifluoroacetic acid (17.6 ml) under ice-cooling, and the mixture was stirred at ambient temperature for 2 hours. To the reaction mixture was added diisopropyl ether, and the precipitated substance was collected by filtration, which was washed with diisopropyl ether. To this substance were added ethyl acetate and water, and then adjusted to pH 7.5 with a saturated aqueous sodium bicarbonate. The separated aqueous layer was washed with ethyl acetate, and the remaining ethyl acetate in the aqueous solution was completely removed by evaporation, followed by adjusting to pH 2.2 with 10% hydrochloric acid. The precipitated substance was collected by filtration and then dried to obtain 7-[2-(2-aminothiazol-4-yl)-2-(trans-3-carboxyallyloxyimino)acetamido]-3-vinyl-3-cephem-4-carboxylic acid (syn isomer) (2.31 g).

IR (Nujol): 3250, 1760, 1690, 1650 cm$^{-1}$

NMR δppm (DMSO—d$_6$): 3.73 (2H, q, J=16.0 Hz), 4.84 (2H, m), 5.24 (1H, d, J=4.0 Hz), 5.34 (1H, d, J=12.0 Hz), 5.47–6.23 (3H, m), 6.63–7.34 (2H, m), 6.83 (1H, s), 9.77 (1H, d, J=8.0 Hz)

Example 222

A mixture of benzhydryl 7-[2-(6-aminopyridin-2-yl)-2-tert-butoxycarbonylmethoxyiminoacetamido]-3-vinyl-3-cephem-4-carboxylate (syn isomer) (6.0 g), anisole (10 ml) and trifluoroacetic acid (60 ml) was stirred at ambient temperature for an hour. The reaction mixture was poured into diisopropyl ether (600 ml) with stirring, and the precipitated substance was collected by filtration, washed with diisopropyl ether and then dissolved in water (100 ml), followed by adjusting to pH 7.5 with 5% aqueous sodium bicarbonate and washing with ethyl acetate (50 ml). The resultant aqueous solution was adjusted to pH 2.5 with conc. hydrochloric acid, and extracted with ethyl acetate (200 ml) and tetrahydrofuran (200 ml). The remaining aqueous solution was further adjusted to pH 1.5 with conc. hydrochloric acid and extracted with tetrahydrofuran (100 ml). The combined extracts were washed with a saturated aqueous sodium chloride and then dried over magnesium sulfate. Removal of the solvent gave a residue, which was washed with acetone and diisopropyl ether to obtain 7-[2-(6-aminipyridin-2-yl)-2-carboxymethoximinoacetamido]-3-vinyl-3-cephem-4-carboxylic acid (syn isomer) (2.4 g), mp 173°-178° C. (dec.).

IR (Nujol): 3300, 1763 (broad), 1660 (broad) cm$^{-1}$

NMR δppm (DMSO—d$_6$): 3.68 (2H, m), 4.77 (2H, broad s), 5.25 (1H, d, J=5 Hz), 5.30 (1H, d, J=11 Hz), 5.87 (1H, d, J=18 Hz), 5.83 (1H, dd, J=5 Hz, 8 Hz), 6.5-8.0 (3H, m), 9.7 (1H, d, J=8 Hz)

Example 223

7-[2-(2-Aminothiazol-4-yl)-2-(3-carboxypropoxyimino)acetamido]-3-vinyl-3-cephem-4-carboxylic acid (syn isomer) (1.75 g) was obtained by reacting benzhydryl 7-[2-(2-aminothiazol-4-yl)-2-(3-tert-butoxycarbonylpropoxyimino)acetamido]-3-vinyl-3-cephem-4-carboxylate (syn isomer) (3.2 g) with trifluoroacetic acid (12.8 ml) in the presence of anisole (3.2 ml) according to similar manners to those of Examples 220 to 222.

IR (Nujol): 3300, 1760, 1660 cm$^{-1}$

NMR δppm (DMSO—d$_6$): 1.95 (2H, m), 2.37 (2H, t, J=6.0 Hz), 3.73 (2H, q, J=17.0 Hz), 4.13 (2H, t, J=6.0 Hz), 5.23 (1H, d, J=5.0 Hz), 5.23-6.00 (3H, m), 6.79 (1H, s), 7.00 (1H, dd, J=11.0 Hz, 18.0 Hz), 9.65 (1H, d, J=8.0 Hz)

Example 224

7-[2-(2-Amino-5-chlorothiazol-4-yl)-2-carboxymethoxyiminoacetamido]-3-vinyl-3-cephem-4-carboxylic acid (syn isomer) (2.2 g) was obtained by reacting benzhydryl 7-[2-(2-amino-5-chlorothiazol-4-yl)-2-tert-butoxycarbonylmethoxyiminoacetamido]-3-vinyl-3-cephem-4-carboxylate (syn isomer) (4.6 g) with trifluoroacetic acid (14.4 g) in the presence of anisole (2.7 g) according to similar manners to those of Examples 220 to 222.

IR (Nujol): 3400, 3180, 1770, 1685, 1650, 1610 cm$^{-1}$

NMR δppm (DMSO—d$_6$): 3.70 (2H, q, J=18 Hz), 4.63 (2H, s), 5.18 (1H, d, J=5 Hz), 5.33 (1H, d, J=11 Hz), 5.56 (1H, d, J=18 Hz), 5.83 (1H, dd, J=5 Hz, 8 Hz), 6.95 (1H, dd, J=11 Hz, 18 Hz), 9.45 (1H, d, J=8 Hz)

Example 225

Trifluoroacetic acid (16.0 ml) was added to a solution of benzhydryl 7-[2-[5-{N-(N,N-dimethylaminomethylene)amino}-1,2,4-thiadiazol-3-yl]-2-tert-butoxycarbonylmethoxyiminoacetamido]-3-vinyl-3-cephem-4-carboxylate (syn isomer) (4.0 g) in methylene chloride (8.0 ml) and anisole (4.0 ml) under ice-cooling, and the mixture was stirred at ambient temperature for 1.5 hours. The reaction mixture was added dropwise to diisopropyl ether (200 ml), and the precipitated substance was collected by filtration and then added to a mixture of water and ethyl acetate, followed by adjusting to pH 7.5 with a saturated aqueous sodium bicarbonate. The separated aqueous layer was saturated with sodium chloride and adjusted to pH 2.5 with 10% hydrochloric acid, followed by extraction with a mixed solvent of ethyl acetate and tetrahydrofuran (1:2 by volume). The extract was washed with a saturated aqueous sodium chloride and then dried over magnesium sulfate. Removal of the solvent gave a residue, which was washed with diethyl ether and collected by filtration to obtain 7-[2-(5-formamido-1,2,4-thiadiazol-3-yl)-2-carboxymethoxyiminoacetamido]-3-vinyl-3-cephem-4-carboxylic acid (syn isomer) (1.75 g).

IR (Nujol): 3200, 1770, 1670 cm$^{-1}$

NMR δppm (DMSO—d$_6$): 3.70 (2H, m), 4.75 (2H, s), 5.24 (1H, d, J=5.0 Hz), 5.33 (1H, d, J=12.0 Hz), 5.61 (1H, d, J=18.0 Hz), 5.91 (1H, dd, J=5.0 Hz, 8.0 Hz), 6.96 (1H, dd, J=12.0 Hz, 18.0 Hz), 8.87 (1H, s), 9.70 (1H, d, J=8.0 Hz), 13.47 (1H, broad s)

Example 226

To a solution of benzhydryl 7-[2-tert-butoxycarbonylmethoxyimino)-2-(2-formamidothiazol-4-yl)acetamido]-3-vinyl-3-cephem-4-carboxylate (syn isomer) (2 g) and anisole (8.0 ml) in dioxane (8 ml) and tert-butyl alcohol (8.0 ml) was added p-toluenesulfonic acid (2.2 g), followed by stirring at 60° C. for 5 hours. To the reaction mixture were added ethyl acetate and water, and then adjusted to pH 7.5 with a saturated aqueous sodium bicarbonate. The aqueous layer was separated and washed with ethyl acetate, and thereto were added ethyl acetate and tetrahydrofuran, followed by adjusting to pH 2.2 with 10% hydrochloric acid. After the aqueous layer was saturated with sodium chloride, the organic layer was separated, washed with a saturated aqueous sodium chloride and then dried over magnesium sulfate. Removal of the solvent gave a residue, which was pulverized with diisopropyl ether and collected by filtration. To this substance was added water and then adjusted to pH 5.5 with 2N aqueous sodium hydroxide. The aqueous solution was subjected to column chromatography on a nonionic adsorption resin, "Diaion HP-20" (20 ml), and elution was carried out with water (40 ml). To the elute were added ethylacetate and tetrahydrofuran, followed by adjusting to pH 2.2 with 10% hydrochloric acid. After the aqueous layer was saturated with sodium chloride, the organic layer was separated, washed with a saturated aqueous sodium chloride and then dried over magnesium sulfate. Removal of the solvent gave a residue, which was pulverized with diisopropyl ether and collected by filtration to obtain 7-[2-(2-aminothiazol-4-yl)-2-carboxymethoxyiminoacetamido]-3-vinyl-3-cephem-4-carboxylic acid (syn isomer) (0.31 g).

IR (Nujol): 3350, 1770, 1680, 1640 cm$^{-1}$

NMR δppm (DMSO—d$_6$): 3.70 (2H, q, J=18 Hz), 4.62 (2H, s), 5.21 (1H, d, J=5 Hz), 5.82 (1H, dd, J=5 Hz, 8 Hz), 5-6 (2H, m), 6.82 (1H, s), 7.22 (2H, broad s), 6.5-7.5 (1H, m), 9.5 (1H, d, J=8 Hz)

The following compounds were obtained by reacting 7-acylamino-3-vinylcephalosporanic acid derivatives having a formamido group, a tert-butoxycarbonyl group and a benzhydryl ester with p-toluenesulfonic acid in the presence of anisole according to a similar manner to that of Example 226.

Example 227

7-[2-(2-Aminothiazol-4-yl)-2-(trans-3-carboxyallyloxyimino)acetamido]-3-vinyl-3-cephem-4-carboxylic acid (syn isomer)

IR (Nujol): 3250, 1760, 1690, 1650 cm$^{-1}$

Example 228

7-[2-(6-Aminopyridin-2-yl)-2-carboxymethoxyiminoacetamido]-3-vinyl-3-cephem-4-carboxylic acid (syn isomer)

IR (Nujol): 3300, 1763 (broad), 1660 (broad) cm$^{-1}$

Example 229

7-[2-(2-Aminothiazol-4-yl)-2-(3-carboxypropoxyimino)acetamido]-3-vinyl-3-cephem-4-carboxylic acid (syn isomer)

IR (Nujol): 3300, 1760, 1660 cm$^{-1}$

Example 230

7-[2-(2-Amino-5-chlorothiazol-4-yl)-2-carboxymethoxyiminoacetamido]-3-vinyl-3-cephem-4-carboxylic acid (syn isomer)

IR (Nujol): 3400, 3180, 1770, 1685, 1650, 1610 cm$^{-1}$

Example 231

A mixture of benzhydryl 7-[2-(3-tert-butoxycarbonylpropoxyimino)-2-(2-formamidothiazol-4-yl)acetamido]-3-vinyl-3-cephem-4-carboxylate (syn isomer) (3.5 g), conc. hydrochloric acid (1.0 g), methanol (30 ml) and tetrahydrofuran (15.0 ml) was stirred at ambient temperature for 2.5 hours. To the reaction mixture was added ethyl acetate, followed by adjusting to pH 7.5 with a saturated aqueous sodium bicarbonate. The separated organic layer was washed with a saturated aqueous sodium chloride and then dried over magnesium sulfate. Removal of the solvent gave a residue, which was pulverized with diisopropyl ether to obtain benzhydryl 7-[2-(3-tert-butoxycarbonylpropoxyimino)-2-(2-aminothiazol-4-yl)acetamido]-3-vinyl-3-cephem-4-carboxylate (syn isomer) (3.33 g).

IR (Nujol): 3340, 3250, 1780, 1720, 1680, 1620 cm$^{-1}$

NMR δppm (DMSO—d$_6$): 1.40 (9H, s), 1.87 (2H, m), 2.35 (2H, t, J=7.0 Hz), 3.76 (2H, m), 4.11 (2H, t, J=7.0 Hz), 5.30 (1H, d, J=5.0 Hz), 5.32 (1H, d, J=12.0 Hz), 5.66 (1H, d, J=18.0 Hz), 5.91 (1H, dd, J=5.0 Hz, 8.0 Hz), 6.78 (1H, s), 6.79 (1H, dd, J=12.0 Hz, 18.0 Hz), 6.98 (1H, s), 7.39 (10H, s), 9.66 (1H, d, J=8.0 Hz)

Example 232

A mixture of benzhydryl 7-[2-(trans-3-tert-butoxycarbonylallyloxyimino)-2-(2-formamidothiazol-4-yl)acetamido]-3-vinyl-3-cephem-4-carboxylate (syn isomer) (4.7 g), conc. hydrochloric acid (1.34 g), methanol (30 ml) and tetrahydrofuran (10 ml) was stirred at ambient temperature for 2.5 hours. To the reaction mixture was added ethyl acetate, followed by adjusting to pH 7.5 with a saturated aqueous sodium bicarbonate. The separated organic layer was washed with a saturated aqueous sodium chloride and then dried over magnesium sulfate. Removal of the solvent gave a residue, which was pulverized with diisopropyl ether to obtain benzhydryl 7-[2-(trans-3-tert-butoxycarbonylallyloxyimino)-2-(2-aminothiazol-4-yl)acetamido]-3-vinyl-3-cephem-4-carboxylate (syn isomer) (4.50 g).

IR (Nujol): 3250, 1770, 1670, 1610 cm$^{-1}$

NMR δppm (DMSO—d$_6$): 1.45 (9H, s), 3.76 (2H, m), 4.86 (2H, m), 5.34 (1H, d, J=12.0 Hz), 5.35 (1H, d, J=5.0 Hz), 5.68 (1H, d, J=18.0 Hz), 5.77–6.30 (2H, m), 6.54–7.17 (2H, m), 6.86 (1H, s), 7.00 (1H, s), 7.17–7.70 (10H, m), 9.81 (1H, d, J=8.0 Hz)

Example 233

To a suspension of benzhydryl 7-[2-(6-formamidopyridin-2-yl)-2-tert-butoxycarbonylmethoxyiminoacetamido]-3-vinyl-3-cephem-4-carboxylate (syn isomer) (4.8 g) in methanol (300 ml) was added conc. hydrochloric acid (2.88 ml), and the mixture was stirred at 35° C. for an hour. The reaction mixture was adjusted to pH 5.5 with 5% aqueous sodium bicarbonate, and the methanol was removed by distillation under reduced pressure, followed by extraction with ethyl acetate (300 ml). The extract was washed with a saturated aqueous sodium chloride and then dried over magnesium sulfate. Removal of the solvent gave benzhydryl 7-[2-(6-aminopyridin-2-yl)-2-tert-butoxycarbonylmethoxyiminoacetamido]-3-vinyl-3-cephem-4-carboxylate (syn isomer) (4.5 g), mp 125°–129° C.

IR (Nujol): 3350, 1778, 1721, 1682, 1615 cm$^{-1}$

NMR δppm (DMSO—d$_6$): 1.45 (9H, s), 3.55, 3.97 (2H, ABq, J=18 Hz), 4.65 (2H, broad s), 5.29 (1H, d, J=5 Hz), 5.29 (1H, d, J=11 Hz), 5.95 (1H, d, J=18 Hz), 5.98 (1H, dd, J=5 Hz, 8 Hz), 6.9 (1H, m), 6.97 (1H, s), 6.8–7.7 (3H, m), 7.4 (10H, m), 9.47 (1H, d, J=8 Hz)

Example 234

Benzhydryl 7-[2-(2-aminothiazol-4-yl)-2-cyanomethoxyiminoacetamido]-3-vinyl-3-cephem-4-carboxylate (syn isomer) (2.17 g) was obtained by reacting benzhydryl 7-[2-(2-formamidothiazol)-4-yl)-2-cyanomethoxyiminoacetamido]-3-vinyl-3-cephem-4-carboxylate (syn isomer) (3.0 g) with conc. hydrochloric acid (0.35 g) according to similar manners to those of Examples 231 to 233.

IR (Nujol): 3430, 3250, 1780, 1720, 1680, 1660 cm$^{-1}$

NMR δppm (DMSO—d$_6$): 3.77 (2H, m), 5.02 (2H, s), 5.10–6.08 (2H, m), 5.28 (1H, d, J=5.0 Hz), 5.85 (1H, dd, J=5.0 Hz, 8.0 Hz), 6.83 (1H, dd, J=10.0 Hz, 18.0 Hz), 6.89 (1H, s), 6.95 (1H, s), 7.09–7.63 (10H, m), 9.83 (1H, d, J=8.0 Hz)

Example 235

Benzhydryl 7-[2-(2-amino-5-chlorothiazol-4-yl)-2-tert-butoxycarbonylmethoxyiminoacetamido]-3-vinyl-3-cephem-4-carboxylate (syn isomer) (4.6 g) was obtained by reacting benzhydryl 7-[2-(2-formamido-5-chlorothiazol-4-yl)-2-tert-butoxycarbonylmethoxyiminoacetamido]-3-vinyl-3-cephem-4-carboxylate (syn isomer) (5.5 g) with conc. hydrochloric acid (2.3 ml) according to similar manners to those of Examples 231 to 233.

IR (Nujol): 3425, 3270, 1780, 1720, 1675, 1620, 1540 cm$^{-1}$

NMR δppm (DMSO—d$_6$): 1.43 (9H, s), 3.77 (2H, m), 4.63 (2H, s), 5.30 (1H, d, J=5 Hz), 5.32 (1H, d, J=11 Hz), 5.68 (1H, d, J=17 Hz), 6.00 (1H, dd, J=5 Hz, 8 Hz), 6.85 (1H, dd, J=11 Hz, 17 Hz), 7.03 (1H, s), 7.22–7.90 (10H, m), 9.60 (1H, d, J=8 Hz)

Example 236

Benzhydryl 7-[2-(6-aminopyridin-2-yl)-2-methoxyiminoacetamido]-3-vinyl-3-cephem-4-carboxylic (syn isomer) (4.5 g), mp 183°–188° C., was obtained by reacting benzhydryl 7-[2-(6-formamidopyridin-2-yl)-2-methoxyiminoacetamido]-3-vinyl-3-cephem-4-carboxylate (syn isomer) (5.7 g) with conc. hydrochloric acid (4.3 ml) according to similar manners to those of Examples 231 to 233.

IR (Nujol): 3250, 1775, 1720 (shoulder), 1680 (broad) cm$^{-1}$

NMR δppm (DMSO—d$_6$): 3.8 (2H, m), 3.93 (3H, s), 5.3 (1H, d, J=5 Hz), 5.3 (1H, d, J=11 Hz), 5.63 (1H, d, J=18 Hz), 5.95 (1H, dd, J=11 Hz, 18 Hz), 6.5–8.2 (3H, m), 6.9 (1H, m), 7.0 (1H, s), 7.4 (10H, s), 9.57 (1H, d, J=8 Hz)

The following compounds were obtained by reacting 7-acylamino-3-vinylcephalosporanic acid derivatives having a formamido group with conc. hydrochloric acid according to similar manners to those of Examples 231 to 233.

Example 237

Benzhydryl 7-[2-(5-amino-1,2,4-thiadiazol-5-yl)-2-methoxyiminoacetamido]-3-vinyl-3-cephem-4-carboxylate (syn isomer)

IR (Nujol): 3300, 3175, 1770, 1720, 1670, 1610, 1510 cm$^{-1}$

Example 238

7-[2-(5-Amino-1,2,4-thiadiazol-3-yl)-2-methoxyiminoacetamido]-3-vinyl-3-cephem-4-carboxylic acid (syn isomer)

IR (Nujol): 3350, 3250, 1770, 1670, 1620, 1530 cm$^{-1}$

Example 239

7-[2-(2-Aminothiazol-4-yl)-2-cyanomethoxyiminoacetamido]-3-vinyl-3-cephem-4-carboxylic acid (syn isomer)

IR (Nujol): 3330, 2020, 1770, 1670, 1620 cm$^{-1}$

Example 240

7-[2-(6-Aminopyridin-2-yl)-2-methoxyiminoacetamido]-3-vinyl-3-cephem-4-carboxylic acid (syn isomer)

IR (Nujol): 3350, 3250, 1780 (broad), 1667 (broad) cm$^{-1}$

Example 241

7-[2-(2-Aminothiazol-4-yl)-2-(trans-3-carboxyallyloxyimino)acetamido]-3-vinyl-3-cephem-4-carboxylic acid (syn isomer)

IR (Nujol): 3250, 1760, 1690, 1650 cm$^{-1}$

Example 242

7-[2-(6-Aminopyridin-2-yl)-2-carboxymethoxyiminoacetamido]-3-vinyl-3-cephem-4-carboxylic acid (syn isomer)

IR (Nujol): 3300, 1763 (broad), 1660 (broad) cm$^{-1}$

Example 243

7-[2-(2-Aminothiazol-4-yl)-2-(3-carboxypropoxyimino)acetamido]-3-vinyl-3-cephem-4-carboxylic acid (syn isomer)

IR (Nujol): 3300, 1760, 1660 cm$^{-1}$

Example 244

7-[2-(2-Amino-5-chlorothiazol-4-yl)-2-carboxymethoxyiminoacetamido]-3-vinyl-3-cephem-4-carboxylic acid (syn isomer)

IR (Nujol): 3400, 3180, 1770, 1685, 1650, 1610 cm$^{-1}$

Example 245

Pivaloyloxymethyl 7-[2-(5-Amino-1,2,4-thiadiazol-3-yl)-2-methoxyiminoacetamido]-3-vinyl-3-cephem-4-carboxylate (syn isomer)

IR (Nujol): 3400–3100, 1770, 1760, 1680, 1620 1530 cm$^{-1}$

Example 246

To a suspension of benzhydryl 7-[2-(5-amino-1,2,4-thiadiazol-3-yl)-2-methoxyiminoacetamido]-3-vinyl-3-cephem-4-carboxylate (syn isomer) (6.2 g) in methylene chloride (60 ml) were added anisole (9.3 g) and trifluoroacetic acid (24.5 g), and the mixture was stirred at ambient temperature for 1.5 hours. After removal of the solvent, the residue was added dropwise to diisopropyl ether (600 ml), and the precipitated substance was collected by filtration. This substance was suspended in water (50 ml) and then adjusted to pH 7.5 with 2N aqueous sodium hydroxide, followed by washing twice with a mixture of ethyl acetate (50 ml) and tetrahydrofuran (50 ml). To the resultant aqueous solution were added ethyl acetate (50 ml) and tetrahydrofuran (50 ml), and the mixture was saturated with sodium chloride and adjusted to pH 1.0 with 10% hydrochloric acid. The organic layer was separated, and the remaining aqueous solution was extracted twice with a mixture of ethyl acetate and tetrahydrofuran. The combined organic solution was washed with an aqueous sodium chloride and then dried over magnesium sulfate. Removal of the solvent gave a residue, which was pulverized with diethyl ether to obtain 7-[2-(5-amino-1,2,4-thiadiazol-3-yl)-2-methoxyiminoacetamido]-3-vinyl-3-cephem-4-carboxylic acid (syn isomer) (3.9 g).

IR (Nujol): 3350, 3250, 1770, 1670, 1620, 1530 cm$^{-1}$
NMR δppm (DMSO—d$_6$): 3.71 (2H, m), 3.93 (3H, s), 5.18 (1H, d, J=5 Hz), 5.32 (1H, d, J=11 Hz), 5.55 (1H, d, J=17 Hz), 5.82 (1H, dd, J=5 Hz, 8 Hz), 6.95 (1H, dd, J=11 Hz, 17 Hz), 9.58 (1H, d, J=8 Hz)

Example 247

7-[2-(2-Aminothiazol-4-yl)-2-cyanomethoxyiminoacetamido]-3-vinyl-3-cephem-4-carboxylic acid (syn isomer) 0.92 g) was obtained by reacting benzhydryl 7-[2-(2-aminothiazol-4-yl)-2-cyanomethoxyiminoacetamido]-3-vinyl-3-cephem-4-carboxylate (syn isomer) (2.1 g) with trifluoroacetic acid (8.4 ml) in the presence of anisole (2.1 ml) according to a similar manner to that of Example 246.

IR (Nujol): 3330, 2020, 1770, 1670, 1620 cm$^{-1}$
NMR δppm (DMSO—d$_6$): 3.73 (2H, q, J=18.0 Hz), 5.02 (2H, s), 5.23 (1H, d, J=5.0 Hz), 5.34 (1H, d, J=12.0 Hz), 5.37–6.80 (1H, m), 5.79 (1H, dd, J=5.0 Hz, 8.0 Hz), 6.63–7.38 (1H, m), 6.91 (1H, s), 9.83 (1H, d, J=8.0 Hz)

Example 248

7-[2-(6-Aminopyridin-2-yl)-2-methoxyiminoacetamido]-3-vinyl-3-cephem-4-carboxylic acid (syn isomer) (0.85 g), mp 183°–188° C. (dec.), was obtained by reacting benzhydryl 7-[2-(6-aminopyridin-2-yl)-2-methoxyiminoacetamido]-3-vinyl-3-cephem-4-carboxylate (syn isomer) (4.5 g) with trifluoroacetic acid (15 ml) in the presence of anisole (5 ml) according to a similar manner to that of Example 246.

IR (Nujol): 3350, 3250, 1780 (broad), 1667 (broad) cm$^{-1}$
NMR δppm (DMSO—d$_6$): 3.58, 3.97 (2H, ABq, J=18 Hz), 4.12 (3H, s), 5.28 (1H, d, J=5 Hz), 5.36 (1H, d, J=11 Hz), 5.62 (1H, d, J=18 Hz), 5.87 (1H, dd, J=5 Hz, 8 Hz), 6.7–8.2 (6H, m), 9.93 (1H, d, J=8 Hz)

Example 249

To a suspension of 7-[2-methoxyimino-2-(5-amino-1,2,4-thiadiazol-3-yl)acetamido]-3-vinyl-3-cephem-4-carboxylic acid (syn isomer) (2.3 g) in water (30 ml) was added sodium bicarbonate (0.47 g), and the mixture was stirred for a while. The insoluble substance was removed by filtration, and then the filtrate was lyophilized to prepare sodium salt of the above compound (2.0 g).

This product was dissolved in N,N-dimethylformamide (20 ml), and thereto was added dropwise a solution of iodomethyl pivalate (1.23 g) in N,N-dimethylformamide (3 ml) under ice-cooling, followed by stirring below 5° C. for 10 minutes. To the reaction mixture were added ethyl acetate (50 ml) and water (50 ml), and the organic layer was separated, and washed three times with a saturated aqueous sodium bicarbonate (30 ml) and three times with an aqueous sodium chloride (30 ml), followed by drying over magnesium sulfate. Removal of the solvent gave a residue, which was pulverized with diisopropyl ether to obtain pivaloyloxymethyl 7-[2-methoxyimino-2-(5-amino-1,2,4-thiadiazol-3-yl)acetamido]-3-vinyl-3-cephem-4-carboxylate (syn isomer) (1.4 g), mp 125°–133° C. (dec.).

IR (Nujol): 3400–3100, 1770, 1760, 1680, 1620, 1530 cm$^{-1}$

NMR δppm (DMSO—d$_6$): 1.15 (9H, s), 3.77 (2H, q, J=17 Hz), 3.93 (3H, s), 5.23 (1H, d, J=5 Hz), 5.38 (1H, d, J=11 Hz), 5.7 (1H, d, J=17 Hz), 5.7–6.1 (3H, m), 6.85 (1H, dd, J=11 Hz, 17 Hz), 8.15 (2H, broad s), 9.67 (1H, d, J=8 Hz)

Example 250

2-(5-Amino-1,2,4-thiadiazol-3-yl)-2-tert-butoxycarbonylmethoxyimino)acetic acid (syn isomer) (2.5 g) was added to a solution of phosphorus pentachloride (1.7 g) in methylene chloride at −18° C., followed by stirring at −5° to −15° C. for an hour. After dried diisopropyl ether (75 ml) was added thereto at −10° to −5° C., the mixture was stirred at ambient temperature for 10 minutes. The precipitates were collected by filtration and then washed with diisopropyl ether.

On the other hand, trimethylsilylacetamide (5.8 g) was added to a suspension of benzhydryl 7-amino-3-vinyl-3-cephem-4-carboxylate hydrochloride (2.7 g) in methylene chloride (27 ml), followed by stirring for a while. To this solution was added the precipitates obtained above at −10° C., and the mixture was stirred at the same temperature for half an hour. To the reaction mixture were added water (80 ml) and ethyl acetate (200 ml), followed by separation of the organic layer. Thereto was added water, and the mixture was adjusted to pH 7.5 with a saturated aqueous sodium bicarbonate. The separated organic layer was washed with a saturated aqueous sodium chloride and then dried over magnesium sulfate. Removal of the solvent gave benzhydryl 7-[2-(5-amino-1,2,4-thiadiazol-3-yl)-2-tert-butoxycarbonylmethoxyiminoacetamido]-3-vinyl-3-cephem-4-carboxylate (syn isomer) (3.53 g).

IR (Nujol): 3400, 1770, 1720, 1670, 1620 cm$^{-1}$

NMR δppm (DMSO—d$_6$): 1.46 (9H, s), 3.77 (2H, q, J=19.0 Hz), 4.67 (2H, s), 5.30 (1H, d, J=5.0 Hz), 5.33 (1H, d, J=11.0 Hz), 5.66 (1H, d, J=17.0 Hz), 5.96 (1H, dd, J=5.0 Hz, 9.0 Hz), 6.80 (1H, dd, J=11.0 Hz, 17.0 Hz), 6.99 (1H, s), 7.43 (10H, s), 8.23 (2H, broad s), 9.63 (1H, d, J=9.0 Hz)

Example 251

To a suspension of 2-(4-aminopyrimidin-2-yl)-2-tert-butoxycarbonylmethoxyiminoacetic acid (syn isomer) (1.3 g) in ethyl acetate (25 ml) was added phosphorus oxychloride (0.5 ml) under ice-cooling with stirring, followed by stirring at 0° to 5° C. for half an hour. After trimethylsilylacetamide (28 mg) was added thereto, the mixture was stirred at the same temperature for half an hour. To the mixture was added phosphorus oxychloride (0.5 ml) at 0° to 5° C., followed by stirring at the same temperature for 15 minutes. Thereto was added N,N-dimethylformamide (0.37 ml) at 0° to 5° C., followed by stirring under ice-cooling for half an hour to prepare the activated acid solution. This solution was added at a time to a solution of benzhydryl 7-amino-3-vinyl-3-cephem-4-carboxylate (1.32 g) and trimethylsilylacetamide (3.5 g) in methylene chloride (30 ml) at −20° C., followed by stirring at −10° C. for 40 minutes.

The reaction mixture was poured into ethyl acetate, and the separated organic layer was washed with 5% aqueous sodium bicarbonate and 5% aqueous sodium chloride, followed by drying over magnesium sulfate. After removal of the solvent, the residual oil was subjected to column chromatography on silica gel (100 ml) using a mixed solvent of diisopropyl ether and ethyl acetate as an eluent. The fractions containing a desired compound were collected and then evaporated to obtain benzhydryl 7-[2-(4-aminopyrimidin-2-yl)-2-tert-butoxycarbonylmethoxyiminoacetamido]-3-vinyl-3-cephem-4-carboxylate (syn isomer) (0.4 g), mp 155° to 158° C.

IR (Nujol): 3250, 1780, 1723, 1690, 1628 cm$^{-1}$

NMR δppm (DMSO—d$_6$): 1.46 (9H, s), 3.44, 3.66 (2H, ABq, J=18 Hz), 4.78 (2H, s), 5.12 (1H, d, J=5 Hz), 5.27 (1H, d, J=11 Hz), 5.40 (1H, d, J=18 Hz), 6.10 (1H, dd, J=5 Hz, 8 Hz), 6.67 (1H, d, J=6 Hz), 6.96 (1H, s), 6.98 (1H, dd, J=11 Hz, 18 Hz), 7.3 (10H, m), 8.28 (1H, d, J=6 Hz), 8.50 (1H, d, J=8 Hz)

Example 252

Benzhydryl 7-[2-(O,O-diethylphosphonomethoxyimino)-2-(2-formamidothiazol-4-yl)acetamido]-3-vinyl-3-cephem-4-carboxylate (syn isomer) (4.3 g), mp 135° to 142° C., was obtained by reacting benzhydryl -7-amino-3-vinyl-3-cephem-4-carboxylate (4.7 g) with an activated acid solution, which was prepared from 2-(O,O-diethylphosphonomethoxyimino)-2-(2-formamidothiazol-4-yl)acetic acid (syn isomer) (5.5 g), phosphorus oxychloride (2.07 ml) and N,N-dimethylformamide (1.75 ml) in tetrahydrofuran (55 ml) in a conventional manner, according to similar manners to those of Examples 250 and 251.

IR (Nujol): 3400, 3160, 1785, 1723, 1675 cm$^{-1}$

NMR δppm (DMSO—d$_6$): 1.25 (6H, t, J=6 Hz), 3.73 (2H, m), 4.13 (4H, m), 4.57 (2H, d, J=7 Hz), 5.28 (1H, d, J=5 Hz), 5.2–5.8 (2H, m), 5.90 (1H, m), 6.80 (1H, dd, J=11 Hz, 18 Hz), 6.95 (1H, s), 7.37 (10H, m), 7.47 (1H, s), 8.53 (1H, s), 9.80 (1H, d, J=8 Hz), 12.7 (1H, broad s)

Example 253

Trifluoroacetic acid (13.6 ml) was added to a solution of benzhydryl 7-[2-(5-amino-1,2,4-thiadiazol-3-yl)-2-tert-butoxycarbonylmethoxyiminoacetamido]-3-vinyl-3-cephem-4-carboxylate (syn isomer) (3.4 g) in methylene chloride (7.0 ml) and anisole (3.4 ml) under ice-cooling, followed by stirring at ambient temperature for 1.5 hours. The reaction mixture was added dropwise to diisopropyl ether (150 ml), and the precipitates were collected by filtration and then added to a mixture of water and ethyl acetate. After adjusting to pH 7.5 with a saturated aqueous sodium bicarbonate, the aqueous layer was separated and then adjusted to pH 2.0 with 10% hydrochloric acid. The precipitates were collected by filtration, washed with cold water and then dried to obtain 7-[2-(5-amino-1,2,4-thiadiazol-3-yl)-2-carboxymethoxyiminoacetamido]-3-vinyl-3-cephem-4-carboxylic acid (syn isomer) (1.39 g).

IR (Nujol): 3380, 3280, 1760, 1720, 1670 cm$^{-1}$

NMR δppm (DMSO—d₆): 3.73 (2H, q, J=18.5 Hz), 4.69 (2H, s), 5.21 (1H, d, J=5.0 Hz), 5.33 (1H, d, J=12.0 Hz), 5.60 (1H, d, J=18.0 Hz), 5.86 (1H, dd, J=5.0 Hz, 8.0 Hz), 6.98 (1H, dd, J=12.0 Hz, 18.0 Hz), 8.16 (2H, broad s), 9.56 (1H, d, J=18.0 Hz)

Example 254

To a solution of benzhydryl 7-[2-(O,O-diethylphosphonomethoxyimino)-2-(2-formamidothiazol-4-yl)acetamido]-3-vinyl-3-cephem-4-carboxylate (syn isomer) (4.2 g) in methylene chloride (20 ml) and anisole (2 ml) was added trifluoroacetic acid (5 ml) under ice-cooling, followed by stirring at 10° C. for 1.5 ours. The reaction mixture was added dropwise to diisopropyl ether (400 ml), and the precipitates were collected by filtration and washed with diisopropyl ether, followed by drying under reduced pressure to obtain 7-[2-(O,O-diethylphosphonomethoxyimino)-2-(2-formamidothiazol-4-yl)acetamido]-3-vinyl-3-cephem-4-carboxylic acid (syn isomer) (2.8 g), mp 173° to 176° C.

IR (Nujol): 3160, 1775 (broad), 1680 (broad) cm⁻¹

NMR δppm (DMSO—d₆): 1.28 (6H, t, J=6 Hz), 3.76 (2H, m), 4.17 (4H, m), 4.58 (2H, d, J=7 Hz), 5.23 (1H, d, J=5 Hz), 5.36 (1H, d, J=11 Hz), 5.63 (1H, d, J=18 Hz), 5.87 (1H, dd, J=5 Hz, 8 Hz), 7.0 (1H, dd, J=11 Hz, 18 Hz), 7.70 (1H, s), 8.56 (1H, s), 9.82 (1H, d, J=8 Hz), 12.7 (1H, broad s)

Example 255

To a solution of 7-[2-(O,O-diethylphosphonomethoxyimino)-2-(2-formamidothiazol-4-yl)acetamido]-3-vinyl-3-cephem-4-carboxylic acid (syn isomer) (1.725 g) in methylene chloride (26 ml) were added bis(trimethylsilyl)acetamide (3.05 g) and trimethylsilyl iodide (3.0 g) at 25° to 28° C., followed by stirring at ambient temperature for 18 hours. Removal of the solvent gave a residual oil, which was dissolved in methanol (25 ml). After addition of conc. hydrochloric acid (2 ml), the mixture was stirred at 30° C. for 2 hours. Removal of the solvent gave a residue, which was dissolved in water (50 ml) and adjusted to pH 5.5 with 1N aqueous sodium hydroxide. This aqueous solution was subjected to column chromatography on a nonionic adsorption resin "Diaion HP-20". After washing with water, elution was carried out with 10% aqueous methanol. The eluates containing a desired compound were collected and then lyophilized to obtain 7-[2-phosphonomethoxyimino-2-(2-aminothiazol-4-yl)acetamido]-3-vinyl-3-cephem-4-carboxylic acid (syn isomer) (1.0 g), mp 185° C. (dec.).

IR (Nujol): 3300 (broad), 1780, 1658, 1600 cm⁻¹

NMR δppm (D₂O+NaHCO₃): 3.70 (2H, m), 4.32 (2H, d, J=8 Hz), 5.28 (1H, d, J=5 Hz), 5.43 (1H, d, J=18 Hz), 5.50 (1H, d, J=11 Hz), 5.83 (1H, d, J=5 Hz), 6.93 (1H, dd, J=11 Hz, 18 Hz), 7.0 (1H, s)

The following compound was obtained by reacting 7-acylamino-3-vinylcephalosporanic acid derivatives having a formamido group with conc. hydrochloric acid according to similar manners to those of Examples 231 to 233.

Example 256

7-[2-(5-Amino-1,2,4-thiadiazol-3-yl)-2-carboxymethoxyiminoacetamido]-3-vinyl-3-cephem-4-carboxylic acid (syn isomer)

IR (Nujol): 3380, 3280, 1760, 1720, 1670 cm⁻¹

Example 257

To a suspension of benzhydryl 7-[2-(2-aminothiazol-4-yl)-2-methoxyiminoacetamido]-3-vinyl-3-cephem-4-carboxylate (syn isomer) (0.9 g) in methylene chloride (10 ml) and anisole (0.66 g) was added trifluoroacetic acid (2.5 g) under ice-cooling, followed by stirring at ambient temperature for an hour. The reaction mixture was added dropwise to diisopropyl ether (100 ml), and the precipitates were collected by filtration and suspended in a mixture of ethyl acetate and water, followed by adjusting to pH 7 with a saturated aqueous sodium bicarbonate. The separated aqueous solution was saturated with sodium chloride, and thereto was added a mixed solvent of ethyl acetate and tetrahydrofuran (8:2 by volume). After adjusting to pH 3.2 with 10% hydrochloric acid, the organic layer was separated out, washed with a saturated aqueous sodium chloride and then dried over magnesium sulfate. Removal of the solvent gave a residue, which was washed with diisopropyl ether to obtain 7-[2-(2-aminothiazol-4-yl)-2-methoxyiminoacetamido]-3-vinyl-3-cephem-4-carboxylic acid (syn isomer (0.4 g).

IR (Nujol): 3400–3100, 1780, 1660, 1630, 1540 cm⁻¹

NMR δppm (DMSO—d₆): 3.72 (2H, q, J=18 Hz), 3.87 (3H, s), 5.20 (1H, d, J=5 Hz), 5.33 (1H, d, J=11 Hz), 5.58 (1H, d, J=18 Hz), 5.78 (1H, dd, J=5 Hz, 8 Hz), 6.77 (1H, s), 6.95 (1H, dd, J=11 Hz, 18 Hz), 9.62 (1H, d, J=8 Hz)

Example 258

Vilsmeier reagent was prepared from phosphorus oxychloride (1.8 g) and N,N-dimethylformamide (0.8 g) in ethyl acetate (3.2 ml) in a conventional manner. 2-(2-Cyclopenten-1-yloxyimino)-2-(2-formamidothiazol-4-yl)acetic acid (syn isomer) (2.7 g) was added to the stirred suspension of Vilsmeier reagent in dry tetrahydrofuran (30 ml) under ice-cooling and stirred for 30 min. at same temperature [Solution A]. Trimethylsilylacetamide (8.1 g) was added to the stirred suspension of 7-amino-3-vinyl-3-cephem-4-carboxylic acid (2.0 g) in ethyl acetate, and the mixture was stirred for 10 minutes at 35° to 40° C. To the mixture was added the solution A at a time at −10° C. and stirred at same temperature for 0.5 hour. Water (40 ml) was added to the reaction mixture, and the separated organic layer was added to water. The mixture was adjusted to pH 7.5 with a saturated aqueous sodium bicarbonate. The separated aqueous layer was adjusted to pH 2.0 with 10% hydrochloric acid and extracted with ethyl acetate. The extract was washed with a saturated aqueous sodium chloride, and dried over magnesium sulfate. The solvent was removed to give precipitates of 7-[2-(2-cyclopenten-1-yloxyimino)-2-(2-formamidothiazol-4-yl)acetamido]-3-vinyl-3-cephem-4-carboxylic acid (syn isomer) (3.20 g).

IR (Nujol): 3200, 1780, 1680, 1650 cm⁻¹

NMR δppm (DMSO—d₆): 1.79–2.78 (4H, m), 3.73 (2H, q, J=20.0 Hz), 5.22 (1H, d, J=5.0 Hz), 5.33 (1H, d, J=12.0 Hz), 5.60 (1H, d, J=18.0 Hz), 5.71–6.28 (4H, m), 6.96 (1H, d, J=12.0 Hz, 18.0 Hz), 7.40 (1H, s), 8.53 (1H, s), 9.63 (1H, d, J=8.0 Hz)

Example 259

Benzhydryl 7-[2-(5-tritylamino-1,2,4-thiadiazol-3-yl)acetamido]-3-vinyl-3-cephem-4-carboxylate (5.1 g) was obtained by reacting benzhydryl 7-amino-3-vinyl-3-cephem-4-carboxylate monohydrochloride (3.17 g) with the acid chloride prepared from 2-(5-tritylamino-1,2,4-thiadiazol-3-yl)acetic acid (2.7 g) and phosphorus pentachloride (1.75 g) according to a similar manner to that of Example 258.

IR (Nujol): 1760, 1710, 1670 cm$^{-1}$

NMR δppm (DMSO—d$_6$): 3.35 (2H, m), 3.73 (2H, m), 5.18 (1H, d, J=5 Hz), 5.27 (1H, d, J=11 Hz), 5.62 (1H, d, J=18 Hz), 5.72 (1H, dd, J=5 Hz), 8 Hz), 6.77 (1H, dd, J=11 Hz, 18 Hz), 6.93 (1H, s), 7.3 (10H, s), 7.63 (1H, d, J=8 Hz), 8.05 (1H, s)

Example 260

To a suspension of benzhydryl 7-amino-3-vinyl-3-cephem-4-carboxylate monohydrochloride (2.15 g) in methylene chloride (100 ml) was added 2,6-lutidine (0.54 g) under ice-cooling. To the resultant solution were added 2-(5-tritylamino-1,3,4-thiadiazol-2-yl)acetic acid (2.4 g), N,N'-dicyclohexylcarbodiimide (1.03 g), tetrahydrofuran (200 ml) and N,N-dimethylformamide (60 ml), and the mixture was stirred at ambient temperature for a day. Removal of the solvent gave a residue, to which a mixed solvent of ethyl acetate, tetrahydrofuran and water was added. The insoluble substances were removed by filtration, and the filtrate was washed with dilute hydrochloric acid, a saturated aqueous sodium bicarbonate and an aqueous sodium chloride, followed by drying over magnesium sulfate. Removal of the solvent gave a residue, which was washed with diisopropyl ether to obtain benzhydryl 7-[2-(5-tritylamino-1,3,4-thiadiazol-2-yl)acetamido]-3-vinyl-3-cephem-4-carboxylate (2.6 g).

IR (Nujol): 3300-3150, 1780, 1720, 1660, 1620, 1510 cm$^{-1}$

Example 261

Benzhydryl 7-[2-(5-tritylamino-2H-tetrazol-2-yl)acetamido]-3-vinyl-3-cephem-4-carboxylate (4.4 g) was obtained by reacting benzhydryl 7-amino-3-vinyl-3-cephem-4-carboxylate monohydrochloride (3.5 g) with 2-(5-tritylamino-2H-tetrazol-2-yl)acetic acid (3.5 g) in the presence of 2,6-lutidene (0.9 g) and N,N'-dicyclohexylcarbodiimide (1.7 g) according to a similar manner to that of Example 260.

IR (Nujol): 3325, 1780, 1710, 1620, 1560 cm$^{-1}$

NMR δppm (DMSO—d$_6$): 3.78 (2H, m), 5.02-5.92 (6H, m), 6.78 (1H, dd, J=11 Hz, 17 Hz), 6.97 (1H, s), 7.05-7.65 (25H, m), 9.33 (1H, d, J=8 Hz)

Example 262

A mixture of 7-[2-(2-cyclopenten-1-yloxyimino)-2-(2-formamidothiazol-4-yl)acetamido]-3-vinyl-3-cephem-4-carboxylic acid (syn isomer) (3.1 g) in methanol (22 ml), tetrahydrofuran (10 ml) and conc. hydrochloric acid (1.3 g) was stirred for 2.5 hours at ambient temperature. The reaction mixture was added to a mixture of water and ethyl acetate, and adjusted to pH 7.5 with a saturated aqueous sodium bicarbonate. The separated aqueous layer wa adjusted to pH 3.0 with 10% hydrochloric acid. The precipitates were filtered off, washed with water and dried over phosphorus pentoxide in vacuo to give 7-[2-(2-cyclopenten-1-yloxyimino)-2-(2-aminothiazol-4-yl)acetamido]-3-vinyl-3-cephem-4-carboxylic acid (syn isomer) (2.7 g).

IR (Nujol): 3270, 1765, 1650 cm$^{-1}$

NMR δppm (DMSO—d$_6$): 1.92-2.75 (4H, m), 3.73 (2H, q, J=18.0 Hz), 5.21 (1H, d, J=5.0 Hz), 5.21-6.33 (6H, m), 6.80 (1H, s), 6.96 (1H, dd, J=11.0 Hz, 18.0 Hz), 9.62 (1H, d, J=8.0 Hz).

Example 263

To a suspension of benzhydryl 7-[2-(5-tritylamino-1,3,4-thiadiazol-2-yl)acetamido]-3-vinyl-3-cephem-4-carboxylate (2.6 g) in methylene chloride (30 ml) and anisole (2.1 g) was added trifluoroacetic acid (7.6 g) under ice-cooling, followed by stirring at ambient temperature for 1.5 hours. The reaction mixture was poured into diisopropyl ether (300 ml), and the precipitates were collected by filtration and suspended in water (40 ml). After adjusting to pH 7 with 10% aqueous sodium hydroxide, the aqueous solution was washed with ethyl acetate and then adjusted to pH 5 with 10% hydrochloric acid. The organic solvent included in the resultant aqueous solution was completely removed by evaporation, and the resultant aqueous solution was adjusted to pH 4 with dilute acetic acid, which was chromatographed on a non-ionic adsorption resin "Diaion HP-20" (50 ml). After washing with water, elution was carried out with 30% isopropyl alcohol, and the fractions containing a desired compound were collected and then concentrated under reduced pressure. The concentrate was lyophilized to obtain 7-[2-(5-amino-1,3,4-thiadiazol-2-yl)-acetamido]-3-vinyl-3-cephem-4-carboxylic acid (0.31 g).

IR (Nujol): 3300, 3200, 1760, 1650, 1610, 1600, 1550, 1510 cm$^{-1}$

NMR δppm (DMSO—d$_6$): 3.55 (2H, broad s), 3.88 (2H, s), 5.05 (1H, d, J=11 Hz), 5.05 (1H, d, J=5 Hz), 5.30 (1H, d, J=17 Hz), 5.55 (1H, dd, J=5 Hz, 8 Hz), 7.17 (1H, dd, J=11 Hz, 17 Hz), 9.27 (1H, d, J=8 Hz)

Example 264

7-[2-(5-Amino-1,2,4-thiadiazol-3-yl)acetamido]-3-vinyl-3-cephem-4-carboxylic acid (0.55 g) was obtained by reacting benzhydryl 7-[2-(5-tritylamino-1,2,4-thiadiazol-3-yl)acetamido]-3-vinyl-3-cephem-4-carboxylate (5 g) with trifluoroacetic acid (14.7 g) in the presence of anisole (5.57 g) according to a similar manner to that of Example 263.

IR (Nujol): 1760, 1640 cm$^{-1}$

NMR δppm (DMSO—d$_6$): 3.55 (2H, s), 3.68 (2H, m), 5.13 (1H, d, J=5 Hz), 5.28 (1H, d, J=11 Hz), 5.55 (1H, d, J=18 Hz), 5.68 (1H, dd, J=5 Hz, 8 Hz), 6.95 (1H, dd, J=11 Hz, 18 Hz), 7.9 (2H, broad s), 9.05 (1H, d, J=8 Hz)

Example 265

7-[2-(5-Amino-2H-tetrazol-2-yl)acetamido]-3-vinyl-3-cephem-4-carboxylic acid (0.7 g), mp 230°-242° C. (dec.), was obtained by reacting benzhydryl 7-[2-(5-tritylamino-2H-tetrazol-2-yl)acetamido]-3-vinyl-3-cephem-4-carboxylate (8.3 g) with trifluoroacetic acid (24.9 g) in the presence of anisole (9.4 g) according to a similar manner to that of Example 263.

IR (Nujol): 3400-3100, 1770, 1680, 1620, 1550 cm$^{-1}$

NMR δppm (DMSO—d$_6$): 3.7 (2H, m), 4.8-6.05 (6H, m), 7.0 (1H, dd, J=11 Hz, 17 Hz), 9.57 (1H, d, J=8 Hz)

Example 266

Conc. hydrochloric acid (0.18 g) was added to a solution of benzhydryl 7-[2-(tert-butoxycarbonyl)methoxyimino)-2-(2-aminothiazol-4-yl-acetamido]-3-vinyl-3-cephem-4-carboxylate (syn isomer) (3.0 g) in formic acid (12 ml) at 10° C. and stirred for 2.5 hours at ambient temperature. The reaction mixture was poured into diisopropyl ether (100 ml). The precipitates were collected by filtration, washed with diisopropyl ether and dried to give 7-[2-carboxymethoxyimino-2-(2-aminothiazol-4-yl)acetamido]-3-vinyl-3-cephem-4-carboxylic acid mono-hydrochloride (syn isomer) (1.6 g).

IR (Nujol): 1760, 1670, 1630 cm$^{-1}$

NMR δppm (DMSO—d$_6$): 3.74 (2H, m), 4.75 (2H, s), 5.25 (1H, d, J=5.0 Hz), 5.36 (1H, d, J=12.0 Hz), 5.61 (1H, d, J=18.0 Hz), 5.80 (1H, dd, J=5.0 Hz, 8.0 Hz), 6.70-7.47 (1H, m), 7.06 (1H, s), 9.78 (1H, d, J=8.0 Hz)

This reaction could be carried out by using the following reagents and solvents.

| Reagents | Solvents | Yield (%) |
| --- | --- | --- |
| conc. hydrochloric acid | acetic acid | 30 |
| p-toluenesulfonic acid | formic acid | 90 |
| " | acetic acid | 50 |
| methanesulfonic acid | formic acid | 89 |
| " | acetic acid | 65 |

Example 267

2-Aminooxyacetic acid hemihydrochloride (1.7 g) was added to a solution of 7-[(2-aminothiazol-4-yl)glyoxylamido]-3-vinyl-3-cephem-4-carboxylic acid (2.0 g) and sodium acetate trihydrate (0.7 g) in water (40 ml), and the mixture was adjusted to pH 5.2 with 10% aqueous sodium hydroxide and then stirred for 3.5 hours at 50° C. During the stirring, the mixture was adjusted to pH 5.0 to 5.4 with the same. The reaction mixture was further adjusted to pH 2.2 with 10% hydrochloric acid under ice-cooling. The precipitates were collected by filtration, washed with water and then dried over phosphorus pentoxide in vacuo to give 7-[2-(2-aminothiazol-4-yl)-2-carboxymethoxyiminoacetamido]-3-vinyl-3-cephem-4-carboxylic acid (syn isomer) (1.13 g).

IR (Nujol): 3350, 1770, 1680, 1640 cm$^{-1}$

The following compounds were obtained by reacting 7-acylaminocephalosporanic acid derivatives having an oxo group with the corresponding O-substituted hydroxylamine according to a similar manner to that of Example 267.

Example 268

7-[2-(2-Aminothiazol-4-yl)-2-methoxyiminoacetamido]-3-vinyl-3-cephem-4-carboxylic acid (syn isomer)

IR (Nujol): 3400-3100, 1780, 1660, 1630, 1540 cm$^{-1}$

Example 269

Pivaloyloxymethyl 7-[2-(2-aminothiazol-4-yl)-2-methoxyiminoacetamido]-3-vinyl-3-cephem-4-carboxylate (syn isomer)

IR (Nujol): 3400-3100, 1770, 1745, 1670, 1610, 1530 cm$^{-1}$

Example 270

Acetoxymethyl 7-[2-(2-aminothiazol-4-yl)-2-methoxyiminoacetamido]-3-vinyl-3-cephem-4-carboxylate (syn isomer)

IR (Nujol): 3300, 1765 (broad), 1660, 1610, 1535 cm$^{-1}$

Example 271

Propionyloxymethyl 7-[2-(2-aminothiazol-4-yl)-2-methoxyiminoacetamido]-3-vinyl-3-cephem-4-carboxylate (syn isomer)

IR (Nujol): 3350, 1770 (broad), 1650, 1620, 1530 cm$^{-1}$

Example 272

Isobutyryloxymethyl 7-[2-(2-aminothiazol-4-yl)-2-methoxyiminoacetamido]-3-vinyl-3-cephem-4-carboxylate (syn isomer)

IR (Nujol): 3400-3100, 1780-1740, 1670, 1610, 1530 cm$^{-1}$

Example 273

1-Acetoxypropyl 7-[2-(2-aminothiazol-4-yl)-2-methoxyiminoacetamido]-3-vinyl-3-cephem-4-carboxylate (syn isomer)

IR (Nujol): 3300, 1765, 1670, 1610 cm$^{-1}$

Example 274

L-2-Amino-2-carboxyethyl 7-[2-(2-aminothiazol-4-yl)-2-methoxyiminoacetamido]-3-vinyl-3-cephem-4-carboxylate (syn isomer)

IR (Nujol): 3200, 1770, 1735, 1650 (broad) cm$^{-1}$

Example 275

Phthalid-3-yl 7-[2-(2-aminothiazol-4-yl)-2-methoxyiminoacetamido]-3-vinyl-3-cephem-4-carboxylate (syn isomer)

IR (Nujol): 3300, 1775, 1670, 1610, 1530 cm$^{-1}$

Example 276

7-[2-(2-Aminothiazol-4-yl)-2-allyloxyiminoacetamido]-3-vinyl-3-cephem-4-carboxylic acid (syn isomer)

IR (Nujol): 3250, 1770, 1655, 1605, 1545 cm$^{-1}$

Example 277

7-[2-(2-Aminothiazol-4-yl)-2-propargyloxyiminoacetamido]-3-vinyl-3-cephem-4-carboxylic acid (syn isomer)

IR (Nujol): 3250, 1760, 1680, 1620, 1530 cm$^{-1}$

Example 278

7-[2-(2-Aminothiazol-4-yl)-2-ethoxyiminoacetamido]-3-vinyl-3-cephem-4-carboxylic acid (syn isomer)

IR (Nujol): 3300, 1770, 1660, 1545 cm$^{-1}$

Example 279

Pivaloyloxymethyl 7-[2-(2-aminothiazol-4-yl)-2 ethoxyiminoacetamido]-3-vinyl-3-cephem-4-carboxylate (syn isomer)

IR (Nujol): 3300, 1780, 1740, 1670, 1610, 1530 cm$^{-1}$

Example 280

7-[2-(2-Aminothiazol-4-yl)-2-hexyloxyiminoacetamido]-3-vinyl-3-cephem-4-carboxylic acid (syn isomer)

IR (Nujol): 3250, 1770, 1660, 1530 cm$^{-1}$

Example 281

7-[2-(2-Aminothiazol-4-yl)-2-(1-carboxyethoxyimino)acetamido]-3-vinyl-3-cephem-4-carboxylic acid (syn isomer)

IR (Nujol): 3260, 3160, 1770, 1670 cm$^{-1}$

Example 282

7-[2-(2-Aminothiazol-4-yl)-2-(1-carboxy-1-methylethoxyimino)acetamido]-3-vinyl-3-cephem-4-carboxylic acid (syn isomer)

IR (Nujol): 3300, 3200, 1770, 1670, 1640 cm$^{-1}$

Example 283

7-[2-(2-Aminothiazol-4-yl)-2-(3-carboxypropoxyiminoacetamido]-3-vinyl-3-cephem-4-carboxylic acid (syn isomer)

IR (Nujol): 3300, 1760, 1660 cm$^{-1}$

Example 284

7-[2-(2-Aminothiazol-4-yl)-2-ethoxycarbonylmethoxyiminoacetamido]-3-vinyl-3-cephem-4-carboxylic acid (syn isomer)

IR (Nujol): 3250, 1770, 1670, 1530 cm$^{-1}$

Example 285

Benzhydryl 7-[2-(2-aminothiazol-4-yl)-2-(3-benzhydryloxycarbonyl-3-tert-butoxycarbonylaminopropoxyimino)acetamido]-3-vinyl-3-cephem-4-carboxylate (syn isomer)

IR (Nujol): 3300, 1780, 1719, 1680 cm$^{-1}$

Example 286

Benzhydryl 7-[2-(2-aminothiazol-4-yl)-2-(2-benzhydryloxycarbonyl-2-tert-butoxycarbonylaminoethoxycarbonylmethoxyimino)acetamido]-3-vinyl-3-cephem-4-carboxylate (syn isomer)

IR (Nujol): 3360, 1750 (broad) cm$^{-1}$

Example 287

7-[2-(2-Aminothiazol-4-yl)-2-(pyridin-2-ylmethoxyimino)acetamido]-3-vinyl-3-cephem-4-carboxylic acid (syn isomer)

IR (Nujol): 3300, 1770, 1650, 1620, 1540 cm$^{-1}$

Example 288

7-[2-(2-Aminothiazol-5-yl)-2-methoxyiminoacetamido]-3-vinyl-3-cephem-4-carboxylic acid (syn isomer)

IR (Nujol): 3300, 1780, 1645, 1580, 1515 cm$^{-1}$

Example 289

7-[2-(2-Aminothiazol-4-yl)-2-cyanomethoxyiminoacetamido]-3-vinyl-3-cephem-4-carboxylic acid (syn isomer)

IR (Nujol): 3330, 2020, 1770, 1670, 1620 cm$^{-1}$

Example 290

7-[2-(2-Aminothiazol-4-yl)-2-(3-carboxyallyloxyiminoacetamido]-3-vinyl-3-cephem-4-carboxylic acid (syn isomer)

IR (Nujol): 3250, 1760, 1690, 1650 cm$^{-1}$

Example 291

7-[2-(2-Amino-5-chlorothiazol-4-yl)-2-carboxymethoxyiminoacetamido]-3-vinyl-3-cephem-4-carboxylic acid (syn isomer)

IR (Nujol): 3400, 3180, 1770, 1685, 1650, 1610 cm$^{-1}$

Example 292

7-[2-(2-Formamidothiazol-4-yl)-2-(O,O-diethylphosphonomethoxyimino)acetamido]-3-vinyl-3-cephem-4-carboxylic acid (syn isomer)

IR (Nujol): 3160, 1775 (broad), 1680 (broad) cm$^{-1}$

Example 293

7-[2-(2-Aminothiazol-4-yl)-2-(2-cyclopenten-1-yloxyimino)acetamido]-3-vinyl-3-cephem-4-carboxylic acid (syn isomer)

IR (Nujol): 3270, 1765, 1650 cm$^{-1}$

Example 294

7-[2-(5-Amino-1,2,4-thiadiazol-3-yl)-2-methoxyiminoacetamido]-3-vinyl-3-cephem-4-carboxylic acid (syn isomer)

IR (Nujol): 3350, 3250, 1770, 1670, 1620, 1530 cm$^{-1}$

Example 295

Pivaloyloxymethyl 7-[2-(5-amino-1,2,4-thiadiazol-3-yl)-2-methoxyiminoacetamido]-3-vinyl-3-cephem-4-carboxylate (syn isomer).

IR (Nujol): 3400-3100, 1770, 1760, 1680, 1620, 1530 cm$^{-1}$

Example 296

7-[2-(5-Amino-1,2,4-thiadiazol-3-yl)-2-carboxymethoxyiminoacetamido]-3-vinyl-3-cephem-4 -carboxylic acid (syn isomer)

IR (Nujol): 3380, 3280, 1760, 1720, 1670 cm$^{-1}$

Example 297

7-[2-(5-Amino-1,2,4-oxadiazol-3-yl)-2-methoxyiminoacetamido]-3-vinyl-3-cephem-4 -carboxylic acid (syn isomer)

IR (Nujol): 3250, 1770, 1660, 1550 cm$^{-1}$

Example 298

7-[2-(6Aminopyridin-2-yl)-2-methoxyiminoacetamido]-3-vinyl-3-cephem-4 -carboxylic acid (syn isomer)

IR (Nujol): 3350, 3250, 1780 (broad), 1667 (broad) cm$^{-1}$

Example 299

7-[2-(6-Aminopyridin-2-yl)-2-carboxymethoxyiminoacetamido]-3-vinyl-3-cephem-4 -carboxylic acid (syn isomer)

IR (Nujol): 3300, 1763 (broad), 1660 (broad) cm$^{-1}$

Example 300

Benzhydryl 7-[2-(2-formamidothiazol-4-yl)-2-methoxyiminoacetamido]-

7-[2-(5-Amino-1,2,4-thiadiazol-3-yl)-2-carboxymethoxyiminoacetamido]-3-vinyl-3-cephem-4 -carboxylate acid (syn isomer)

IR (Nujol): 3250, 1780, 1710, 1700, 1660, 1540 cm$^{-1}$

Example 301

Benzhydryl 7-[2-(2-formamidothiazol-4-yl)-2-tert-butoxycarbonylmethoxyiminoacetamido]-

7-[2-(5-Amino-1,2,4-thiadiazol-3-yl)-2-carboxymethoxyiminoacetamido]-3-vinyl-3-cephem-4 -carboxylate acid (syn isomer)

IR (Nujol): 3250, 1780, 1720, 1680, 1540 cm$^{-1}$

Example 302

Benzhydryl
7-[2-(2-aminothiazol-4-yl)-2-tert-butoxycarbonylmethoxyiminoacetamido]-

7-[2-(5-Amino-1,2,4-thiadiazol-3-yl)-2-carboxymethoxyiminoacetamido]-3-vinyl-3-cephem-4-carboxylate acid (syn isomer)

IR (Nujol): 3440, 3260, 3100, 1780, 1720, 1660, 1530 cm$^{-1}$

Example 303

2-(1-tert-Butoxycarbonylethoxyimino)-2-(5-amino-1,2,4-thiadiazol-3-yl)acetic acid (syn isomer) (2.2 g) was added to the stirred suspension of phosphorus pentachloride (1.6 g) in methylene chloride (22 ml) at −15° C., and the mixture was stirred for 30 minutes at −5° to −15° C. Dry diisopropyl ether was added to the reaction mixture at −10° C., and the precipitates were collected by filtration, washed with dry diisopropyl ether. On the other hand, trimethylsilylacetamide (5.4 g) was added to the stirred suspension of benzhydryl 7-amino-3-vinyl-3-cephem-4-carboxylate hydrochloride (2.5 g) in methylene chloride (25 ml). To the solution obtained were added the above precipitates at −10° C. and stirred at −5° to −10° C. for 40 minutes. Water was added to the resultant solution and the separated organic layer was washed with a saturated aqueous sodium bicarbonate and a saturated aqueous sodium chloride, dried over magnesium sulfate, and then evaporated to give benzhydryl 7-[2-(1-tert-butoxycarbonylethoxyimino)-2-(5-amino-1,2,4-thiadiazol-3-yl)acetamido]-3-vinyl-3-cephem-4-carboxylate (syn isomer) (2.51 g).

IR (Nujol): 1770, 1720, 1680, 1610 cm$^{-1}$

Example 304

7-[2-(4-tert-Butoxycarbonylaminothizol-2-yl)-2-methoxyiminoacetamido]-3-vinyl-3cephem-4-carboxylic acid (syn isomer) (0.95 g) was obtained by reacting 7-amino-3-vinyl-3-cephem-4-carboxylic acid (0.7 g) with 2-(4-tert-butoxycarbonylaminothiazol-2-yl)-2-methoxyiminoacetic acid (syn isomer) (0.9 g) according to a similar manner to that of Example 7.

IR (Nujol): 3250, 1785, 1720, 1690, 1600, 1535 cm$^{-1}$

N.M.R. δppm DMSO—d$_6$): 1.45 (9H, s), 3.72 (2H, q, J=17 Hz), 3.95 (3H, s), 5.18 (1H, d, J=5 Hz), 5.28 (1H, d, J=11 Hz), 5.52 (1H, d, J=17 Hz), 5.82 (1H, dd, J=5 Hz,8 Hz), 5.90 (1H, dd, J=11 Hz, 17 Hz), 7.28 (1H, s), 9.71 (1H, d, J=8 Hz), 10.27 (1H, s).

Example 305

Trifluoroacetic acid (9.6 ml) was added to a solution of benzhydryl 7-[2-(1-tert-butoxycarbonylethoxyimino)-2-(5-amino-1,2,4-thiadiazol-3-yl)acetamido]-3-vinyl-3-cephem-4-carboxylate (syn isomer) (2.4 g) in methylene chloride (5 ml) and anisole (2.4 ml) under ice-cooling, and the mixture was stirred for 1 hour at room temperature. The resultant solution was added dropwise to diisopropyl ether (100 ml) and the precipitates were collected by filtration. The precipitates were added to a mixture of water and ethyl acetate and then adjusted to pH 7.5 with 10% aqueous sodium hydroxide. The separated aqueous layer was saturated with sodium chloride and adjusted to pH 1.5 with 10% hydrochloric acid, followed by extraction with a mixed solvent of ethyl acetate and tetrahydrofuran (1:1 by volume). The extract was washed with a saturated aqueous sodium chloride and dried over magnesium sulfate.

Removal of the solvent gave 7-[2-(1-carboxyethoxyimino)-2-(5-amino-1,2,4-thiadiazol-3-yl)acetamido]-3-vinyl-3-cephem-4-carboxylic acid (syn isomer) (0.55 g).

IR (Nujol): 3330, 3200, 1770, 1670, 1610 cm$^{-1}$

| NMR δ ppm (DMSO-d6): | 1.37(3H, m), 3.70(2H, m), |
|---|---|
| | 4.80(1H, m), 5.07–6.07(4H, m), |
| | 6.96(1H, d,d J=12.0Hz, 18.0Hz), |
| | 8.17(2H, broad s), |
| | 9.47(d, J=8.0Hz) ⎫ (1H) |
| | 9.55(d, J=8.0Hz) ⎭ |

Example 306

To ethanol (2 l) was added 7-[2-(2-aminothiazol-4-yl)-2-carboxymethoxyiminoacetamido]-3-vinyl-3-cephem-4-carboxylic acid (syn isomer) (70 g), and the mixture was stirred at 40° C. for 30 minutes. The insoluble substance was collected by filtration and washed with ethanol. The washings and the filtrate were combined, and thereto was added water (4.2 l) at 40° C., followed by stirring at ambient temperature for an hour. The precipitates were collected by filtration to obtain crystalline trihydrate of 7-[2-(2-aminothiazol-4-yl)-2-carboxymethoxyiminoacetamido]-3-vinyl-3-cephem-4-carboxylic acid (syn isomer) (61.6 g).

| X-ray spectrum: | |
|---|---|
| 2θ° | I/I$_0$ (relative intensity) |
| 29.9° | 0.40 |
| 28.7 | 0.17 |
| 28.4 | 0.23 |
| 28.0 | 0.15 |
| 27.3 | 0.69 |
| 26.4 | 0.53 |
| 26.1 | 0.43 |
| 24.7 | 0.42 |
| 23.7 | 0.53 |
| 23.4 | 0.70 |
| 23.1 | 0.50 |
| 22.7 | 0.69 |
| 22.2 | 0.82 |
| 21.4 | 0.40 |
| 21.0 | 0.50 |
| 20.5 | 0.54 |
| 20.0 | 0.30 |
| 19.5 | 1.00 |
| 17.5 | 0.10 |
| 15.4 | 0.48 |
| 15.0 | 0.93 |
| 8.9 | 0.93 |
| 7.5 | 0.15 |
| 5.8 | 0.34 |

Example 307

Vilsmeir reagent was prepared from phosphorus oxychloride (1.28 ml) and N,N-dimethylformamide (1.06 ml) in tetrahydrofuran (35 ml) in a usual manner. To the resultant suspension was added 2-benzhydryloxycarbonylmethoxyimino-2-(2-formamidothiazol-4-yl)acetic acid (syn isomer) (5 g) under ice-cooling, and the mixture was stirred at the same temperature for 30 minutes to prepare the activated acid solution. This solution was added at a time to a solution of benzhydryl 7-amino-3-vinyl-3-cephem-4-carboxylate hydrochloride (4.89 g) and trimethylsilylacetamide (9.2 g) in ethyl acetate (40 ml) at −20° C., followed by stirring at −20° to −10° C.

for an hour. After water and ethyl acetate were added to the reaction mixture, the separated organic layer was washed with 5% aqueous sodium carbonate and an aqueous sodium chloride, followed by drying over magnesium sulfate. Removal of the solvent gave benzhydryl 7-[2-benzhydryloxycarbonylmethoxyimino-2-(2-formamidothiazol-4-yl)acetamido]-3-vinyl-3-cephem-4-carboxylate (syn isomer) (8.7 g).

IR (Nujol): 3250, 1780, 1720, 1680, 1620, 1540 cm$^{-1}$

NMR δppm (DMSO—d$_6$): 3.70 (2H, m), 4.95 (2H, broad s), 5.25 (1H, d, J=5 Hz), 5.26 (1H, d, J=11 Hz), 5.50 (1H, d, J=18 Hz), 5.95 (1H, dd, J=5, 8 Hz), 6.78 (1H, dd, J=11, 18 Hz), 6.90 (1H, s), 6.95 (1H, s), 7.2–7.7 (11H, m), 8.50 (1H, s), 9.72 (1H, d, J=8 Hz)

Example 308

Benzhydryl 7-[2-benzyloxycarbonylmethoxyimino-2-(2-formamidothiazol-4-yl)acetamido]-3-vinyl-3-cephem-4-carboxylate (syn isomer) (6.95 g) was obtained by reacting benzhydryl 7-amino-3-vinyl-3-cephem-4-carboxylate hydrochloride (4.3 g) with the activated acid solution prepared from 2-benzyloxycarbonylmethoxyimino-2-(2-formamidothiazol-4-yl)acetic acid (syn isomer) (4.0 g), phosphorus oxychloride (1.9 g) and N,N-dimethylformamide (0.9 g) according to a similar manner to that of Example 307.

IR (Nujol): 3250, 1775, 1710, 1680, 1610 cm$^{-1}$

NMR δppm (DMSO—d$_6$): 3.80 (2H, q, J=18 Hz), 4.36 (2H, s), 5.27 (2H, s), 5.35 (1H, d, J=11 Hz), 5.35 (1H, d, J=5Hz), 5.67 (1H, d, J=17 Hz), 6.00 (1H, dd, J=5, 8 Hz), 6.83 (1H, dd, J=11, 17 Hz), 7.00 (1H, s, 7.21–7.70 (16H, m), 8.60 (1H, s), 9.80 (1H, d, J=8 Hz), 12.73 (1H, s)

Example 309

Benzhydryl 7-[2-(1-tert-butoxycarbonylethoxyimino)-2-(2-formamido-5-chlorothiazol-4-yl)acetamido]-3-vinyl-3-cephem-4-carboxylate (syn isomer) (1.1 g) was obtained by reacting benzhydryl 7-amino-3-vinyl-3-cephem-4-carboxylate hydrochloride (1.1 g) with the activated acid solution prepared from 2-(1-tert-butoxycarbonylethoxyimino)-2-(2-formamido-5-chlorothiazol-4-yl)acetic acid (syn isomer) (1.1 g), phosphorus oxychloride (0.53 g) and N,N-dimethylformamide (0.25 g) according to a similar manner to that of Example 307.

IR (Nujol): 1780, 1710, 1680 cm$^{-1}$

NMR δppm (DMSO—d$_6$): 1.33–1.70 (12H, m), 3.80 (2H, m), 4.68 (1H, m), 5.18–5.19 (4H, m), 6.78 (1H, dd, J=11.0, 17.0 Hz), 7.00 (1H, s), 7.41 (10H, s), 8.58 (1H, s), 9.60, 9.73 (1H, d, J=8.0 Hz), 12.87 (1H, broad s)

Example 310

To a stirred solution of benzhydryl 7-[2-benzhydryloxycarbonylmethoxyimino-2-(2-formamidothiazol-4-yl)acetamido]-3-vinyl-3-cephem-4-carboxylate (syn isomer) (8.14 g) in methanol (50 ml) and tetrahydrofuran (10 ml) was added 35% hydrochloric acid (2.3 ml). After stirring at 30° C. for an hour, the reaction mixture was poured into ice-water and then adjusted to pH 3.5 with a saturated aqueous sodium bicarbonate. The precipitates were collected by filtration and then dried to give benzhydryl 7-[2-benzhydryloxycarbonylmethoxyimino-2-(2-aminothiazol-4-yl)acetamido]-3-vinyl-3-cephem-4-carboxylate (syn isomer) (7.08 g).

IR (Nujol): 3300, 1780, 1720, 1680, 1620 cm$^{-1}$

NMR δppm (DMSO—d$_6$): 3.72 (2H, broad s), 4.95 (2H, s), 5.30 (1H, d, J=11 Hz), 5.32 (1H, d, J=5 Hz), 5.56 (1H, d, J=18 Hz), 5.85 (1H, d, J=8, 5 Hz), 6.82 (1H, dd, J=11, 18 Hz), 6.87 (1H, s), 6.90 (1H, s), 6.95 (1H, s), 7.2–7.7 (10H, m), 9.8 (1H, d, J=8 Hz)

Example 311

Benzhydryl 7-[2-benzyloxycarbonylmethoxyimino-2-(2-aminothiazol-4-yl)acetamido]-3-vinyl-3-cephem-4-carboxylate (syn isomer) (4.2 g) was obtained by reacting benzhydryl 7-[2-benzyloxycarbonylmethoxyimino-2-(2-formamidothiazol-4-yl)acetamido]-3-vinyl-3-cephem-4-carboxylate (syn isomer) (4.9 g) with conc.hydrochloric acid (2.2. ml) according to a similar manner to that of Example 310.

IR (Nujol): 3300, 1780, 1720, 1680, 1620 cm$^{-1}$

NMR δppm (DMSO—d$_6$): 3.72 (2H, m), 4.83 (2H, s), 5.23 (2H, s), 5.30 (1H, d, J=5 Hz), 5.32 (1H, d, J=12 Hz), 5.67 (1H, d, J=18 Hz), 6.87 (1H, dd, J=12, 18 Hz), 6.87 (1H, s), 7.00 (1H, s), 7.13–7.77 (15H, m), 9.7 (1H, d, J=8 Hz)

Example 312

Benzhydryl 7-[2-(1-tert-butoxycarbonylethoxyimino)-2-(2-amino-5-chlorothiazol-4-yl)acetamido]-3-vinyl-3-cephem-4-carboxylate (syn isomer) (1.69 g) was prepared by reacting benzhydryl 7-[2-(1-tert-butoxycarbonylethoxyimino)-2-(2-formamido-5-chlorothiazol-4-yl)acetamido]-3-vinyl-3-cephem-4-carboxylate (syn isomer) (1.9 g) with conc. hydrochloric acid (0.8 g) according to a similar manner to that of Example 310.

IR (Nujol): 3420, 3250, 3150, 1770, 1715, 1670, 1620 cm$^{-1}$

NMR δppm (DMSO—d$_6$): 1.43 (12H, s), 3.68 (2H, m), 4.57 (1H, m), 5.17–5.77 (2H, m), 5.25 (1H, d, J=5.0 Hz), 5.87 (1H, dd, J=5.0, 8.0 Hz), 6.69 (1H, dd, J=11.0, 16.0 Hz), 6.93 (1H, s), 7.35 (10H, s), 9.34, 9.47 (1H, d, J=8 Hz)

Example 313

To a solution of benzhydryl 7-[2-benzhydryloxycarbonylmethoxyimino-2-(2-aminothiazol-4-yl)acetamido]-3-vinyl-3-cephem-4-carboxylate (syn isomer) (3 g) in formic acid (12 ml) was added 35% hydrochloric acid (1 ml) at 0° C. After stirring at ambient temperature for an hour, the reaction mixture was poured into diisopropyl ether. The precipitates were collected by filtration, washed with diisopropyl ether and then dissolved in water (15 ml). The aqueous solution was adjusted to pH 3.5 with 5% aqueous sodium bicarbonate. The precipitates were collected by filtration and dried to give 7-[2-carboxymethoxyimino-2-(2-aminothiazol-4-yl)acetamido]-3-vinyl-3-cephem-4-carboxylic acid (syn isomer) (1.5 g).

IR (Nujol): 3200, 1770, 1670 cm$^{-1}$

Example 314

Trifluoroacetic acid (6.4 ml) was added to a solution of benzhydryl 7-[2-(1-tert-butoxycarbonylethoxyimino)-2-(2-amino-5-chlorothiazol-4-yl)acetamido]-3-vinyl-3-cephem-4-carboxylate (syn isomer) (1.6 g) in methylene chloride (3.0 ml) and anisole (1.6 ml) under ice-cooling, and the mixture was stirred at ambient temperature for 1.5 hours. To the reaction mixture was added diisopropyl ether (50 ml), and the precipitates were collected by filtration and added to a mixture of water and ethyl acetate. After adjusting to pH 7.5 with 10% aqueous sodium hydroxide, the separated aqueous layer was adjusted to pH 2.2 with 10% hydrochloric acid and then saturated with sodium chloride, followed by extraction with a mixture of ethyl acetate and tetrahydrofuran (1:1). The extract was washed with a saturated aqueous sodium chloride and then dried over magnesium sulfate. Removal of the solvent gave 7-[2-(1-carboxyethoxyimino)-2-(2-amino-5-chlorothiazol-4-yl)acetamido]-3-vinyl-3-cephem-4-carboxylic acid (syn isomer) (0.52 g).

IR (Nujol): 3300, 3200, 1770, 1670 cm$^{-1}$

NMR δppm (DMSO-d$_6$): 1.40(d, J=7.0Hz) ⎫
1.47(d, J=7.0Hz) ⎬ (3H),
3.62(2H, q, J=18.0Hz), 4.67(1H, m), 5.20(1H, d, J=5.0Hz), 5.11–5.92(3H, m), 6.92(1H, m), 9.47(1H, m)

Example 315

To a solution of benzhydryl 7-(2-benzyloxycarbonylmethoxyimino-4-bromo-3-oxobutyramido)-3-vinyl-3-cephem-4-carboxylate (2.5 g) in tetrahydrofuran (25 ml) was added a solution of thiourea (0.78 g) and sodium acetate (0.34 g) in water (10 ml), followed by stirring at 35° C. for 4 hours. The reaction mixture was extracted with ethyl acetate, and the extract was washed with a saturated aqueous sodium chloride and dried over magnesium sulfate. Removal of the solvent gave benzhydryl 7-[2-benzyloxycarbonylmethoxyimino-2-(2-aminothiazol-4-yl)acetamido]-3-vinyl-3-cephem-4-carboxylate (syn isomer) (2.0 g).

IR (Nujol): 3300, 1780, 1720, 1680, 1620 cm$^{-1}$

Example 316

To a solution of benzhydryl 7-[4-bromo-2-(2,2,2-trichloroethoxycarbonylmethoyimino)-3-oxobutyramido]-3-vinyl-3-cephem-4-carboxylate (26.0 g) in tetrahydrofuran (100 ml) was added a solution of thiourea (3.1 g) and sodium acetate (3.3 g) in water (100 ml), and the mixture was stirred at 35° C. for 3 hours. The reaction mixture was extracted with ethyl acetate, and the extract was washed with water, followed by drying over magnesium sulfate. Removal of the solvent gave benzhydryl 7-[2-(2-aminothiazol-4-yl)-2-(2,2,2-trichloroethoxycarbonylmethoxyimino)acetamido]-3-vinyl-3-cephem-4-carboxylate (syn isomer) (12.5 g).

IR (Nujol): 3200, 1773, 1716, 1640 cm$^{-1}$
NMR δppm (DMSO—d$_6$): 3.51, 3.88 (2H, ABq, J=18 Hz), 4.83 (2H, s), 4.95 (2H, s), 5.22 (1H, d, J=5 Hz), 5.23 (1H, d, J=10 Hz), 5.55 (1H, d, J=18 Hz), 5.82 (1H, dd, J=5, 8 Hz), 6.68 (1H, dd, J=10, 18 Hz), 6.75 (1H, s), 6.87 (1H, s), 7.3 (10H, m), 9.50 (1H, d, J=8 Hz).

Example 317

To a mixture of 2-(2-aminothiazol-4-yl)-2-(2,2,2-trichloroethoxycarbonylmethoxyimino)acetic acid (syn isomer) (1.13 g) and phosphorus oxychloride (0.56 g) in ethyl acetate (20 ml) was added trimethylsilylacetamide (0.30 g) at 4° C., and the mixture was stirred at 4° to 6° C. for 15 minutes. To the mixture was added additional phosphorus oxychloride (0.56 g), followed by stirring at the same temperature for 15 minutes. Thereto was added N,N-dimethylformamide (0.26 g), and the mixture was stirred at 4° to 6° C. for 50 minutes to prepare the activated acid solution. This solution was added to a solution of benzhydryl 7-amino-3-vinyl-3-cephem-4-carboxylate hydrochloride (1.1 g) and trimethylsilylacetamide (2.0 g) in ethyl acetate (20 ml) at −20° C., and the mixture was stirred at −20° to 0° C. for an hour. After addition of ethyl acetate and water, the organic layer was separated and washed with a saturated aqueous sodium bicarbonate and an aqueous sodium chloride, followed by drying over magnesium sulfate. The solution was evaporated, and the residue was pulverized with diethyl ether to give benzhydryl 7-[2-(2-aminothiazol-4-yl)-2-(2,2,2-trichloroethoxycarbonylmethoxyimino)acetamido]-3-vinyl-3-cephem-4-carboxylate (syn isomer) (1.6 g).

IR (Nujol): 3200, 1773, 1716, 1640 cm$^{-1}$

Example 318

A solution of benzhydryl 7-[2-(2-aminothiazol-4-yl)-2-(2,2,2-trichloroethoxycarbonylmethoxyimino)acetamido]-3-vinyl-3-cephem-4-carboxylate (syn isomer) (2.5 g) in trifluoroacetic acid (7.5 ml) and anisole (2.5 ml) was stirred at ambient temperature for 30 minutes. The reaction mixture was poured into diisopropyl ether, and the precipitates were collected by filtration, followed by dissolving them in a saturated aqueous sodium bicarbonate (50 ml). The aqueous solution was washed with ethyl acetate, adjusted to pH 2.0 with 10% hydrochloric acid and then extracted with ethyl acetate. The extract was washed with a saturated aqueous sodium chloride and then dried over magnesium sulfate. Removal of the solvent gave 7-[2-(2-aminothiazol-4-yl)-2-(2,2,2-trichloroethoxycarbonylmethoxyimino)acetamido]-3-vinyl-3-cephem-4-carboxylic acid (syn isomer) (1.55 g).

IR (Nujol): 3270, 1760 (broad), 1663 (broad) cm$^{-1}$
NMR δppm (DMSO—d$_6$): 3.68 (2H, m), 4.87 (2H, s), 4.93 (2H, s), 5.17 (1H, d, J=5 Hz), 5.28 (1H, d, J=12 Hz), 5.53 (1H, d, J=18 Hz), 5.73 (1H, dd, J=5, 8 Hz), 6.83 (1H, s), 6.87 (1H, dd, J=12, 18 Hz), 9.53 (1H, d, J=8 Hz)

Example 319

To a solution of 7-[2-(2-aminothiazol-4-yl)-2-(2,2,2-trichloroethoxycarbonylmethoxyimino)acetamido]-3-vinyl-3-cephem-4-carboxylic acid (syn isomer) (0.5 g) in tetrahydrofuran (2.5 ml) were added zinc powder (0.5 g) and an aqueous ammonium chloride (0.3 g) in water (4 ml) at ambient temperature with stirring, and the stirring was continued at ambient temperature for 30 minutes. After the zinc powder was removed by filtration, the filtrate was adjusted to pH 2.3 with 10% hydrochloric acid and then extracted with ethyl acetate. The extract was washed with a saturated aqueous sodium chloride, followed by drying over magnesium sulfate. The solution was evaporated under reduced pressure, and the residue was triturated with diisopropyl ether to give 7-[2-(2-aminothiazol-4-yl)-2-carboxymethoxyiminoacetamido]-3-vinyl-3-cephem-4-carboxylic acid (syn isomer) (0.11 g).

IR (Nujol): 3200, 1770, 1670 cm$^{-1}$

Example 320

7-[2-(2-Aminothiazol-4-yl)-2-carboxymethoxyiminoacetamido]-3-vinyl-3-cephem-4-carboxylic acid (syn isomer) (0.19 g) was obtained by reacting 7-[2-(2-aminothiazol-4-yl)-2-(2,2,2-trichloroethoxycarbonylmethoxyimino)acetamido]-3-vinyl-3-cephem-4-carboxylic acid (syn isomer) (1.0 g) with zinc powder (1.0 g) and 1M aqueous potassium biphosphate (10 ml) according to a similar manner to that of Example 119.

IR (Nujol): 3200, 1770, 1670 cm$^{-1}$

Example 321

7-[2-(2-Formamidothiazol-4-yl)-2-benzhydryloxycarbonylmethoxyiminoacetamido]-3-vinyl-3-cephem-4- carboxylic acid (syn isomer) (10.5 g) was obtained by reacting 7-amino-3-vinyl-3-cephem-4-carboxylic acid (4.53 g) with the activated acid solution prepared from 2-(2-formamidothiazol-4-yl)-2-benzhydryloxycarbonyl-methoxyiminoacetic acid (syn isomer) (10.55 g), phosphorus oxychloride (4.4 g) and N,N-dimethylformamide (2.1 g) in ethyl acetate according to a similar manner to that of Example 307.

IR (Nujol): 3500, 3200, 1770, 1730, 1680 cm$^{-1}$

NMR δppm (DMSO—d$_6$): 3.71 (2H, m), 4.96 (2H, s), 5.15 (1H, d, J=11 Hz), 5.25 (1H, d, J=5 Hz), 5.57 (1H, d, J=17 Hz), 5.89 (1H, dd, J=5, 8 Hz), 6.92 (1H, s), 7.00 (1H, dd, J=11, 17 Hz), 7.12–7.68 (10H, m), 8.54 (1H, s), 9.75 (1H, d, J=8 Hz), 11.78 (1H, broad s)

Example 322

Trifluoroacetic acid (5.75 g) was added to a solution of pivaloyloxymethyl 7-[2-(2-aminothiazol-4-yl)-2-benzhydryloxycarbonylmethoxyiminoacetamido]-3-vinyl-3-cephem-4-carboxylate (syn isomer) (3.7 g) in methylene chloride (14.8 ml) and anisole (1.09 g) under ice-cooling, and the mixture was stirred for an hour at ambient temperature. Then the reaction mixture was added dropwise to diisopropyl ether (160 ml). The precipitate were collected by filtration and washed with diisopropyl ether, followed by adding them to a mixture of water (60 ml) and ethyl acetate (60 ml). The resultant mixture was adjusted to pH 7.0 with a saturated aqueous sodium bicarbonate. The separated aqueous solution was further adjusted to pH 2.5 with 10% hydrochloric acid. The precipitates were collected by filtration, washed with water and then dried over phosphorus pentoxide in vacuo to give pivaloyloxymethyl 7-[2-(2-aminothiazol-4-yl)-2-carboxymethoxyiminoacetamido]-3-vinyl-3-cephem-4-carboxylate (syn isomer) (2.13 g).

IR (Nujol): 3300, 3200, 1780, 1750, 1670 cm$^{-1}$

NMR δppm (DMSO-d$_6$): 1.2 (9H, s), 3.8 (2H, q, J=18 Hz), 4.63 (2H, s), 5.26 (1H, d, J=5 Hz), 5.56 (1H,d, J=11 Hz), 5.63 (1H, d, J=17 Hz), 5.73–6.14 (3H,m), 6.83 (1H,s), 6.87 (1H, dd, J=11,17 Hz), 7.27(2H, broad s), 9.55 (1H, d, J=8 Hz).

Example 323

To a solution of 7-[2-(2-formamidothiazol-4-yl)-2-benzhydryloxycarbonylmethoxyiminoacetamido]-3-vinyl-3-cephem-4-carboxylic acid (syn isomer) (11.7 g) in methanol (120 ml) was added conc. hydrochloric acid (3.97 ml) at 30° C., and the mixture was stirred for 3 hours at the same temperature. The reaction mixture was concentrated under reduced pressure. After water (150 ml) and ethyl acetate (100 ml) were added to the residual oil, the mixture was adjusted to pH 7.0 with a saturated aqueous sodium bicarbonate. The precipitates were collected by filtration and washed with ethyl acetate, followed by drying over phosphorus pentoxide to give sodium 7-[2-(2-aminothiazol-4-yl)-2-benzhydryloxycarbonylmethoxyiminoacetamido]-3-vinyl-3-cephem-4-carboxylate (syn isomer) (4.14 g)

IR (Nujol): 3450, 3270, 1750, 1670 cm$^{-1}$

NMR δppm (DMSO—d$_6$): 3.42 (2H, broad s), 4.82 (2H, s), 4.95 (1H, d, J=11 Hz), 5.02 (1H, d, J=5 Hz), 5.08 (1H, d, J=17 Hz), 5.57 (1H, d d, J=5, 8 Hz), 6.73 (1H, s), 6.83 (1H, s), 6.90 (1H, dd, J=11, 17 Hz), 7.05–7.52 (10H, m), 9.40 (1H, d, J=8 Hz)

Example 324

To a solution of sodium 7-[2-(2-aminothiazol-4-yl)-2-benzhydryloxycarbonylmethoxyiminoacetamido]-3-vinyl-3-cephem-4-carboxylate (syn isomer) (4.1 g) in N,N-dimethylformamide (41 ml) was added iodomethyl pivalate (1.55 g) at 0° C., and the mixture was stirred for 15 minutes at same temperature. The reaction mixture was poured into water (150 ml) and extracted with ethyl acetate (200 ml). The extract was washed with a saturated aqueous sodium bicarbonate and water, followed by drying over magnesium sulfate. The solution was evaporated in vacuo to give pivaloyloxymethyl 7-[2-(2-aminothiazol-4-yl)-2-benzhydryloxycarbonylmethoxyiminoacetamido]-3-vinyl-3-cephem-4-carboxylate (syn isomer) (3.75 g).

IR (Nujol): 3425, 3300, 1780, 1740, 1680 cm$^{-1}$

NMR δppm (DMSO—d$_6$): 1.17 (9H, s), 3.74 (2H, q, J=18 Hz), 4.82 (2H, s), 5.17 (1H, d, J=11 Hz), 5.21 (1H, d, J=5 Hz), 5.60 (1H, d, J=17 Hz), 5.84 (1H, dd, J=5, 8 Hz), 5.85 (2H, s), 6.76 (1H, s), 6.76 (1H, dd, J=11, 17 Hz), 6.84 (1H, s), 7.1–7.63 (10H, m), 9.56 (1H, d, J=8 Hz)

Example 325 tert-Butoxycarbonylmethyl 7-[2-(2-aminothiazol-4-yl)-2-benzhydryloxycarbonylmethoxyiminoacetamido]-3-vinyl-3-cephem-4-carboxylate (syn isomer) (3.4 g) was obtained by reacting sodium 7-[2-(2-aminothiazol-4-yl)-2-benzhydryloxycarbonylmethoxyiminoacetamido]-3-vinyl-3-cephem-4-carboxylate (syn isomer) (3.5 g) with tert-butyl bromoacetate (2.1 g) according to a similar manner to that of Example 324.

IR (Nujol): 3450, 3330, 1782, 1740, 1661, 1602 cm$^{-1}$

NMR δppm (DMSO—d$_6$): 1.44 (9H, s), 3.56, 3.88 (2H, ABq, J=14 Hz), 4.71 (2H, s), 4.84 (2H, s), 5.24 (1H, d, J=5 Hz), 5.36 (1H, d, J=11 Hz), 5.65 (1H, d, J=18 Hz), 5.83 (1H, dd, J=5, 8 Hz), 6.78 (1H, s), 6.87 (1H, s), 7.0 (1H, m), 7.42 (10H, m), 9.59 (1H, d, J=8 Hz)

Example 326

A solution of tert-butoxycarbonylmethyl 7-[2-(2-aminothiazol-4-yl)-2-benzhydryloxycarbonylmethoxyiminoacetamido]-3-vinyl-3-cephem-4-carboxylate (syn isomer) (3.0 g) in trifluoroacetic acid (10 ml) and anisole (5 ml) was stirred at 25° to 30° C. for an hour. The reaction mixture was poured into diisopropyl ether (150 ml), and the precipitates were collected by filtration and dissolved in 5% aqueous sodium bicarbonate (50 ml). The aqueous solution was washed with ethyl acetate and then adjusted to pH 2.3 with 10% hydrochloric acid. The precipitated substance was collected by filtration and washed with water to give carboxymethyl 7-[2-(2-aminothiazol-4-yl)-2-carboxymethoxyiminoacetamido]-3-vinyl-3-cephem-4-carboxylate (syn isomer) (1.7 g).

IR (Nujol): 3300, 1775, 1723, 1673 cm$^{-1}$

NMR δppm (DMSO—d$_6$): 3.60, 3.97 (2H, ABq, J=18 Hz), 4.57 (2H, s), 4.75 (2H, s), 5.27 (1H, d, J=5 Hz), 5.38 (1H, d, J=10 Hz), 5.60 (1H, d, J=20 Hz), 5.82 (1H, dd, J=5, 8 Hz), 6.80 (1H, s), 7.03 (1H, dd, J=10, 20 Hz), 9.50 (1H, d, J=8 Hz)

Preparation 90

(1) To a solution of tert-butyl 2-hydroxyimino-3-oxobutyrate (syn isomer) (187 g) in ethyl acetate (280 ml) and N,N-dimethylformamide (187 ml) was added potassium carbonate (166 g) at ambient temperature. To the suspension was dropwise added methyl monochloroacetate (109 g) and the reaction mixture was stirred at ambient temperature for 7.5 hours.

To the resultant suspensions was added ethyl acetate (280 ml) and the inorganic salts were filtered off. The organic solution was washed with a saturated aqueous solution of sodium chloride four times. The organic layer was dried over magnesium sulfate and concentrated under reduced pressure to give tert-butyl 2-methoxycarbonylmethoxyimino-3-oxobutyrate (syn isomer) (246 g).

IR (film): 1760, 1740, 1690, 1610 cm$^{-1}$

NMR (DMSO—d$_6$, δ): 1.40 (9H, s), 1.23 (3H, s), 3.62 (3H, s), 4.86 (2H, s)

(2) To a solution of tert-butyl 2-methoxycarbonylmethoxyimino-3-oxobutyrate (syn isomer) (10 g) in glacial acetic acid (5 ml) was added 30% hydrobromic acid in acetate acid (10 ml) at ambient temperature with stirring. The reaction mixture was stirred at 40° C. for 3 hours. The resultant solution was concentrated under reduced pressure and the residual oil was dissolved into ethyl acetate (100 ml). The ethyl acetate layer was washed with a saturated aqueous solution of sodium chloride four times and dried over magnesium sulfate. The solvent was evaporated under reduced pressure to give a crude oil (8.6 g). The oil was dissolved in methylene chloride (100 ml). To the solution was added potassium carbonate (1.87 g) and the suspension was stirred at ambient temperature for 30 minutes. The solution was diluted with n-hexane (100 ml). The solvent was decanted and the residual glassy mass was dissolved in ethyl acetate and 10% hydrochloric acid. The separated organic layer was washed with a saturated aqueous solution of sodium chloride and dried over magnesium sulfate. The solvent was concentrated under reduced pressure to give 2-methoxycarbonylmethoxyimino-3-oxobutyric acid (syn isomer) (4.0 g) as an oil.

IR (film): 3500, 1720 (broad) cm$^{-1}$

NMR (DMSO—d$_6$, δ): 2.46 (3H, s), 3.83 (3H, s) 5.06 (2H, s)

To a solution of tert-butyl 2-methoxycarbonylmethoxyimino-3-oxobutyrate (syn isomer) (51.9 g) in glacial acetic acid (52 ml) was slowly added sulfuryl chloride (72.2 ml) at 40° C. with stirring. The reaction mixture was stirred at the same temperature for an hour. The resultant solution was concentrated under reduced pressure and the residual oil was dissolved in ethyl acetate (300 ml). The ethyl acetate layer was washed with 10% hydrochloric acid once and washed with a saturated aqueous solution of sodium chloride four times. The separated organic layer was dissolved over magnesium sulfate and concentrated under reduced pressure. The residual oil was diluted with n-hexane (100 ml) and evaporated under reduced pressure. The white crystalline precipitates were washed with diisopropyl ether (100 ml). The precipitates were collected by filtration, dried under reduced pressure to give crystalline 4-chloro-2-methoxycarbonylmethoxyimino-3-oxobutyric acid (syn isomer) (13.4 g), mp 127° to 128.5° C.

IR (Nujol): 1745, 1720, 1701, 1604 cm$^{-1}$

NMR (DMSO—d$_6$, δ): 3.66 (3H, s), 4.79 (2H, s), 4.92 (2H, s)

Preparation 91

Vilsmeir reagent prepared from N,N-dimethylformamide (3.76 ml) and phosphorus oxychloride (4.46 ml) was suspended in dry tetrahydrofuran (50 ml). To the suspension was added 4-chloro-2-methoxycarbonylmethoxyimino-3-oxobutyric acid (syn isomer) (10.5 g), and the mixture was stirred under ice-cooling to prepare the activated acid solution. This solution was added at a time to a solution of 7-amino-3-vinyl-3-cephem-4-carboxylic acid (10 g) and trimethylsilylacetamide (35 g) in ethyl acetate (110 ml) at −30° C. After the reaction mixture was stirred at −15° C. for an hour, the resultant solution was poured into water (100 ml) and then extracted with ethyl acetate (200 ml). The extract was washed with a saturated aqueous sodium chloride and dried over magnesium sulfate. The solvent was evaporated under reduced pressure and the residue was triturated with diisopropyl ether to give 7-(4-chloro-2-methoxycarbonylmethoxyimino-3-oxobutyramido)-3-vinyl-3-cephem-4-carboxylic acid (syn isomer) (16.75 g).

I.R. (Nujol): 3200, 1760, 1727, 1702, 1650 cm$^{-1}$

N.M.R. (DMSO—d$_6$, δ): 3.66(3H, s), 3.50,3.88(2H,ABq, J=18 Hz), 4.73 (2H,s), 4.88(2H,s)m 5.15 (1H,d, J=5 Hz), 5.26(1H,d,J=11 Hz), 5.55(1H,d,J=18 Hz), 5.90(1H,dd,J=5 Hz, 8 Hz), 6.90(1H,dd,J=11 Hz, 18 Hz), 9.42(1H,d,J=8 Hz)

Preparation 92

Vilsmeir reagent prepared from N,N-dimethylformamide (3.4 g) and phosphorus oxychloride (7.1 g) was suspended in dry tetrahydrofuran (30 ml). To the suspension was added 4-chloro-2-methoxycarbonylmethoxyimino-3-oxobutyric acid (syn isomer) (10 g) under ice-cooling, and the mixture was stirred at the same temperature for an hour to prepare the activated acid solution. This solution was added at a time to a solution of benzhydryl 7-amino-3-vinyl-3-cephem-4-carboxylate hydrochloride (16.3 g) and trimethylsilylacetamide (40 g) in ethyl acetate (163 ml) at −30° C. After the reaction mixture was stirred at −15° C. for an hour, the resultant solution was poured into water (100 ml) and then extracted with ethyl acetate (200 ml). The extract was washed with a saturated aqueous sodium bicarbonate and a saturated aqueous sodium chloride. The organic layer was dried over magnesium sulfate and evaporated under reduced pressure to give benzhydryl 7-(4-chloro-2-methoxycarbonylmethoxyimino-3-oxobutyramido)-3-vinyl-3-cephem-4-carboxylate (syn isomer) (21.8 g).

I.R. (Nujol): 3260, 1770, 1750, 1708, 1660 cm$^{-1}$

N.M.R. (DMSO—d$_6$, δ): 3.55, 3.94(2H, ABq, J=18 Hz), 3.65 (3H, s), 4.75 (2H,s), 4.87(2H,s), 5.22 (1H,d, J=5 Hz), 5.23(1H,d,J=11 Hz), 5.57(1H,d,J=17 Hz), 5.85(1H,dd,J=5 Hz, 8 Hz), 6.71(1H,dd,J=11 Hz, 17 Hz), 6.90(1H,s), 7.28(10H.m), 9.46(1H,d,J=8 Hz)

Preparation 93

(1) To a mixture of p-nitrobenzyl alcohol (45 g) and N,N-dimethylaniline (37.2 ml) in a mixture of diisopropyl ether and diethyl ether (300 ml) was added dropwise bromoacetyl bromide (25 ml) at 30° to 35° C., and the reaction mixture was stirred at the same temperature for an hour. After the reaction mixture was poured into ice-water, the separated organic layer was washed with 5% aqueous sodium bicarbonate. The solution was evaporated under reduced pressure to give p-nitrobenzyl bromoacetate. To a solution of this residue in N,N-dimethylformamide (150 ml) was added N-hydroxyphthalimide 39.3 g) and triethylamine (50 ml), and the reaction mixture was stirred for an hour at room temperature. The resultant mixture was poured into ice-water, and the precipitates were collected by filtration and washed with water to give p-nitrobenzyl 2-phthalimidooxyacetate (69.26 g).

(2) To 34.32 g of this product in tetrahydrofuran (103 ml) was added a solution of 100% hydrazine hydrate (5.37 g) in methanol (7 ml), and the mixture was stirred at ambient temperature for 30 minutes. To the reaction mixture was added 20% hydrochloric acid (70 ml) under ice-cooling, and the mixture was stirred at the same temperature for 10 minutes. The insoluble material was filtered off. To the filtrate were added pyridine (15 ml) and (2-formamidothiazol-4-yl)glyoxylic acid (15 g) and the mixture was stirred at ambient temperature for 2.5 hours. The resultant mixture was adjusted to pH 7.5 with 10% aqueous sodium hydroxide and washed with ethyl acetate. The resultant aqueous solution was acidified to pH 2.0 with 10% hydrochloric acid and then extracted with ethyl acetate. Conventional work-up of the extract gave 2-(p-nitrobenzyloxycarbonylmethoxyimino)-2-(2-formamidothiazol-4-yl)acetic acid (syn isomer) (21.7 g).

I.R. (Nujol): 1770, 1680, 1630, 1600, 1510, 1200 cm$^{-1}$
N.M.R. (DMSO—d$_6$, δ): 4.95(2H,s), 5.40(2H,s), 7.52(1H,s), 7.65, 8.20(4H,dd,J=9 Hz), 8.55(1H,s), 12.60(1H, broad s)

Example 327

To a suspension of 7-(4-chloro-2-methoxycarbonylmethoxyimino-3-oxobutyramido)-3-vinyl-3-cephem-4-carboxylic acid (syn isomer) (2.0 g) in water (20 ml) were added thiourea (0.683 g) and sodium acetate (1.84 g) at 40° C. with stirring. The reaction mixture was stirred at the same temperature for 1.5 hours. The resultant solution was adjusted to pH 2.8 with 10% hydrochloric acid and stirred under ice-cooling for 20 minutes. The precipitates were collected by filtration, washed with water and dried over phosphorus pentoxide under reduced pressure to give 7-[2-(2-aminothiazol-4-yl)-2-methoxycarbonylmethoxyiminoacetamido]-3-vinyl-3-cephem-4-carboxylic acid (syn isomer) (1.9 g).

I.R. (Nujol): 3240, 1760(broad), 1724, 1650(broad) cm$^{-1}$
N.M.R. (DMSO—d$_6$, δ): 3.50, 3.88(2H,ABq, J=18 Hz), 3.65 (3H, s), 4.67(2H,s), 5.17(1H,d,J=5 Hz), 5.28(1H, d,J=11 Hz), 5.51(1H,d,J=18 Hz), 5.75(1H,dd,J=5 Hz, 8 Hz), 6.73(1H,s), 6.88(1H,dd,J=11 Hz, 18 Hz), 9.50(1H,d,J=8 Hz)

Example 328

To a solution of benzhydryl 7-(4-chloro-2-methoxycarbonylmethoxyimino-3-oxobutyramido)-3-vinyl-3-cephem-4-carboxylate (syn isomer) (2.0 g) in a mixture of tetrahydrofuran (10 ml) and water (10 ml) were added thiourea (0.5 g) and sodium acetate (1.34 g). The mixture was stirred at 40° C. for 4 hours. The resultant solution was extracted with ethyl acetate (100 ml), and the extract was washed with a saturated aqueous sodium chloride twice. After the resultant solution was dried over magnesium sulfate, the solvent was removed by distillation under reduced pressure to give benzhydryl 7-[2-(2-aminothiazol-4-yl)-2-methoxycarbonylmethoxyiminoacetamido]-3-vinyl-3-cephem-4-carboxylate (syn isomer) (2.0 g).

I.R. (Nujol): 3440, 3260, 1778, 1740, 1720, 1662, 1620 cm$^{-1}$
N.M.R. (DMSO—d$_6$, δ): 3.3-3.9(2H,m), 3.63(3H,s), 4.67 5.60 (1H,d, J=18 Hz), 5.86(1H,dd,J=5 Hz, 8 Hz), 6.50-7.03(1H,m), 6.76(1H,s), 6.88(1H,s), 7.28(10H,m), 9.56(1H,d,J=8 Hz)

Example 329

A mixture of 7-[2-(2-aminothiazol-4-yl)-2-methoxycarbonylmethoxyiminoacetamido]-3-vinyl-3-cephem-4-carboxylic acid (syn isomer) (2.0 g) and sodium bicarbonate (1.8 g) in water (40 ml) was stirred at 40° to 45° C. for 7 hours. The reaction mixture was adjusted to pH 5.0 with acetic acid. This solution was subjected to column chromatography on macroporous nonionic adsorption resin "Diaion HP-20" (20 ml and eluted with water. The eluate was acidified to pH 2.2 with 10% hydrochloric acid under ice-cooling. The precipitates were collected by filtration and dried to give 7-[2-(2-aminothiazol-4-yl)-2-carboxymethoxyiminoacetamido]-3-vinyl-3-cephem-4-carboxylic acid (syn isomer) (0.9 g), which was identified by comparing the physico-chemical data with those of the object compound in Example 90.

Example 330

A mixture of 7-[2-(2-aminothiazol-4-yl)-2-ethoxycarbonylmethoxyiminoacetamido]-3-vinyl-3-cephem-4-carboxylic acid (syn isomer) (1.45 g) and sodium bicarbonate (0.63 g) in water (5 ml) was stirred at ambient temperature for 7 days. The reaction mixture was adjusted to pH 6.0 with acetic acid. The solution was subjected to column chromatography on macroporous nonionic adsorption resin "Diaion HP-20" (30 ml) and eluted with water. The eluate was acidified to pH 2.2 with 10% hydrochloric acid under ice-cooling. The precipitates were collected by filtration and dried to give 7-[2-(2-aminothiazol-4-yl)-2-carboxymethoxyiminoacetamido]-3-vinyl-3-cephem-4-carboxylic acid (syn isomer) (0.7 g), which was identified by comparing the physico-chemical data with those of the object compound in Example 90.

Example 331

Vilsmeir reagent was prepared from N,N-dimethylformamide (1.67 ml) and phosphorus oxychloride (1.98 ml) in dry tetrahydrofuran (50.4 ml) in a conventional manner. 2-(p-Nitrobenzyloxycarbonylmethoxyimino)-2-(2-formamidothiazol-4-yl)acetic acid (syn isomer) (7.35 g) was added to the stirred suspension of Vilsmeir reagent under ice-cooling, followed by stirring for 30 minutes at the same temperature. To a solution of 7-amino-3-vinyl-3-cephem-4-carboxylic acid (3.4 g) and trimethylsilylacetamide (11.8 g) in ethyl acetate (35 ml) was added the activated acid solution obtained above at −20° C., and the reaction mixture was stirred at −20° C. to −10° C. for an hour. After water and ethyl acetate were added to the resultant solution, the separated organic layer was washed with water and then dried. A conventional work-up of the solution gave 7-[2-(p-nitrobenzyloxycarbonylmethoxyimino)-2-(2-formamidothiazol-4-yl)acetamido]-3-vinyl-3-cephem-4-carboxylic acid (syn isomer) (6.8 g) as yellowish powder.

I.R. (Nujol): 3250, 1765, 1680, 1520 cm$^{-1}$
N.M.R. (DMSO—d$_6$+D$_2$O,δ): 3.70(2H,m), 4.87(2H,s), 5.12(1H,d,=5 Hz), 5.28(1H,d,J=11 Hz), 5.35(2H,s), 5.58(1H,d,J=18 Hz), 5.83(1H,dd,J=8 Hz, 5 Hz), 6.95(1H,dd,J=18 Hz, 11 Hz), 7.45(1H,s), 7.63(2H,d,J=9 Hz), 8.17(2H,d,J=9 Hz), 8.50(1H,s), 9.68(1H,d,J=8 Hz)

Example 332

7-[2-(p-Nitrobenzyloxycarbonylmethoxyimino)-2-(2-aminothiazol-4-yl)acetamido]-3-vinyl-3-cephem-4-carboxylic acid hydrochloride (syn isomer) (4.47 g) was obtained by reacting 7-[2-(p-nitrobenzyloxycarbonylmethoxyimino)-2-(2-formamidothiazol-4-yl)acetamido]-3-vinyl-3-cephem-4-carboxylic acid (syn isomer) (6.7 g)

with conc. hydrochloric acid (2.4 ml) in methanol (67 ml) according to a similar manner to that of Example 64.

I.R. (Nujol): 3300, 1780, 1750, 1660, 1610 cm$^{-1}$

N.M.R. (DMSO—d$_6$, δ):3.75(2H,s), 4.86(2H,s), 5.30(1H,d,J=5 Hz), 5.35(1H,d,J=11 Hz), 5.43(2H,s), 5.62(1H,d,J=18 Hz), 5.85(1H,dd,J=8 Hz, 5 Hz), 6.93(1H,s), 7.02(1H,dd,J=18 Hz, 11 Hz ), 7.70 (2H,d,J=9 Hz), 8.25(2H,d,J=9 Hz), 9.73(1H,d,J=8 Hz)

Example 333

Pivaloyloxymethyl 7-[2-(2-aminothiazol)-4-yl)-2-(p-nitrobenzyloxycarbonylmethoxyimino)acetamido]-3-vinyl-3-cephem-4-carboxylate (syn isomer) (3.18 g) was obtained by reacting sodium 7-[2-(2-aminothiazol-4-yl)-2-(p-nitrobenzyloxycarbonylmethoxyimino)acetamido]-3-vinyl-3-cephem-4-carboxylate (syn isomer) (4.9 g), which was prepared from 7-[2-(2-aminothiazol-4-yl)-2-(p-nitrobenzyloxycarbonylmethoxyimino)acetamido]-3-vinyl-3-cephem-4-carboxylic acid (syn isomer) (4.4 g) and sodium bicarbonate (0.61 g), according to a similar manner to that of Example 158.

I.R. (Nujol): 3300, 1770, 1740, 1680 cm$^{-1}$

N.M.R. (DMSO—d$_6$+D$_2$O,δ): 1.17(9H,s), 3.70(2H,m), 4.83(2H,s), 5.27(1H,d,J=5 Hz), 5.37(2H,s), 5.4(1H,d,J=11 Hz), 5.87(1H,dd,J=8 Hz, 5 Hz), 5.88(2H,m,), 6.83(1H,s), 6.90(1H,dd,J=18 Hz, 11 Hz), 7.27(2H,m), 7.68(2H,d,J=8 Hz), 8.22(2H,d,J=8 Hz), 9.67(1H,d,J=8 Hz)

What is claimed is:

1. A compound of the formula:

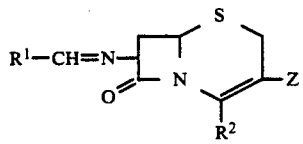

in which
$R^2$ is carboxy or a protected carboxy group,
$R^8$ is aryl and
Z is a group of the formula:

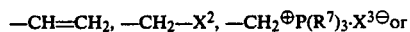

wherein $X^2$ and $X^3$ are each halogen and $R^7$ is aryl,
or a salt thereof.

2. A compound of the formula:

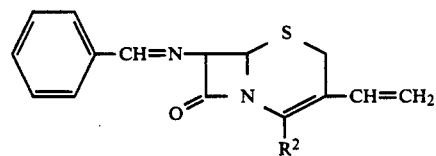

in which $R^2$ is carboxy or a protected carboxy group, or a salt thereof.

3. A compound of the formula:

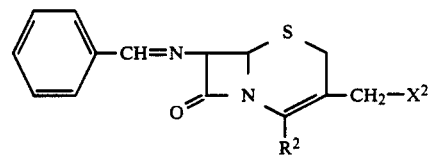

in which
$R^2$ is carboxy or a protected carboxy group and
$X^2$ is halogen,
or a salt thereof.

* * * * *